(12) United States Patent
Bennett et al.

US010941157B2

(10) Patent No.: US 10,941,157 B2
(45) Date of Patent: *Mar. 9, 2021

(54) PESTICIDAL COMPOSITIONS AND USES THEREOF

(71) Applicant: Gilead Apollo, LLC, Foster City, CA (US)

(72) Inventors: Jennifer Lynn Bennett, Chesterfield, MO (US); Karen C. Fitzsimmons, Defiance, MO (US); Shomir Ghosh, Brookline, MA (US); Jeremy Robert Greenwood, Brooklyn, NY (US); William P. Haakenson, Jr., St. Louis, MO (US); Geraldine C. Harriman, Charlestown, RI (US); Silvana Marcel Leit De Moradei, Burlington, MA (US); Barry J. Shortt, New Melle, MO (US); Urszula J. Slomczynska, Ballwin, MO (US); Jeffrey Michael Stein, Wildwood, MO (US)

(73) Assignee: Gilead Apollo, LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,722

(22) Filed: Jul. 9, 2018

(65) Prior Publication Data

US 2019/0040078 A1 Feb. 7, 2019

Related U.S. Application Data

(63) Continuation of application No. 15/359,531, filed on Nov. 22, 2016, now abandoned.

(60) Provisional application No. 62/259,935, filed on Nov. 25, 2015.

(51) Int. Cl.

| C07D 495/04 | (2006.01) |
|---|---|
| A01N 43/90 | (2006.01) |
| A01N 25/00 | (2006.01) |
| A01N 47/24 | (2006.01) |
| A01N 37/46 | (2006.01) |
| A01N 37/50 | (2006.01) |
| A01N 43/56 | (2006.01) |
| A01N 43/653 | (2006.01) |
| A01N 43/82 | (2006.01) |
| A01N 43/88 | (2006.01) |
| A01N 51/00 | (2006.01) |
| A01N 63/02 | (2006.01) |

(52) U.S. Cl.
CPC .......... *C07D 495/04* (2013.01); *A01N 43/90* (2013.01)

(58) Field of Classification Search
None
See application file for complete search history.

(56) References Cited

U.S. PATENT DOCUMENTS

| 4,670,560 | A | 6/1987 | Press et al. |
|---|---|---|---|
| 6,180,635 | B1 | 1/2001 | Cheshire et al. |
| 6,197,780 | B1 | 3/2001 | Munter et al. |
| 8,623,880 | B2 | 1/2014 | Chaudhari et al. |
| 8,969,557 | B2 | 3/2015 | Harriman et al. |
| 9,346,822 | B2 | 5/2016 | Cho et al. |
| 9,453,026 | B2 | 9/2016 | Harriman et al. |
| 9,957,277 | B2 | 5/2018 | Ernst et al. |
| 10,208,044 | B2 | 2/2019 | Greenwood et al. |
| 10,208,053 | B2 | 2/2019 | Strohbach et al. |
| 2003/0187254 | A1 | 10/2003 | Perry et al. |
| 2003/0191142 | A1 | 10/2003 | Cheshire et al. |
| 2005/0124636 | A1 | 6/2005 | Sharma et al. |
| 2006/0039943 | A1 | 2/2006 | Applebaum et al. |
| 2007/0208040 | A1 | 9/2007 | Elzein et al. |
| 2008/0287465 | A1 | 11/2008 | Tumey et al. |
| 2013/0123231 | A1 | 5/2013 | Harriman et al. |
| 2016/0075661 | A1 | 3/2016 | Oberholzer |
| 2016/0108060 | A1 | 4/2016 | Greenwood et al. |
| 2016/0108061 | A1 | 4/2016 | Greenwood et al. |
| 2016/0185783 | A1 | 6/2016 | Greenwood et al. |
| 2016/0185799 | A1 | 6/2016 | Greenwood et al. |
| 2016/0297834 | A1 | 10/2016 | Harriman et al. |
| 2017/0145028 | A1 | 5/2017 | Ghosh et al. |
| 2017/0166582 | A1 | 6/2017 | Ghosh et al. |
| 2017/0166583 | A1 | 6/2017 | Ghosh et al. |
| 2017/0166584 | A1 | 6/2017 | Ghosh et al. |
| 2017/0166585 | A1 | 6/2017 | Bennett et al. |
| 2017/0267690 | A1 | 9/2017 | Alexander et al. |
| 2018/0354973 | A1 | 12/2018 | Bradner et al. |
| 2019/0016732 | A1 | 1/2019 | Bhat et al. |
| 2019/0241582 | A1 | 8/2019 | Ghosh et al. |
| 2019/0330224 | A1 | 10/2019 | Ghosh et al. |
| 2019/0375759 | A1 | 12/2019 | Ghosh et al. |

(Continued)

FOREIGN PATENT DOCUMENTS

| CN | 1106663 A | 8/1995 |
|---|---|---|
| CN | 1301162 A | 6/2001 |

(Continued)

OTHER PUBLICATIONS

Extended European Search Report dated Mar. 20, 2018 for EP Application No. 17209455.9. (7 pages).

(Continued)

*Primary Examiner* — Erin E Hirt
(74) *Attorney, Agent, or Firm* — Sheppard Mullin Richter & Hampton LLP

(57) ABSTRACT

Provided herein are compounds that exhibit activity as fungicides and are useful, for example, in methods for the control of fungal pathogens in plants and can be applied to said plants in a variety of ways.

16 Claims, No Drawings

(56) References Cited

U.S. PATENT DOCUMENTS

| | | |
|---|---|---|
| 2020/0010478 A1 | 1/2020 | Ghosh et al. |
| 2020/0017519 A1 | 1/2020 | Ghosh et al. |
| 2020/0102323 A1 | 4/2020 | Bhat et al. |

FOREIGN PATENT DOCUMENTS

| | | |
|---|---|---|
| CN | 101198614 A | 6/2008 |
| EP | 0640606 A1 | 3/1995 |
| EP | 02351743 A1 | 8/2011 |
| JP | 62-289583 A | 12/1987 |
| JP | 02-225485 A | 9/1990 |
| JP | 08-073467 A | 3/1996 |
| JP | 09-110873 A | 4/1997 |
| JP | 2002-500666 A | 1/2002 |
| JP | 2002-541258 A | 12/2002 |
| JP | 2004-518732 A | 6/2004 |
| JP | 2007-302703 A | 11/2007 |
| JP | 2009-528389 A | 8/2009 |
| WO | WO 97/007119 A1 | 2/1997 |
| WO | WO 97/040846 A1 | 11/1997 |
| WO | WO 98/54190 A1 | 12/1998 |
| WO | WO 00/61583 A1 | 10/2000 |
| WO | WO 02/064598 A1 | 8/2002 |
| WO | WO 2004/014916 A1 | 2/2004 |
| WO | WO 2006/014647 A2 | 2/2006 |
| WO | WO 2007/103776 A2 | 9/2007 |
| WO | WO 2008/143262 A1 | 11/2008 |
| WO | WO 2011/080277 A1 | 7/2011 |
| WO | WO 2011/143553 | 11/2011 |
| WO | WO 2013/071169 | 5/2013 |
| WO | WO 2014/182943 | 11/2014 |
| WO | WO 2014/182950 | 11/2014 |
| WO | WO 2015/003879 | 1/2015 |
| WO | WO 2015/007451 | 1/2015 |

OTHER PUBLICATIONS

Lange, et al. Bioisosteric replacements of the pyrazole moiety of rimonabant: synthesis, biological properties, and molecular modeling investigations of thiazoles, triazoles, and imidazoles as potent and selective CB1 cannabinoid receptor antagonists. J Med Chem. Mar. 24, 2005;48(6):1823-38.

Cambridge Medchem Consulting. "Tuning the Basicity of Amines" (https://www.cambridgemedchemconsulting.com/resources/tuning_bases.html) Updated Apr. 4, 2011.

Caplus record for US 2007/020840 A1 by Elzein et al. (retrieved Nov. 2013).

Cho et al., "Thieno[2,3-d]pyrimidine-3-acetic acids. A new class of nonpeptide endothelin receptor antagonists," Chemical & Pharmaceutical Bulletin, vol. 46, No Month Listed 1998 (pp. 1724-1737).

Corbett, "Review of recent acetyl-CoA carboxylase inhibitor patents: mid-2007-2008," Expert Opinion on Therapeutic Patents, vol. 19, No. 7, No Month Listed 2009 (pp. 943-956).

Database Chemcats [Online], Chemical Abstracts Services, Columbus, Ohio, USA, XP002765978, retrieved from STN Database accession No. AX101218917, Oct. 5, 2016, Aldlab Chemicals Building Blocks.

Database Chemcats [Online], Chemical Abstracts Services, Columbus, Ohio, USA, XP002765979, retrieved from STN Database accession No. K01.513.094, Apr. 7, 2016, Aurora Screening Library.

Database Chemcats [Online], Chemical Abstracts Services, Columbus, Ohio, USA, XP002765980, retrieved from STN Database accession No. A05.862.801, Oct. 20, 2016, Aurora Building Blocks.

Database Chemcats [Online], Chemical Abstracts Services, Columbus, Ohio, USA, XP002765981, retrieved from STN Database accession No. A29.986.104, Oct. 20, 2016, Aurora Building Blocks.

Extended European Search Report dated Feb. 26, 2015 for EP Application No. 12848361.7. (6 pages).

Fernandez et al., "Bayesian-regularized Genetic Neural Networks Applied to the Modeling on Non-Peptide Antagonists for the Human Luteinizing Hormone-releasing Hormone Receptor", Journal of Molecular Graphics and Modelling, 2006, 25(4), 410-422.

International Search Report and Written Opinion dated Feb. 1, 2017 for PCT/US2016/063424. (11 pages).

International Search Report and Written Opinion dated Feb. 4, 2013 for PCT/US2012/064528. (14 pages).

International Search Report and Written Opinion for PCT/US2016/058867 dated Feb. 2, 2017, 18 pages.

International Search Report and Written Opinion for PCT/US2016/063386 dated Jan. 26, 2017, 11 pages.

International Search Report and Written Opinion for PCT/US2016/063410 dated Jan. 25, 2017, 11 pages.

International Search Report and Written Opinion for PCT/US2016/063388 dated Jan. 20, 2017, 10 pages.

Kakehi, "Reactions of 2-Amino-,2-Alkylamino-, and 2-Piperidino-1-aza-azulenes with Aryl and Chlorosulfonyl Isocyanates", Journal of Heterocyclic Chemistry, 1996, 33(4), 1323-1331.

Malamas et al., "Quinazolineacetic Acids and Related Analogues as Aldose Reductase Inhibitors", Journal of Medicinal Chemistry, 1991, 34(4), 1492-1503.

Registry (STN) [online], 2009.05.08, retrieval date Apr. 22, 2016, CAS registration Nos. 1144464-32-3, 1089988-38-4, 1089987-08-5, 1089986-32-2, 1089984-45-1, 1089983-19-6, 1089981-89-4, 1089978-89-1, 1089978-06-2, 1089978-06-2, 1089978-05-1, 1089977-32-1 and the like.

Sasaki et al., "Discovery of a Thieno[2,3-d] pyrimidine-2,4-dione Bearing a p-Methoxyureidophenyl Moiety at the 6-Position: A Highly Potent and Orally Bioavailable Non-Peptide Antagonist for the Human Luteinizing Hormone-Releasing Hormone Receptor", Journal of Medicinal Chemistry, 2003, 46(1), 113-124.

Vlasov et al., "The Synthesis of Novel 3-Substituted 1-Alkyl-5-Methyl-6-(3-Aryl-1,2,4-Oxadiazole-5-Yl)Thieno[2,3-D]Pyrimidine-2,4(1H3H)-Diones and Their Antimicrobial Activity", Journal of Organic and Pharmaceutical Chemistry, 2011, 9(3):51-55, with English translation, 6 pages.

You et al., "Section II Lead Optimization", Medicinal Chemistry, 2nd version, Chemical Industry Press, pp. 25-29, 2008.

Extended European Search Report dated Dec. 10, 2019 for EP Application No. 19190936.5. (7 pages).

Wei, et al., Advances in Antimicrobial Agents Targeted Acetyl CoA Carboxylase. World Pesticides, Jun. 30, 2014; vol. 36, No. 3; 16-19. (In Chinese with English Translation).

PESTICIDAL COMPOSITIONS AND USES THEREOF

CROSS REFERENCE TO RELATED APPLICATIONS

This application is a continuation of U.S. patent application Ser. No. 15/359,531, filed Nov. 22, 2016, which claims the benefit under 35 U.S.C. § 119(e) to U.S. Provisional Application Ser. No. 62/259,935, filed Nov. 25, 2015, the entirety of which is incorporated herein by reference.

FIELD

Provided herein are compounds that exhibit activity as pesticides and are useful, for example, in methods for the control of fungal pathogens and diseases caused by fungal pathogens in plants.

BACKGROUND

Acetyl-CoA carboxylase ("ACCase") is an essential catalyst for the rate-limiting step of fatty acid biosynthesis in both eukaryotes and prokaryotes. Phytopathogenic *fungi* can infect crop plants either in the field or after harvesting, resulting in considerable economic losses to farmers and producers worldwide. In addition to the agricultural impact, when food and feed contaminated with *fungi* or the toxins they produce are ingested by humans or livestock, a number of debilitating diseases or death can occur. Approximately 10,000 species of *fungi* are known to damage crops and affect quality and yield. Crop rotation, breeding of resistant cultivars, the application of agrochemicals and combinations of these strategies is commonly employed to stem the spread of fungal pathogens and the diseases they cause. Additional chemistry and methods of using such as a modulator for ACCase or to control *fungi* are important for, among other things, protection in agriculture.

For example, the rapid onset of resistance to chemical fungicides has often lowered the efficacy of some chemical fungicides. This threat, as well as emergence and spread of additional fungal diseases, accentuates the need for new means of fungal control.

SUMMARY

A compound is provided, the compound having Formula I:

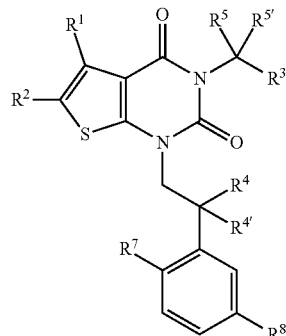

Formula I or a salt thereof, wherein:

$R^1$ is hydrogen, $C_1$-$C_4$ alkyl, $C_1$-$C_4$ alkoxy, $C_1$-$C_4$ haloalkyl, or $C_1$-$C_4$ haloalkoxy;

$R^2$ is heteroaryl, alkyl, cycloalkyl, or heterocyclyl, each of which may be optionally independently substituted with one or more of hydroxyl, halogen, $C_1$-$C_4$ alkyl, $C_1$-$C_4$ alkoxy, $C_1$-$C_4$ haloalkyl, $C_1$-$C_4$ haloalkoxy, oxo, or cyano; or $R^2$ is —C(O)$R^{21}$, wherein $R^{21}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or heterocyclyl, each of which may be optionally independently substituted with one or more of hydroxyl, $C_1$-$C_4$ alkyl, $C_1$-$C_4$ alkoxy, oxo, or cyano;

$R^3$ is —C(O)$R^{31}$, —C(O)N($R^{32}R^{33}$), or —$R^{34}$SO$_2$N($R^{32}R^{33}$), wherein $R^{31}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or 1-heterocycl-1-yl, each of which may be optionally independently substituted with one or more of hydroxyl, $C_1$-$C_4$ alkyl, $C_1$-$C_4$ alkoxy, oxo, or cyano; $R^{32}$ and $R^{33}$ are each independently hydrogen, $C_1$-$C_6$ alkyl, $C_2$-$C_6$ alkenyl, or $C_3$-$C_6$ cycloalkyl, each of which may be optionally independently substituted with one or more of hydroxyl, halogen, $C_1$-$C_4$ alkoxy, oxo, or cyano; and $R^{34}$ is a bond, $C_1$-$C_4$ alkyl, $C_1$-$C_4$ haloalkyl, or $C_2$-$C_4$ alkenyl;

$R^4$ is hydrogen or —OR$^6$, wherein $R^6$ is hydrogen, $C_1$-$C_6$ alkyl, $C_2$-$C_6$ alkenyl, $C_3$-$C_6$ cycloalkyl, $C_4$-$C_{10}$ cycloalkylalkyl, or heterocyclyl, each of which may be optionally independently substituted with one or more of an oxygen atom, hydroxyl, $C_1$-$C_4$ alkyl, $C_1$-$C_4$ alkoxy, oxo, cyano, —N($R^{61}R^{62}$), —C(O)N($R^{61}R^{62}$), or —SO$_2R^{63}$, wherein $R^{61}$ and $R^{62}$ are each independently hydrogen or $C_1$-$C_6$ alkyl, and $R^{63}$ is $C_1$-$C_6$ alkyl;

$R^{4'}$ is hydrogen or $C_1$-$C_4$ alkyl, which may be optionally substituted with one or more of hydroxyl, $C_1$-$C_4$ alkoxy, or cyano;

$R^5$ and $R^{5'}$ are each independently hydrogen or $C_1$-$C_4$ alkyl;

$R^7$ is hydroxyl or $C_1$-$C_4$ alkyl, which may be optionally substituted with one or more of hydroxyl, $C_1$-$C_4$ alkoxy, oxo, or cyano; or $R^7$ is —OR$^{10}$, wherein $R^{10}$ is $C_1$-$C_4$ alkyl, $C_1$-$C_4$ haloalkyl, $C_3$-$C_6$ cycloalkylmethyl, heterocyclyl, or aryl($C_1$-$C_4$)alkyl, each of which may be optionally independently substituted with one or more of hydroxyl, an oxygen atom, $C_1$-$C_4$ alkyl, $C_1$-$C_4$ alkoxy, oxo, or cyano; and $R^8$ is hydrogen, halogen, or cyano.

A compound is provided, the compound having Formula Ia, or Ib:

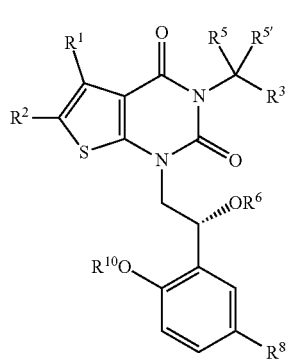

Formula Ia

-continued

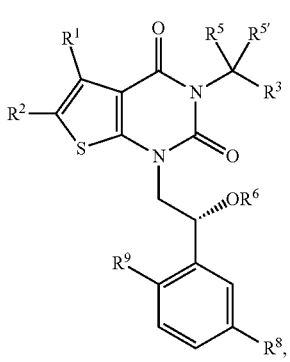

Formula Ib or a salt thereof, wherein:

$R^1$ is methyl;

$R^2$ is oxazolyl, pyrazolyl, triazolyl, cyclobutyl, —$CH_2OH$, —$CH_2O(C_1-C_4)$alkyl, or —$C(O)R^{21}$ wherein $R^{21}$ is $C_1-C_4$ alkoxy;

$R^3$ is —$C(O)R^{31}$, —$C(O)N(R^{32}R^{33})$, or $R^{34}SO_2N(R^{32}R^{33})$, wherein $R^{31}$ is hydroxyl, ethoxy, benzoxy, 1-pyrrolidinyl, 1-piperidinyl, 1-morpholinyl, 2,5-dihydro-1H-pyrrol-1-yl, or 3-hydroxyazetidin-1-yl, $R^{32}$ is hydrogen or methyl, and $R^{33}$ is hydrogen, methyl, ethyl, isopropyl, isobutyl, 2-propenyl, or cyclobutyl; or $R^{34}$ is a bond, or $C_1-C_4$ alkyl;

$R^5$ and $R^{5'}$ are each independently hydrogen or methyl;

$R^6$ is hydrogen, $C_1-C_4$ alkyl, which may be substituted with one or more of hydroxyl, methoxy, oxo, cyano, or —$SO_2CH_3$; $R^6$ is cyclohexyl or cyclohexylmethyl, which may be substituted with one or more of hydroxyl or oxo; $R^6$ is 2-propenyl; or $R^6$ is tetrahydropyranyl;

$R^8$ is hydrogen or F;

$R^9$ is hydroxyl, methyl, ethyl, or —$(CH_2)_3CN$; and $R^{10}$ is methyl or ethyl, each of which may be substituted with one or more of hydroxyl, methyl, methoxy, cyano, phenyl, oxo, or oxetan-3-yl; or $R^{10}$ is tetrahydropyranyl.

A compound is provided, wherein the compound is selected from the group consisting of:

(R)-ethyl-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-2,4-dioxo-1,2,3,4-tetrahydrothieno[2,3-d]pyrimidine-6-carboxylate;

(R)-2-(1-(2-(5-fluoro-2-methoxyphenyl)-2-isopropoxyethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-isopropoxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-6-(2H-1,2,3-triazol-2-yl)thieno[2,3-d]pyrimidine-2,4(1H,3H)-dione;

(R)—N-ethyl-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3 (2H)-yl)-2-methylpropanamide;

(R)-2-(1-(2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-2-(1-(2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3(2H)-yl)-N-isopropyl-2-methylpropanamide;

(S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3(2H)-yl)-N-isopropyl-N-methylpropanamide;

(R)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)—N-cyclobutyl-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)propanamide;

(R)-2-(1-((R)-2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3(2H)-yl)-N-isopropylpropanamide;

(R)-2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-ethyl-1-(2-(2-cyanoethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-(5-fluoro-2-methoxyphenyl)-2-(2-hydroxyethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(5-fluoro-2-methoxyphenyl)-2-hydroxyethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(S)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(R)-2-(1-(2-(2-cyanoethoxy)-2-(2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide;

(R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

3-((R)-1-(5-fluoro-2-methoxyphenyl)-2-(5-methyl-2,4-dioxo-3-((R)-1-oxo-1-(pyrrolidin-1-yl)propan-2-yl)-6-(2H-1,2,3-triazol-2-yl)-3,4-dihydrothieno[2,3-d]pyrimidin-1(2H)-yl)ethoxy)propanenitrile;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide;

(R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide;

(R)-2-(1-(2-(cyanomethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((S)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-(2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(2-cyanoethoxy)-2-(5-fluoro-2-methoxyphenyl)ethyl)-3-((R)-1-(isopropylamino)-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(5-fluoro-2-methoxyphenyl)ethyl)-3-((R)-1-(isopropyl(methyl)amino)-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(5-fluoro-2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;

(S)-2-(1-((R)-2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-ethyl-5-fluorophenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(cyanomethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-((R)-2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-isopropylpropanamide;

(R)-ethyl-1-(2-((S)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-((R)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

2-(1-((R)-2-((S)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(S)-2-(1-(2-(2-cyanoethoxy)-2-(5-fluoro-2-methoxyphenyl)propyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((S)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(5-fluoro-2-methoxyphenyl)-2-(2-(methylsulfonyl)ethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-(2-(5-fluoro-2-methoxyphenyl)-2-(2-(methylsulfonyl)ethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethylpropanamide;

(R)—N-ethyl-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-2-methylpropanamide;

(R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutyl-2-methylpropanamide;

(R)-2-(1-((R)-2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutylpropanamide;

(R)-2-(1-((R)-2-(5-fluoro-2-methoxyphenyl)-2-(2-methoxyethoxy)ethyl)-5-methyl-2,4-dioxo-6-(1H-pyrazol-1-yl)-1,4-dihydrothieno[2,3-d]pyrimidin-3 (2H)-yl)-N-isopropylpropanamide;

(R)-2-(1-(2-hydroxy-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-isopropyl-2-methylpropanamide; and (R)-1-(5-fluoro-2-methoxyphenyl)-2-(3-(1-(isopropylamino)-2-methyl-1-oxopropan-2-yl)-5-methyl-2,4-dioxo-6-(2H-1,2,3-triazol-2-yl)-3,4-dihydrothieno[2,3-d]pyrimidin-1(2H)-yl)ethyl acetate.

A composition is provided, wherein the composition comprises a compound as described herein.

A method of controlling fungal pathogens is provided, the method comprising administering to a plant, a seed or soil a composition comprising an effective amount of a compound as described herein.

A method for modulating ACCase in a biological organism is provided, the method comprising administering to the biological organism a composition comprising an effective amount of a compound as described herein.

A treated seed is provided, wherein the seed comprises a compound or a composition as described herein.

Other objects and features will be in part apparent and in part pointed out hereinafter.

DETAILED DESCRIPTION

Provided herein are compounds that exhibit pesticidal activity, in particular fungicidal activity. The compounds may be used, for example, in the preparation of compositions and in accordance with methods for control of fungal pathogens, as set forth in detail below.

For example, provided herein are compounds of Formula I:

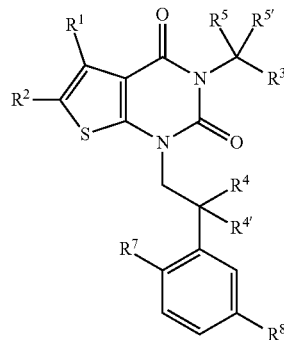

Formula I or a salt thereof, wherein:

$R^1$ is hydrogen, $C_1$-$C_4$ alkyl, $C_1$-$C_4$ alkoxy, $C_1$-$C_4$ haloalkyl, or $C_1$-$C_4$ haloalkoxy;

$R^2$ is heteroaryl, alkyl, cycloalkyl, or heterocyclyl, each of which may be optionally independently substituted with one or more of hydroxyl, halogen, $C_1$-$C_4$ alkyl, $C_1$-$C_4$ alkoxy, $C_1$-$C_4$ haloalkyl, $C_1$-$C_4$ haloalkoxy, oxo, or cyano; or $R^2$ is —C(O)$R^{21}$, wherein $R^{21}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or heterocyclyl, each of which may be optionally independently substituted with one or more of hydroxyl, $C_1$-$C_4$ alkyl, $C_1$-$C_4$ alkoxy, oxo, or cyano;

$R^3$ is —C(O)$R^{31}$, —C(O)N($R^{32}R^{33}$), or —$R^{34}$SO$_2$N($R^{32}R^{33}$), wherein $R^{31}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or 1-heterocycl-1-yl, each of which may be optionally independently substituted with one or more of hydroxyl, $C_1$-$C_4$ alkyl, $C_1$-$C_4$ alkoxy, oxo, or cyano; $R^{32}$ and $R^{33}$ are each independently hydrogen, $C_1$-$C_6$ alkyl, $C_2$-$C_6$ alkenyl, or $C_3$-$C_6$ cycloalkyl, each of which may be optionally independently substituted with one or more of hydroxyl, halogen, $C_1$-$C_4$ alkoxy, oxo, or cyano; and $R^{34}$ is a bond, $C_1$-$C_4$ alkyl, $C_1$-$C_4$ haloalkyl, or $C_2$-$C_4$ alkenyl;

$R^4$ is hydrogen or —OR$^6$, wherein $R^6$ is hydrogen, $C_1$-$C_6$ alkyl, $C_2$-$C_6$ alkenyl, $C_3$-$C_6$ cycloalkyl, $C_4$-$C_{10}$ cycloalkylalkyl, or heterocyclyl, each of which may be optionally independently substituted with one or more of an oxygen atom, hydroxyl, $C_1$-$C_4$ alkyl, $C_1$-$C_4$ alkoxy, oxo, cyano, —N($R^{61}R^{62}$), —C(O)N($R^{61}R^{62}$), or —SO$_2R^{63}$, wherein $R^{61}$ and $R^{62}$ are each independently hydrogen or $C_1$-$C_6$ alkyl, and $R^{63}$ is $C_1$-$C_6$ alkyl;

$R^{4'}$ is hydrogen or $C_1$-$C_4$ alkyl, which may be optionally substituted with one or more of hydroxyl, $C_1$-$C_4$ alkoxy, or cyano;

$R^5$ and $R^{5'}$ are each independently hydrogen or $C_1$-$C_4$ alkyl;

$R^7$ is hydroxyl or $C_1$-$C_4$ alkyl, which may be optionally substituted with one or more of hydroxyl, $C_1$-$C_4$ alkoxy, oxo, or cyano; or $R^7$ is —OR$^{10}$, wherein $R^{10}$ is $C_1$-$C_4$ alkyl, $C_1$-$C_4$ haloalkyl, $C_3$-$C_6$ cycloalkylmethyl, heterocyclyl, or aryl($C_1$-$C_4$)alkyl, each of which may be optionally independently substituted with one or more of hydroxyl, an oxygen atom, $C_1$-$C_4$ alkyl, $C_1$-$C_4$ alkoxy, oxo, or cyano; and $R^8$ is hydrogen, halogen, or cyano.

In some embodiments, $R^1$ can be $C_1$-$C_4$ alkyl. In some embodiments, for example, $R^1$ is methyl.

In some embodiments, $R^2$ can be —C(O)$R^{21}$, wherein $R^{21}$ is $C_1$-$C_4$ alkoxy. In some embodiments, $R^2$ is —CH$_2$OH. In some embodiments, $R^2$ is —CH$_2$O($C_1$-$C_4$)alkyl. In some embodiments, $R^2$ is cyclobutyl. In other embodiments, $R^2$ can be unsubstituted heteroaryl. In some embodiments, $R^2$ can be a 5-membered heteroaryl. For example, $R^2$ can be oxazolyl, pyrazolyl, triazolyl, isoxazolyl, or thienyl. In some embodiments, for example, $R^2$ is selected from the group consisting of oxazolyl, pyrazolyl, and triazolyl. In some embodiments, $R^2$ is 2-oxazolyl. In some embodiments, $R^2$ is 1-pyrazolyl. In other embodiments, $R^2$ is 2H-1,2,3-triazol-2-yl.

In some embodiments, $R^3$ can be —C(O)$R^{31}$, wherein $R^{31}$ is hydroxyl, alkoxy, or an optionally independently substituted 1-heterocycl-1-yl. For example, in some embodiments $R^{31}$ can be hydroxyl or alkoxy (e.g., ethoxy or benzoxy). In other embodiments, $R^{31}$ can be 2,5-dihydro-1H-pyrrolyl, 1-piperidinyl, 1-pyrrolidinyl, 1-morpholinyl, or 1-azetidinyl, each of which may be optionally independently substituted with hydroxyl, methoxy, methyl, or cyano. In other embodiments, $R^3$ is —C(O)N($R^{32}R^{33}$), wherein $R^{32}$ and $R^{33}$ are independently selected from hydrogen, $C_1$-$C_6$ alkyl, $C_2$-$C_6$ alkenyl, and $C_3$-$C_6$ cycloalkyl. In some embodiments, $R^3$ is —C(O)N($R^{32}R^{33}$), wherein $R^{32}$ is hydrogen or methyl, and $R^{33}$ is hydrogen, methyl, ethyl, propyl, isopropyl, butyl, isobutyl, t-butyl, cyclopropyl, cyclobutyl, 2-propenyl, or —$CH_2CN$. In some embodiments, $R^3$ is —C(O)NH$R^{33}$, wherein $R^{33}$ is hydrogen, methyl, ethyl, isopropyl, isobutyl, cyclopropyl, cyclobutyl, 2-propenyl, or —$CH_2CN$. In other embodiments, $R^3$ is —C(O)N($CH_3$)($R^{33}$), wherein $R^{33}$ is methyl, isopropyl, or 2-propenyl. In some embodiments, $R^3$ is —C(O)NH$_2$. In other embodiments, $R^3$ is —C(O)N($CH_3$)$_2$. In other embodiments, $R^3$ can be —$R^{34}SO_2NH_2$ wherein $R^{34}$ is a bond or $C_1$-$C_4$ alkyl. In some embodiments, $R^3$ is —$CH_2SO_2NH_2$. In other embodiments, $R^3$ is —$SO_2NH_2$.

In some embodiments, $R^4$ and $R^{4'}$ are both hydrogen. In some embodiments, $R^4$ is —$OR^6$ and $R^{4'}$ is hydrogen, wherein $R^6$ is hydrogen, $C_1$-$C_6$ alkyl, $C_2$-$C_6$ alkenyl, $C_3$-$C_6$ cycloalkyl, $C_4$-$C_{10}$ cycloalkylalkyl, or heterocyclyl, each of which may be optionally independently substituted with hydroxyl, methoxy, oxo, cyano, —N($CH_3$)$_2$, —C(O)NH$_2$, or —$SO_2CH_3$. In some embodiments, $R^6$ is hydrogen. In some embodiments, $R^6$ can be $C_1$-$C_6$ alkyl or $C_2$-$C_6$ alkenyl, each of which may be optionally independently substituted with hydroxyl, methoxy, oxo, cyano, —N($CH_3$)$_2$, —C(O)NH$_2$, or —$SO_2CH_3$. For example, $R^6$ can be ethyl, isopropyl, isobutyl, —$CH_2CH_2OH$, —$CH_2CH_2OCH_3$, —$(CH_2)_3OCH_3$, —$CH_2CH(CH_3)OH$, $CH_2C(CH_3)_2OH$, —$CH_2CH=CH_2$, —$C(O)CH_3$, —$C(O)CH_2OH$, —$CH_2CN$, —$CH_2CH_2CN$, —$CH_2CH(CH_3)CN$, —$CH_2C(CH_3)_2CN$, —$CH_2CH_2N(CH_3)_2$, —$CH_2CH_2C(O)NH_2$, or —$CH_2CH_2SO_2CH_3$. In some embodiments, $R^6$ is $C_3$-$C_6$ cycloalkyl or $C_4$-$C_{10}$ cycloalkylalkyl, which may be optionally independently substituted with hydroxyl or oxo. For example, $R^6$ can comprise an optionally substituted cyclohexyl moiety (e.g., $R^6$ can be 4-hydroxycyclohexyl, 4-oxycyclohexyl, (4-oxocyclohexyl)methyl, or (4-hydroxycyclohexyl)methyl). In other embodiments, $R^6$ is heterocyclyl (e.g., tetrahydropyranyl). For example, $R^6$ can be tetrahydro-2H-pyran-4-yl. In other embodiments, $R^4$ is hydroxyl or —$OCH_2CH_2CN$; and $R^{4'}$ is methyl, —$CH_2OH$, or —$CH_2CH_2OH$. For example, $R^4$ is —OH and $R^{4'}$ is —$CH_2OH$; $R^4$ is —OH and $R^{4'}$ is —$CH_2CH_2OH$; or $R^4$ is —$OCH_2CH_2CN$ and $R^{4'}$ is methyl.

$R^5$ and $R^{5'}$ can be independently selected from the group consisting of hydrogen and methyl. In some embodiments, $R^5$ and $R^{5'}$ are both methyl. In some embodiments, $R^5$ and $R^{5'}$ are both hydrogen. In other embodiments, $R^5$ is methyl and $R^{5'}$ is hydrogen.

In some embodiments, $R^7$ is hydroxyl. In some embodiments, $R^7$ is $C_1$-$C_4$ alkyl, which may be optionally substituted with cyano. For example, $R^7$ is methyl, ethyl, or —$(CH_2)_3CN$. In other embodiments, $R^7$ is —$OR^{10}$, wherein $R^{10}$ is $C_1$-$C_4$ alkyl, heterocyclyl, or benzyl, each of which may be optionally independently substituted with hydroxyl, methoxy, oxo, oxetanyl, and cyano. For example, $R^{10}$ can be selected from the group consisting of methyl, —CH($CH_3$)$_2$, —$CH_2CH_2OH$, —$CH_2CH_2OCH_3$, —$C(O)CH_3$, —$CH_2$(oxetan-3-yl), —$CH_2CN$, and —$CH_2CH_2CN$. In some embodiments, for example, $R^{10}$ is methyl. In other embodiments, $R^{10}$ is heterocyclyl (e.g., tetrahydropyranyl). For example, $R^{10}$ can be tetrahydro-2H-pyran-4-yl. In other embodiments, $R^{10}$ is benzyl.

$R^8$ can be selected from the group consisting of hydrogen and F.

The compound of Formula I can be a compound of Formula Ia, or Ib:

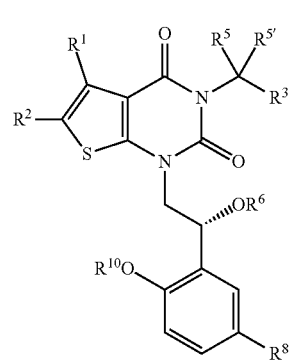

Formula Ia

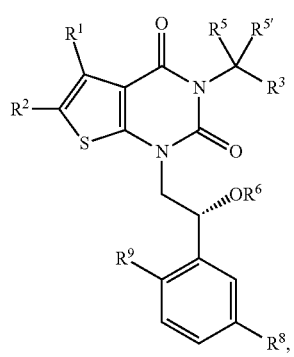

Formula Ib or a salt thereof, wherein:

$R^1$ is methyl;

$R^2$ is oxazolyl, pyrazolyl, triazolyl, cyclobutyl, —$CH_2OH$, —$CH_2O(C_1$-$C_4)$alkyl, or —C(O)$R^{21}$, wherein $R^{21}$ is $C_1$-$C_4$ alkoxy;

$R^3$ is —C(O)$R^{31}$, —C(O)N($R^{32}R^{33}$), or —$R^{34}SO_2N$($R^{32}R^{33}$), wherein $R^{31}$ is hydroxyl, ethoxy, benzoxy, 1-pyrrolidinyl, 1-piperidinyl, 1-morpholinyl, 2,5-dihydro-1H-pyrrol-1-yl, 3-hydroxyazetidin-1-yl, $R^{32}$ is hydrogen or methyl, and $R^{33}$ is hydrogen, methyl, ethyl, isopropyl, isobutyl, 2-propenyl, or cyclobutyl; or $R^{34}$ is a bond or $C_1$-$C_4$ alkyl;

$R^5$ and $R^{5'}$ are each independently hydrogen or methyl;

$R^6$ is hydrogen, $C_1$-$C_4$ alkyl, which may be substituted with one or more of hydroxyl, methoxy, oxo, cyano, or —$SO_2CH_3$; $R^6$ is cyclohexyl or cyclohexylmethyl, which may be substituted with one or more of hydroxyl or oxo; $R^6$ is 2-propenyl; or $R^6$ is tetrahydropyranyl;

$R^8$ is hydrogen or F;

$R^9$ is hydroxyl, methyl, ethyl, or —$(CH_2)_3CN$; and $R^{10}$ is methyl or ethyl, each of which may be substituted with one or more of hydroxyl, methyl, methoxy, cyano, phenyl, oxo, or oxetan-3-yl; or $R^{10}$ is tetrahydropyranyl.

The compound of Formula I can be a compound of Formula Ia or a salt thereof. $R^2$ can be 1-pyrazolyl, 2H-1,2,3-triazol-2-yl, 2-oxazolyl, or —C(O)O$CH_2CH_3$. In some embodiments, $R^2$ is 1-pyrazolyl, corresponding to a compound of Formula Ia-i:

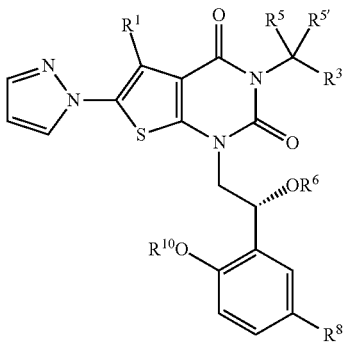

Formula Ia-i or a salt thereof, wherein each of $R^1$, $R^3$, $R^5$, $R^{5'}$, $R^6$, $R^8$, and $R^{10}$ is as defined above and described in embodiments herein, both singly and in combination. In some embodiments, $R^2$ is 2H-1,2,3-triazol-2-yl, corresponding to a compound of Formula Ia-ii:

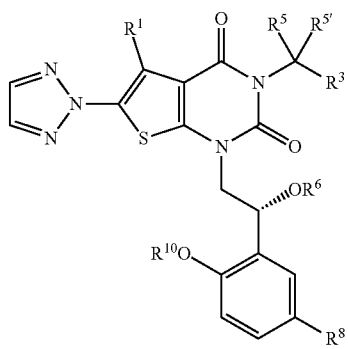

Formula Ia-ii or a salt thereof, wherein each of $R^1$, $R^3$, $R^5$, $R^{5'}$, $R^6$, $R^8$, and $R^{10}$ is as defined above and described in embodiments herein, both singly and in combination. In some embodiments, $R^2$ is 2-oxazolyl, corresponding to a compound of Formula Ia-iii:

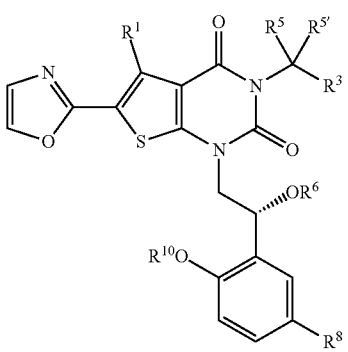

Formula Ia-iii or a salt thereof, wherein each of $R^1$, $R^3$, $R^5$, $R^{5'}$, $R^6$, $R^8$, and $R^{10}$ is as defined above and described in embodiments herein, both singly and in combination. In other embodiments, $R^2$ is —C(O)OCH$_2$CH$_3$, corresponding to a compound of Formula Ia-iv:

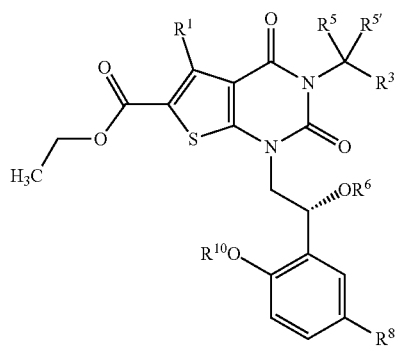

Formula Ia-iv or a salt thereof, wherein each of $R^1$, $R^3$, $R^5$, $R^{5'}$, $R^6$, $R^8$, and $R^{10}$ is as defined above and described in embodiments herein, both singly and in combination.

The compound of Formula I can be a compound of Formula Ib or a salt thereof. $R^2$ can be 1-pyrazolyl, 2H-1,2,3-triazol-2-yl, 2-oxazolyl, or —C(O)OCH$_2$CH$_3$. In some embodiments, $R^2$ is 2H-1,2,3-triazol-2-yl, corresponding to a compound of Formula Ib-ii:

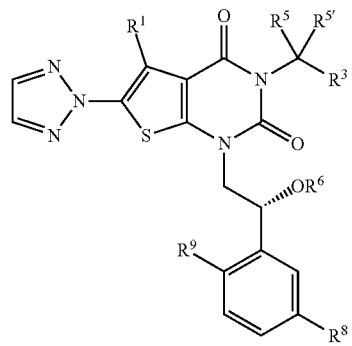

Formula Ib-ii or a salt thereof, wherein each of $R^1$, $R^3$, $R^5$, $R^{5'}$, $R^6$, $R^8$, and $R^9$ is as defined above and described in embodiments herein, both singly and in combination.

In some embodiments, $R^3$ can be —C(O)N($R^{32}R^{33}$), wherein $R^{32}$ is hydrogen or methyl, and $R^{33}$ is ethyl, isopropyl, or cyclobutyl. In some embodiments, $R^3$ is —C(O)NHCH$_2$CH$_3$. In some embodiments, $R^3$ is —C(O)NHC(CH$_3$)$_2$. In some embodiments, $R^3$ is —C(O)N(CH$_3$)C(CH$_3$)$_2$. In some embodiments, $R^3$ is —C(O)NH(cyclobutyl).

In other embodiments, $R^3$ can be —C(O)$R^{31}$ wherein $R^{31}$ is 1-pyrrolidinyl or 1-piperidinyl. In some embodiments, $R^3$ is —C(O)$R^{31}$ wherein $R^{31}$ is 1-pyrrolidinyl.

In some embodiments, $R^5$ and $R^{5'}$ are both methyl. In some embodiments, $R^5$ and $R^{5'}$ are both hydrogen. In other embodiments, $R^5$ is methyl and $R^{5'}$ is hydrogen.

In some embodiments, $R^6$ can be hydrogen, isopropyl, —CH$_2$CH$_2$OH, —CH$_2$CH$_2$OCH$_3$, —(CH$_2$)$_3$OCH$_3$, —C(O)CH$_3$, —CH$_2$CN, —CH$_2$CH$_2$CN, —CH$_2$CH(CH$_3$)CN, —CH$_2$C(CH$_3$)$_2$CN, —CH$_2$CH$_2$SO$_2$CH$_3$, or tetrahydro-2H-pyran-4-yl. In some embodiments, $R^6$ is hydrogen. In some embodiments, $R^6$ is isopropyl. In some embodiments, $R^6$ is —CH$_2$CH$_2$OH. In some embodiments, $R^6$ is —CH$_2$CH$_2$OCH$_3$. In some embodiments, $R^6$ is —(CH$_2$)$_3$OCH$_3$. In some embodiments, $R^6$ is —C(O)CH$_3$. In some embodiments, $R^6$ is —CH$_2$CN. In some embodiments, $R^6$ is —CH$_2$CH$_2$CN. In some embodiments, R$^6$ is —CH$_2$CH(CH$_3$)CN. In some embodiments, R$^6$ is —CH$_2$C(CH$_3$)$_2$CN. In some embodiments, R$^6$ is —CH$_2$CH(CH$_3$)CN. In some embodiments, R$^6$ is —CH$_2$CH$_2$SO$_2$CH$_3$. In some embodiments, R$^6$ is tetrahydro-2H-pyran-4-yl.

In some embodiments, R$^8$ is hydrogen. In other embodiments, R$^8$ is F.

In some embodiments, R$^9$ is ethyl.

In some embodiments, R$^{10}$ is methyl.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons. Non-limiting examples of C$_1$-C$_{10}$ alkyl groups include methyl, ethyl, propyl, isopropyl, butyl, sec-butyl, tert-butyl, 3-pentyl, hexyl and octyl groups. For example, the term "alkyl" as used herein, by itself or as part of another group, can refer to a straight or branched chain radical comprising from one to six carbon atoms.

The term "alkenyl" as employed herein, by itself or as part of another group, refers to both straight and branched chain radicals of up to ten carbons, and which comprise at least one carbon-carbon double bond.

The term "hydroxyalkyl" as employed herein, refers to both straight and branched chain alkyl radicals having a hydroxyl substituent. The hydroxyl substituent can be bound to any carbon of the alkyl chain. Non-limiting examples include —CH$_2$OH, —CH$_2$CH$_2$OH, —CH$_2$CH(OH)CH$_3$ and —CH$_2$CH(OH)CH$_2$CH$_3$. For example, the term "hydroxyalkyl" as employed herein can refer to a straight or branched chain radical comprising from one to four carbon atoms and having one or more hydroxyl substituents.

The term "haloalkyl" as employed herein, by itself or as part of another group, refers to an alkyl group, as defined herein, substituted with at least one halogen. Non-limiting examples of haloalkyl groups include trifluromethyl and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy.

The term "haloalkoxy" as employed herein, by itself or as part of another group, refers to an alkoxy group as defined herein, wherein the alkyl moiety of the alkoxy group is further substituted with at least one halogen. Non-limiting example of haloalkoxy groups include trifluoromethoxy, and 2,2-dichloroethoxy.

The term "cycloalkyl" as used herein refers to an alkyl group comprising a closed ring comprising from 3 to 8 carbon atoms. Non-limiting examples of cycloalkyl groups include cyclopropyl, cyclobutyl, cyclopentyl, cyclohexyl, cycloheptyl, (cyclohexyl)methyl, and (cyclohexyl)ethyl.

The term "cycloalkylalkyl" as used herein refers to an alkyl group, as defined herein, substituted with a cycloalkyl group, as defined herein. Non-limiting examples of cycloalkylalkyl groups include (cyclobutyl)methyl, (cyclohexyl)methyl, and (cyclohexyl)ethyl.

As used herein, the term "heterocyclyl," "heterocycloalkyl," or "heterocycle" refers to a saturated or partially saturated 3 to 7 membered monocyclic, or 7 to 10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and includes any bicyclic group in which any of the above-defined heterocyclic rings is fused to a benzene ring, and wherein the heterocyclic ring can be substituted on carbon or on a nitrogen atom if the resulting compound is stable. Non-limiting examples of common saturated or partially saturated heterocyclic groups include azetinyl, oxetanyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "aryl" as employed herein by itself or as part of another group refers to monocyclic, bicyclic or tricyclic aromatic groups containing from 6 to 14 carbons in the ring.

Common aryl groups include C$_{6-14}$ aryl, typically C$_{6-10}$ aryl. Typical C$_{6-14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms. Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "oxo" as employed herein refers to an oxygen atom joined by a double bond to a carbon atom. For example, an oxo substituent can be bound to any carbon of an alkyl chain. Non-limiting examples include —CH$_2$C(O)H, —C(O)CH$_3$, —CH$_2$C(O)CH$_3$, —CH$_2$CH$_2$C(O)CH$_3$, and —CH$_2$C(O)CH$_2$CH$_3$.

Non-limiting examples of species encompassed by the present disclosure are disclosed in Table 1.

TABLE 1

Compounds of Formula I

| Cmpd No. | R Groups | Substituent | Compound Structure |
|---|---|---|---|
| I-001 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>$C(O)NHCH(CH_3)_2$<br>$OCH(CH_3)_2$<br>H<br>$CH_3, CH_3$<br>$OCH_3$<br>H | 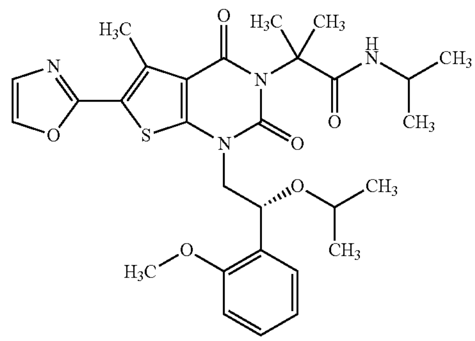 [SMILES: COc1ccccc1[C@H](Cn1c(=O)n(C(C)(C)C(=O)NC(C)C)c(=O)c2c(C)c(-c3ncco3)sc21)OC(C)C] |
| I-002 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)(1\text{-piperidinyl})$<br>$OCH(CH_3)_2$<br>H<br>$CH_3, CH_3$<br>$OCH_3$<br>F | 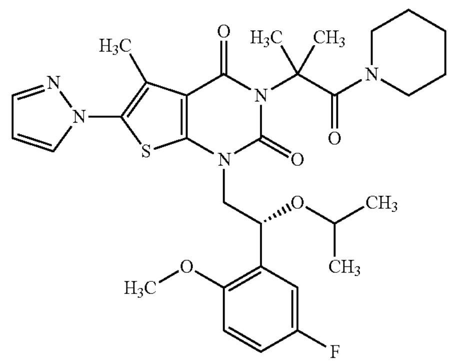 [SMILES: COc1ccc(F)cc1[C@H](Cn1c(=O)n(C(C)(C)C(=O)N2CCCCC2)c(=O)c2c(C)c(-n3cccn3)sc21)OC(C)C] |
| I-003 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)(1\text{-pyrrolidinyl})$<br>O-tetrahydro-2H-pyran-4-yl<br>H<br>$CH_3, CH_3$<br>$OCH_3$<br>H | 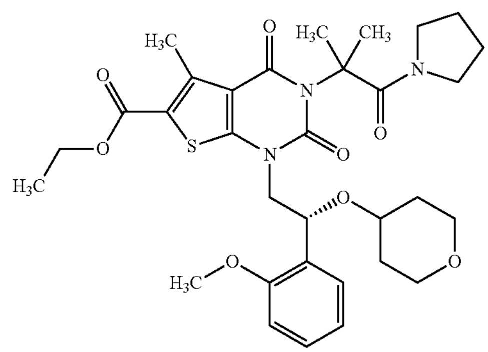 [SMILES: CCOC(=O)c1sc2c(c1C)c(=O)n(C(C)(C)C(=O)N1CCCC1)c(=O)n2C[C@H](OC1CCOCC1)c1ccccc1OC] |
| I-004 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>$C(O)(1\text{-piperidinyl})$<br>O-tetrahydro-2H-pyran-4-yl<br>H<br>$CH_3, CH_3$<br>$OCH_3$<br>H | 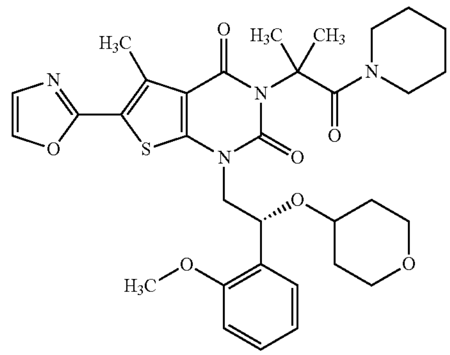 [SMILES: COc1ccccc1[C@H](Cn1c(=O)n(C(C)(C)C(=O)N2CCCCC2)c(=O)c2c(C)c(-c3ncco3)sc21)OC1CCOCC1] |

TABLE 1-continued

Compounds of Formula I

| Cmpd No. | R Groups | Substituent |
|---|---|---|
| I-005 | R¹ | CH₃ |
| | R² | 2-oxazolyl |
| | R³ | C(O)(1-pyrrolidinyl) |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | H |
| I-006 | R¹ | CH₃ |
| | R² | C(O)OCH₂CH₃ |
| | R³ | C(O)(1-piperidinyl) |
| | R⁴ | OCH(CH₃)₂ |
| | R⁴' | H |
| | R⁵, R⁵' | CH₃, CH₃ |
| | R⁷ | OCH₃ |
| | R⁸ | H |
| I-007 | R¹ | CH₃ |
| | R² | C(O)OCH₂CH₃ |
| | R³ | C(O)(1-pyrrolidinyl) |
| | R⁴ | OCH(CH₃)₂ |
| | R⁴' | H |
| | R⁵, R⁵' | CH₃, CH₃ |
| | R⁷ | OCH₃ |
| | R⁸ | H |
| I-008 | R¹ | CH₃ |
| | R² | C(O)OCH₂CH₃ |
| | R³ | C(O)NHCH(CH₃)₂ |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | H |

TABLE 1-continued

Compounds of Formula I

| Cmpd No. | R Groups | Substituent |
|---|---|---|
| I-009 | $R^1$ | $CH_3$ |
| | $R^2$ | $C(O)OCH_2CH_3$ |
| | $R^3$ | $C(O)NHCH(CH_3)_2$ |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-010 | $R^1$ | $CH_3$ |
| | $R^2$ | 2-oxazolyl |
| | $R^3$ | $C(O)NHCH_2CH_3$ |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | H |
| I-011 | $R^1$ | $CH_3$ |
| | $R^2$ | 2-oxazolyl |
| | $R^3$ | $C(O)NHCH(CH_3)_2$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | H |
| I-012 | $R^1$ | $CH_3$ |
| | $R^2$ | 2-oxazolyl |
| | $R^3$ | $C(O)NHCH(CH_3)_2$ |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | H |

TABLE 1-continued

Compounds of Formula I

| Cmpd No. | R Groups | Substituent |
|---|---|---|
| I-013 | R¹ | CH₃ |
| | R² | 2-oxazolyl |
| | R³ | C(O)NHCH(CH₃)₂ |
| | R⁴ | O-4-oxocyclohexyl |
| | R⁴' | H |
| | R⁴'' | CH₃, CH₃ |
| | R⁵, R⁵' | OCH₃ |
| | R⁷ | H |
| | R⁸ | |
| I-014 | R¹ | CH₃ |
| | R² | 1-pyrazolyl |
| | R³ | C(O)NHCH(CH₃)₂ |
| | R⁴ | OCH(CH₃)₂ |
| | R⁴' | H |
| | R⁵, R⁵' | CH₃, CH₃ |
| | R⁷ | OCH₃ |
| | R⁸ | F |
| I-015 | R¹ | CH₃ |
| | R² | 2-oxazolyl |
| | R³ | C(O)NHCH(CH₃)₂ |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | F |
| I-016 | R¹ | CH₃ |
| | R² | 2-oxazolyl |
| | R³ | C(O)(1-piperidinyl) |
| | R⁴ | OCH(CH₃)₂ |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-017 | R¹ | CH₃ |
| | R² | 2-oxazolyl |
| | R³ | C(O)(1-pyrrolidinyl) |
| | R⁴ | OCH(CH₃)₂ |
| | R⁴' | H |
| | R⁵, R⁵' | CH₃, CH₃ |
| | R⁷ | OCH₃ |
| | R⁸ | F |
| I-018 | R¹ | CH₃ |
| | R² | 2-oxazolyl |
| | R³ | C(O)NHCH(CH₃)₂ |
| | R⁴ | OCH(CH₃)₂ |
| | R⁴' | H |
| | R⁵, R⁵' | CH₃, CH₃ |
| | R⁷ | OCH₃ |
| | R⁸ | F |
| I-019 | R¹ | CH₃ |
| | R² | 2H-1,2,3-triazol-2-yl |
| | R³ | C(O)NHCH₂CH₃ |
| | R⁴ | OCH(CH₃)₂ |
| | R⁴' | H |
| | R⁵, R⁵' | CH₃, CH₃ |
| | R⁷ | OCH₃ |
| | R⁸ | F |
| I-020 | R¹ | CH₃ |
| | R² | 2H-1,2,3-triazol-2-yl |
| | R³ | C(O)NHCH(CH₃)₂ |
| | R⁴ | OCH(CH₃)₂ |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-021 | $R^1$ | $CH_3$ |
| | $R^2$ | 2H-1,2,3-triazol-2-yl |
| | $R^3$ | C(O)(1-morpholinyl) |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | F |
| I-022 | $R^1$ | $CH_3$ |
| | $R^2$ | 2H-1,2,3-triazol-2-yl |
| | $R^3$ | C(O)(1-piperidinyl) |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | F |
| I-023 | $R^1$ | $CH_3$ |
| | $R^2$ | 2H-1,2,3-triazol-2-yl |
| | $R^3$ | C(O)(1-pyrrolidinyl) |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | F |
| I-024 | $R^1$ | $CH_3$ |
| | $R^2$ | 2-oxazolyl |
| | $R^3$ | $C(O)NHCH(CH_3)_2$ |
| | $R^4$ | O-4-oxocyclohexyl |
| | $R^{4'}$ | H |
| | $R^5, R^{5'}$ | $CH_3, CH_3$ |
| | $R^7$ | $OCH_3$ |
| | $R^8$ | F |

TABLE 1-continued

Compounds of Formula I

| Cmpd No. | R Groups | Substituent | Compound Structure |
|---|---|---|---|
| I-025 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH₂CH₃<br>O CH₂CH(CH₃)₂<br>H<br>CH₃, CH₃<br>OCH₃<br>F | 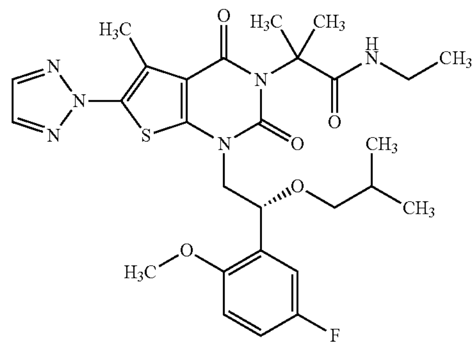 [SMILES: CCNC(=O)C(C)(C)n1c(=O)c2c(C)c(-n3nccn3)sc2n(C[C@H](OCC(C)C)c2cc(F)ccc2OC)c1=O] |
| I-026 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>O CH₂CH(CH₃)₂<br>H<br>CH₃, CH₃<br>OCH₃<br>F | 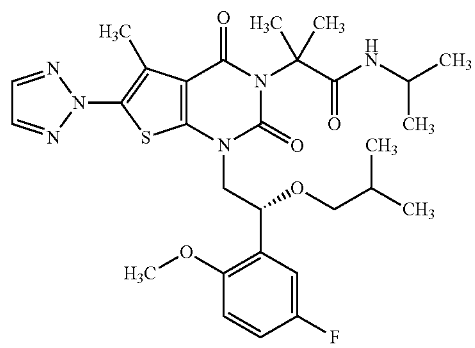 [SMILES: COc1ccc(F)cc1[C@H](Cn1c(=O)n(C(C)(C)C(=O)NC(C)C)c(=O)c2c(C)c(-n3nccn3)sc21)OCC(C)C] |
| I-027 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-piperidinyl)<br>O CH₂CH(CH₃)₂<br>H<br>CH₃, CH₃<br>OCH₃<br>F | 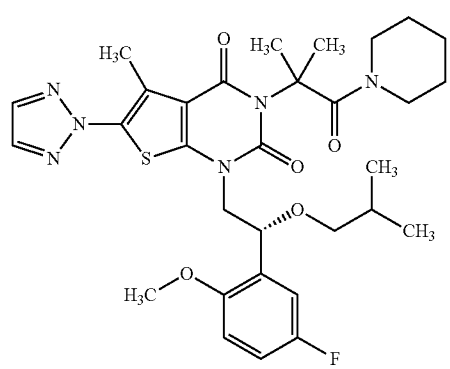 [SMILES: COc1ccc(F)cc1[C@H](Cn1c(=O)n(C(C)(C)C(=O)N2CCCCC2)c(=O)c2c(C)c(-n3nccn3)sc21)OCC(C)C] |
| I-028 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>O CH₂CH(CH₃)₂<br>H<br>CH₃, CH₃<br>OCH₃<br>F | 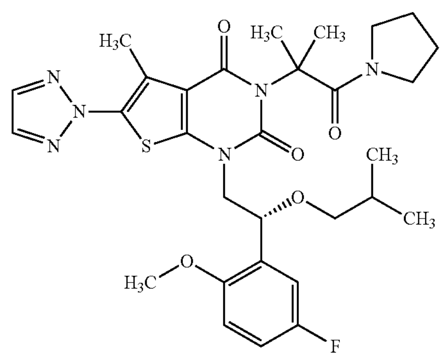 [SMILES: COc1ccc(F)cc1[C@H](Cn1c(=O)n(C(C)(C)C(=O)N2CCCC2)c(=O)c2c(C)c(-n3nccn3)sc21)OCC(C)C] |

TABLE 1-continued

Compounds of Formula I

| Cmpd No. | R Groups | Substituent | Compound Structure |
|---|---|---|---|
| I-029 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>O-tetrahydro-2H-pyran-4-yl<br>H<br>$CH_3, CH_3$<br>$OCH_3$<br>H | 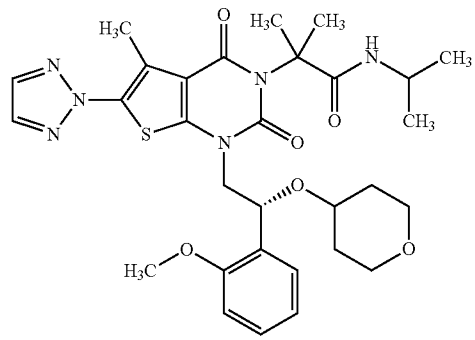 [SMILES: COc1ccccc1[C@H](Cn1c(=O)n(C(C)(C)C(=O)NC(C)C)c(=O)c2c(C)c(-n3nccn3)sc21)OC1CCOCC1] |
| I-030 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>O-tetrahydro-2H-pyran-4-yl<br>H<br>$CH_3, CH_3$<br>$OCH_3$<br>F | 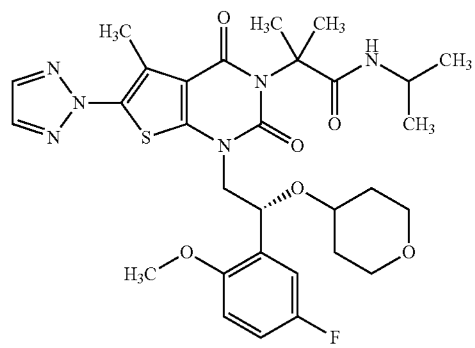 |
| I-031 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NH_2$<br>O-tetrahydro-2H-pyran-4-yl<br>H<br>$CH_3, CH_3$<br>$OCH_3$<br>H | 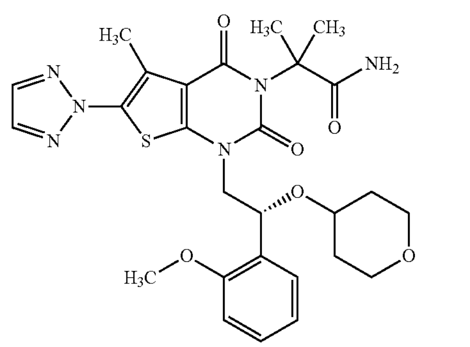 [SMILES: COc1ccccc1[C@H](Cn1c(=O)n(C(C)(C)C(N)=O)c(=O)c2c(C)c(-n3nccn3)sc21)OC1CCOCC1] |
| I-032 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH_2CH_3$<br>O-tetrahydro-2H-pyran-4-yl<br>H<br>$CH_3, CH_3$<br>$OCH_3$<br>H | 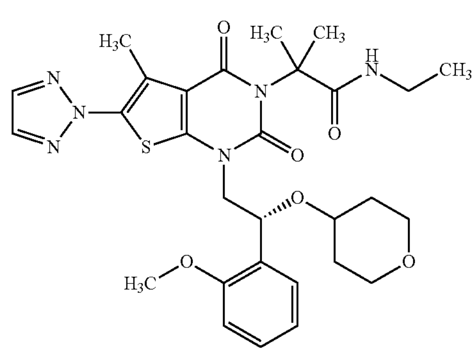 [SMILES: CCNC(=O)C(C)(C)n1c(=O)c2c(C)c(-n3nccn3)sc2n(C[C@H](OC2CCOCC2)c2ccccc2OC)c1=O] |

TABLE 1-continued

Compounds of Formula I

| Cmpd No. | R Groups | Substituent | Compound Structure |
|---|---|---|---|
| I-033 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-piperidinyl)<br>O-tetrahydro-2H-pyran-4-yl<br>H<br>CH₃, CH₃<br>OCH₃<br>H | 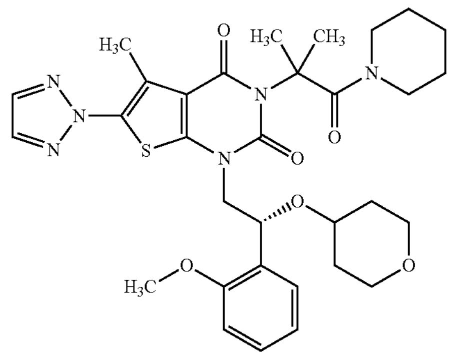 |
| I-034 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>O-tetrahydro-2H-pyran-4-yl<br>H<br>CH₃, CH₃<br>OCH₃<br>H | 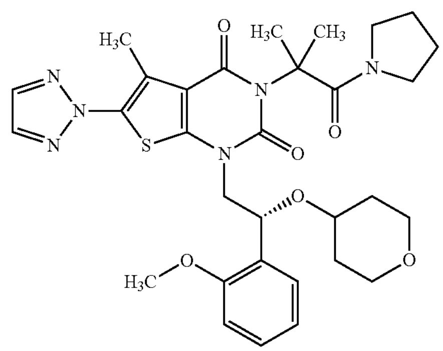 |
| I-035 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH₂CH₃<br>O-tetrahydro-2H-pyran-4-yl<br>H<br>CH₃, CH₃<br>OCH₃<br>F | 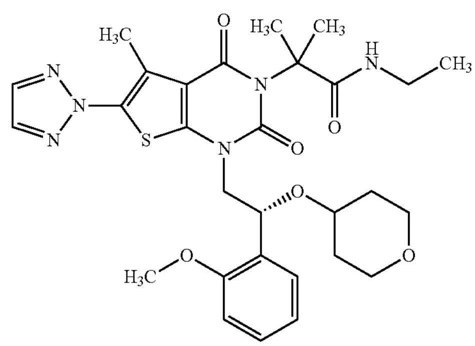 [SMILES: CCNC(=O)C(C)(C)n1c(=O)c2c(C)c(-n3nccn3)sc2n(C[C@H](OC2CCOCC2)c2ccccc2OC)c1=O] |
| I-036 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-piperidinyl)<br>O-tetrahydro-2H-pyran-4-yl<br>H<br>CH₃, CH₃<br>OCH₃<br>F | 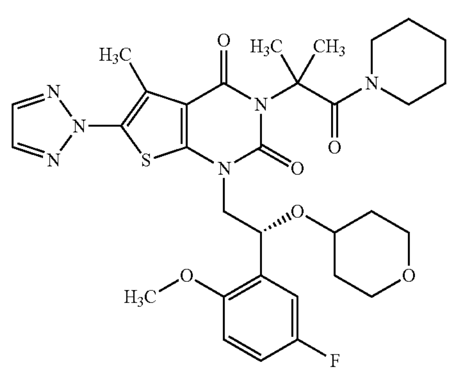 |

TABLE 1-continued

Compounds of Formula I

| Cmpd No. | R Groups | Substituent |
|---|---|---|
| I-037 | $R^1$ | $CH_3$ |
| | $R^2$ | 2H-1,2,3-triazol-2-yl |
| | $R^3$ | C(O)(1-pyrrolidinyl) |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |
| I-038 | $R^1$ | $CH_3$ |
| | $R^2$ | 2H-1,2,3-triazol-2-yl |
| | $R^3$ | $C(O)NHC_4H_7$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |
| I-039 | $R^1$ | $CH_3$ |
| | $R^4$ | 2H-1,2,3-triazol-2-yl |
| | $R^3$ | $C(O)NHC_6H_{11}$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |
| I-040 | $R^1$ | $CH_3$ |
| | $R^2$ | 2H-1,2,3-triazol-2-yl |
| | $R^3$ | $C(O)NHCH_2CH(CH_3)_2$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |

TABLE 1-continued

Compounds of Formula I

| Cmpd No. | R Groups | Substituent |
|---|---|---|
| I-041 | R$^1$ | CH$_3$ |
| | R$^2$ | 2H-1,2,3-triazol-2-yl |
| | R$^3$ | C(O)NHCH$_2$CH(CH$_3$)$_2$ |
| | R$^4$ | O-tetrahydro-2H-pyran-4-yl |
| | R$^{4'}$ | H |
| | R$^5$, R$^{5'}$ | CH$_3$, CH$_3$ |
| | R$^7$ | OCH$_3$ |
| | R$^8$ | H |
| I-042 | R$^1$ | CH$_3$ |
| | R$^2$ | 2H-1,2,3-triazol-2-yl |
| | R$^3$ | C(O)NHC$_4$H$_7$ |
| | R$^4$ | O-tetrahydro-2H-pyran-4-yl |
| | R$^{4'}$ | H |
| | R$^5$, R$^{5'}$ | CH$_3$, CH$_3$ |
| | R$^7$ | OCH$_3$ |
| | R$^8$ | H |
| I-043 | R$^1$ | CH$_3$ |
| | R$^2$ | 2H-1,2,3-triazol-2-yl |
| | R$^3$ | C(O)NHC$_6$H$_{11}$ |
| | R$^4$ | O-tetrahydro-2H-pyran-4-yl |
| | R$^{4'}$ | H |
| | R$^5$, R$^{5'}$ | CH$_3$, CH$_3$ |
| | R$^7$ | OCH$_3$ |
| | R$^8$ | H |
| I-044 | R$^1$ | CH$_3$ |
| | R$^2$ | 1-pyrazolyl |
| | R$^3$ | C(O)(1-pyrrolidinyl) |
| | R$^4$ | OCH(CH$_3$)$_2$ |
| | R$^{4'}$ | H |
| | R$^5$, R$^{5'}$ | CH$_3$, CH$_3$ |
| | R$^7$ | OCH$_3$ |
| | R$^8$ | F |

TABLE 1-continued

Compounds of Formula I

| Cmpd No. | R Groups | Substituent | Compound Structure |
|---|---|---|---|
| I-045 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>O-tetrahydro-2H-pyran-4-yl<br>H<br>CH₃, CH₃<br>OCH₃<br>F | 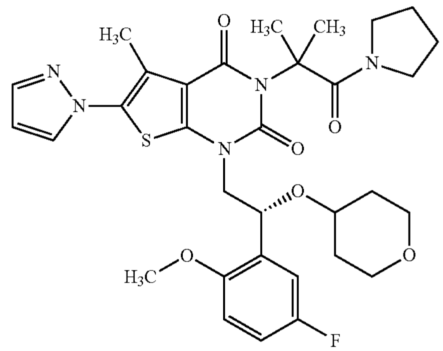 [SMILES: COc1ccc(F)cc1[C@H](Cn1c(=O)n(C(C)(C)C(=O)N2CCCC2)c(=O)c2c(C)c(-n3cccn3)sc21)OC1CCOCC1] |
| I-046 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH(CH₃)₂<br>H<br>CH₃, CH₃<br>OCH₃<br>H | 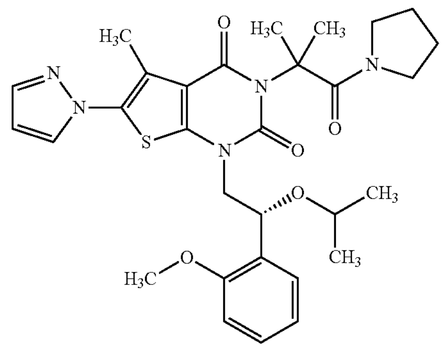 [SMILES: COc1ccccc1[C@H](Cn1c(=O)n(C(C)(C)C(=O)N2CCCC2)c(=O)c2c(C)c(-n3cccn3)sc21)OC(C)C] |
| I-047 | R¹<br>R²<br>R³<br>R⁴<br>R⁴'<br>R⁵, R⁵'<br>R⁷<br>R⁸ | CH₃<br>1-pyrazolyl<br>C(O)(1-piperidinyl)<br>OCH(CH₃)₂<br>H<br>CH₃, CH₃<br>OCH₃<br>H | 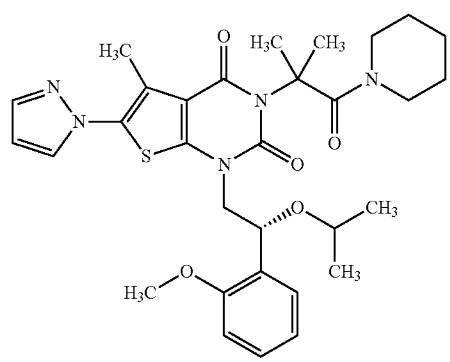 [SMILES: COc1ccccc1[C@H](Cn1c(=O)n(C(C)(C)C(=O)N2CCCCC2)c(=O)c2c(C)c(-n3cccn3)sc21)OC(C)C] |
| I-048 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>O-4-oxocyclohexyl<br>H<br>CH₃, CH₃<br>OCH₃<br>F | 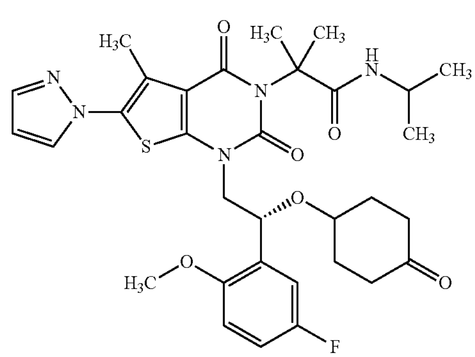 [SMILES: COc1ccc(F)cc1[C@H](Cn1c(=O)n(C(C)(C)C(=O)NC(C)C)c(=O)c2c(C)c(-n3cccn3)sc21)OC1CCC(=O)CC1] |

TABLE 1-continued

Compounds of Formula I

| Cmpd No. | R Groups | Substituent | Compound Structure |
|---|---|---|---|
| I-049 | R$^1$<br>R$^2$<br>R$^3$<br>R$^4$<br>R$^{4'}$<br>R$^5$, R$^{5'}$<br>R$^7$<br>R$^8$ | CH$_3$<br>1-pyrazolyl<br>C(O)NHCH(CH$_3$)$_2$<br>O-cis-4-hydroxycyclohexyl<br>H<br>CH$_3$, CH$_3$<br>OCH$_3$<br>F | 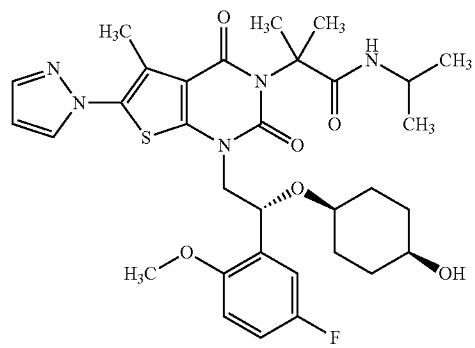 |
| I-050 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)NHCH(CH$_3$)$_2$<br>O-4-oxocyclohexyl<br>H<br>CH$_3$, CH$_3$<br>OCH$_3$<br>F | 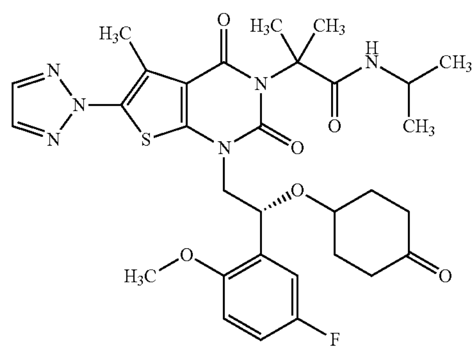 [SMILES: COc1ccc(F)cc1[C@H](Cn1c(=O)n(C(C)(C)C(=O)NC(C)C)c(=O)c2c(C)c(-n3nccn3)sc21)OC1CCC(=O)CC1] |
| I-051 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)(1-pyrrolidinyl)<br>O-4-oxocyclohexyl<br>H<br>CH$_3$, CH$_3$<br>OCH$_3$<br>F | 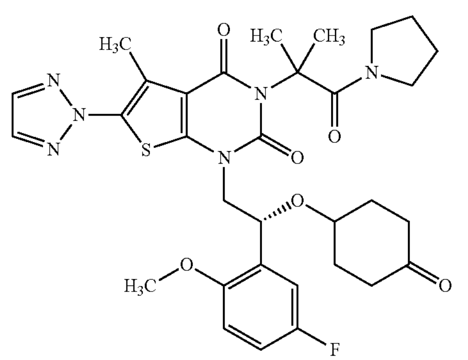 [SMILES: COc1ccc(F)cc1[C@H](Cn1c(=O)n(C(C)(C)C(=O)N2CCCC2)c(=O)c2c(C)c(-n3nccn3)sc21)OC1CCC(=O)CC1] |
| I-052 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)(1-piperidinyl)<br>O-4-oxocyclohexyl<br>H<br>CH$_3$, CH$_3$<br>OCH$_3$<br>F | 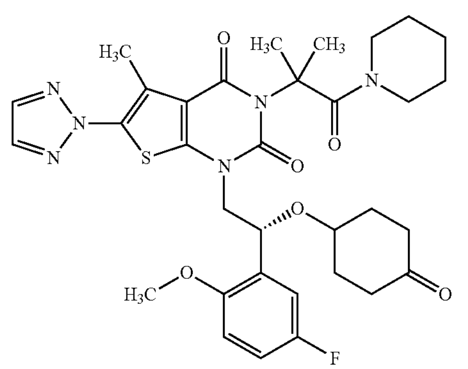 [SMILES: COc1ccc(F)cc1[C@H](Cn1c(=O)n(C(C)(C)C(=O)N2CCCCC2)c(=O)c2c(C)c(-n3nccn3)sc21)OC1CCC(=O)CC1] |

TABLE 1-continued

Compounds of Formula I

| Cmpd No. | R Groups | Substituent | Compound Structure |
|---|---|---|---|
| I-053 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>C(O)(1-pyrrolidinyl)<br>$OCH_2CH_3$<br>H<br>$CH_3, CH_3$<br>$OCH_3$<br>F | 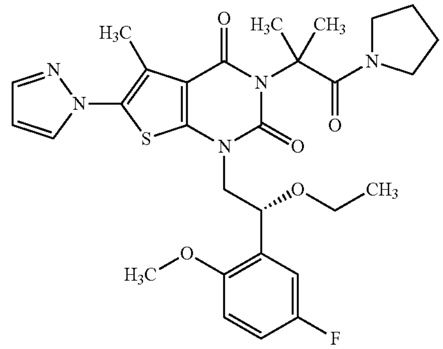 [SMILES: CCO[C@@H](Cn1c(=O)n(C(C)(C)C(=O)N2CCCC2)c(=O)c2c(C)c(-n3cccn3)sc21)c1cc(F)ccc1OC] |
| I-054 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2CH_3$<br>H<br>$CH_3, CH_3$<br>$OCH_3$<br>F | 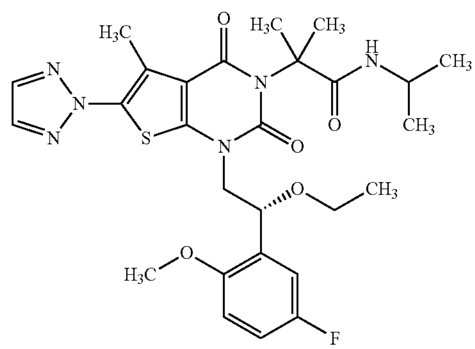 [SMILES: CCO[C@@H](Cn1c(=O)n(C(C)(C)C(=O)NC(C)C)c(=O)c2c(C)c(-n3nccn3)sc21)c1cc(F)ccc1OC] |
| I-055 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)(1-pyrrolidinyl)<br>$OCH_2CH_3$<br>H<br>$CH_3, CH_3$<br>$OCH_3$<br>F | 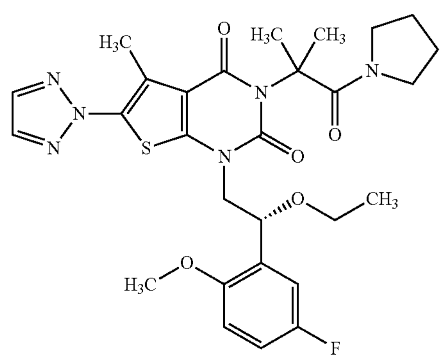 [SMILES: CCO[C@@H](Cn1c(=O)n(C(C)(C)C(=O)N2CCCC2)c(=O)c2c(C)c(-n3nccn3)sc21)c1cc(F)ccc1OC] |
| I-056 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)(1-pyrrolidinyl)<br>$OCH(CH_3)_2$<br>H<br>$CH_3, H$<br>$CH_3$<br>F | 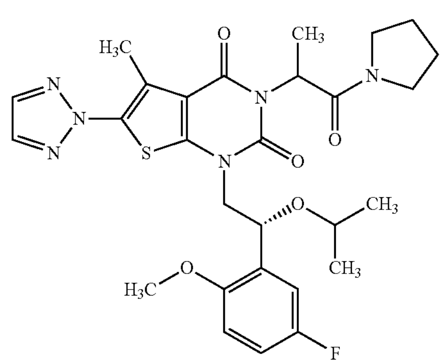 [SMILES: COc1ccc(F)cc1[C@H](Cn1c(=O)n(C(C)C(=O)N2CCCC2)c(=O)c2c(C)c(-n3nccn3)sc21)OC(C)C] |

TABLE 1-continued

Compounds of Formula I

| Cmpd No. | R Groups | Substituent | Compound Structure |
|---|---|---|---|
| I-057 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>S—CH₃, H<br>OCH₃<br>F | 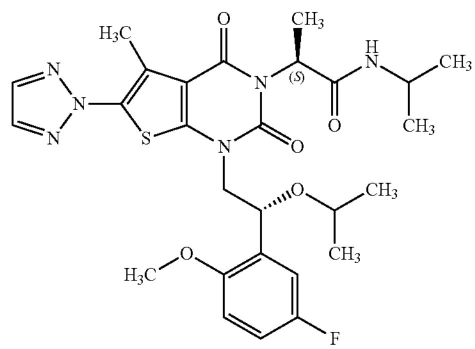 |
| I-058 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH(CH₃)₂<br>H<br>S—CH₃, H<br>OCH₃<br>F | 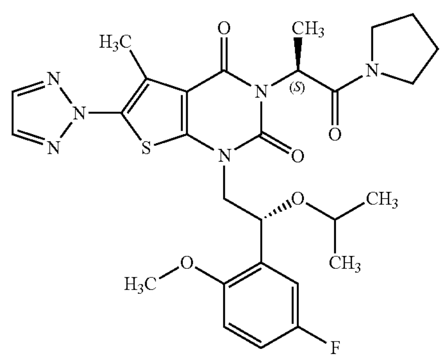 |
| I-059 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH(CH₃)₂<br>H<br>H, H<br>OCH₃<br>F | 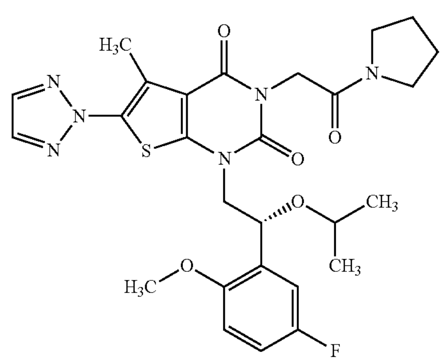 |
| I-060 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>H, H<br>CH₃<br>F | 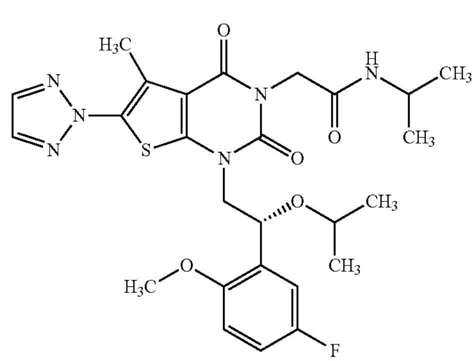 [SMILES: COc1ccc(F)cc1[C@H](Cn1c(=O)n(CC(=O)NC(C)C)c(=O)c2c(C)c(-n3nccn3)sc21)OC(C)C] |

TABLE 1-continued

Compounds of Formula I

| Cmpd No. | R Groups | Substituent | Compound Structure |
|---|---|---|---|
| I-061 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>R—CH₃, H<br>OCH₃<br>F | 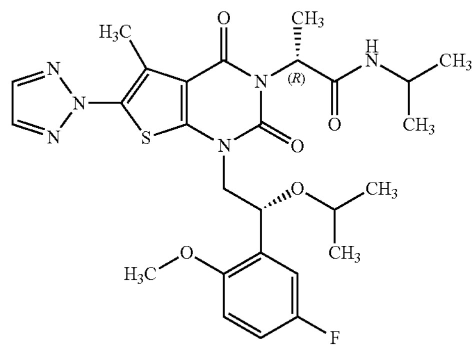 |
| I-062 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH(CH₃)₂<br>H<br>CH₃, H<br>OCH₃<br>F | 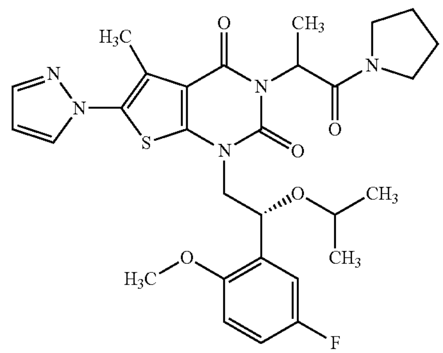 [SMILES: COc1ccc(F)cc1[C@H](Cn1c(=O)n(C(C)C(=O)N2CCCC2)c(=O)c2c(C)c(-n3cccn3)sc21)OC(C)C] |
| I-063 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH(CH₃)₂<br>H<br>S—CH₃, H<br>OCH₃<br>F | 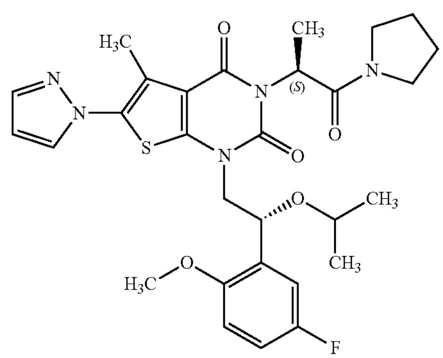 |
| I-064 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OH<br>H<br>CH₃, CH₃<br>OCH₃<br>F | 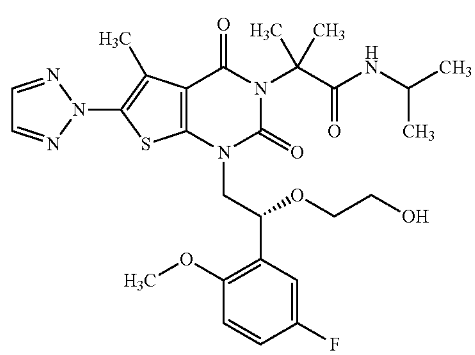 |

TABLE 1-continued

Compounds of Formula I

| Cmpd No. | R Groups | Substituent | Compound Structure |
|---|---|---|---|
| I-065 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)NHCH(CH$_3$)$_2$<br>OCH$_2$CH(R-CH$_3$)OH<br>H<br>CH$_3$, CH$_3$<br>OCH$_3$<br>F | 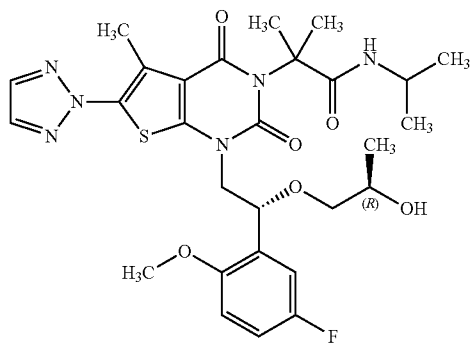 |
| I-066 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)NHCH(CH$_3$)$_2$<br>OCHC$_2$CH(S-CH$_3$)OH<br>H<br>CH$_3$, CH$_3$<br>OCH$_3$<br>F | 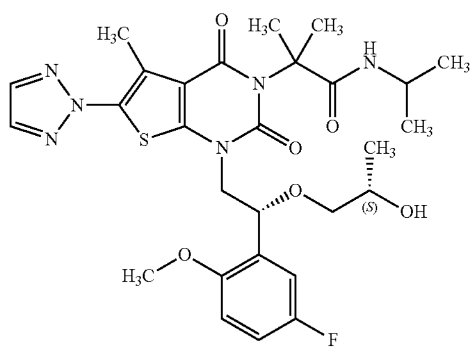 |
| I-067 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)(2,5-dihydro-1H-pyrrol-1-yl)<br>OCH(CH$_3$)$_2$<br>H<br>CH$_3$, CH$_3$<br>OCH$_3$<br>F | 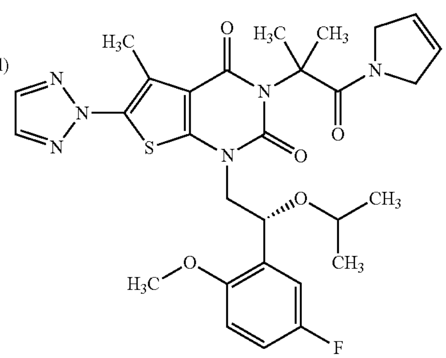 |
| I-068 | R$^1$<br>R$^2$<br>R$^3$<br>R$^4$<br>R$^{4'}$<br>R$^5$, R$^{5'}$<br>R$^7$<br>R$^8$ | CH$_3$<br>2H-1,2,3-triazol-2-yl<br>C(O)NHCH(CH$_3$)$_2$<br>OCH(CH$_3$)$_2$<br>H<br>CH$_3$, CH$_3$<br>OCH$_2$CH$_2$OCH$_3$<br>F | 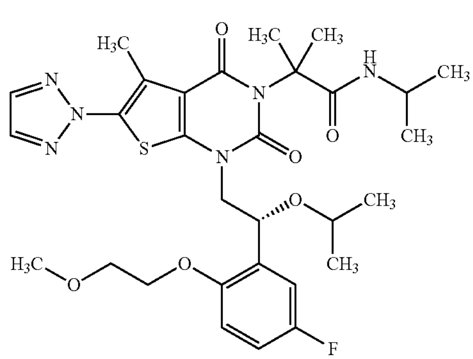 [SMILES: COCCOc1ccc(F)cc1[C@H](Cn1c(=O)n(C(C)(C)C(=O)NC(C)C)c(=O)c2c(C)c(-n3nccn3)sc21)OC(C)C] |

TABLE 1-continued

Compounds of Formula I

| Cmpd No. | R Groups | Substituent | Compound Structure |
|---|---|---|---|
| I-069 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>CH₃, CH₃<br>OCH₂CH(CH₂)₂O<br>F | 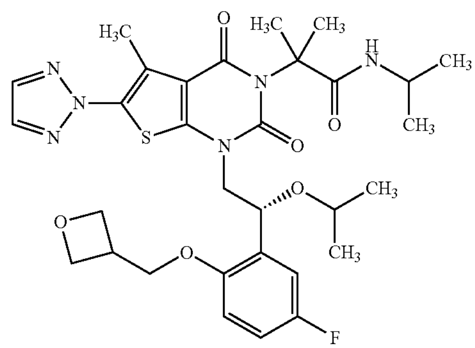 [SMILES: Cc1c(-n2nccn2)sc2c1c(=O)n(C(C)(C)C(=O)NC(C)C)c(=O)n2C[C@H](OC(C)C)c1cc(F)ccc1OCC1COC1] |
| I-070 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>CH₃, CH₃<br>OCH₂CN<br>F | 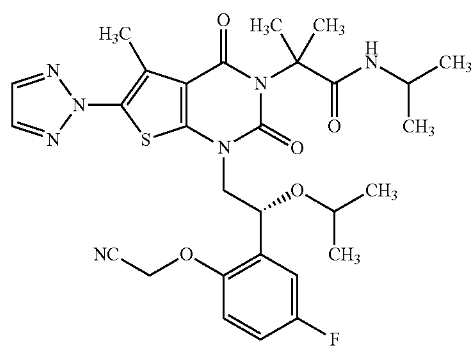 |
| I-071 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>CH₃, CH₃<br>OCH₂CH₂OH<br>F | 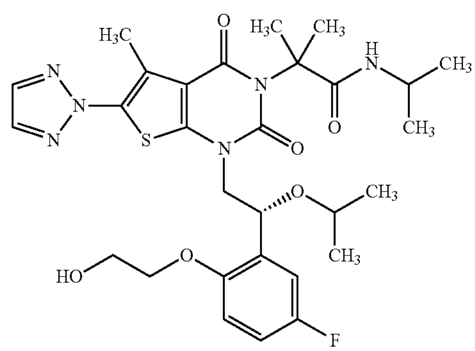 [SMILES: Cc1c(-n2nccn2)sc2c1c(=O)n(C(C)(C)C(=O)NC(C)C)c(=O)n2C[C@H](OC(C)C)c1cc(F)ccc1OCCO] |
| I-072 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂C(CH₃)₂OH<br>H<br>CH₃, CH₃<br>OCH₃<br>F | 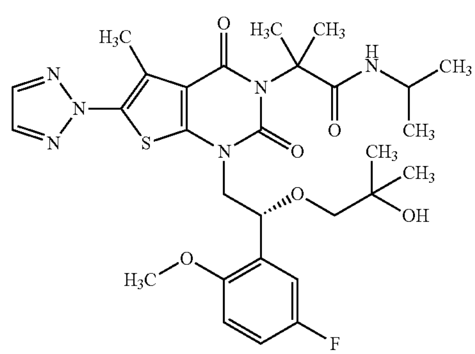 [SMILES: COc1ccc(F)cc1[C@H](Cn1c(=O)n(C(C)(C)C(=O)NC(C)C)c(=O)c2c(C)c(-n3nccn3)sc21)OCC(C)(C)O] |

TABLE 1-continued

Compounds of Formula I

| Cmpd No. | R Groups | Substituent | Compound Structure |
|---|---|---|---|
| I-073 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂C(CH₃)₂OH<br>H<br>CH₃, CH₃<br>OCH₃<br>F | 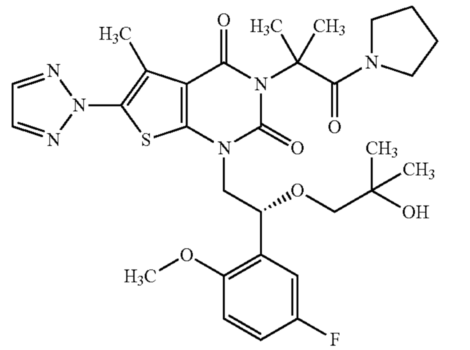 [SMILES: COc1ccc(F)cc1[C@H](Cn1c(=O)n(C(C)(C)C(=O)N2CCCC2)c(=O)c2c(C)c(-n3nccn3)sc21)OCC(C)(C)O] |
| I-074 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OCH₃<br>H<br>CH₃, CH₃<br>OCH₃<br>F | 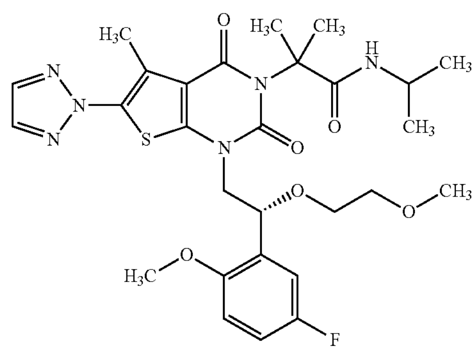 [SMILES: COCCO[C@@H](Cn1c(=O)n(C(C)(C)C(=O)NC(C)C)c(=O)c2c(C)c(-n3nccn3)sc21)c1cc(F)ccc1OC] |
| I-075 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(2,5-dihydro-1H-pyrrol-1-yl)<br>O-tetrahydro-2H-pyran-4-yl<br>H<br>CH₃, CH₃<br>OCH₃<br>F | 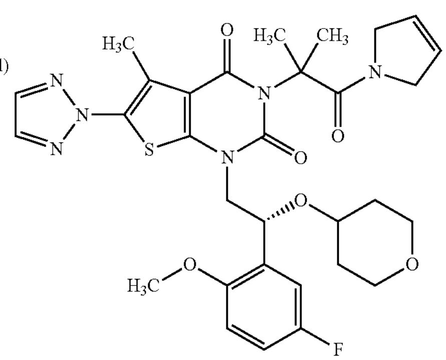 |
| I-076 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>O-tetrahydro-2H-pyran-4-yl<br>H<br>CH₃, CH₃<br>OCH₂CH₂OCH₃<br>F | 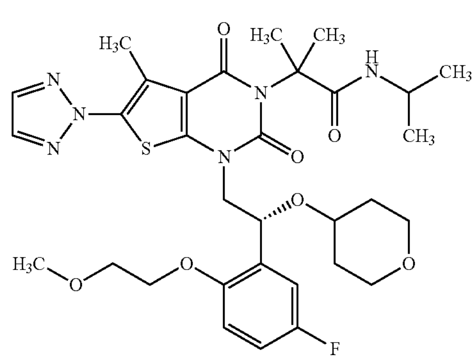 [SMILES: COCCOc1ccc(F)cc1[C@H](Cn1c(=O)n(C(C)(C)C(=O)NC(C)C)c(=O)c2c(C)c(-n3nccn3)sc21)OC1CCOCC1] |

TABLE 1-continued

Compounds of Formula I

| Cmpd No. | R Groups | Substituent | Compound Structure |
|---|---|---|---|
| I-077 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2CH=CH_2$<br>H<br>$CH_3, CH_3$<br>$OCH_3$<br>F | 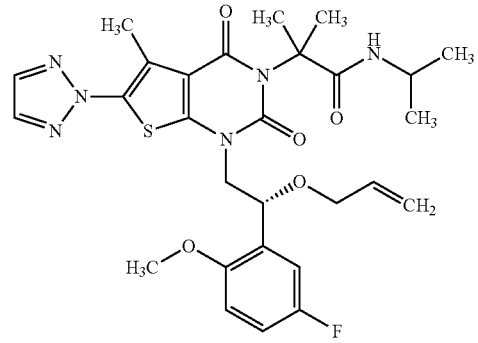 [SMILES: C=CCO[C@@H](Cn1c(=O)n(C(C)(C)C(=O)NC(C)C)c(=O)c2c(C)c(-n3nccn3)sc21)c1cc(F)ccc1OC] |
| I-078 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHC_3H_5$<br>$OCH(CH_3)_2$<br>H<br>$CH_3, CH_3$<br>$OCH_3$<br>F | 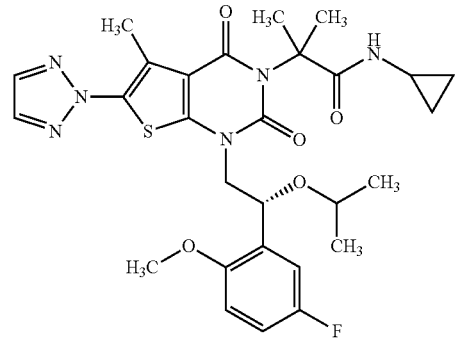 [SMILES: COc1ccc(F)cc1[C@H](Cn1c(=O)n(C(C)(C)C(=O)NC2CC2)c(=O)c2c(C)c(-n3nccn3)sc21)OC(C)C] |
| I-079 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NH\ CH_2CH=CH_2$<br>O-tetrahydro-2H-pyran-4-yl<br>H<br>$CH_3, CH_3$<br>$OCH_3$<br>F | 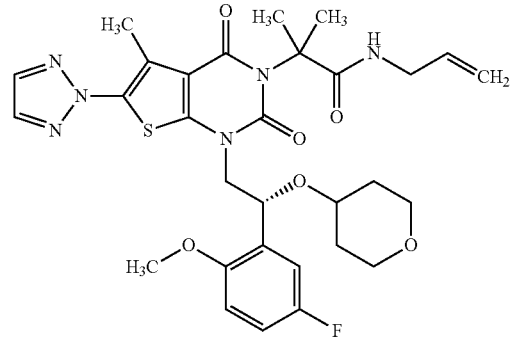 [SMILES: C=CCNC(=O)C(C)(C)n1c(=O)c2c(C)c(-n3nccn3)sc2n(C[C@H](OC2CCOCC2)c2cc(F)ccc2OC)c1=O] |
| I-080 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)N(CH_2CH=CH_2)(CH_3)$<br>O-tetrahydro-2H-pyran-4-yl<br>H<br>$CH_3, CH_3$<br>$OCH_3$<br>F | 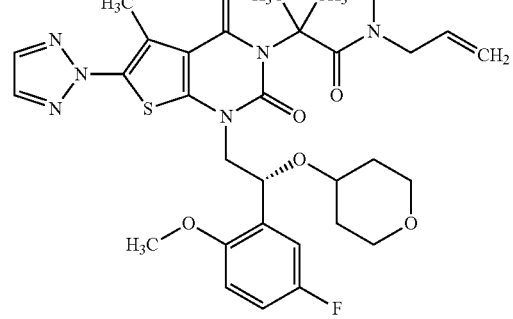 |

TABLE 1-continued

Compounds of Formula I

| Cmpd No. | R Groups | Substituent | Compound Structure |
|---|---|---|---|
| I-081 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(2,5-dihydro-1H-pyrrol-1-yl)<br>OCH₂CH(R—CH₃)OH<br>H<br>CH₃, CH₃<br>OCH₃<br>F | 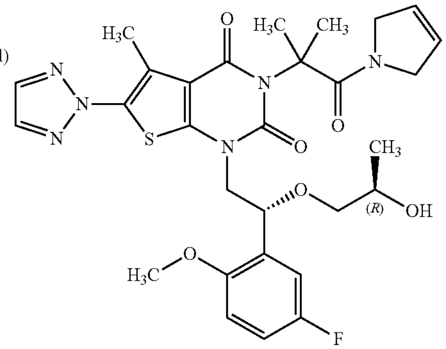 |
| I-082 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OCH₃<br>H<br>CH₃, H<br>OCH₃<br>F | 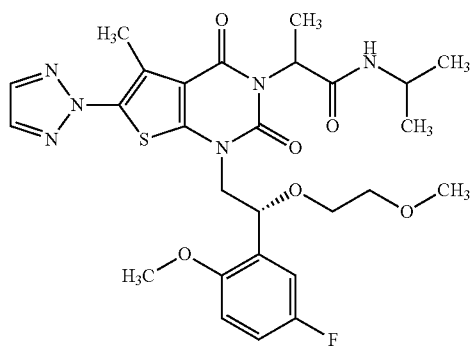 [SMILES: COCCO[C@@H](Cn1c(=O)n(C(C)C(=O)NC(C)C)c(=O)c2c(C)c(-n3nccn3)sc21)c1cc(F)ccc1OC] |
| I-083 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂CH₂OCH₃<br>H<br>CH₃, CH₃<br>OCH₃<br>F | 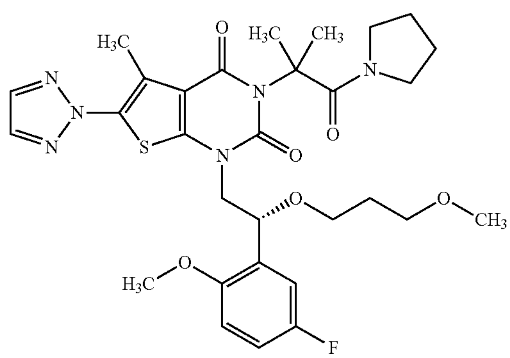 [SMILES: COCCCO[C@@H](Cn1c(=O)n(C(C)(C)C(=O)N2CCCC2)c(=O)c2c(C)c(-n3nccn3)sc21)c1cc(F)ccc1OC] |
| I-084 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CH₂OCH₃<br>H<br>CH₃, CH₃<br>OCH₃<br>F | 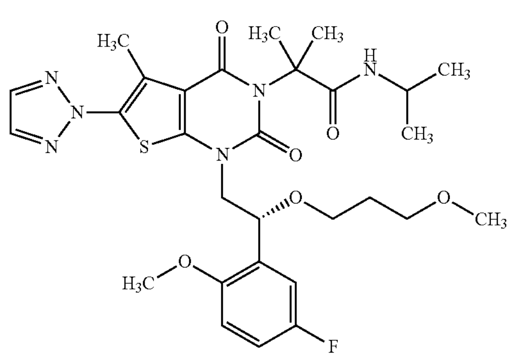 [SMILES: COCCCO[C@@H](Cn1c(=O)n(C(C)(C)C(=O)NC(C)C)c(=O)c2c(C)c(-n3nccn3)sc21)c1cc(F)ccc1OC] |

TABLE 1-continued

Compounds of Formula I

| Cmpd No. | R Groups | Substituent | Compound Structure |
|---|---|---|---|
| I-085 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)OCH₂CH₃<br>OCH₂CH₂OH<br>H<br>CH₃, CH₃<br>OCH₃<br>F | 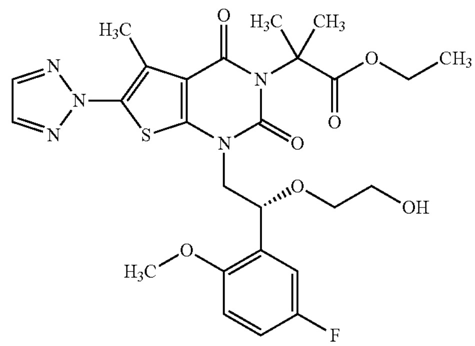 [SMILES: CCOC(=O)C(C)(C)n1c(=O)c2c(C)c(-n3nccn3)sc2n(C[C@H](OCCO)c2cc(F)ccc2OC)c1=O] |
| I-086 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OCH₃<br>H<br>H, H<br>OCH₃<br>F | 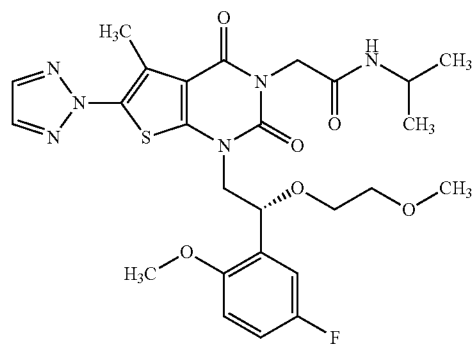 [SMILES: COCCO[C@@H](Cn1c(=O)n(CC(=O)NC(C)C)c(=O)c2c(C)c(-n3nccn3)sc21)c1cc(F)ccc1OC] |
| I-087 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OH<br>H<br>H, H<br>OCH₃<br>F | 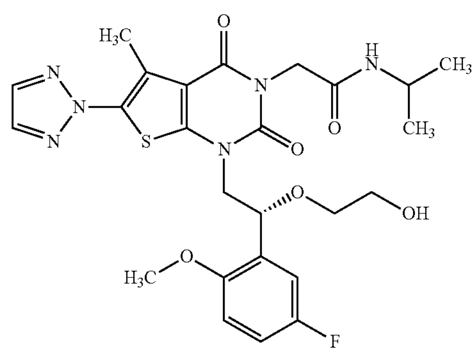 [SMILES: COc1ccc(F)cc1[C@H](Cn1c(=O)n(CC(=O)NC(C)C)c(=O)c2c(C)c(-n3nccn3)sc21)OCCO] |
| I-088 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂OH<br>H<br>H, H<br>OCH₃<br>F | 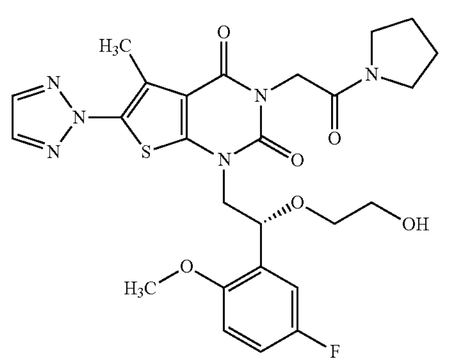 [SMILES: COc1ccc(F)cc1[C@H](Cn1c(=O)n(CC(=O)N2CCCC2)c(=O)c2c(C)c(-n3nccn3)sc21)OCCO] |

TABLE 1-continued

Compounds of Formula I

| Cmpd No. | R Groups | Substituent |
|---|---|---|
| I-089 | $R^1$ | $CH_3$ |
| | $R^2$ | 2H-1,2,3-triazol-2-yl |
| | $R^3$ | $C(O)N(CH_3)CH(CH_3)_2$ |
| | $R^4$ | $OCH_2CH_2OH$ |
| | $R^{4'}$ | H |
| | $R^5, R^{5'}$ | S—$CH_3$, H |
| | $R^7$ | $OCH_3$ |
| | $R^8$ | F |
| I-090 | $R^1$ | $CH_3$ |
| | $R^2$ | 2H-1,2,3-triazol-2-yl |
| | $R^3$ | $C(O)N(CH_3)CH(CH_3)_2$ |
| | $R^4$ | $OCH_2CH_2OH$ |
| | $R^{4'}$ | H |
| | $R^5, R^{5'}$ | R—$CH_3$, H |
| | $R^7$ | $OCH_3$ |
| | $R^8$ | F |
| I-091 | $R^1$ | $CH_3$ |
| | $R^2$ | 2H-1,2,3-triazol-2-yl |
| | $R^3$ | $C(O)NHC_4H_7$ |
| | $R^4$ | $OCH_2CH_2OH$ |
| | $R^{4'}$ | H |
| | $R^5, R^{5'}$ | S—$CH_3$, H |
| | $R^7$ | $OCH_3$ |
| | $R^8$ | F |
| I-092 | $R^1$ | $CH_3$ |
| | $R^2$ | 2H-1,2,3-triazol-2-yl |
| | $R^3$ | $C(O)NHC_4H_7$ |
| | $R^4$ | $OCH_2CH_2OH$ |
| | $R^{4'}$ | H |
| | $R^5, R^{5'}$ | R—$CH_3$, H |
| | $R^7$ | $OCH_3$ |
| | $R^8$ | F |

TABLE 1-continued

Compounds of Formula I

| Cmpd No. | R Groups | Substituent | Compound Structure |
|---|---|---|---|
| I-093 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CH₂OCH₃<br>H<br>S—CH₃, H<br>OCH₃<br>F | 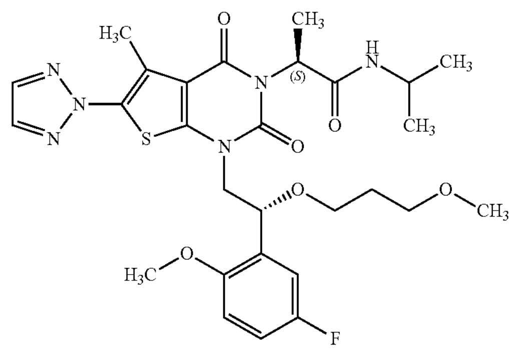 |
| I-094 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CH₂OCH₃<br>H<br>R—CH₃, H<br>OCH₃<br>F | 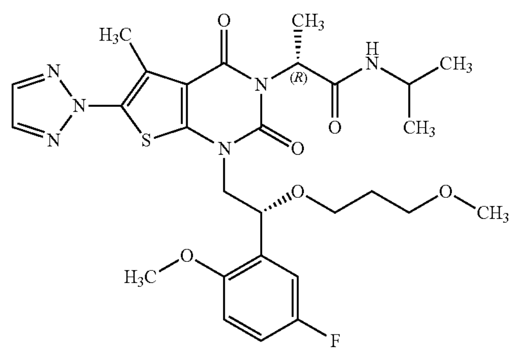 |
| I-095 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CN<br>H<br>CH₃, CH₃<br>OCH₃<br>F | 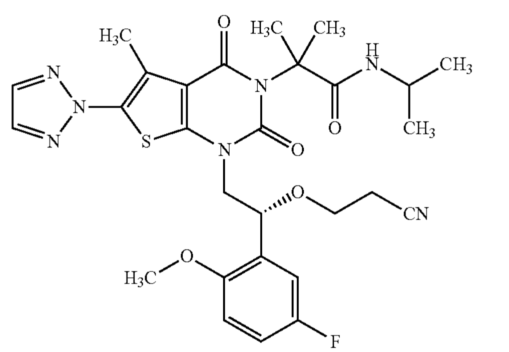 |
| I-096 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OH<br>H<br>S—CH₃, H<br>OCH₃<br>F | 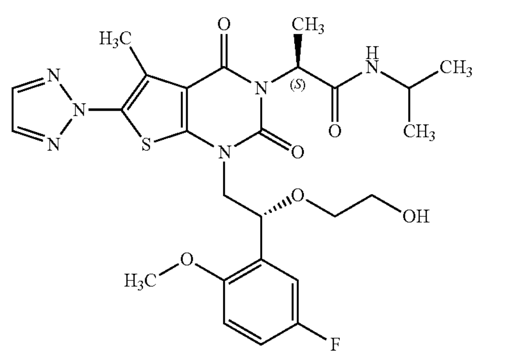 |

TABLE 1-continued

Compounds of Formula I

| Cmpd No. | R Groups | Substituent |
|---|---|---|
| I-097 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OH<br>H<br>R—CH₃, H<br>OCH₃<br>F |
| I-098 | R¹<br>R²<br>R³<br>R⁴<br>R⁴'<br>R⁵, R⁵'<br>R⁷<br>R⁸ | CH₃<br>2-oxazolyl<br>C(O)NHC₄H₇<br>OCH(CH₃)₂<br>H<br>CH₃, CH₃<br>OCH₃<br>H |
| I-099 | R¹<br>R²<br>R³<br>R⁴<br>R⁴'<br>R⁵, R⁵'<br>R⁷<br>R⁸ | CH₃<br>2-oxazolyl<br>C(O)NHC₄H₇<br>O-tetrahydro-2H-pyran-4-yl<br>H<br>CH₃, CH₃<br>OCH₃<br>H |
| I-100 | R¹<br>R²<br>R<br>R⁴<br>R⁴'<br>R⁵, R⁵'<br>R⁷<br>R⁸ | CH₃<br>2-oxazolyl<br>C(O)NH₂<br>O-cis-4-hydroxycyclohexyl<br>H<br>CH₃, CH₃<br>OCH₃<br>H |

TABLE 1-continued

Compounds of Formula I

| Cmpd No. | R Groups | Substituent |
|---|---|---|
| I-101 | R¹ | CH₃ |
| | R² | 2-oxazolyl |
| | R³ | C(O)NH₂ |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | F |
| I-102 | R¹ | CH₃ |
| | R² | 2H-1,2,3-triazol-2-yl |
| | R³ | C(O)NH₂ |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | F |
| I-103 | R¹ | CH₃ |
| | R² | 2-oxazolyl |
| | R³ | C(O)NH₂ |
| | R⁴ | O-cis-4-hydroxycyclohexyl |
| | R⁴' | H |
| | R⁵, R⁵' | CH₃, CH₃ |
| | R⁷ | OCH₃ |
| | R⁸ | F |
| I-104 | R¹ | CH₃ |
| | R² | 2-oxazolyl |
| | R³ | C(O)NH₂ |
| | R⁴ | O-cis-4-hydroxycyclohexylmethyl |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent | Compound Structure |
|---|---|---|---|
| I-105 | R¹<br>R²<br>R³<br>R⁴<br>R⁴'<br>R⁵, R⁵'<br>R⁷<br>R⁸ | CH₃<br>2-oxazolyl<br>C(O)NHCH₂CH₃<br>O-4-oxocyclohexyl<br>H<br>CH₃, CH₃<br>OCH₃<br>H | 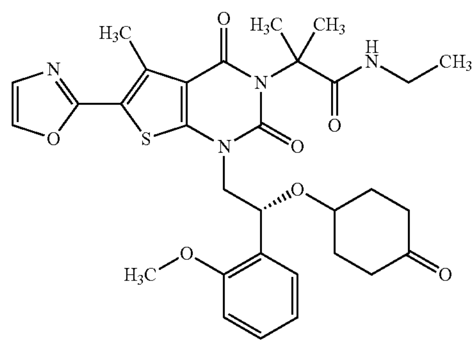 [SMILES: CCNC(=O)C(C)(C)n1c(=O)c2c(C)c(-c3ncco3)sc2n(C[C@H](OC2CCC(=O)CC2)c2ccccc2OC)c1=O] |
| I-106 | R¹<br>R²<br>R³<br>R⁴<br>R⁴'<br>R⁵, R⁵'<br>R⁷<br>R⁸ | CH₃<br>2-oxazolyl<br>C(O)(1-piperidinyl)<br>O-4-oxocyclohexyl<br>H<br>CH₃, CH₃<br>OCH₃<br>H | 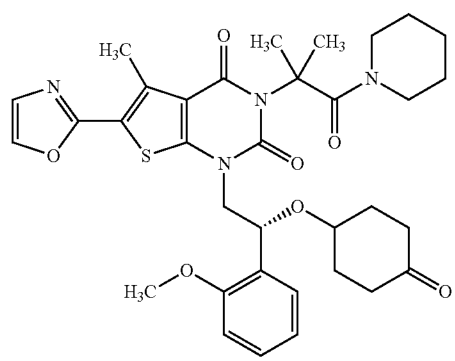 [SMILES: COc1ccccc1[C@H](Cn1c(=O)n(C(C)(C)C(=O)N2CCCCC2)c(=O)c2c(C)c(-c3ncco3)sc21)OC1CCC(=O)CC1] |
| I-107 | R¹<br>R²<br>R³<br>R⁴<br>R⁴'<br>R⁵, R⁵'<br>R⁷<br>R⁸ | CH₃<br>2-oxazolyl<br>C(O)O-benzyl<br>O-4-oxocyclohexyl<br>H<br>CH₃, CH₃<br>OCH₃<br>H | 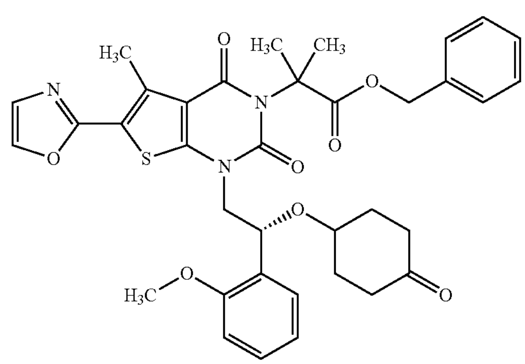 [SMILES: COc1ccccc1[C@H](Cn1c(=O)n(C(C)(C)C(=O)OCc2ccccc2)c(=O)c2c(C)c(-c3ncco3)sc21)OC1CCC(=O)CC1] |
| I-108 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH₂CH₃<br>OCH(CH₃)₂<br>H<br>CH₃, CH₃<br>OCH₃<br>H | 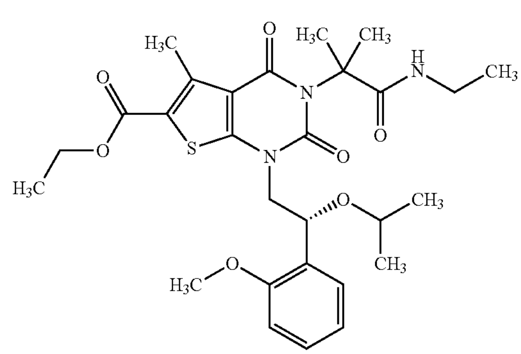 [SMILES: CCNC(=O)C(C)(C)n1c(=O)c2c(C)c(C(=O)OCC)sc2n(C[C@H](OC(C)C)c2ccccc2OC)c1=O] |

TABLE 1-continued

Compounds of Formula I

| Cmpd No. | R Groups | Substituent |
|---|---|---|
| I-109 | $R^1$ | $CH_3$ |
| | $R^2$ | $C(O)OCH_2CH_3$ |
| | $R^3$ | C(O)(1-morpholinyl) |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-110 | $R^1$ | $CH_3$ |
| | $R^2$ | 2-oxazolyl |
| | $R^3$ | C(O)((1-piperidinyl) |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | H |
| I-111 | $R^1$ | $CH_3$ |
| | $R^2$ | 2-oxazolyl |
| | $R^3$ | C(O)(1-pyrrolidinyl) |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | H |
| I-112 | $R^1$ | $CH_3$ |
| | $R^2$ | 2-oxazolyl |
| | $R^3$ | C(O(1-pyrrolidinyl) |
| | $R^4$ | O-4-oxocyclohexyl |
| | $R^{4'}$ | H |
| | $R^5, R^{5'}$ | $CH_3, CH_3$ |
| | $R^7$ | $OCH_3$ |
| | $R^8$ | H |

TABLE 1-continued

Compounds of Formula I

| Cmpd No. | R Groups | Substituent | Compound Structure |
|---|---|---|---|
| I-113 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NH_2$<br>$OCH(CH_3)_2$<br>H<br>$CH_3, CH_3$<br>F | 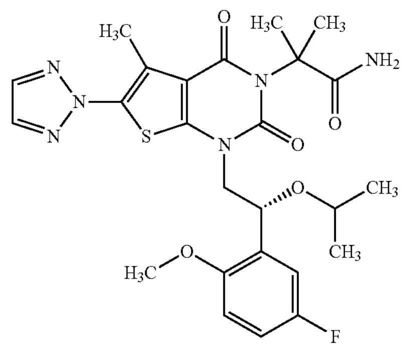 [SMILES: COc1ccc(F)cc1[C@H](Cn1c(=O)n(C(C)(C)C(N)=O)c(=O)c2c(C)c(-n3nccn3)sc21)OC(C)C] |
| I-114 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)(3-hydroxyazetidin-1-yl)<br>O-tetrahydro-2H-pyran-4-yl<br>H<br>$CH_3, CH_3$<br>$OCH_3$<br>F | 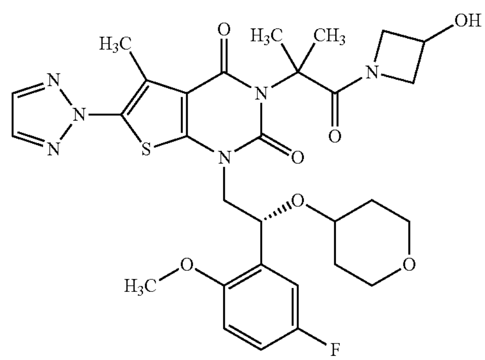 [SMILES: COc1ccc(F)cc1[C@H](Cn1c(=O)n(C(C)(C)C(=O)N2CC(O)C2)c(=O)c2c(C)c(-n3nccn3)sc21)OC1CCOCC1] |
| I-115 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>O-tetrahydro-2H-pyran-4-yl<br>H<br>$CH_3, CH_3$<br>$OCH_3$<br>F | 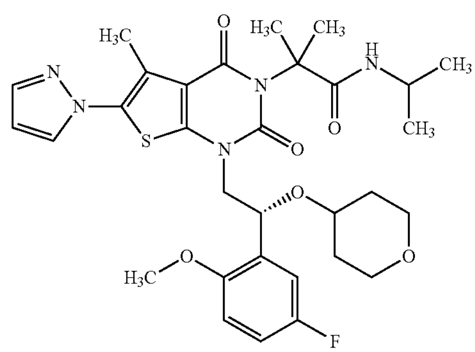 [SMILES: COc1ccc(F)cc1[C@H](Cn1c(=O)n(C(C)(C)C(=O)NC(C)C)c(=O)c2c(C)c(-n3cccn3)sc21)OC1CCOCC1] |
| I-116 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>C(O)(1-pyrrolidinyl)<br>O-tetrahydro-2H-pyran-4-yl<br>H<br>$CH_3, CH_3$<br>$OCH_3$<br>H | 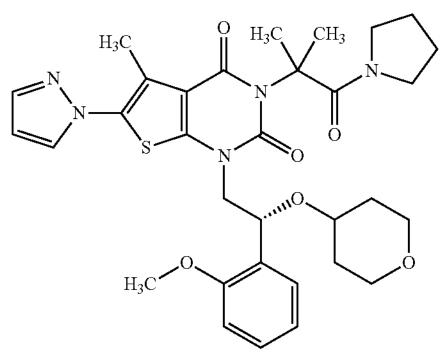 [SMILES: COc1ccccc1[C@H](Cn1c(=O)n(C(C)(C)C(=O)N2CCCC2)c(=O)c2c(C)c(-n3cccn3)sc21)OC1CCOCC1] |

TABLE 1-continued

Compounds of Formula I

| Cmpd No. | R Groups | Substituent |
|---|---|---|
| I-117 | $R^1$ | $CH_3$ |
| | $R^2$ | 1-pyrazolyl |
| | $R^3$ | C(O)(1-piperidinyl) |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | H |
| I-118 | $R^1$ | $CH_3$ |
| | $R^2$ | 1-pyrazolyl |
| | $R^3$ | $C(O)NHCH(CH_3)_2$ |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-119 | $R^1$ | $CH_3$ |
| | $R^2$ | 1-pyrazolyl |
| | $R^3$ | $C(O)NHCH(CH_3)_2$ |
| | $R^4$ | $O CH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-120 | $R^1$ | $CH_3$ |
| | $R^2$ | 1-pyrazolyl |
| | $R^3$ | C(O)(1-pyrrolidinyl) |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |

TABLE 1-continued

Compounds of Formula I

| Cmpd No. | R Groups | Substituent |
|---|---|---|
| I-121 | R¹ | CH₃ |
| | R² | 1-pyrazolyl |
| | R³ | C(O)(1-piperidinyl) |
| | R⁴ | OCH(CH₃)₂ |
| | R⁴' | H |
| | R⁵, R⁵' | CH₃, CH₃ |
| | R⁷ | OCH₃ |
| | R⁸ | H |
| I-122 | R¹ | CH₃ |
| | R² | 1-pyrazolyl |
| | R³ | C(O)(1-pyrrolidinyl) |
| | R⁴ | O-4-oxocyclohexyl |
| | R⁴' | H |
| | R⁵, R⁵' | CH₃, CH₃ |
| | R⁷ | OCH₃ |
| | R⁸ | F |
| I-123 | R¹ | CH₃ |
| | R² | 1-pyrazolyl |
| | R³ | C(O)(1-pyrrolidinyl) |
| | R⁴ | O-cis-4-hydroxycyclohexyl |
| | R⁴' | H |
| | R⁵, R⁵' | CH₃, CH₃ |
| | R⁷ | OCH₃ |
| | R⁸ | F |
| I-124 | R¹ | CH₃ |
| | R² | 2H-1,2,3-triazol-2-yl |
| | R³ | C(O)NH₂ |
| | R⁴ | O-4-oxocyclohexyl |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent | Compound Structure |
|---|---|---|---|
| I-125 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>$OCH_2CH_3$<br>H<br>$CH_3, CH_3$<br>$OCH_3$<br>F | 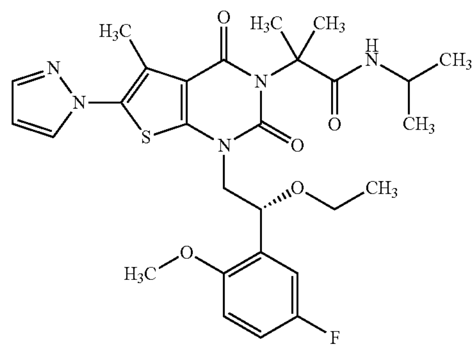 |
| I-126 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>$OCH(CH_3)_2$<br>H<br>$CH_3, H$<br>$OCH_3$<br>F | 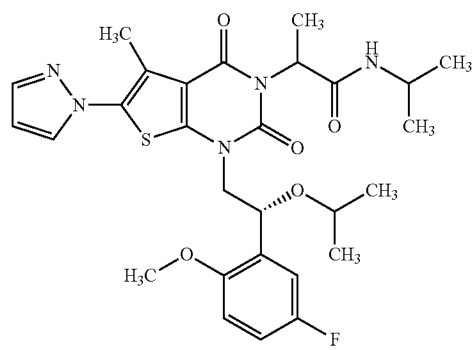 [SMILES: COc1ccc(F)cc1[C@H](Cn1c(=O)n(C(C)C(=O)NC(C)C)c(=O)c2c(C)c(-n3cccn3)sc21)OC(C)C] |
| I-127 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>$OCH(CH_3)_2$<br>H<br>R—$CH_3$, H<br>$OCH_3$<br>F | 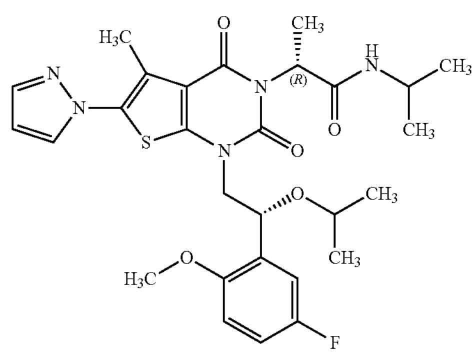 |
| I-128 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)(1\text{-pyrrolidinyl})$<br>$OCH(CH_3)_2$<br>H<br>H, H<br>$OCH_3$<br>F | 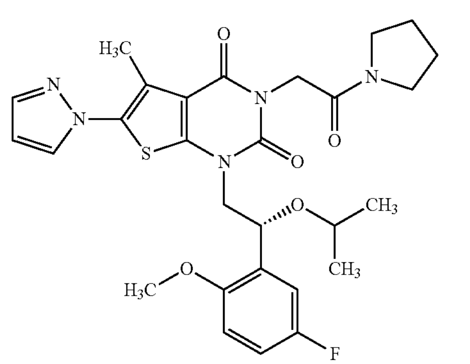 [SMILES: COc1ccc(F)cc1[C@H](Cn1c(=O)n(CC(=O)N2CCCC2)c(=O)c2c(C)c(-n3cccn3)sc21)OC(C)C] |

TABLE 1-continued

Compounds of Formula I

| Cmpd No. | R Groups | Substituent | Compound Structure |
|---|---|---|---|
| I-129 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>$OCH_2CH_2OH$<br>H<br>$CH_3, CH_3$<br>$OCH_3$<br>F | 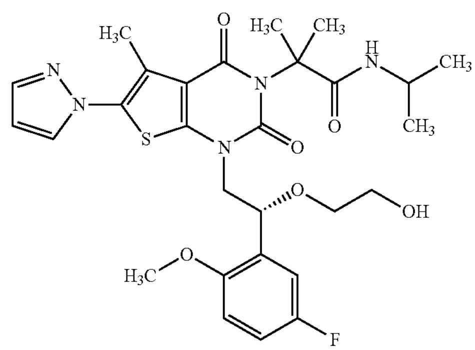 |
| I-130 | $R^1$<br>$R^2$<br>$R^3$<br>$R^4$<br>$R^{4'}$<br>$R, R^{5'}$<br>$R^7$<br>$R^8$ | $CH_3$<br>2H-1,2,3-triazol-2-yl<br>$C(O)(1$-pyrrolidinyl)<br>$OCH_2CH_2OH$<br>H<br>$CH_3, CH_3$<br>$OCH_3$<br>F | 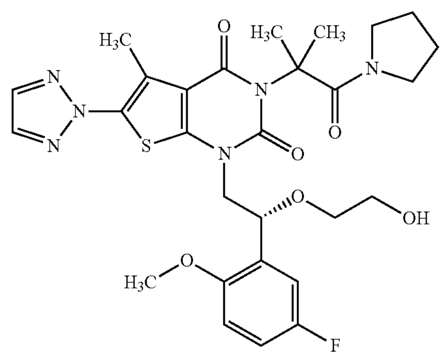 |
| I-131 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)N(CH_3)_2$<br>$OCH(CH_3)_2$<br>H<br>$CH_3, CH_3$<br>$OCH_3$<br>F | 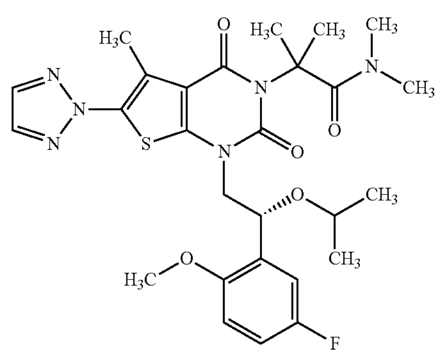 [SMILES: COc1ccc(F)cc1[C@H](Cn1c(=O)n(C(C)(C)C(=O)N(C)C)c(=O)c2c(C)c(-n3nccn3)sc21)OC(C)C] |
| I-132 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH_3$<br>$OCH(CH_3)_2$<br>H<br>$CH_3, CH_3$<br>$OCH_3$<br>F | 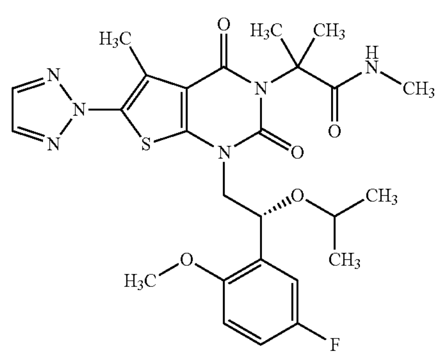 [SMILES: CNC(=O)C(C)(C)n1c(=O)c2c(C)c(-n3nccn3)sc2n(C[C@H](OC(C)C)c2cc(F)ccc2OC)c1=O] |

TABLE 1-continued

Compounds of Formula I

| Cmpd No. | R Groups | Substituent | Compound Structure |
|---|---|---|---|
| I-133 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH(S—CH₃)OH<br>H<br>CH₃, CH₃<br>OCH₃<br>F | 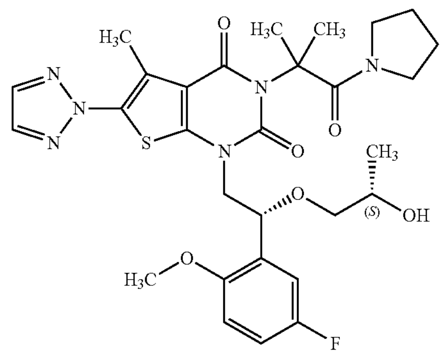 |
| I-134 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>OCH₂CH(R—CH₃)OH<br>H<br>CH₃, CH₃<br>OCH₃<br>F | 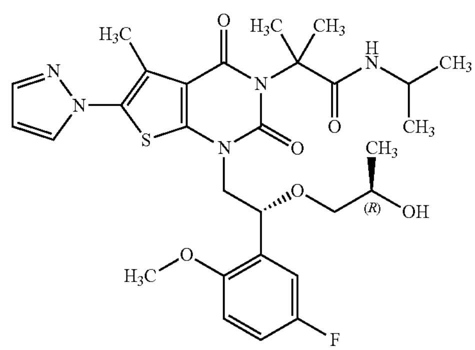 |
| I-135 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH₂CH(R—CH₃)OH<br>H<br>CH₃, CH₃<br>OCH₃<br>F | 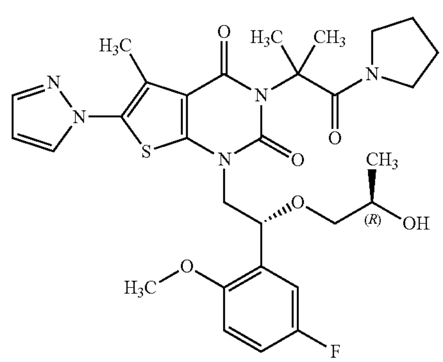 |
| I-136 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>OCH₂CH(S—CH₃)OH<br>H<br>CH₃, CH₃<br>OCH₃<br>F | 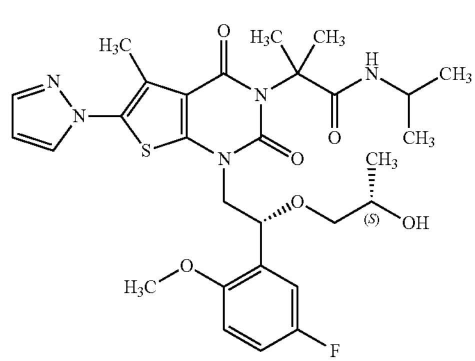 |

TABLE 1-continued

Compounds of Formula I

| Cmpd No. | R Groups | Substituent | Compound Structure |
|---|---|---|---|
| I-137 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>OCH₂C(CH₃)₂OH<br>H<br>CH₃, CH₃<br>OCH₃<br>F | 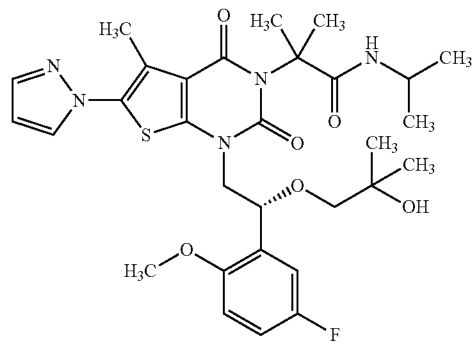 [SMILES: COc1ccc(F)cc1[C@H](Cn1c(=O)n(C(C)(C)C(=O)NC(C)C)c(=O)c2c(C)c(-n3cccn3)sc21)OCC(C)(C)O] |
| I-138 | R¹<br>R²<br>R³<br>R⁴<br>R⁴'<br>R⁵, R⁵'<br>R⁷<br>R¹⁴ | CH₃<br>1-pyrazolyl<br>C(O)(1-pyrrolidinyl)<br>OCH₂C(CH₃)₂OH<br>H<br>CH₃, CH₃<br>OCH₃<br>F | 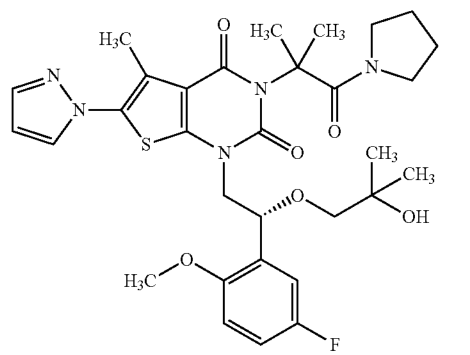 [SMILES: COc1ccc(F)cc1[C@H](Cn1c(=O)n(C(C)(C)C(=O)N2CCCC2)c(=O)c2c(C)c(-n3cccn3)sc21)OCC(C)(C)O] |
| I-139 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂OCH₃<br>H<br>CH₃, H<br>OCH₃<br>F | 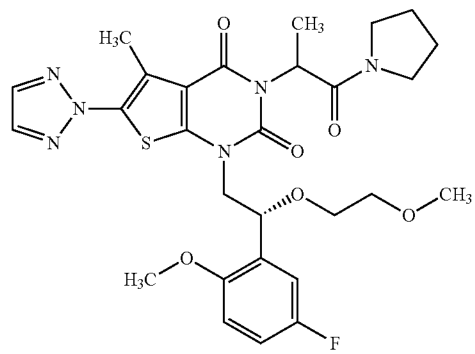 [SMILES: COCCO[C@@H](Cn1c(=O)n(C(C)C(=O)N2CCCC2)c(=O)c2c(C)c(-n3nccn3)sc21)c1cc(F)ccc1OC] |
| I-140 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂OCH₃<br>H<br>R—CH₃, H<br>OCH₃<br>F | 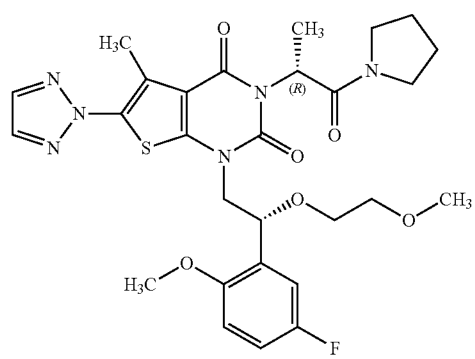 |

TABLE 1-continued

Compounds of Formula I

| Cmpd No. | R Groups | Substituent | Compound Structure |
|---|---|---|---|
| I-141 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)(1-pyrrolidinyl)<br>$OCH_2CH_2OCH_3$<br>H<br>H, H<br>$OCH_3$<br>F | 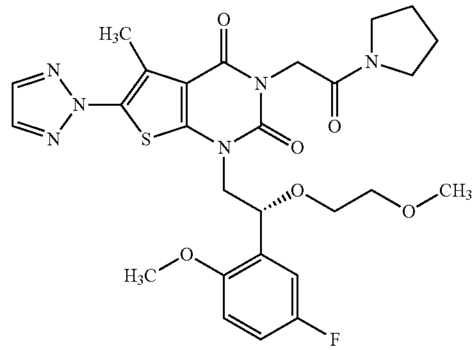 [SMILES: COCCO[C@@H](Cn1c(=O)n(CC(=O)N2CCCC2)c(=O)c2c(C)c(-n3nccn3)sc21)c1cc(F)ccc1OC] |
| I-142 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2CH_2C(O)NH_2$<br>H<br>$CH_3, CH_3$<br>$OCH_3$<br>F | 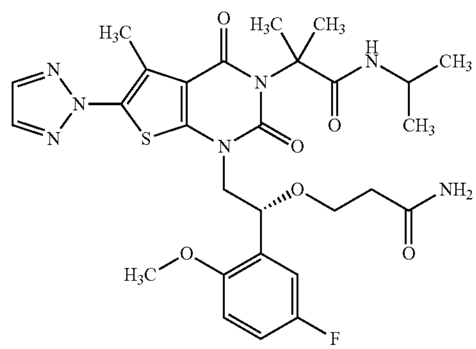 [SMILES: COc1ccc(F)cc1[C@H](Cn1c(=O)n(C(C)(C)C(=O)NC(C)C)c(=O)c2c(C)c(-n3nccn3)sc21)OCCC(N)=O] |
| I-143 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>C(O)(1-morpholinyl)<br>$OCH(CH_3)_2$<br>H<br>$CH_3, CH_3$<br>$OCH_3$<br>H | 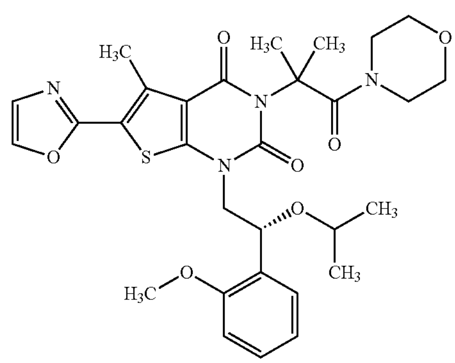 [SMILES: COc1ccccc1[C@H](Cn1c(=O)n(C(C)(C)C(=O)N2CCOCC2)c(=O)c2c(C)c(-c3ncco3)sc21)OC(C)C] |
| I-144 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>$C(O)NHCH_2CH_3$<br>$OCH(CH_3)_2$<br>H<br>$CH_3, CH_3$<br>$OCH_3$<br>H | 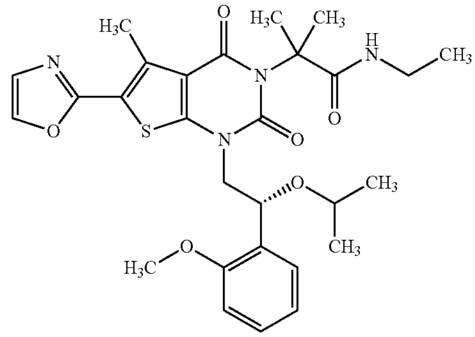 [SMILES: CCNC(=O)C(C)(C)n1c(=O)c2c(C)c(-c3ncco3)sc2n(C[C@H](OC(C)C)c2ccccc2OC)c1=O] |

TABLE 1-continued

Compounds of Formula I

| Cmpd No. | R Groups | Substituent |
|---|---|---|
| I-145 | $R^1$ | $CH_3$ |
| | $R^2$ | 2-oxazolyl |
| | $R^3$ | $C(O)NH_2$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | H |
| I-146 | $R^1$ | $CH_3$ |
| | $R^2$ | 1-pyrazolyl |
| | $R^3$ | $C(O)NH_2$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |
| I-147 | $R^1$ | $CH_3$ |
| | $R^2$ | $C_4H_7$ |
| | $R^3$ | $C(O)NH_2$ |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | F |
| I-148 | $R^1$ | $CH_3$ |
| | $R^2$ | 2-oxazolyl |
| | $R^3$ | $CH_2SO_2NH_2$ |
| | $R^4$ | O-tetrahydro-2H-pyran-4-yl |
| | $R^{4'}$ | H |
| | $R^5, R^{5'}$ | H, H |
| | $R^7$ | $OCH_3$ |
| | $R^8$ | F |

TABLE 1-continued

Compounds of Formula I

| Cmpd No. | R Groups | Substituent | Compound Structure |
|---|---|---|---|
| I-149 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>$C(O)NH_2$<br>O-(4-oxocyclohexyl)methyl<br>H<br>$CH_3, CH_3$<br>$OCH_3$<br>F | 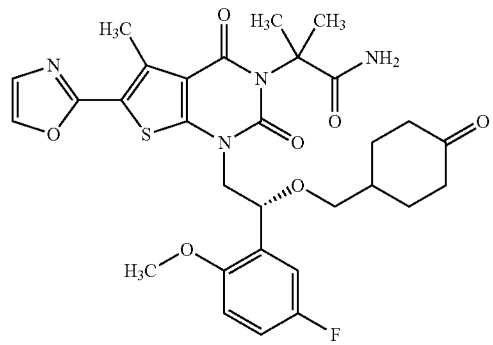 [SMILES: COc1ccc(F)cc1[C@H](Cn1c(=O)n(C(C)(C)C(N)=O)c(=O)c2c(C)c(-c3ncco3)sc21)OCC1CCC(=O)CC1] |
| I-150 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NH_2$<br>O-cis-4-hydroxycyclohexyl<br>H<br>$CH_3, CH_3$<br>$OCH_3$<br>F | 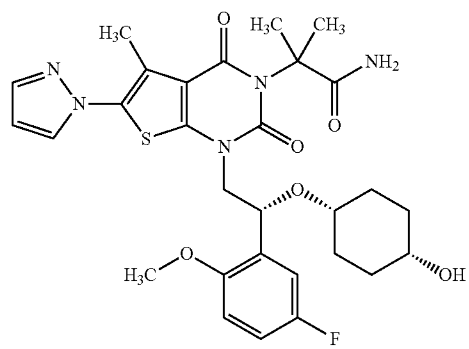 [SMILES: COc1ccc(F)cc1[C@H](Cn1c(=O)n(C(C)(C)C(N)=O)c(=O)c2c(C)c(-n3cccn3)sc21)O[C@H]1CC[C@@H](O)CC1] |
| I-151 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>C(O)(1-morpholinyl)<br>$OCH(CH_3)_2$<br>H<br>$CH_3, CH_3$<br>$OCH_3$<br>F | 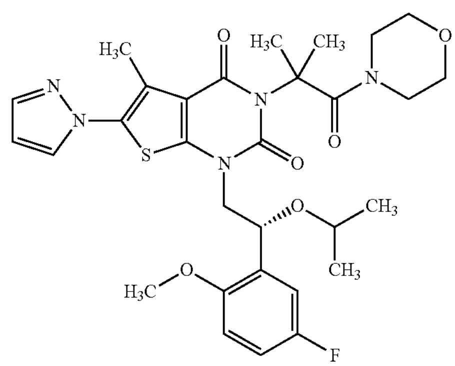 [SMILES: COc1ccc(F)cc1[C@H](Cn1c(=O)n(C(C)(C)C(=O)N2CCOCC2)c(=O)c2c(C)c(-n3cccn3)sc21)OC(C)C] |
| I-152 | $R^1$<br>$R^2$<br>$R^3$<br>$R^4$<br>$R^{4'}$<br>$R^5, R^{5'}$<br>$R^7$<br>$R^8$ | $CH_3$<br>2-oxazolyl<br>C(O)(1-morpholinyl)<br>O-tetrahydro-2H-pyran-4-yl<br>H<br>$CH_3, CH_3$<br>$OCH_3$<br>H | 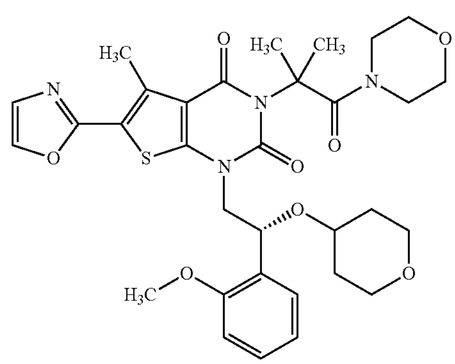 [SMILES: COc1ccccc1[C@H](Cn1c(=O)n(C(C)(C)C(=O)N2CCOCC2)c(=O)c2c(C)c(-c3ncco3)sc21)OC1CCOCC1] |

TABLE 1-continued

Compounds of Formula I

| Cmpd No. | R Groups | Substituent |
|---|---|---|
| I-153 | $R^1$ | $CH_3$ |
| | $R^2$ | $C(O)OCH_2CH_3$ |
| | $R^3$ | $C(O)OH$ |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-154 | $R^1$ | $CH_3$ |
| | $R^2$ | 2-oxazolyl |
| | $R^3$ | $C(O)NH_2$ |
| | $R^4$ | O-4-oxocyclohexyl |
| | $R^{4'}$ | H |
| | $R^5, R^{5'}$ | $CH_3, CH_3$ |
| | $R^7$ | $OCH_3$ |
| | $R^8$ | H |
| I-155 | $R^1$ | $CH_3$ |
| | $R^2$ | $C(O)OCH_2CH_3$ |
| | $R^3$ | $C(O)NH_2$ |
| | $R^4$ | $OCH(CH_3)_2$ |
| | $R^{4'}$ | H |
| | $R^5, R^{5'}$ | $CH_3, CH_3$ |
| | $R^7$ | $OCH_3$ |
| | $R^8$ | H |
| I-156 | $R^1$ | $CH_3$ |
| | $R^2$ | 2H-1,2,3-triazol-2-yl |
| | $R^3$ | C(O)(3-hydroxyazetidin-1-yl) |
| | $R^4$ | O-tetrahydro-2H-pyran-4-yl |
| | $R^{4'}$ | H |
| | $R^5, R^{5'}$ | $CH_3, CH_3$ |
| | $R^7$ | $OCH_3$ |
| | $R^8$ | H |

TABLE 1-continued

Compounds of Formula I

| Cmpd No. | R Groups | Substituent |
|---|---|---|
| I-157 | R¹ | CH₃ |
| | R² | 1-pyrazolyl |
| | R³ | C(O)NHCH(CH₃)₂ |
| | R⁴ | O-tetrahydro-2H-pyran-4-yl |
| | R⁴' | H |
| | R⁵, R⁵' | CH₃, CH₃ |
| | R⁷ | OCH₃ |
| | R⁸ | H |
| I-158 | R¹ | CH₃ |
| | R² | 2H-1,2,3-triazol-2-yl |
| | R³ | C(O)OH |
| | R⁴ | O-4-oxocyclohexyl |
| | R⁴' | H |
| | R⁵, R⁵' | CH₃, CH₃ |
| | R⁷ | OCH₃ |
| | R⁸ | F |
| I-159 | R¹ | CH₃ |
| | R² | 1-pyrazolyl |
| | R³ | C(O)(1-pyrrolidinyl) |
| | R⁴ | OCH₂CH₂OH |
| | R⁴' | H |
| | R⁵, R⁵' | CH₃, CH₃ |
| | R⁷ | OCH₃ |
| | R⁸ | F |
| I-160 | R¹ | CH₃ |
| | R² | 2H-1,2,3-triazol-2-yl |
| | R³ | C(O)NHCH₂CN |
| | R⁴ | OCH(CH₃)₂ |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent | Compound Structure |
|---|---|---|---|
| I-161 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>C(O)(1-pyrrolidinyl)<br>$OCH_2CH(S—CH_3)OH$<br>H<br>$CH_3, CH_3$<br>$OCH_3$<br>F | 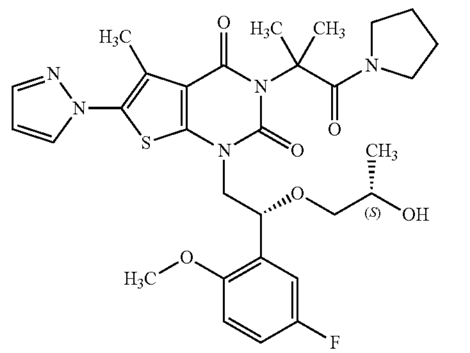 |
| I-162 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>C(O)(2,5-dihydro-1H-pyrrol-1-yl)<br>O-tetrahydro-2H-pyran-4-yl<br>H<br>$CH_3, CH_3$<br>$OCH_3$<br>F | 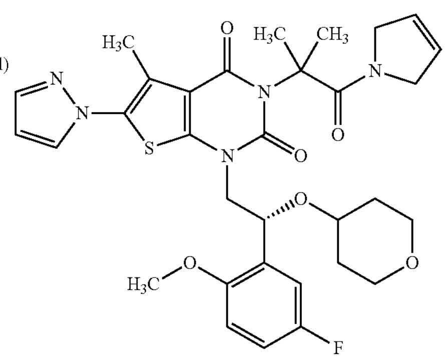 |
| I-163 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>$OCH_2CH_2OCH_3$<br>H<br>$CH_3, CH_3$<br>$OCH_3$<br>F | 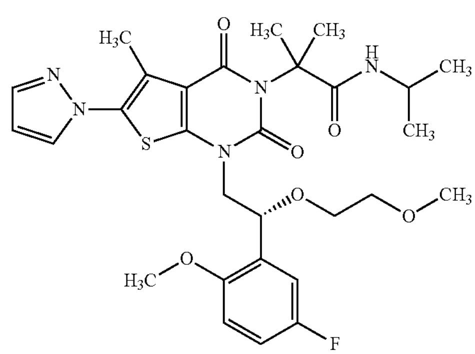 [SMILES: COCCO[C@@H](Cn1c(=O)n(C(C)(C)C(=O)NC(C)C)c(=O)c2c(C)c(-n3cccn3)sc21)c1cc(F)ccc1OC] |
| I-164 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)(1-pyrrolidinyl)<br>$OCH_2CH_2OCH_3$<br>H<br>$CH_3, CH_3$<br>$OCH_3$<br>F | 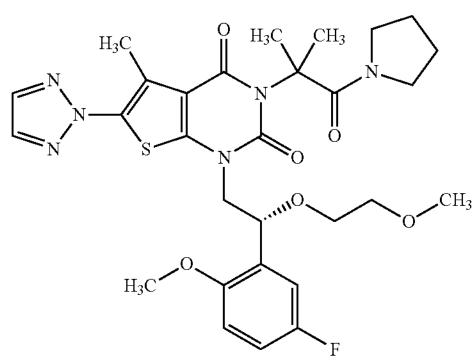 [SMILES: COCCO[C@@H](Cn1c(=O)n(C(C)(C)C(=O)N2CCCC2)c(=O)c2c(C)c(-n3nccn3)sc21)c1cc(F)ccc1OC] |

TABLE 1-continued

Compounds of Formula I

| Cmpd No. | R Groups | Substituent | Compound Structure |
|---|---|---|---|
| I-165 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NH₂<br>OCH₂CH(CH₃)₂<br>H<br>CH₃, CH₃<br>OCH₃<br>F | 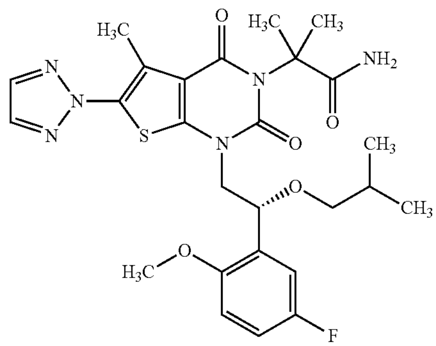 [SMILES: COc1ccc(F)cc1[C@H](Cn1c(=O)n(C(C)(C)C(N)=O)c(=O)c2c(C)c(-n3nccn3)sc21)OCC(C)C] |
| I-166 | R¹<br>R²<br>R³<br>R⁴<br>R⁴'<br>R⁵, R⁵'<br>R⁷<br>R⁸ | CH₃<br>1-pyrazolyl<br>C(O)(1-piperidinyl)<br>O-tetrahydro-2H-pyran-4-yl<br>H<br>CH₃, CH₃<br>OCH₃<br>F | 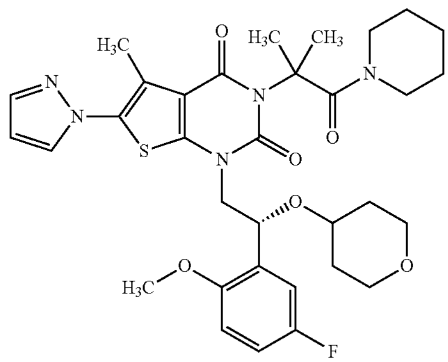 [SMILES: COc1ccc(F)cc1[C@H](Cn1c(=O)n(C(C)(C)C(=O)N2CCCCC2)c(=O)c2c(C)c(-n3cccn3)sc21)OC1CCOCC1] |
| I-167 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH(R—CH₃)OH<br>H<br>CH₃, CH₃<br>OCH₃<br>F | 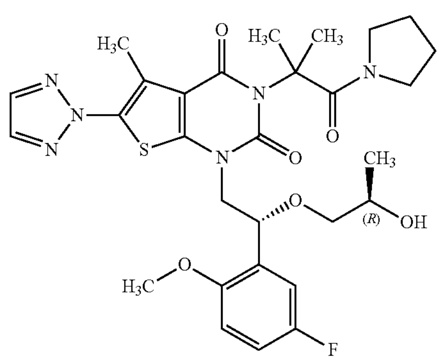 |
| I-168 | R¹<br>R²<br>R³<br>R⁴<br>R⁴'<br>R⁵, R⁵'<br>R⁷<br>R⁸ | CH₃<br>C(O)OCH₂CH₃<br>C(O)(1-piperidinyl)<br>O-tetrahydro-2H-pyran-4-yl<br>H<br>CH₃, CH₃<br>OCH₃<br>H | 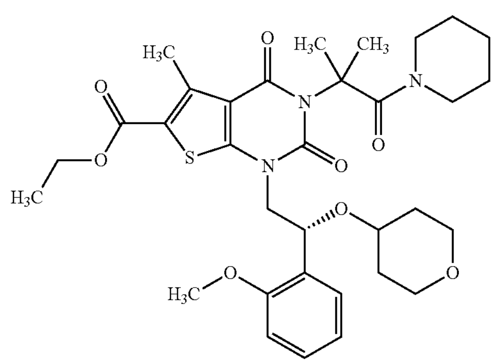 [SMILES: CCOC(=O)c1sc2c(c1C)c(=O)n(C(C)(C)C(=O)N1CCCCC1)c(=O)n2C[C@H](OC1CCOCC1)c1ccccc1OC] |

TABLE 1-continued

Compounds of Formula I

| Cmpd No. | R Groups | Substituent |
|---|---|---|
| I-169 | $R^1$ | $CH_3$ |
|  | $R^2$ | 2-oxazolyl |
|  | $R^3$ | $C(O)NHCH_2CH_3$ |
|  | $R^4$ | O-tetrahydro-2H-pyran-4-yl |
|  | $R^{4'}$ | H |
|  | $R^5, R^{5'}$ | $CH_3, CH_3$ |
|  | $R^7$ | $OCH_3$ |
|  | $R^8$ | H |
| I-170 | $R^1$ | $CH_3$ |
|  | $R^2$ | 1-pyrazolyl |
|  | $R^3$ | $C(O)NH_2$ |
|  | $R^4$ | O-4-oxocyclohexyl |
|  | $R^{4'}$ | H |
|  | $R^5, R^{5'}$ | $CH_3, CH_3$ |
|  | $R^7$ | $OCH_3$ |
|  | $R^8$ | F |
| I-171 | $R^1$ | $CH_3$ |
|  | $R^2$ | 2H-1,2,3-triazol-2-yl |
|  | $R^3$ | $C(O)NHCH(CH_3)_2$ |
|  | $R^4$ | $OCH_2CH_2OCH_3$ |
|  | $R^{4'}$ | H |
|  | $R^5, R^{5'}$ | R—$CH_3$, H |
|  | $R^7$ | $OCH_3$ |
|  | $R^8$ | F |
| I-172 | $R^1$ | $CH_3$ |
|  | $R^2$ | 2H-1,2,3-triazol-2-yl |
|  | $R^3$ | $C(O)NHCH(CH_3)_2$ |
|  | $R^4$ | $OCH_2CH_2OCH_3$ |
|  | $R^{4'}$ | H |
|  | $R^5, R^{5'}$ | S—$CH_3$, H |
|  | $R^7$ | $OCH_3$ |
|  | $R^8$ | F |

TABLE 1-continued

Compounds of Formula I

| Cmpd No. | R Groups | Substituent | Compound Structure |
|---|---|---|---|
| I-173 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2CH_2N(CH_3)_2$<br>H<br>$CH_3, CH_3$<br>$OCH_3$<br>F | 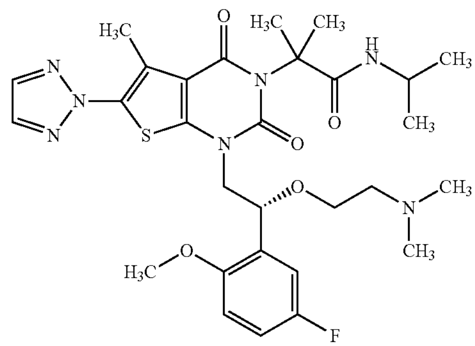 [SMILES: COc1ccc(F)cc1[C@H](Cn1c(=O)n(C(C)(C)C(=O)NC(C)C)c(=O)c2c(C)c(-n3nccn3)sc21)OCCN(C)C] |
| I-174 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NH_2$<br>O-tetrahydro-2H-pyran-4-yl<br>H<br>$CH_3, CH_3$<br>$OCH_3$<br>H | 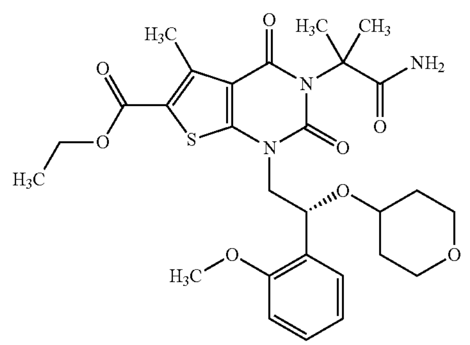 [SMILES: CCOC(=O)c1sc2c(c1C)c(=O)n(C(C)(C)C(N)=O)c(=O)n2C[C@H](OC1CCOCC1)c1ccccc1OC] |
| I-175 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NHCH_2CH_3$<br>O-tetrahydro-2H-pyran-4-yl<br>H<br>$CH_3, CH_3$<br>$OCH_3$<br>H | 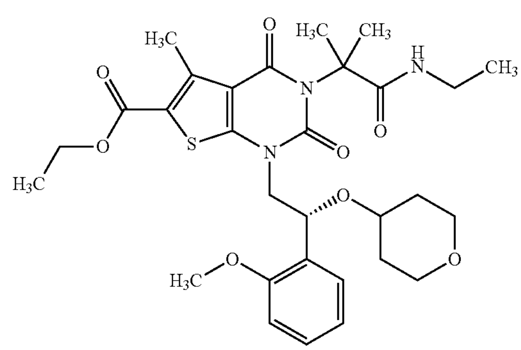 [SMILES: CCNC(=O)C(C)(C)n1c(=O)c2c(C)c(C(=O)OCC)sc2n(C[C@H](OC2CCOCC2)c2ccccc2OC)c1=O] |
| I-176 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NH_2$<br>$OCH_2CH_2OCH_3$<br>H<br>$CH_3, CH_3$<br>$OCH_3$<br>F | 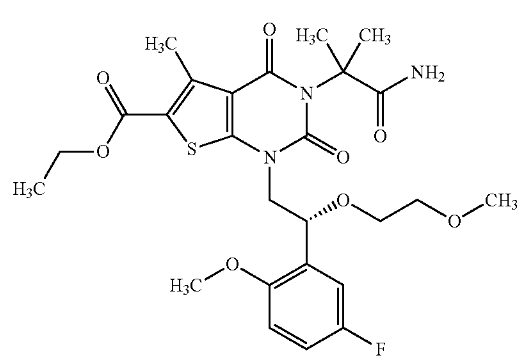 [SMILES: CCOC(=O)c1sc2c(c1C)c(=O)n(C(C)(C)C(N)=O)c(=O)n2C[C@H](OCCOC)c1cc(F)ccc1OC] |

TABLE 1-continued

Compounds of Formula I

| Cmpd No. | R Groups | Substituent |
|---|---|---|
| I-177 | R¹ | CH₃ |
| | R² | C(O)OCH₂CH₃ |
| | R³ | C(O)NHCH(CH₃)₂ |
| | R⁴ | OCH₂CH₂OCH₃ |
| | R⁴' | H |
| | R⁵, R⁵' | CH₃, CH₃ |
| | R⁷ | OCH₃ |
| | R⁸ | F |
| I-178 | R¹ | CH₃ |
| | R² | C(O)OCH₂CH₃ |
| | R³ | C(O)(1-pyrrolidinyl) |
| | R⁴ | OCH₂CH₂OH |
| | R⁴' | H |
| | R⁵, R⁵' | CH₃, CH₃ |
| | R⁷ | OCH₃ |
| | R⁸ | F |
| I-179 | R¹ | CH₃ |
| | R² | C(O)OCH₂CH₃ |
| | R³ | C(O)(1-pyrrolidinyl) |
| | R⁴ | OCH₂CH₂OCH₃ |
| | R⁴' | H |
| | R⁵, R⁵' | CH₃, CH₃ |
| | R⁷ | OCH₃ |
| | R⁸ | F |
| I-180 | R¹ | CH₃ |
| | R² | C(O)OCH₂CH₃ |
| | R³ | C(O)NH₂ |
| | R⁴ | OCH₂CH₂CN |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent | Compound Structure |
|---|---|---|---|
| I-181 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NHCH(CH_3)_2$<br>$OCH_2CH_2CN$<br>H<br>$CH_3, CH_3$<br>$OCH_3$<br>F | 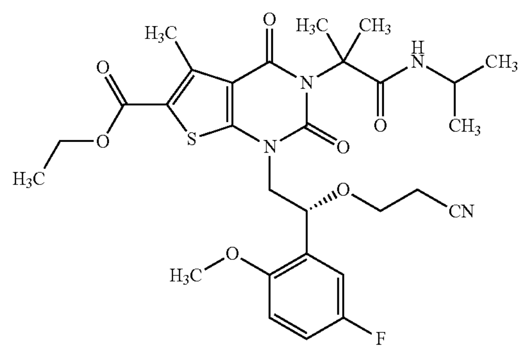 [SMILES: CCOC(=O)c1sc2c(c1C)c(=O)n(C(C)(C)C(=O)NC(C)C)c(=O)n2C[C@H](OCCC#N)c1cc(F)ccc1OC] |
| I-182 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)(1$-pyrrolidinyl)<br>$OCH_2CH_2CN$<br>H<br>$CH_3, CH_3$<br>$OCH_3$<br>F | 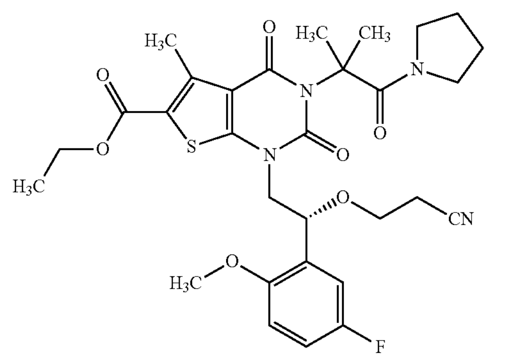 [SMILES: CCOC(=O)c1sc2c(c1C)c(=O)n(C(C)(C)C(=O)N1CCCC1)c(=O)n2C[C@H](OCCC#N)c1cc(F)ccc1OC] |
| I-183 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NH_2$<br>$OCH_2CH_2OH$<br>H<br>$CH_3, CH_3$<br>$OCH_3$<br>F | 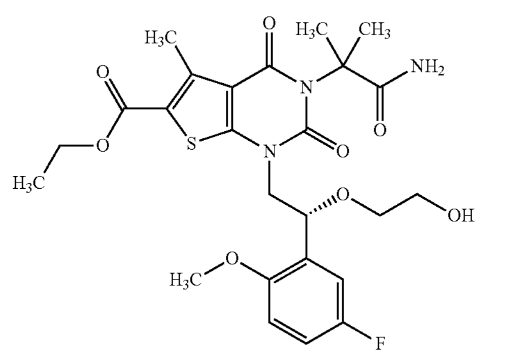 [SMILES: CCOC(=O)c1sc2c(c1C)c(=O)n(C(C)(C)C(N)=O)c(=O)n2C[C@H](OCCO)c1cc(F)ccc1OC] |
| I-184 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NHCH(CH_3)_2$<br>$OCH_2CH_2OH$<br>H<br>$CH_3, CH_3$<br>$OCH_3$<br>F | 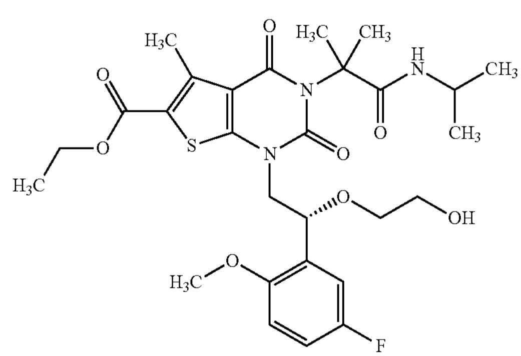 |

TABLE 1-continued

Compounds of Formula I

| Cmpd No. | R Groups | Substituent |
|---|---|---|
| I-185 | $R^1$ | $CH_3$ |
| | $R^2$ | 2H-1,2,3-triazol-2-yl |
| | $R^3$ | $C(O)NHCH(CH_3)_2$ |
| | $R^4$ | OH |
| | $R^{4'}$ | H |
| | $R^5, R^{5'}$ | $CH_3, CH_3$ |
| | $R^7$ | $OCH_3$ |
| | $R^8$ | F |
| I-186 | $R^1$ | $CH_3$ |
| | $R^2$ | $C(O)OCH_2CH_3$ |
| | $R^3$ | $C(O)NHCH(CH_3)_2$ |
| | $R^4$ | OH |
| | $R^{4'}$ | H |
| | $R^5, R^{5'}$ | $CH_3, CH_3$ |
| | $R^7$ | $OCH_3$ |
| | $R^8$ | F |
| I-187 | $R^1$ | $CH_3$ |
| | $R^2$ | 2H-1,2,3-triazol-2-yl |
| | $R^3$ | $C(O)NHCH(CH_3)_2$ |
| | $R^4$ | OH |
| | $R^{4'}$ | H |
| | $R^5, R^{5'}$ | $CH_3, CH_3$ |
| | $R^7$ | $OCH_3$ |
| | $R^8$ | F |
| I-188 | $R^1$ | $CH_3$ |
| | $R^2$ | 2H-1,2,3-triazol-2-yl |
| | $R^3$ | $C(O)N(CH_3)CH(CH_3)_2$ |
| | $R^4$ | OH |
| | $R^{4'}$ | H |
| | $R^5, R^{5'}$ | R—$CH_3$, H |
| | $R^7$ | $OCH_3$ |
| | $R^8$ | F |

TABLE 1-continued

Compounds of Formula I

| Cmpd No. | R Groups | Substituent |
|---|---|---|
| I-189 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)N(CH₃)CH(CH₃)₂<br>OH<br>H<br>S—CH₃, H<br>OCH₃<br>F |
| I-190 | R¹<br>R²<br>R³<br>R⁴<br>R⁴'<br>R⁵, R⁵'<br>R⁷<br>R⁸ | CH₃<br>1-pyrazolyl<br>C(O)NH₂<br>OCH₂CH₂CN<br>H<br>CH₃, CH₃<br>OCH₃<br>F |
| I-191 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>OCH₂CH₂CN<br>H<br>CH₃, CH₃<br>OCH₃<br>F |
| I-192 | R¹<br>R²<br>R³<br>R⁴<br>R⁴'<br>R⁵, R⁵'<br>R⁷<br>R⁸ | CH₃<br>1-pyrazolyl<br>C(O)NHCH(CH₃)₂<br>OCH₂CH₂CN<br>H<br>CH₃, CH₃<br>OCH₃<br>H |

TABLE 1-continued

Compounds of Formula I

| Cmpd No. | R Groups | Substituent | Compound Structure |
|---|---|---|---|
| I-193 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CN<br>H<br>CH₃, CH₃<br>OCH₃<br>H | 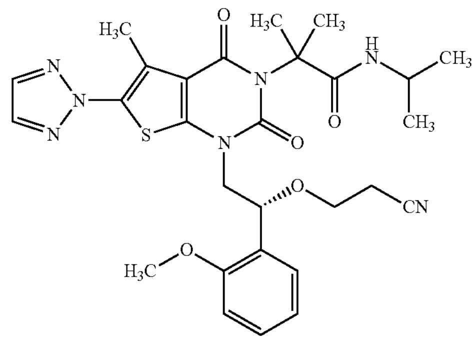 [SMILES: COc1ccccc1[C@H](Cn1c(=O)n(C(C)(C)C(=O)NC(C)C)c(=O)c2c(C)c(-n3nccn3)sc21)OCCC#N] |
| I-194 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH₂CH₂CN<br>H<br>CH₃, CH₃<br>OCH₃<br>F | 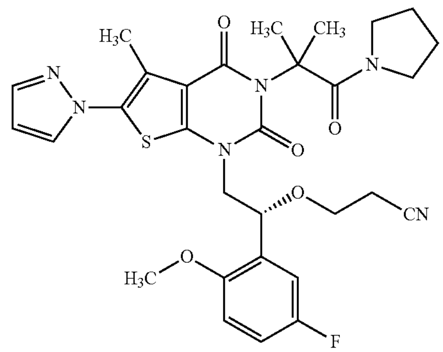 [SMILES: COc1ccc(F)cc1[C@H](Cn1c(=O)n(C(C)(C)C(=O)N2CCCC2)c(=O)c2c(C)c(-n3cccn3)sc21)OCCC#N] |
| I-195 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂CN<br>H<br>CH₃, CH₃<br>OCH₃<br>F | 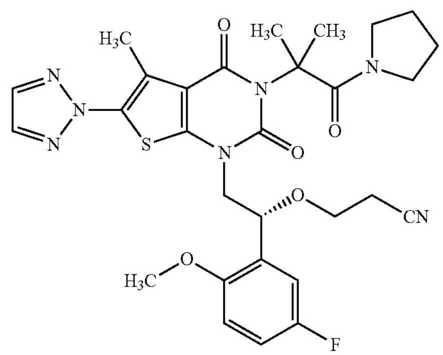 |
| I-196 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂CN<br>H<br>CH₃, CH₃<br>OCH₃<br>H | 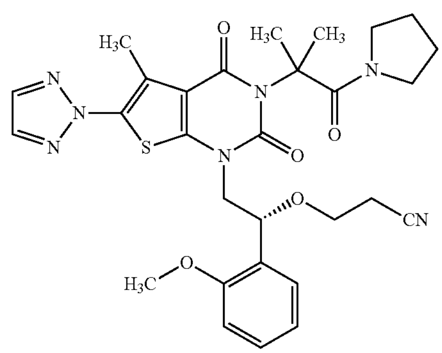 [SMILES: COc1ccccc1[C@H](Cn1c(=O)n(C(C)(C)C(=O)N2CCCC2)c(=O)c2c(C)c(-n3nccn3)sc21)OCCC#N] |

TABLE 1-continued

Compounds of Formula I

| Cmpd No. | R Groups | Substituent |
|---|---|---|
| I-197 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CN<br>H<br>S—CH₃, H<br>OCH₃<br>F |
| I-198 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CN<br>H<br>R—CH₃, H<br>OCH₃<br>F |
| I-199 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NH₂<br>OCH₂CH₂CN<br>H<br>S—CH₃, H<br>OCH₃<br>F |
| I-200 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NH₂<br>OCH₂CH₂CN<br>H<br>R—CH₃, H<br>OCH₃<br>F |

TABLE 1-continued

Compounds of Formula I

| Cmpd No. | R Groups | Substituent | Compound Structure |
|---|---|---|---|
| I-201 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂CN<br>H<br>S—CH₃, H<br>OCH₃<br>F | 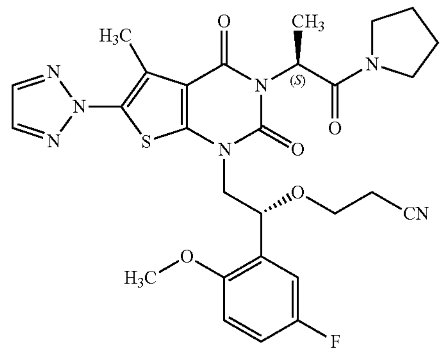 |
| I-202 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂CN<br>H<br>R—CH₃, H<br>OCH₃<br>F | 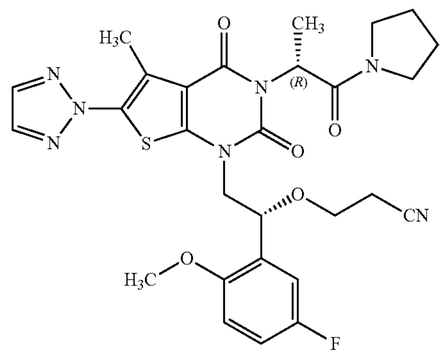 |
| I-203 | R¹<br>R²<br>R³<br>R⁴<br>R⁴'<br>R⁵, R⁵'<br>R⁷<br>R⁸ | CH₃<br>1-pyrazolyl<br>C(O)(1-pyrrolidinyl)<br>OCH₂CH₂CN<br>H<br>CH₃, CH₃<br>OCH₃<br>H | 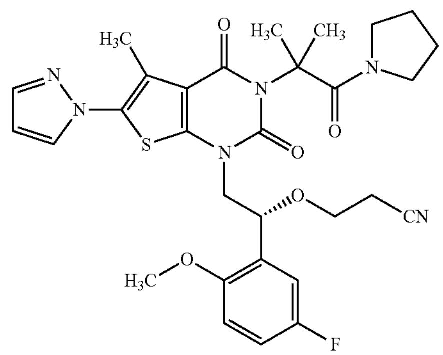 [SMILES: COc1ccc(F)cc1[C@H](Cn1c(=O)n(C(C)(C)C(=O)N2CCCC2)c(=O)c2c(C)c(-n3cccn3)sc21)OCCC#N] |
| I-204 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)N(CH₃)CH(CH₃)₂<br>OCH₂CH₂CN<br>H<br>S—CH₃, H<br>OCH₃<br>F | 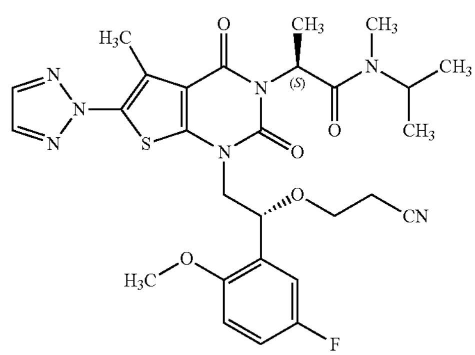 |

TABLE 1-continued

Compounds of Formula I

| Cmpd No. | R Groups | Substituent | Compound Structure |
|---|---|---|---|
| I-205 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)N(CH₃)CH(CH₃)₂<br>OCH₂CH₂CN<br>H<br>R—CH₃, H<br>OCH₃<br>F | 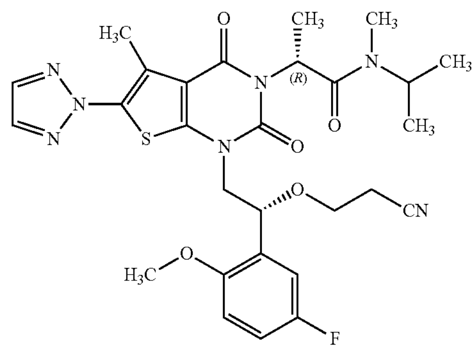 |
| I-206 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH₂CH₃<br>OCH₂CH₂CN<br>H<br>CH₃, CH₃<br>OCH₃<br>F | 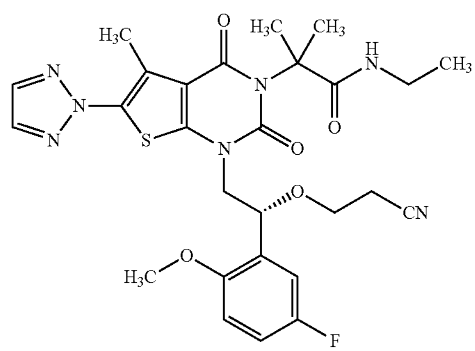 [SMILES: CCNC(=O)C(C)(C)n1c(=O)c2c(C)c(-n3nccn3)sc2n(C[C@H](OCCC#N)c2cc(F)ccc2OC)c1=O] |
| I-207 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH₃<br>OCH₂CH₂CN<br>H<br>CH₃, CH₃<br>OCH₃<br>F | 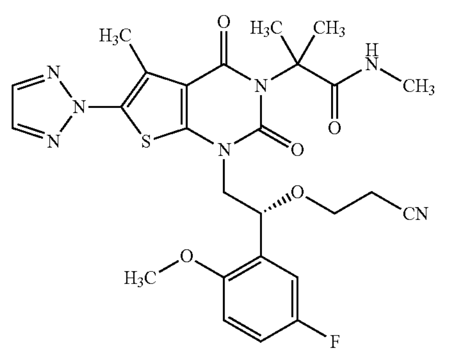 [SMILES: CNC(=O)C(C)(C)n1c(=O)c2c(C)c(-n3nccn3)sc2n(C[C@H](OCCC#N)c2cc(F)ccc2OC)c1=O] |
| I-208 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH₂CH₃<br>OCH₂CH₂CN<br>H<br>CH₃, CH₃<br>OCH₃<br>H | 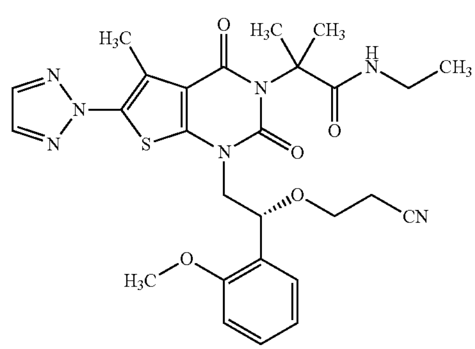 [SMILES: CCNC(=O)C(C)(C)n1c(=O)c2c(C)c(-n3nccn3)sc2n(C[C@H](OCCC#N)c2ccccc2OC)c1=O] |

TABLE 1-continued

Compounds of Formula I

| Cmpd No. | R Groups | Substituent | Compound Structure |
|---|---|---|---|
| I-209 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH$_3$<br>OCH$_2$CH$_2$CN<br>H<br>CH$_3$, CH$_3$<br>OCH$_3$<br>H | 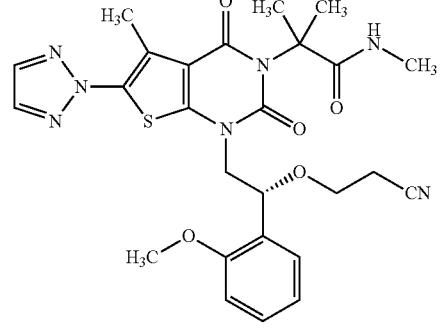 |
| I-210 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH(CH$_3$)$_2$<br>OCH$_2$CN<br>H<br>CH$_3$, CH$_3$<br>OCH$_3$<br>F | 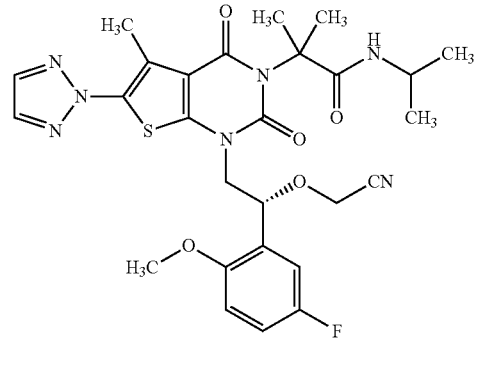 |
| I-211 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH(CH$_3$)$_2$<br>OCH$_2$CH(S—CH$_3$)CN<br>H<br>CH$_3$, CH$_3$<br>OCH$_3$<br>F | 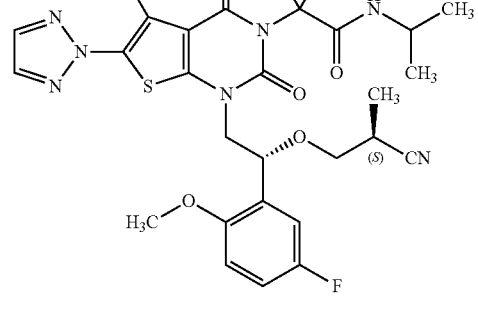 |
| I-212 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH(CH$_3$)$_2$<br>OCH$_2$CH(R—CH$_3$)CN<br>H<br>CH$_3$, CH$_3$<br>OCH$_3$<br>F | 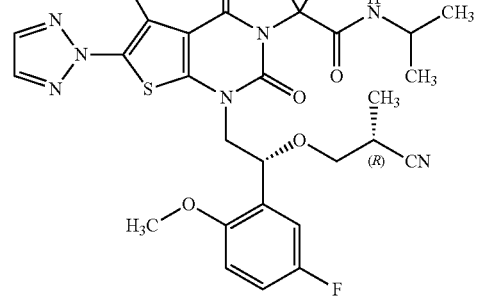 |

TABLE 1-continued

Compounds of Formula I

| Cmpd No. | R Groups | Substituent |
|---|---|---|
| I-213 | R¹ | CH₃ |
| | R² | 2H-1,2,3-triazol-2-yl |
| | R³ | C(O)NHCH(CH₃)₂ |
| | R⁴ | OCH₂C(CH₃)₂CN |
| | R⁴' | H |
| | R⁵, R⁵' | CH₃, CH₃ |
| | R⁷ | OCH₃ |
| | R⁸ | F |
| I-214 | R¹ | CH₃ |
| | R² | 2H-1,2,3-triazol-2-yl |
| | R³ | C(O)(1-pyrrolidinyl) |
| | R⁴ | OH |
| | R⁴' | H |
| | R⁵, R⁵' | CH₃, CH₃ |
| | R⁷ | OCH₃ |
| | R⁸ | F |
| I-215 | R¹ | CH₃ |
| | R² | 2H-1,2,3-triazol-2-yl |
| | R³ | C(O)(1-pyrrolidinyl) |
| | R⁴ | OH |
| | R⁴' | H |
| | R⁵, R⁵' | CH₃, CH₃ |
| | R⁷ | OCH₃ |
| | R⁸ | H |
| I-218 | R¹ | CH₃ |
| | R² | 2H-1,2,3-triazol-2-yl |
| | R³ | C(O)(1-pyrrolidinyl) |
| | R⁴ | OH |
| | R⁴' | H |
| | R⁵, R⁵' | S—CH₃, H |
| | R⁷ | OCH₃ |
| | R⁸ | F |

TABLE 1-continued

Compounds of Formula I

| Cmpd No. | R Groups | Substituent |
|---|---|---|
| I-219 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH(CH₃)₂<br>OCH₂CH₂CN<br>H<br>S—CH₃, H<br>OCH₃<br>F |
| I-220 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH(CH₃)₂<br>OCH₂CH₂CN<br>H<br>R—CH₃, H<br>OCH₃<br>F |
| I-221 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NH₂<br>OH<br>H<br>CH₃, CH₃<br>OCH₃<br>F |
| I-222 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OH<br>H<br>R—CH₃, H<br>OCH₃<br>F |

TABLE 1-continued

Compounds of Formula I

| Cmpd No. | R Groups | Substituent | Compound Structure |
|---|---|---|---|
| I-224 | $R^1$ | $CH_3$ | 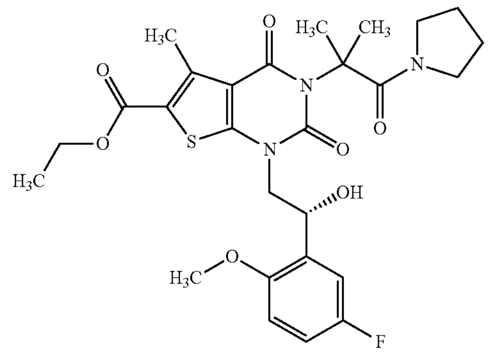 [SMILES: CCOC(=O)c1sc2c(c1C)c(=O)n(C(C)(C)C(=O)N1CCCC1)c(=O)n2C[C@H](O)c1cc(F)ccc1OC] |
| | $R^2$ | $C(O)OCH_2CH_3$ | |
| | $R^3$ | $C(O)$(1-pyrrolidinyl) | |
| | $R^4$ | OH | |
| | $R^{4'}$ | H | |
| | $R^5, R^{5'}$ | $CH_3$, H | |
| | $R^7$ | $OCH_3$ | |
| | $R^8$ | F | |
| I-225 | $R^1$ | $CH_3$ | 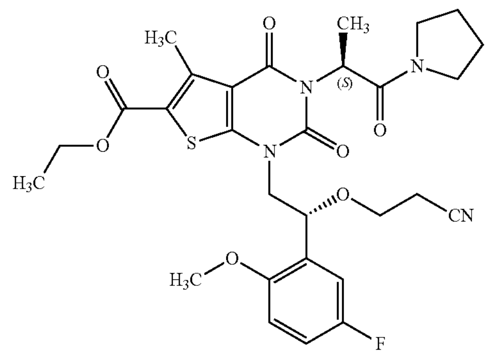 |
| | $R^2$ | $C(O)OCH_2CH_3$ | |
| | $R^3$ | $C(O)$(1-pyrrolidinyl) | |
| | $R^4$ | $OCH_2CH_2CN$ | |
| | $R^{4'}$ | H | |
| | $R^5, R^{5'}$ | S—$CH_3$, H | |
| | $R^7$ | $OCH_3$ | |
| | $R^8$ | F | |
| I-226 | $R^1$ | $CH_3$ | 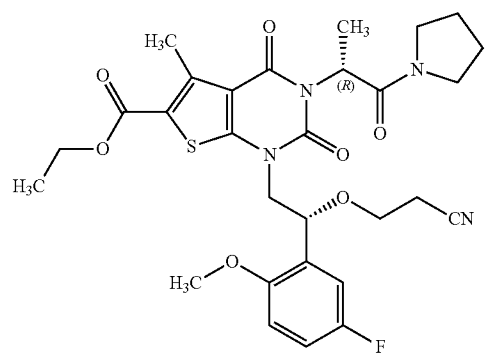 |
| | $R^2$ | $C(O)OCH_2CH_3$ | |
| | $R^3$ | $C(O)$(1-pyrrolidinyl) | |
| | $R^4$ | $OCH_2CH_2CN$ | |
| | $R^{4'}$ | H | |
| | $R^5, R^{5'}$ | R—$CH_3$, H | |
| | $R^7$ | $OCH_3$ | |
| | $R^8$ | F | |
| I-227 | $R^1$ | $CH_3$ | 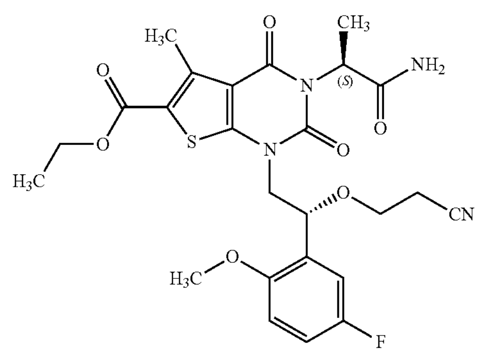 |
| | $R^2$ | $C(O)OCH_2CH_3$ | |
| | $R^3$ | $C(O)NH_2$ | |
| | $R^4$ | $OCH_2CH_2CN$ | |
| | $R^{4'}$ | H | |
| | $R^5, R^{5'}$ | S—$CH_3$, H | |
| | $R^7$ | $OCH_3$ | |
| | $R^8$ | F | |

TABLE 1-continued

Compounds of Formula I

| Cmpd No. | R Groups | Substituent | Compound Structure |
|---|---|---|---|
| I-228 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NH_2$<br>$OCH_2CH_2CN$<br>H<br>R—$CH_3$, H<br>$OCH_3$<br>F | 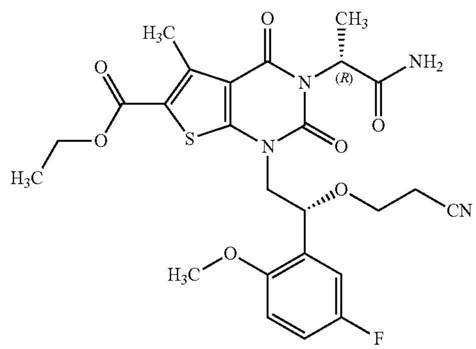 |
| I-229 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)N(CH_3)CH(CH_3)_2$<br>$OCH_2CH_2CN$<br>H<br>R—$CH_3$, H<br>$OCH_3$<br>F | 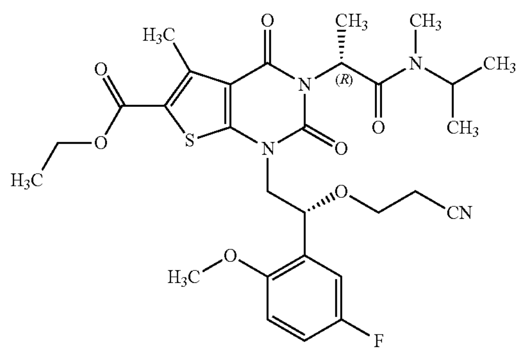 |
| I-230 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)N(CH_3)CH(CH_3)_2$<br>$OCH_2CH_2CN$<br>H<br>S—$CH_3$, H<br>$OCH_3$<br>F | 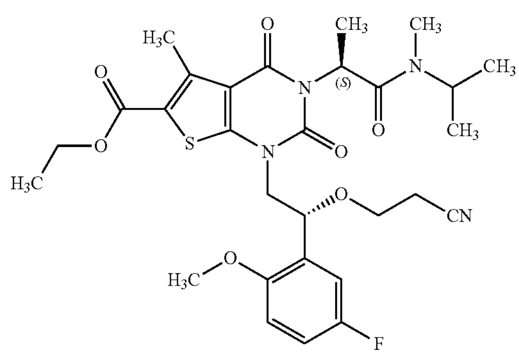 |
| I-231 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NHCH_2CH_3$<br>$OCH_2CH_2CN$<br>H<br>$CH_3, CH_3$<br>$OCH_3$<br>F | 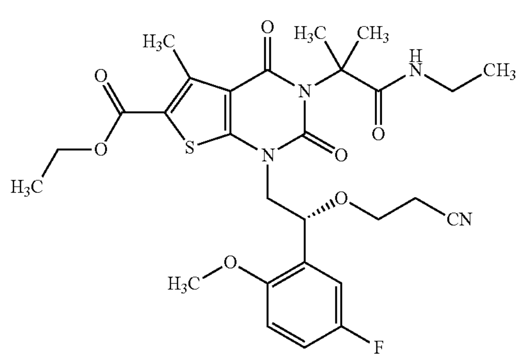 |

TABLE 1-continued

Compounds of Formula I

| Cmpd No. | R Groups | Substituent | Compound Structure |
|---|---|---|---|
| I-232 | R¹<br>R²<br>R³<br>R⁴<br>R⁴'<br>R⁵,R⁵'<br>R⁷<br>R⁸ | CH₃<br>1-pyrazolyl<br>C(O)NHCH₂CH₃<br>OCH₂CH₂CN<br>H<br>CH₃, CH₃<br>OCH₃<br>H | 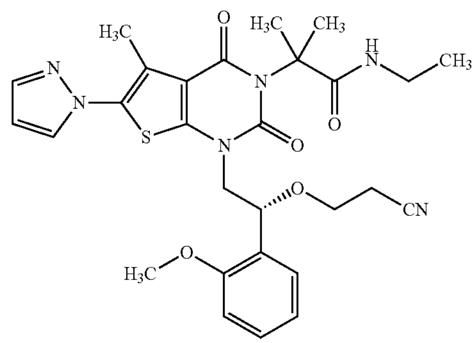 [SMILES: CCNC(=O)C(C)(C)n1c(=O)c2c(C)c(-n3cccn3)sc2n(C[C@H](OCCC#N)c2ccccc2OC)c1=O] |
| I-233 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH(CH₃)₂<br>OCH₂CH₂CN<br>H<br>CH₃, CH₃<br>OCH₃<br>H | 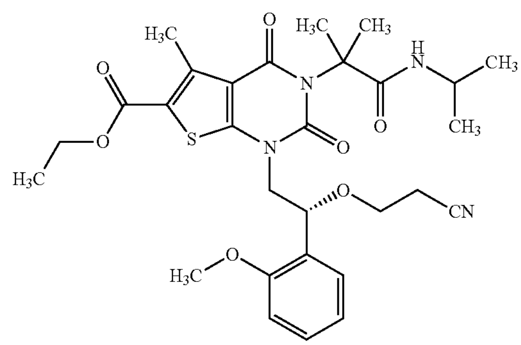 [SMILES: CCOC(=O)c1sc2c(c1C)c(=O)n(C(C)(C)C(=O)NC(C)C)c(=O)n2C[C@H](OCCC#N)c1ccccc1OC] |
| I-234 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH₂CH₃<br>OCH₂CH₂CN<br>H<br>CH₃, CH₃<br>OCH₃<br>H | 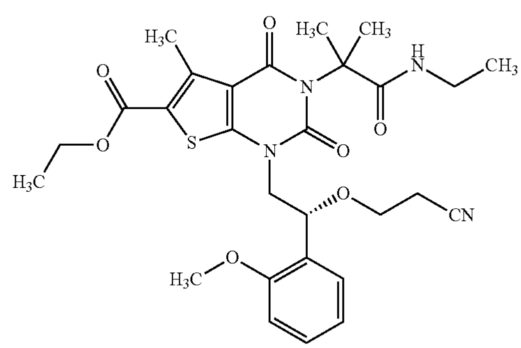 [SMILES: CCNC(=O)C(C)(C)n1c(=O)c2c(C)c(C(=O)OCC)sc2n(C[C@H](OCCC#N)c2ccccc2OC)c1=O] |
| I-235 | R¹<br>R²<br>R³<br>R⁴<br>R⁴'<br>R⁵, R⁵'<br>R⁷<br>R⁸ | CH₃<br>1-pyrazolyl<br>C(O)NHCH₂CH₃<br>OCH₂CH₂CN<br>H<br>CH₃, CH₃<br>OCH₃<br>F | 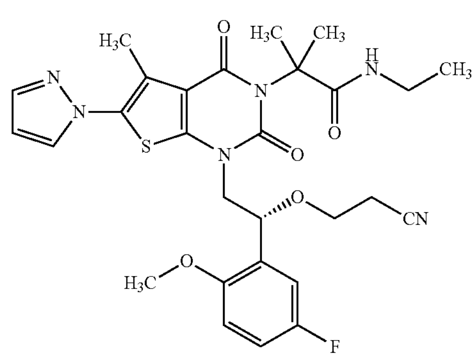 [SMILES: CCNC(=O)C(C)(C)n1c(=O)c2c(C)c(-n3cccn3)sc2n(C[C@H](OCCC#N)c2cc(F)ccc2OC)c1=O] |

TABLE 1-continued

Compounds of Formula I

| Cmpd No. | R Groups | Substituent |
|---|---|---|
| I-238 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)N(CH₃)CH(CH₃)₂<br>OCH₂CH₂CN<br>H<br>R—CH₃, H<br>OCH₃<br>H |
| I-239 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)N(CH₃)CH(CH₃)₂<br>OCH₂CH₂CN<br>H<br>S—CH₃, H<br>OCH₃<br>H |
| I-242 | R¹<br>R²<br>R³<br>R⁴<br>R⁴'<br>R⁵, R⁵'<br>R⁷<br>R⁸ | CH₃<br>1-pyrazolyl<br>C(O)N(CH₃)CH(CH₃)₂<br>OCH₂CH₂CN<br>H<br>R—CH₃, H<br>OCH₃<br>F |
| I-243 | R¹<br>R²<br>R³<br>R⁴<br>R⁴'<br>R⁵, R⁵'<br>R⁷<br>R⁸ | CH₃<br>1-pyrazolyl<br>C(O)N(CH₃)CH(CH₃)₂<br>OCH₂CH₂CN<br>H<br>S—CH₃, H<br>OCH₃<br>F |

TABLE 1-continued

Compounds of Formula I

| Cmpd No. | R Groups | Substituent | Compound Structure |
|---|---|---|---|
| I-244 | $R^1$ | $CH_3$ | 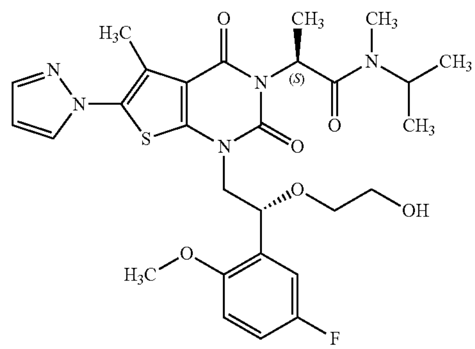 |
| | $R^2$ | 1-pyrazolyl | |
| | $R^3$ | $C(O)N(CH_3)CH(CH_3)_2$ | |
| | $R^4$ | $OCH_2CH_2OH$ | |
| | $R^{4'}$ | H | |
| | $R^5, R^{5'}$ | S—$CH_3$, H | |
| | $R^7$ | $OCH_3$ | |
| | $R^8$ | F | |
| I-245 | $R^1$ | $CH_3$ | 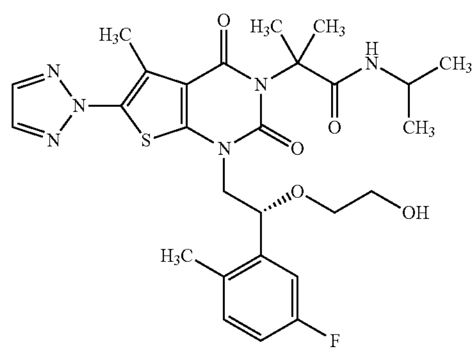 [SMILES: Cc1ccc(F)cc1[C@H](Cn1c(=O)n(C(C)(C)C(=O)NC(C)C)c(=O)c2c(C)c(-n3nccn3)sc21)OCCO] |
| | $R^2$ | 2H-1,2,3-triazol-2-yl | |
| | $R^3$ | $C(O)NHCH(CH_3)_2$ | |
| | $R^4$ | $OCH_2CH_2OH$ | |
| | $R^{4'}$ | H | |
| | $R^5, R^{5'}$ | $CH_3, CH_3$ | |
| | $R^7$ | $CH_3$ | |
| | $R^8$ | F | |
| I-246 | $R^1$ | $CH_3$ | 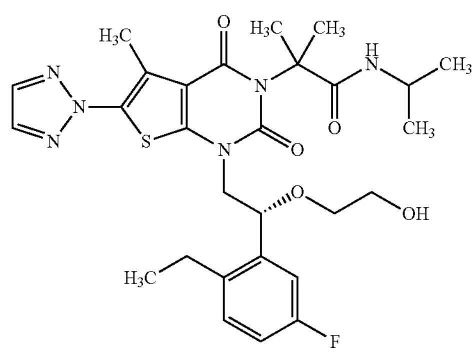 [SMILES: CCc1ccc(F)cc1[C@H](Cn1c(=O)n(C(C)(C)C(=O)NC(C)C)c(=O)c2c(C)c(-n3nccn3)sc21)OCCO] |
| | $R^2$ | 2H-1,2,3-triazol-2-yl | |
| | $R^3$ | $C(O)NHCH(CH_3)_2$ | |
| | $R^4$ | $OCH_2CH_2OH$ | |
| | $R^{4'}$ | H | |
| | $R^5, R^{5'}$ | $CH_3, CH_3$ | |
| | $R^7$ | $CH_2CH_3$ | |
| | $R^8$ | F | |
| I-247 | $R^1$ | $CH_3$ | 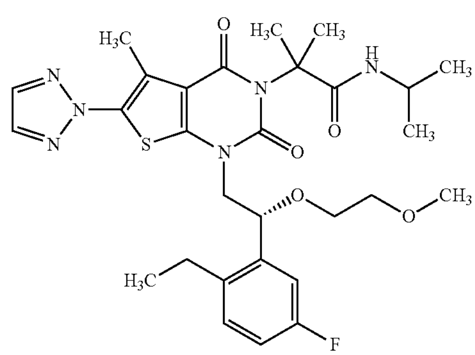 |
| | $R^2$ | 2H-1,2,3-triazol-2-yl | |
| | $R^3$ | $C(O)NHCH(CH_3)_2$ | |
| | $R^4$ | $OCH_2CH_2OCH_3$ | |
| | $R^{4'}$ | H | |
| | $R^5, R^{5'}$ | $CH_3, CH_3$ | |
| | $R^7$ | $CH_2CH_3$ | |
| | $R^8$ | F | |

TABLE 1-continued

Compounds of Formula I

| Cmpd No. | R Groups | Substituent | Compound Structure |
|---|---|---|---|
| I-248 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂OCH₃<br>H<br>CH₃, CH₃<br>CH₃<br>F | 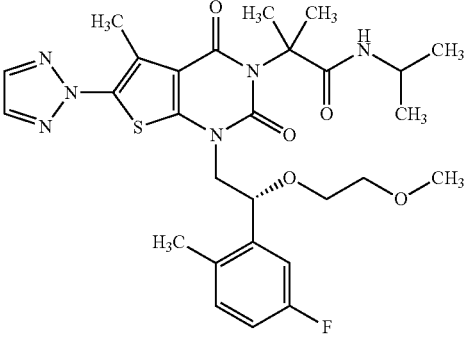 [SMILES: COCCO[C@@H](Cn1c(=O)n(C(C)(C)C(=O)NC(C)C)c(=O)c2c(C)c(-n3nccn3)sc21)c1cc(F)ccc1C] |
| I-249 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)(1-pyrrolidinyl)<br>OCH₂CH₂OCH₃<br>H<br>CH₃, CH₃<br>CH₃<br>F | 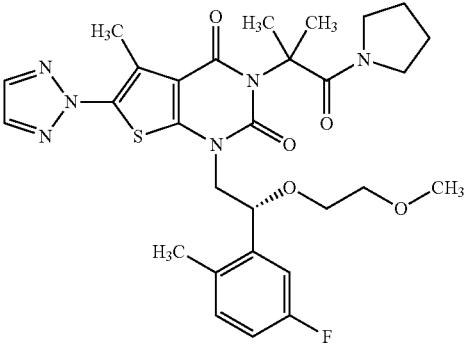 [SMILES: COCCO[C@@H](Cn1c(=O)n(C(C)(C)C(=O)N2CCCC2)c(=O)c2c(C)c(-n3nccn3)sc21)c1cc(F)ccc1C] |
| I-250 | R¹<br>R²<br>R³<br>R⁴<br>R⁴'<br>R⁵, R⁵'<br>R⁷<br>R⁸ | CH₃<br>1-pyrazolyl<br>C(O)N(CH₃)CH(CH₃)₂<br>OCH₂CH₂OH<br>H<br>S—CH₃, H<br>OCH₃<br>F | 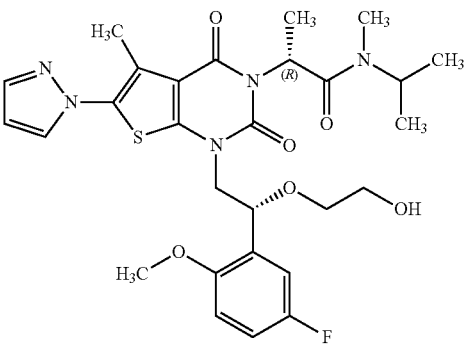 |
| I-251 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH(CH₃)₂<br>OCH₂CN<br>H<br>CH₃, CH₃<br>OCH₃<br>F | 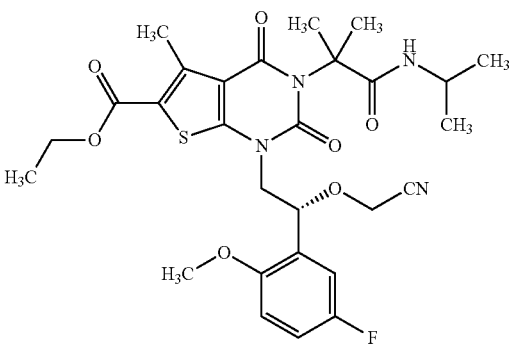 |

TABLE 1-continued

Compounds of Formula I

| Cmpd No. | R Groups | Substituent | Compound Structure |
|---|---|---|---|
| I-253 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2C(CH_3)_2CN$<br>H<br>S—$CH_3$, H<br>$CH_3$<br>F | 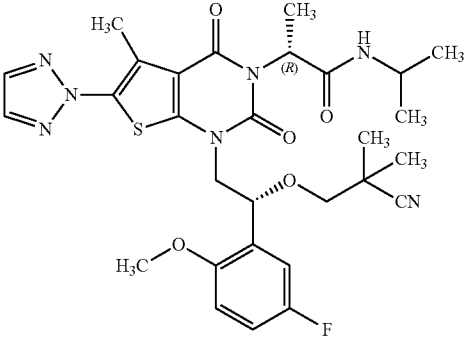 |
| I-254 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>$OCH_2C(CH_3)_2CN$<br>H<br>S—$CH_3$, H<br>$OCH_3$<br>F | 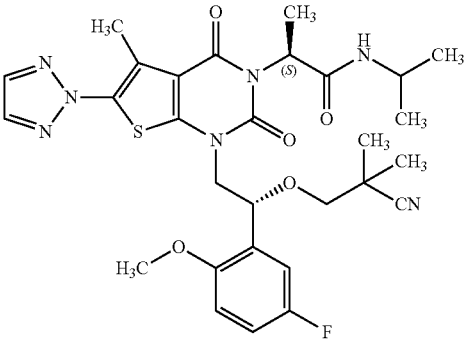 |
| I-255 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NH_2$<br>$OCH_2C(CH_3)_2CN$<br>H<br>R—$CH_3$, H<br>$OCH_3$<br>F | 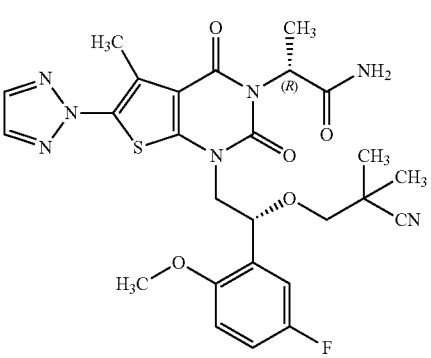 |
| I-256 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NH_2$<br>$OCH_2C(CH_3)_2CN$<br>H<br>S—$CH_3$, H<br>$OCH_3$<br>F | 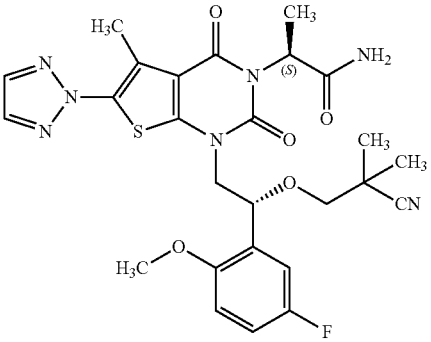 |

TABLE 1-continued

Compounds of Formula I

| Cmpd No. | R Groups | Substituent |
|---|---|---|
| I-257 | R¹ | CH₃ |
| | R² | 1-pyrazolyl |
| | R³ | C(O)NHCH(CH₃)₂ |
| | R⁴ | OCH₂CN |
| | R⁴' | H |
| | R⁵, R⁵' | CH₃, CH₃ |
| | R⁷ | OCH₃ |
| | R⁸ | F |
| I-258 | R¹ | CH₃ |
| | R² | C(O)OCH₂CH₃ |
| | R³ | C(O)NHCH(CH₃)₂ |
| | R⁴ | OCH₂CH(S—CH₃)CN |
| | R⁴' | H |
| | R⁵, R⁵' | CH₃, CH₃ |
| | R⁷ | OCH₃ |
| | R⁸ | F |
| I-259 | R¹ | CH₃ |
| | R² | C(O)OCH₂CH₃ |
| | R³ | C(O)NHCH(CH₃)₂ |
| | R⁴ | OCH₂CH(R—CH₃)CN |
| | R⁴' | H |
| | R⁵, R⁵' | CH₃, CH₃ |
| | R⁷ | OCH₃ |
| | R⁸ | F |
| I-262 | R¹ | CH₃ |
| | R² | 1-pyrazolyl |
| | R³ | C(O)NHCH(CH₃)₂ |
| | R⁴ | OCH₂CH(S—CH₃)CN |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-263 | $R^1$ | $CH_3$ |
| | $R^2$ | 1-pyrazolyl |
| | $R^3$ | $C(O)NHCH(CH_3)_2$ |
| | $R^4$ | $OCH_2CH(R—CH_3)CN$ |
| | $R^{4'}$ | H |
| | $R^5, R^{5'}$ | $CH_3, CH_3$ |
| | $R^7$ | $CH_3$ |
| | $R^8$ | F |
| I-264 | $R^1$ | $CH_3$ |
| | $R^2$ | 2H-1,2,3-triazol-2-yl |
| | $R^3$ | $C(O)NHCH(CH_3)_2$ |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | F |
| I-265 | $R^1$ | $CH_3$ |
| | $R^2$ | 2H-1,2,3-triazol-2-yl |
| | $R^3$ | $C(O)NHCH(CH_3)_2$ |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_3$ |
| | $R^8$ | H |
| I-266 | $R^1$ | $CH_3$ |
| | $R^2$ | 2H-1,2,3-triazol-2-yl |
| | $R^3$ | $C(O)NHCH(CH_3)_2$ |
| | $R^4$ | $OCH_2CH_2C(O)NHOH$ |
| | $R^{4'}$ | H |
| | $R^5, R^{5'}$ | $CH_3, CH_3$ |
| | $R^7$ | $OCH_3$ |
| | $R^8$ | H |

TABLE 1-continued

Compounds of Formula I

| Cmpd No. | R Groups | Substituent |
|---|---|---|
| I-267 | $R^1$ | $CH_3$ |
| | $R^2$ | 2H-1,2,3-triazol-2-yl |
| | $R^3$ | $C(O)NHC_4H_7$ |
| | $R^4$ | $OCH(CH_3)_2$ |
| | $R^{4'}$ | H |
| | $R^5, R^{5'}$ | $CH_3, CH_3$ |
| | $R^7$ | $OCH_2CN$ |
| | $R^8$ | F |
| I-268 | $R^1$ | $CH_3$ |
| | $R^2$ | 2H-1,2,3-triazol-2-yl |
| | $R^3$ | $C(O)NHCH(CH_3)_2$ |
| | $R^4$ | O-cis-4-hydroxycyclohexyl |
| | $R^{4'}$ | H |
| | $R^5, R^{5'}$ | $CH_3, CH_3$ |
| | $R^7$ | $OCH_2CN$ |
| | $R^8$ | F |
| I-269 | $R^1$ | $CH_3$ |
| | $R^2$ | 2H-1,2,3-triazol-2-yl |
| | $R^3$ | $C(O)NHCH(CH_3)_2$ |
| | $R^4$ | $OCH_2C(CH_3)_2CN$ |
| | $R^{4'}$ | H |
| | $R^5, R^{5'}$ | $CH_3, CH_3$ |
| | $R^7$ | $OCH_3$ |
| | $R^8$ | CN |
| I-270 | $R^1$ | $CH_3$ |
| | $R^2$ | 2H-1,2,3-triazol-2-yl |
| | $R^3$ | $C(O)NHCH(CH_3)_2$ |
| | $R^4$ | $OCH_2C(CH_3)_2CN$ |
| | $R^{4'}$ | H |
| | $R^5, R^{5'}$ | $CH_3, CH_3$ |
| | $R^7$ | $OCH_3$ |
| | $R^{14}$ | Br |

TABLE 1-continued

Compounds of Formula I

| Cmpd No. | R Groups | Substituent |
|---|---|---|
| I-271 | R¹ | CH₃ |
| | R² | 2H-1,2,3-triazol-2-yl |
| | R³ | C(O)NHCH(CH₃)₂ |
| | R⁴ | OCH₂CH₂OH |
| | R⁴' | H |
| | R⁵, R⁵' | CH₃, CH₃ |
| | R⁷ | OH |
| | R⁸ | F |
| I-272 | R¹ | CH₃ |
| | R² | 2H-1,2,3-triazol-2-yl |
| | R³ | C(O)NHCH(CH₃)₂ |
| | R⁴ | OCH₂C(CH₃)₂CN |
| | R⁴' | H |
| | R⁵, R⁵' | CH₃, CH₃ |
| | R⁷ | OCH₃ |
| | R⁸ | Cl |
| I-273 | R¹ | CH₃ |
| | R² | 2H-1,2,3-triazol-2-yl |
| | R³ | C(O)NHCH(CH₃)₂ |
| | R⁴ | OCH₂CH₂CN |
| | R⁴' | CH₃ |
| | R⁵, R⁵' | CH₃, CH₃ |
| | R⁷ | OCH₃ |
| | R⁸ | F |
| I-274 | R¹ | CH₃ |
| | R² | 2H-1,2,3-triazol-2-yl |
| | R³ | C(O)NHCH(CH₃)₂ |
| | R⁴ | OCH₂CH₂CN |
| | R⁴' | CH₃ |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent | Compound Structure |
|---|---|---|---|
| I-275 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OH<br>CH₂CH₂OH<br>CH₃, CH₃<br>OCH₃<br>F | 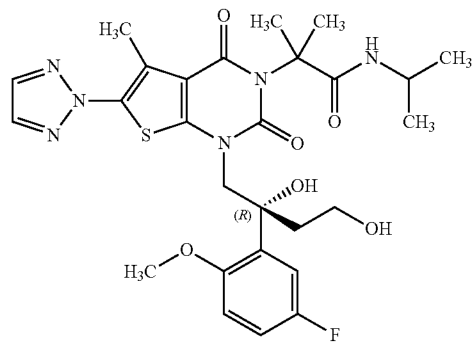 |
| I-276 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OH<br>CH₂CH₂OH<br>CH₃, CH₃<br>OCH₃<br>F | 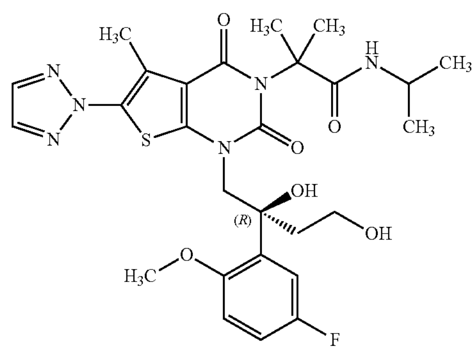 |
| I-277 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH(CH₃)₂<br>H<br>CH₃, CH₃<br>CH₂CH₂CN<br>F | 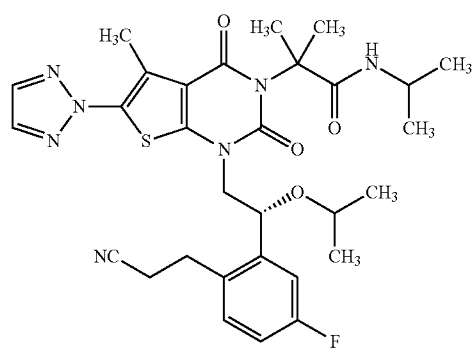 [SMILES: Cc1c(-n2nccn2)sc2c1c(=O)n(C(C)(C)C(=O)NC(C)C)c(=O)n2C[C@H](OC(C)C)c1cc(F)ccc1CCC#N] |
| I-278 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂C(CH₃)₂OH<br>H<br>CH₃, CH₃<br>OCH₂CN<br>F | 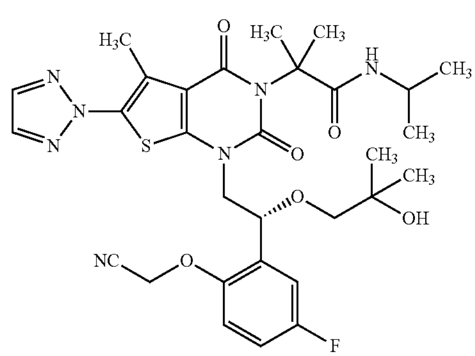 [SMILES: Cc1c(-n2nccn2)sc2c1c(=O)n(C(C)(C)C(=O)NC(C)C)c(=O)n2C[C@H](OCC(C)(C)O)c1cc(F)ccc1OCC#N] |

TABLE 1-continued

Compounds of Formula I

| Cmpd No. | R Groups | Substituent |
|---|---|---|
| I-279 | R¹ | CH₃ |
|  | R² | 2H-1,2,3-triazol-2-yl |
|  | R³ | C(O)NHCH(CH₃)₂ |
|  | R⁴ | OCH₂C(CH₃)₂CN |
|  | R⁴' | H |
|  | R⁵, R⁵' | CH₃, CH₃ |
|  | R⁷ | CH₂CH₃ |
|  | R⁸ | F |
| I-280 | R¹ | CH₃ |
|  | R² | 2H-1,2,3-triazol-2-yl |
|  | R³ | C(O)NHCH(CH₃)₂ |
|  | R⁴ | O-cis-3-hydroxycyclobutyl |
|  | R⁴' | H |
|  | R⁵, R⁵' | CH₃, CH₃ |
|  | R⁷ | OCH₃ |
|  | R⁸ | F |
| I-281 | R¹ | CH₃ |
|  | R² | 2H-1,2,3-triazol-2-yl |
|  | R³ | C(O)NHCH(CH₃)₂ |
|  | R⁴ | OCH₂CH(S—CH₃)CN |
|  | R⁴' | H |
|  | R⁵, R⁵' | CH₃, CH₃ |
|  | R⁷ | CH₂CH₃ |
|  | R⁸ | F |
| I-282 | R¹ | CH₃ |
|  | R² | 2H-1,2,3-triazol-2-yl |
|  | R³ | C(O)NHCH(CH₃)₂ |
|  | R⁴ | OCH₂CH₂CN |
|  | R⁴' | H |
|  | R⁵, R⁵' | CH₃, CH₃ |
|  | R⁷ | OH |
|  | R⁸ | F |

TABLE 1-continued

Compounds of Formula I

| Cmpd No. | R Groups | Substituent |
|---|---|---|
| I-283 | R¹ | CH₃ |
| | R² | 1-pyrazolyl |
| | R³ | C(O)NHCH(CH₃)₂ |
| | R⁴ | OCH₂CH₂CN |
| | R⁴' | H |
| | R⁵, R⁵' | CH₃, CH₃ |
| | R⁷ | OH |
| | R⁸ | F |
| I-284 | R¹ | CH₃ |
| | R² | 2H-1,2,3-triazol-2-yl |
| | R³ | C(O)NHCH(CH₃)₂ |
| | R⁴ | OCH₂CH(R—CH₃)CN |
| | R⁴' | H |
| | R⁵, R⁵' | CH₃, CH₃ |
| | R⁷ | CH₂CH₃ |
| | R⁸ | F |
| I-285 | R¹ | CH₃ |
| | R² | C(O)OCH₂CH₃ |
| | R³ | C(O)NHCH(CH₃)₂ |
| | R⁴ | OCH₂CH₂SO₂CH₃ |
| | R⁴' | H |
| | R⁵, R⁵' | CH₃, CH₃ |
| | R⁷ | OCH₃ |
| | R⁸ | F |
| I-286 | R¹ | CH₃ |
| | R² | 1-pyrazolyl |
| | R³ | C(O)NHCH(CH₃)₂ |
| | R⁴ | OCH₂CH₂SO₂CH₃ |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-287 | R¹ | CH₃ |
| | R² | 2H-1,2,3-triazol-2-yl |
| | R³ | C(O)NHCH(CH₃)₂ |
| | R⁴ | OCH₂CH₂SO₂CH₃ |
| | R⁴' | H |
| | R⁵, R⁵' | CH₃, CH₃ |
| | R⁷ | OCH₃ |
| | R⁸ | F |
| I-289 | R¹ | CH₃ |
| | R² | 2H-1,2,3-triazol-2-yl |
| | R³ | C(O)NHCH₂CH₃ |
| | R⁴ | OCH₂CH₂CN |
| | R⁴' | H |
| | R⁵, R⁵' | R—CH₃, H |
| | R⁷ | OCH₃ |
| | R⁸ | F |
| I-290 | R¹ | CH₃ |
| | R² | 2H-1,2,3-triazol-2-yl |
| | R³ | C(O)NHCH₂CH₃ |
| | R⁴ | OCH₂CH₂CN |
| | R⁴' | H |
| | R⁵, R⁵' | S—CH₃, H |
| | R⁷ | OCH₃ |
| | R⁸ | F |
| I-291 | R¹ | CH₃ |
| | R² | 2H-1,2,3-triazol-2-yl |
| | R³ | C(O)NHCH₂CH₃ |
| | R⁴ | OH |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-292 | R$^1$ | CH$_3$ |
| | R$^2$ | 2H-1,2,3-triazol-2-yl |
| | R$^3$ | C(O)NHCH$_2$CH$_3$ |
| | R$^4$ | OH |
| | R$^{4'}$ | H |
| | R$^5$, R$^{5'}$ | CH$_3$, CH$_3$ |
| | R$^7$ | OCH$_3$ |
| | R$^8$ | F |
| I-293 | R$^1$ | CH$_3$ |
| | R$^2$ | 1-pyrazolyl |
| | R$^3$ | C(O)NH-cyclohexyl |
| | R$^4$ | OCH$_2$CH$_2$OCH$_3$ |
| | R$^{4'}$ | H |
| | R$^5$, R$^{5'}$ | CH$_3$, CH$_3$ |
| | R$^7$ | OCH$_3$ |
| | R$^8$ | F |
| I-294 | R$^1$ | CH$_3$ |
| | R$^2$ | 2H-1,2,3-triazol-2-yl |
| | R$^3$ | C(O)NHCH(CH$_3$)$_2$ |
| | R$^4$ | H |
| | R$^{4'}$ | H |
| | R$^5$, R$^{5'}$ | CH$_3$, CH$_3$ |
| | R$^7$ | OCH$_3$ |
| | R$^8$ | H |
| I-295 | R$^1$ | CH$_3$ |
| | R$^2$ | 1-pyrazolyl |
| | R$^3$ | C(O)NHCH$_2$CH$_3$ |
| | R$^4$ | OCH$_2$CH$_2$CN |
| | R$^{4'}$ | H |
| | R$^5$, R$^{5'}$ | R—CH$_3$, H |
| | R$^7$ | OCH$_3$ |
| | R$^8$ | F |

TABLE 1-continued

Compounds of Formula I

| Cmpd No. | R Groups | Substituent |
|---|---|---|
| I-296 | R¹ | CH₃ |
| | R² | 2H-1,2,3-triazol-2-yl |
| | R³ | C(O)NHCH(CH₃)₂ |
| | R⁴ | H |
| | R⁴' | H |
| | R⁵, R⁵' | CH₃, CH₃ |
| | R⁷ | OCH₃ |
| | R⁸ | F |
| I-297 | R¹ | CH₃ |
| | R² | C(O)OCH₂CH₃ |
| | R³ | C(O)NHCH₂CH₃ |
| | R⁴ | OCH₂CH₂CN |
| | R⁴' | H |
| | R⁵, R⁵' | R—CH₃, H |
| | R⁷ | OCH₃ |
| | R⁸ | F |
| I-298 | R¹ | CH₃ |
| | R² | C(O)OCH₂CH₃ |
| | R³ | C(O)NHCH(CH₃)₂ |
| | R⁴ | H |
| | R⁴' | H |
| | R⁵, R⁵' | CH₃, CH₃ |
| | R⁷ | OCH₃ |
| | R⁸ | F |
| I-299 | R¹ | CH₃ |
| | R² | 1-pyrazolyl |
| | R³ | C(O)NHC₄H₇ |
| | R⁴ | OCH₂CH₂OCH₃ |
| | R⁴' | H |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-300 | R¹ | CH₃ |
| | R² | CH₂OCH₂CH₃ |
| | R³ | C(O)NHCH(CH₃)₂ |
| | R⁴ | OCH₂CH₂CN |
| | R⁴' | H |
| | R⁵, R⁵' | CH₃, CH₃ |
| | R⁷ | OCH₃ |
| | R⁸ | F |
| I-301 | R¹ | CH₃ |
| | R² | 2H-1,2,3-triazol-2-yl |
| | R³ | C(O)NHCH(CH₃)₂ |
| | R⁴ | OCH₂CH₂CN |
| | R⁴' | H |
| | R⁵, R⁵' | CH₃, CH₃ |
| | R⁷ | OH |
| | R⁸ | H |
| I-302 | R¹ | CH₃ |
| | R² | C(O)OCH₂CH₃ |
| | R³ | C(O)NHCH₂CH₃ |
| | R⁴ | OCH₂CH₂CN |
| | R⁴' | H |
| | R⁵, R⁵' | CH₃, CH₃ |
| | R⁷ | OH |
| | R⁸ | F |
| I-303 | R¹ | CH₃ |
| | R² | C(O)OCH₂CH₃ |
| | R³ | C(O)NHCH(CH₃)₂ |
| | R⁴ | OCH₂C(CH₃)₂CN |
| | R⁴' | H |
| | R⁵, R⁵' | CH₃, CH₃ |
| | R⁷ | OCH₃ |
| | R⁸ | H |

TABLE 1-continued

Compounds of Formula I

| Cmpd No. | R Groups | Substituent |
|---|---|---|
| I-304 | R¹<br>R²<br>R³<br>R⁴<br>R⁴'<br>R⁵, R⁵'<br>R⁷<br>R⁸ | CH₃<br>2H-1,2,3-triazol-2-yl<br>C(O)NHCH(CH₃)₂<br>OCH₂CH₂CN<br>H<br>CH₃, CH₃<br>OC(O)CH₃<br>H |
| I-305 | R¹<br>R²<br>R³<br>R⁴<br>R⁴'<br>R⁵, R⁵'<br>R⁷<br>R⁸ | CH₃<br>C(O)OCH₂CH₃<br>C(O)NHCH₂CH₃<br>OCH₂CH₂CN<br>H<br>S—CH₃, H<br>OCH₃<br>F |
| I-306 | R¹<br>R²<br>R³<br>R⁴<br>R⁴'<br>R⁵, R⁵'<br>R⁷<br>R⁸ | CH₃<br>1-pyrazolyl<br>C(O)NHCH₂CH₃<br>OCH₂CH₂CN<br>H<br>S—CH₃, H<br>OCH₃<br>F |
| I-307 | R¹<br>R²<br>R³<br>R⁴<br>R⁴'<br>R⁵, R⁵'<br>R⁷<br>R⁸ | CH₃<br>1-pyrazolyl<br>C(O)NHC₄H₇<br>OCH₂CH₂CN<br>H<br>CH₃, CH₃<br>OCH₃<br>F |

TABLE 1-continued

Compounds of Formula I

| Cmpd No. | R Groups | Substituent |
|---|---|---|
| I-308 | R$^1$ | CH$_3$ |
| | R$^2$ | 1-pyrazolyl |
| | R$^3$ | C(O)NHC$_4$H$_7$ |
| | R$^4$ | OCH$_2$CH$_2$CN |
| | R$^{4'}$ | H |
| | R$^5$, R$^{5'}$ | R—CH$_3$, H |
| | R$^7$ | OCH$_3$ |
| | R$^8$ | F |
| I-309 | R$^1$ | CH$_3$ |
| | R$^2$ | 2H-1,2,3-triazol-2-yl |
| | R$^3$ | C(O)NHCH(CH$_3$)$_2$ |
| | R$^4$ | OC(O)CH$_2$OH |
| | R$^{4'}$ | H |
| | R$^5$, R$^{5'}$ | CH$_3$, CH$_3$ |
| | R$^7$ | OCH$_3$ |
| | R$^8$ | F |
| I-310 | R$^1$ | CH$_3$ |
| | R$^2$ | 1-pyrazolyl |
| | R$^3$ | C(O)NHCH(CH$_3$)$_2$ |
| | R$^4$ | OCH$_2$CH$_2$OCH$_3$ |
| | R$^{4'}$ | H |
| | R$^5$, R$^{5'}$ | R—CH$_3$, H |
| | R$^7$ | OCH$_3$ |
| | R$^8$ | F |
| I-311 | R$^1$ | CH$_3$ |
| | R$^2$ | 1-pyrazolyl |
| | R$^3$ | C(O)NHCH(CH$_3$)$_2$ |
| | R$^4$ | OCH$_2$CH$_2$OCH$_3$ |
| | R$^{4'}$ | H |
| | R$^5$, R$^{5'}$ | S—CH$_3$, H |
| | R$^7$ | OCH$_3$ |
| | R$^8$ | F |

TABLE 1-continued

Compounds of Formula I

| Cmpd No. | R Groups | Substituent |
|---|---|---|
| I-312 | R¹ | CH₃ |
| | R² | 1-pyrazolyl |
| | R³ | C(O)NHC₄H₇ |
| | R⁴ | OCH₂CH₂CN |
| | R⁴' | H |
| | R⁵, R⁵' | S—CH₃, H |
| | R⁷ | OCH₃ |
| | R⁸ | F |
| I-313 | R¹ | CH₃ |
| | R² | 1-pyrazolyl |
| | R³ | C(O)(1-pyrrolidinyl) |
| | R⁴ | OCH₂CH₂CN |
| | R⁴' | H |
| | R⁵, R⁵' | S—CH₃, H |
| | R⁷ | OCH₃ |
| | R⁸ | F |
| I-314 | R¹ | CH₃ |
| | R² | 1-pyrazolyl |
| | R³ | C(O)(1-pyrrolidinyl) |
| | R⁴ | OCH₂CH₂CN |
| | R⁴' | H |
| | R⁵, R⁵' | R—CH₃, H |
| | R⁷ | OCH₃ |
| | R⁸ | F |
| I-315 | R¹ | CH₃ |
| | R² | 2H-1,2,3-triazol-2-yl |
| | R³ | C(O)NHCH(CH₃)₂ |
| | R⁴ | OH |
| | R⁴' | CH₂OH |
| | R⁵, R⁵' | CH₃, CH₃ |
| | R⁷ | OCH₃ |
| | R⁸ | F |

TABLE 1-continued

Compounds of Formula I

| Cmpd No. | R Groups | Substituent |
|---|---|---|
| I-316 | $R^1$ | $CH_3$ |
| | $R^2$ | 2H-1,2,3-triazol-2-yl |
| | $R^3$ | $C(O)NHCH(CH_3)_2$ |
| | $R^4$ | OH |
| | $R^{4'}$ | H |
| | $R^5, R^{5'}$ | $CH_3, CH_3$ |
| | $R^7$ | $OCH_3$ |
| | $R^8$ | H |
| I-317 | $R^1$ | $CH_3$ |
| | $R^2$ | 1H-1,2,4-triazol-1-yl |
| | $R^3$ | $C(O)NHCH(CH_3)_2$ |
| | $R^4$ | $OCH_2CH_2CN$ |
| | $R^{4'}$ | H |
| | $R^5, R^{5'}$ | $CH_3, CH_3$ |
| | $R^7$ | $OCH_3$ |
| | $R^8$ | F |
| I-318 | $R^1$ | $CH_3$ |
| | $R^2$ | 2H-1,2,3-triazol-2-yl |
| | $R^3$ | $C(O)NHCH_2CH_3$ |
| | $R^4$ | $OC(O)CH_3$ |
| | $R^{4'}$ | H |
| | $R^5, R^{5'}$ | $CH_3, CH_3$ |
| | $R^7$ | $OCH_3$ |
| | $R^8$ | F |
| I-319 | $R^1$ | $CH_3$ |
| | $R^2$ | 2H-1,2,3-triazol-2-yl |
| | $R^3$ | $C(O)NHCH(CH_3)_2$ |
| | $R^4$ | $OCH_2CH_2CH_2OH$ |
| | $R^{4'}$ | H |
| | $R^5, R^{5'}$ | $CH_3, CH_3$ |
| | $R^7$ | $OCH_3$ |
| | $R^8$ | F |

TABLE 1-continued

Compounds of Formula I

| Cmpd No. | R Groups | Substituent | Compound Structure |
|---|---|---|---|
| I-320 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>(CO)NHCH(CH$_3$)$_2$<br>OCH$_2$CH$_2$CH$_2$OH<br>H<br>CH$_3$, CH$_3$<br>OCH$_3$<br>F | 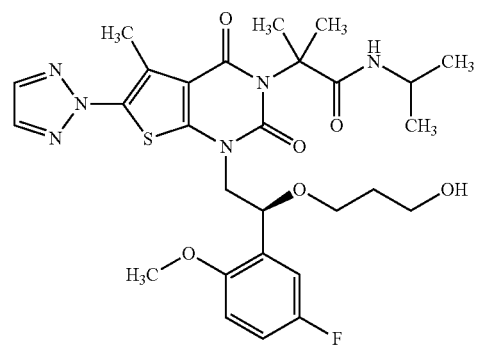 [SMILES: COc1ccc(F)cc1[C@@H](Cn1c(=O)n(C(C)(C)C(=O)NC(C)C)c(=O)c2c(C)c(-n3nccn3)sc21)OCCCO] |
| I-321 | $R^1$<br>$R^2$<br>$R^3$<br>$R^4$<br>$R^{4'}$<br>$R^5, R^{5'}$<br>$R^7$<br>$R^8$ | $CH_3$<br>C(O)OCH$_2$CH$_3$<br>C(O)NHCH(CH$_3$)$_2$<br>OCH$_2$C(CH$_3$)$_2$CN<br>H<br>CH$_3$, CH$_3$<br>OCH$_3$<br>F | 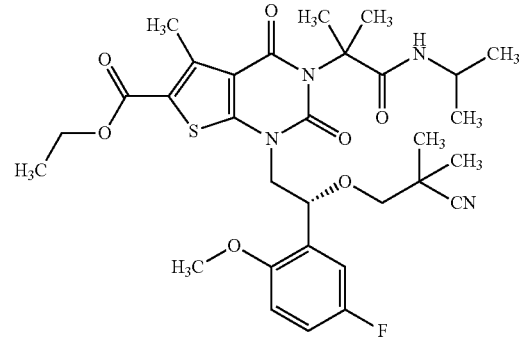 [SMILES: CCOC(=O)c1sc2c(c1C)c(=O)n(C(C)(C)C(=O)NC(C)C)c(=O)n2C[C@H](OCC(C)(C)C#N)c1cc(F)ccc1OC] |
| I-322 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH(CH$_3$)$_2$<br>OC(O)CH$_3$<br>H<br>CH$_3$, CH$_3$<br>OCH$_3$<br>F | 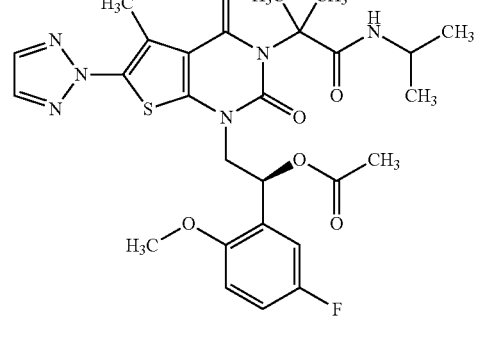 |
| I-323 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>C(O)NHCH(CH$_3$)$_2$<br>OC(O)CH$_3$<br>H<br>CH$_3$, CH$_3$<br>OCH$_3$<br>F | 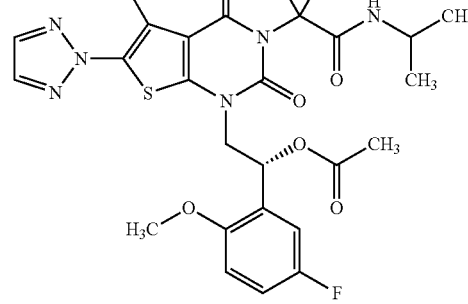 |

TABLE 1-continued

Compounds of Formula I

| Cmpd No. | R Groups | Substituent |
|---|---|---|
| I-324 | R¹ | CH$_3$ |
| | R² | 2H-1,2,3-triazol-2-yl |
| | R³ | C(O)NHCH$_2$CH$_3$ |
| | R⁴ | OC(O)CH$_3$ |
| | R⁴' | H |
| | R⁵, R⁵' | CH$_3$, CH$_3$ |
| | R⁷ | OCH$_3$ |
| | R⁸ | F |
| I-325 | R¹ | CH$_3$ |
| | R² | CH$_2$OH |
| | R³ | C(O)NHCH(CH$_3$)$_2$ |
| | R⁴ | OCH$_2$CH$_2$CN |
| | R⁴' | H |
| | R⁵, R⁵' | CH$_3$, CH$_3$ |
| | R⁷ | OCH$_3$ |
| | R⁸ | F |
| I-326 | R¹ | CH$_3$ |
| | R² | 2H-1,2,3-triazol-2-yl |
| | R³ | C(O)NHCH(CH$_3$)$_2$ |
| | R⁴ | H |
| | R⁴' | H |
| | R⁵, R⁵' | CH$_3$, CH$_3$ |
| | R⁷ | CH$_2$CH$_3$ |
| | R⁸ | F |
| I-328 | R¹ | CH$_3$ |
| | R² | 2H-1,2,3-triazol-2-yl |
| | R³ | C(O)NHCH(CH$_3$)$_2$ |
| | R⁴ | H |
| | R⁴' | H |
| | R⁵, R⁵' | CH$_3$, CH$_3$ |
| | R⁷ | CH$_2$CH$_2$CH$_2$CN |
| | R⁸ | F |

TABLE 1-continued

Compounds of Formula I

| Cmpd No. | R Groups | Substituent |
|---|---|---|
| I-329 | R¹ | CH₃ |
| | R² | 1-pyrazolyl |
| | R³ | C(O)NHCH(CH₃)₂ |
| | R⁴ | H |
| | R⁴' | H |
| | R⁵, R⁵' | CH₃, CH₃ |
| | R⁷ | OCH₃ |
| | R⁸ | F |
| I-330 | R¹ | CH₃ |
| | R² | C(O)OCH₂CH₃ |
| | R³ | C(O)NHCH(CH₃)₂ |
| | R⁴ | OCH₂CH₂CN |
| | R⁴' | H |
| | R⁵, R⁵' | R—CH₃, H |
| | R⁷ | OCH₃ |
| | R⁸ | F |
| I-331 | R¹ | CH₃ |
| | R² | 2H-1,2,3-triazol-2-yl |
| | R³ | C(O)NHCH(CH₃)₂ |
| | R⁴ | H |
| | R⁴' | H |
| | R⁵, R⁵' | CH₃, CH₃ |
| | R⁷ | O-tetrahydro-2H-pyran-4-yl |
| | R⁸ | F |
| I-332 | R¹ | CH₃ |
| | R² | 2H-1,2,3-triazol-2-yl |
| | R³ | C(O)NHCH(CH₃)₂ |
| | R⁴ | H |
| | R⁴' | H |
| | R⁵, R⁵' | CH₃, CH₃ |
| | R⁷ | O-benzyl |
| | R⁸ | F |

TABLE 1-continued

Compounds of Formula I

| Cmpd No. | R Groups | Substituent |
|---|---|---|
| I-333 | R¹ | CH₃ |
| | R² | 1-pyrazolyl |
| | R³ | C(O)NHCH(CH₃)₂ |
| | R⁴ | OCH₂CH₂CN |
| | R⁴' | H |
| | R⁵, R⁵' | R—CH₃, H |
| | R⁷ | OCH₃ |
| | R⁸ | H |
| I-334 | R¹ | CH₃ |
| | R² | 2H-1,2,3-triazol-2-yl |
| | R³ | C(O)NHCH(CH₃)₂ |
| | R⁴ | H |
| | R⁴' | H |
| | R⁵, R⁵' | CH₃, CH₃ |
| | R⁷ | OC(O)CH₃ |
| | R⁸ | F |
| I-335 | R¹ | CH₃ |
| | R² | 2H-1,2,3-triazol-2-yl |
| | R³ | C(O)NHCH(CH₃)₂ |
| | R⁴ | H |
| | R⁴' | H |
| | R⁵, R⁵' | CH₃, CH₃ |
| | R⁷ | C(O)OCH₂CH₃ |
| | R⁸ | F |
| I-336 | R¹ | CH₃ |
| | R² | 1-pyrazolyl |
| | R³ | C(O)NHCH(CH₃)₂ |
| | R⁴ | H |
| | R⁴' | H |
| | R⁵, R⁵' | CH₃, CH₃ |
| | R⁷ | OCH₂CH₂CN |
| | R⁸ | F |

TABLE 1-continued

Compounds of Formula I

| Cmpd No. | R Groups | Substituent | Compound Structure |
|---|---|---|---|
| I-337 | $R^1$<br>$R^2$<br>$R^3$<br>$R^4$<br>$R^{4'}$<br>$R^5, R^{5'}$<br>$R^7$<br>$R^8$ | $CH_3$<br>1-pyrazolyl<br>$C(O)NHCH(CH_3)_2$<br>H<br>H<br>$CH_3, CH_3$<br>$OCH_2CH_2OH$<br>F | 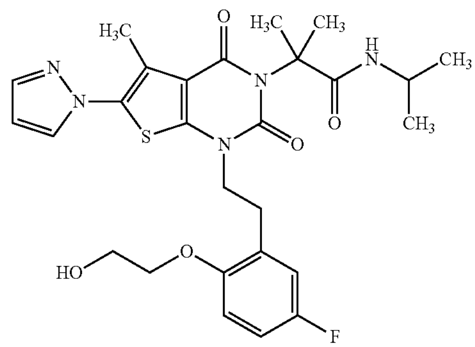 [SMILES: Cc1c(-n2cccn2)sc2c1c(=O)n(C(C)(C)C(=O)NC(C)C)c(=O)n2CCc1cc(F)ccc1OCCC#N] |
| I-338 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>H<br>H<br>$CH_3, CH_3$<br>$O\,CH(CH_3)_2$<br>F | 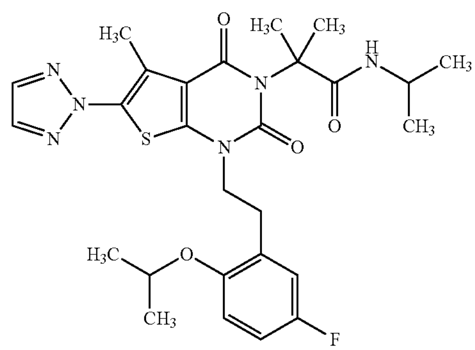 [SMILES: Cc1c(-n2nccn2)sc2c1c(=O)n(C(C)(C)C(=O)NC(C)C)c(=O)n2CCc1cc(F)ccc1OC(C)C] |
| I-339 | $R^1$<br>$R^2$<br>$R^3$<br>$R^4$<br>$R^{4'}$<br>$R^5, R^{5'}$<br>$R^7$<br>$R^8$ | $CH_3$<br>$C(O)OCH_2CH_3$<br>$C(O)NHCH(CH_3)_2$<br>H<br>H<br>$CH_3, CH_3$<br>$OCH_2CH_2CN$<br>F | 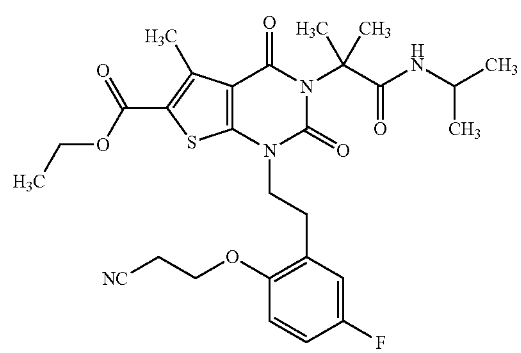 [SMILES: CCOC(=O)c1sc2c(c1C)c(=O)n(C(C)(C)C(=O)NC(C)C)c(=O)n2CCc1cc(F)ccc1OCCC#N] |
| I-340 | $R^1$<br>$R^2$<br>$R^3$<br>$R^4$<br>$R^{4'}$<br>$R^5, R^{5'}$<br>$R^7$<br>$R^8$ | $CH_3$<br>2H-1,2,3-triazol-2-yl<br>$C(O)NHCH(CH_3)_2$<br>H<br>H<br>$CH_3, CH_3$<br>$OCH_2CH_2CN$<br>F | 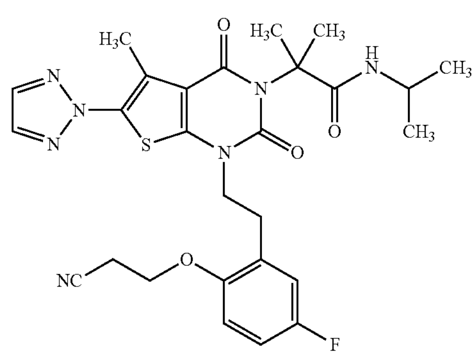 [SMILES: Cc1c(-n2nccn2)sc2c1c(=O)n(C(C)(C)C(=O)NC(C)C)c(=O)n2CCc1cc(F)ccc1OCCC#N] |

TABLE 1-continued

Compounds of Formula I

| Cmpd No. | R Groups | Substituent | Compound Structure |
|---|---|---|---|
| I-341 | $R^1$ | $CH_3$ | 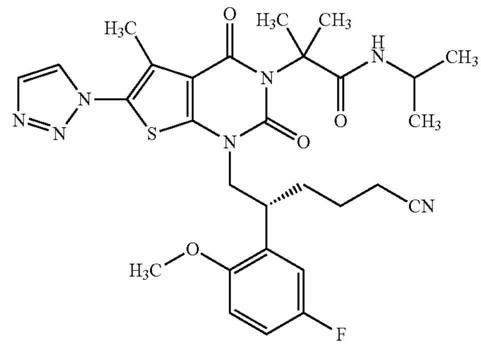 [SMILES: COc1ccc(F)cc1[C@@H](CCCC#N)Cn1c(=O)n(C(C)(C)C(=O)NC(C)C)c(=O)c2c(C)c(-n3ccnn3)sc21] |
| | $R^2$ | 1H-1,2,3-triazol-1-yl | |
| | $R^3$ | $C(O)NHCH(CH_3)_2$ | |
| | $R^4$ | $OCH_2CH_2CN$ | |
| | $R^{4'}$ | H | |
| | $R^5, R^{5'}$ | $CH_3, CH_3$ | |
| | $R^7$ | $OCH_3$ | |
| | $R^8$ | F | |

The compound of Formula I can be (R)-ethyl-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-2,4-dioxo-1,2,3,4-tetrahydrothieno[2,3-d]pyrimidine-6-carboxylate (Formula I-003), (R)-2-(1-(2-(5-fluoro-2-methoxyphenyl)-2-isopropoxyethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide (Formula I-014), (R)-2-(1-(2-(5-fluoro-2-methoxyphenyl)-2-isopropoxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-020), (R)-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-030), (R)-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-6-(2H-1,2,3-triazol-2-yl)thieno[2,3-d]pyrimidine-2,4(1H,3H)-dione (Formula I-034), (R)—N-ethyl-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3(2H)-yl)-2-methylpropanamide (Formula I-035), (R)-2-(1-(2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-064), (R)-2-(1-(2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-074), 2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-082), (R)-2-(1-(2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-084), (S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-089), (R)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-090), (R)—N-cyclobutyl-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)propanamide (Formula I-092), (R)-2-(1-((R)-2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-094), (R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-095), (S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-096), (R)-2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-171).

(R)-ethyl-1-(2-(2-cyanoethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-181), (R)-ethyl-1-(2-(5-fluoro-2-methoxyphenyl)-2-(2-hydroxyethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-184), (R)-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-185), (R)-ethyl-1-(2-(5-fluoro-2-methoxyphenyl)-2-hydroxyethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-186), (R)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-188), (S)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-189), (R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide (Formula I-191), (R)-2-(1-(2-(2-cyanoethoxy)-2-(2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide (Formula I-192), (R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-193), (R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-198), 3-((R)-1-(5-fluoro-2-methoxyphenyl)-2-(5-methyl-2,4-dioxo-3-((R)-1-oxo-1-(pyrrolidin-1-yl)propan-2-yl)-6-(2H-1,2,3-triazol-2-yl)-3,4-dihydrothieno[2,3-d]pyrimidin-1 (2H)-yl)ethoxy)propanenitrile (Formula I-202), (R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-205), (R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide (Formula I-206), (R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide (Formula I-208), (R)-2-(1-(2-(cyanomethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-210), 2-(1-((R)-2-((S)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-211), 2-(1-((R)-2-((R)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-212), (R)-2-(1-(2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-213), (R)-ethyl-1-(2-(2-cyanoethoxy)-2-(5-fluoro-2-methoxyphenyl)ethyl)-3-((R)-1-(isopropylamino)-1-oxopropan-2-yl)-5-methyl-2,4-dioxo-1,2,3,4-tetrahydrothieno[2,3-d]pyrimidine-6-carboxylate (Formula I-220), (R)-ethyl-1-(2-(2-cyanoethoxy)-2-(5-fluoro-2-methoxyphenyl)ethyl)-3-((R)-1-(isopropyl(methyl)amino)-1-oxopropan-2-yl)-5-methyl-2,4-dioxo-1,2,3,4-tetrahydrothieno[2,3-d]pyrimidine-6-carboxylate (Formula I-229), (R)-ethyl-1-(2-(2-cyanoethoxy)-2-(5-fluoro-2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate (Formula I-231), (R)-ethyl-1-(2-(2-cyanoethoxy)-2-(2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-233), (R)-ethyl-1-(2-(2-cyanoethoxy)-2-(2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate (Formula I-234), (S)-2-(1-((R)-2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide (Formula I-239), (R)-2-(1-(2-(2-ethyl-5-fluorophenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-246), (R)-ethyl-1-(2-(cyanomethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-251), (R)-2-(1-((R)-2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide (Formula I-253), (R)-ethyl-1-(2-((S)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-258), (R)-ethyl-1-(2-((R)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-259), 2-(1-((R)-2-((S)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide (Formula I-262), 2-(1-((R)-2-((R)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide (Formula I-263), (S)-2-(1-(2-(2-cyanoethoxy)-2-(5-fluoro-2-methoxyphenyl)propyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-274), 2-(1-((R)-2-((S)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-281), 2-(1-((R)-2-((R)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-284), (R)-ethyl-1-(2-(5-fluoro-2-methoxyphenyl)-2-(2-(methylsulfonyl)ethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate (Formula I-285), (R)-2-(1-(2-(5-fluoro-2-methoxyphenyl)-2-(2-(methylsulfonyl)ethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-287), (R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethylpropanamide (Formula I-289), (R)—N-ethyl-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-2-methylpropanamide (Formula I-292), (R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutyl-2-methylpropanamide (Formula I-307), (R)-2-(1-((R)-2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutylpropanamide (Formula I-308), (R)-2-(1-((R)-2-(5-fluoro-2-methoxyphenyl)-2-(2-methoxyethoxy)ethyl)-5-methyl-2,4-dioxo-6-(1H-pyrazol-1-yl)-1,4-dihydrothieno[2,3-d]pyrimidin-3 (2H)-yl)-N-isopropylpropanamide (Formula I-310), (R)-2-(1-(2-hydroxy-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide (Formula I-316), or (R)-1-(5-fluoro-2-methoxyphenyl)-2-(3-(1-(isopropylamino)-2-methyl-1-oxopropan-2-yl)-5-methyl-2,4-dioxo-6-(2H-1,2,3-triazol-2-yl)-3,4-dihydrothieno[2,3-d]pyrimidin-1(2H)-yl)ethyl acetate (Formula I-323).

Enantiomers and Diastereoisomers

The compounds described herein can be present as a racemic mixture, as a mixture of two enantiomers at different ratios, or as a single enantiomer. In other stance, the compounds described herein can be present as a diastereoisomeric mixture, as a mixture of two or three isomers at different ratios (e.g., S,S-, S,R-, R,R-) or as a single isomer (e.g., R,R-). Compositions that are enriched with respect to one enantiomer or one diastereoisomer, or which comprise substantially a single enantiomer or a single diastereoisomer, may be prepared using any technique known in the art, including chiral separation techniques known in the art (e.g., chiral chromatography or asymmetric synthesis).

Compositions

In another aspect, the present disclosure is generally related to a composition comprising an effective amount of a compound (e.g., a compound of Formula I) as described herein having pesticidal activity, in particular fungicidal activity, for use in administration to a plant, a seed, or soil to control fungal pathogens.

For example, the composition may be an aqueous composition.

Generally, compositions described herein can comprise any adjuvants, excipients, or other desirable components known in the art.

Non-limiting examples of additional ingredients include surfactants, co-surfactants, permeation enhancers, and co-solvents. For example, the composition may comprise as SPAN surfactants, TWEEN surfactants, TRITON surfactants, MAKON surfactants, IGEPAL surfactants, BRIJ surfactants, MORWET surfactants, PLURONIC surfactants, LANEXOL surfactants, ATLOX surfactants, ATLAS surfactants, SURFYNOL surfactants, TERGITOL surfactants, DOWFAX surfactants, TOXIMUL surfactants, SILWET surfactants, SYLGARD surfactants, BREAK THRU surfactants, PHYTOSAN, SOLUPLUS, cyclodextrans, polypropylene glycol, ethyl lactate, methyl soyate/ethyl lactate co-solvent blends (e.g., STEPOSOL), isopropanol, acetone, ethylene glycol, propylene glycol, n-alkylpyrrolidones (e.g., the AGSOLEX series), a petroleum based-oil (e.g., AROMATIC 200) or a mineral oil (e.g., paraffin oil)).

The composition may comprise a surfactant. Non-limiting examples of surfactants include SPAN 20, SPAN 40, SPAN 80, SPAN 85, TWEEN 20, TWEEN 40, TWEEN 80, TWEEN 85, TRITON X 100, MAKON 10, IGEPAL CO 630, BRIJ 35, BRIJ 97, TERGITOL TMN 6, DOWFAX 3B2, PHYSAN and TOXIMUL TA 15.

The composition may comprise a co-solvent. Examples of co-solvents that can be used include ethyl lactate, methyl soyate/ethyl lactate co-solvent blends (e.g., STEPOSOL), isopropanol, acetone, 1,2-propanediol, n-alkylpyrrolidones (e.g., the AGSOLEX series), a petroleum based-oil (e.g., AROMATIC 200) or a mineral oil (e.g., paraffin oil)).

The composition may be formulated, mixed in a tank, combined on a seed by overcoating, or recommended for use with one or more additional active ingredients on a seed, plant, or soil. The additional active ingredients may be, for example, one or more additional pesticides. The composition may comprise one or more additional pesticides. The pesticide may be, for example, an insecticide, a fungicide, an herbicide, or an additional nematicide.

Non-limiting examples of insecticides and nematicides include avermectins, carbamates, benzoylureas, butenolides, diacylhydrazines, diamides, macrocyclic lactones, mitochondrial complex I electron transport inhibitors, neonicotinoids, organophosphates, oxazoles, oxadiazoles, phenylpyrazoles, pyridine azomethine derivatives, pyrethrins, spinosyns, sulfoximines, synthetic pyrethroids, tetronic and tetramic acids. For example, insecticides and nematicides include abamectin, aldicarb, aldoxycarb, bifenthrin, broflanilide, carbofuran, chlorantraniliprole, clothianidin, cyantraniliprole, cyclaniliprole, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodiclofen, spirotetramat, tefluthrin, thiacloprid, tetraniliprole, thiamethoxam, tioxazafen, and thiodicarb.

The composition may comprise an insecticide and/or acaricide that inhibits ACCase activity. Non-limiting examples include tetramic acids such as spirotetramat, and tetronic acids including spiromesifen and spirodiclofen.

The composition may comprise one or more nematicidal compounds as described in U.S. Pub. Nos. 2009/0048311 A1 or 2011/028320 A1, or WO 2012/030887 A1, the contents of which are herein incorporated by reference.

For example, the composition may comprise 3-phenyl-5-(thiophen-2-yl)-1,2,4-oxadiazole.

Non-limiting examples of herbicides include ACCase inhibitors, acetanilides, ALS or AHAS modulators or inhibitors, auxin transport inhibitors, carotenoid biosynthesis inhibitors, cell division inhibitors, cellulose inhibitors, EPSPS modulators or inhibitors, fatty acid and lipid biosynthesis inhibitors, glutamine synthetase modulators or inhibitors, 4-hydroxyphenylpyruvate dioxygenase inhibitors (HPPD inhibitors, mitosis inhibitors, protoporphyrinogen oxidase (PPO) modulators or inhibitors, oxidative phosphorylation uncouplers, photosystem I (PS I) and photosystem II (PS II) modulators or inhibitors, and synthetic auxins. Non-limiting examples of herbicides include acetochlor, clethodim, dicamba, 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione (trifludimoxazin), ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate, flumioxazin, fomesafen, glyphosate, glufosinate, halauxifen, isoxaflutole, mesotrione, metolachlor, quizalofop, saflufenacil, sulcotrione, tembotrione, topramezone, and 2,4-D.

The composition may comprise an herbicide that inhibits ACCase activity. Non-limiting examples include herbicidal aryloxyphenoxypropionates such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, and trifop, herbicidal cyclohexanediones such as alloxydim, butroxydim, clethodim, cloproxydim, cycloxydim, profoxydim, sethoxydim, tepraloxydim, and tralkoxydim, as well as the herbicide pinoxaden.

The herbicides cycloxydim and sethoxydim are known to exhibit moderate antifungal activity alone, and, without being bound to a particular theory, it is believed that the combination of these species with the compounds described herein may enhance fungal control by the additional suppression of ACCase.

The composition may comprise one or more additional fungicides. Non-limiting examples of additional fungicides include aromatic hydrocarbons, anilino-pyrimidines, benzamides, benzimidazoles, benzothiadiazole, carbamates, carboxamides, carboxylic acid amides, cinnamic acid amides, cyanoacetmide oximes, demethylation inhibitors, dicarboxamides, 2,6-dinitroanilines, dinitrophenyl crotonates, dithiocarbamates, mandelic acid amides, morpholines, phenylacetamides, phenylamides, phenyl benzamides, phenylpyrroles, phosphonates, phosphorothiolates, phthalimides, pyrazole carboxamides, pyridine carboxamides, pyridine ethyl benzamides, oxathiin carboxamides, quinine outside inhibitors (e.g. strobilurins), quinone inside inhibitors, thiadiazole carboxamides, thiazolidines, thiocarbamates, thiophanates, thiophene carboxamides, triazoles, and triazolinthiones. Particular examples of fungicides include acibenzolar-S-methyl, ametoctradin, amisulbrom, azaconazole, azoxystrobin, benalaxyl, bixafen, boscalid, captan, carbendazim, carboxin, coumoxystrobin, cyazofamid, cyflufenamid, cymoxanil, cyproconazole, cyprodinil, difenconazole, dimethomorph, dimoxystrobin, dinocap, enoxastrobin, epoxiconazole, ethaboxam, famoxadone, fenamidone, fenaminstrobin, fenpropimorph, fluazinam, fludioxonil, flufenoxystrobin, fluopicolide, fluopyram, fluoxastrobin, fluopyram, fluoxastrobin, fluquinconazole, flutianil, flutolanil, flutriazole, fluxapyroxad, fosetyl-A1, furametpyr, hexaconazole, ipconazole, iprodione, iprovalicarb, isopyrazam, isotianil, kresoxim-methyl, mancozeb, mandestrobin, mandipropamid, mefenoxam, metalaxyl, metconazole, methasulfocarb, metominostrobin, myclobutanil, orysastrobin, oxycarboxin, penflufen, penthiopyrad, picoxystrobin, probenzole, propiconazole, prothiocarb, prothioconazole, pyraclostrobin, pyrametostrobin, pyraoxystrobin, pyrazophos, pyribencarb, pyrimethanil, sedaxane, silthiofam, simeconazole, tebuconazole, thiabendazole, thifluzamide, thiophanate, thiophanate-methyl, thiram, tolfenpyrad, tolclofos-methyl, triclopyricarb, tridemorph, trifloxystrobin, and triticonazole.

The composition may comprise one or more additional fungicides that modulate or inhibit ACCase activity.

The composition may also comprise one or more additional active substances, including biological control agents, microbial extracts, natural products, plant growth activators and/or plant defense agents. Non-limiting examples of biological control agents include Bacteria, fungi, beneficial nematodes, and viruses.

For example, the biological control agent can be a bacterium of the genus *Actinomycetes, Agrobacterium, Arthrobacter, Alcaligenes, Aureobacterium, Azobacter, Bacillus, Beijerinckia, Bradyrhizobium, Brevibacillus, Burkholderia, Chromobacterium, Clostridium, Clavibacter, Comamonas, Corynebacterium, Curtobacterium, Enterobacter, Flavobacterium, Gluconobacter, Hydrogenophage, Klebsiella, Metarhizium, Methylobacterium, Paenibacillus, Pasteuria, Photorhabdus, Phyllobacterium, Pseudomonas, Rhizobium, Serratia, Sphingobacterium, Stenotrophomonas, Streptomyces, Variovax,* and *Xenorhabdus.* For example, the *Bacteria* may be *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Bradyrhizobium japonicum, Chromobacterium subtsugae, Metarhizium anisopliae, Pasteuria nishizawae, Pasteuria penetrans, Pasteuria usage, Pseudomonas fluorescens,* and *Streptomyces lydicus.*

The biological control agent can be a fungus of the genus *Alternaria, Ampelomyces, Aspergillus, Aureobasidium, Beauveria, Colletotrichum, Coniothyrium, Gliocladium, Metarhizium, Muscodor, Paecilomyces, Penicillium, Trichoderma, Typhula, Ulocladium,* and *Verticillium.* For example, the fungus may be *Beauveria bassiana, Coniothyrium minitans, Gliocladium virens, Muscodor albus, Paecilomyces lilacinus, Trichoderma polysporum,* or *Trichoderma virens.*

The biological control agents can be plant growth activators or plant defense agents including, but not limited to harpin, *Reynoutria sachalinensis,* jasmonate, lipochitooligosaccharides, salicylic acid and/or isoflavones.

Methods of Use

The compounds described herein (e.g., compounds as described herein of Formula I) can be used in accordance with methods of controlling fungal pathogens. For example, compounds as described herein of Formula I are believed to exhibit control of phytopathogenic *fungi* as described herein.

The compounds disclosed herein can be administered to a plant, a seed, or soil in a composition as described herein to control fungal pathogens, including using the compounds as described herein with any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

Compounds and compositions described herein can be administered to seeds, plants, or the environment of plants (e.g., soil) wherein the control of phytopathogenic *fungi* is desired. For example, provided herein is a method of controlling fungal pathogens, the method comprising administering to a plant, a seed or soil a composition comprising an effective amount of a compound as described herein.

Non-limiting examples of plants that may be protected from fungal pathogens in accordance with the methods described herein include monocotyledonous crops such as corn, wheat, barley, rye, rice, *sorghum,* oat; sugarcane and turf; and dicotyledonous crops such as cotton, sugar beet, peanut, potato, sweet potato, yam, sunflower, soybean, alfalfa, canola, grapes, tobacco; vegetables including Solanaceae vegetables such as eggplant, tomato, green pepper and pepper; Cucurbitaceae vegetables such as cucumber, pumpkin, zucchini, watermelon, melon and squash; Brassicaceae vegetables such as radish, turnip, horseradish, Chinese cabbage, cabbage, leaf mustard, broccoli and cauliflower; Asteraceae vegetables such as artichoke and lettuce; Liliaceae vegetables such as leek, onion, garlic and asparagus; Apiaceae vegetables such as carrot, parsley, celery and parsnip; Chenopodiaceae vegetables such as spinach and chard; Lamiaceae vegetables such as mint and basil; flowers such as *petunia,* morning glory, carnation, *chrysanthemum* and rose; foliage plants; fruit trees such as pome fruits (e.g., apple, pear and Japanese pear), stone fruits (e.g., peach, plum, nectarine, cherry, apricot and prune), *Citrus* (e.g., orange, lemon, lime and grapefruit), tree nuts (e.g., chestnut, pecan, walnut, hazel, almond, pistachio, cashew and *Macadamia*), berries such as blueberry, cranberry, blackberry, strawberry and raspberry; persimmon; olive; *loquat*; banana;

coffee; palm; coco; the other trees such tea, mulberry, flower trees, and landscape trees (e.g., ash, birch, dogwood, *eucalyptus, Ginkgo*, lilac, maple, oak, poplar, *Formosa* sweetgum, sycamore, fir, hemlock fir, needle juniper, pine, spruce, yew).

Non-limiting examples of the plant diseases that may be controlled by the methods described herein include diseases caused by phytopathogenic *fungi* (in particular of the classes of Ascomycetes, Deuteromycetes, Oomycetes and Basidiomycetes) such as *Magnaporthe grisea, Cochliobolus miyabeanus, Rhizoctonia solani* and *Gibberella fujikuroi* on rice; *Erysiphe graminis, Fusarium graminearum, F. avenacerum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Pyrenophora teres* on wheat and barley; *Diaporthe citri, Elsinoe fawcetti, Penicillium digitatum, P. italicum, Phytophthora parasitica* and *Phytophthora citrophthora* on citrus; *Monilinia mali, Valsa ceratosperma, Podosphaera leucotricha, Alternaria alternata* apple pathotype, *Venturia inaequalis, Colletotrichum acutatum* and *Phytophtora cactorum* on apple; *Venturia nashicola, V. pirina, Alternaria alternata* Japanese pear pathotype, *Gymnosporangium haraeanum* and *Phytophthora cactorum* on pear; *Monilinia fructicola, Cladosporium carpophilum* and *Phomopsis* sp. on peach; *Elsinoe ampelina, Glomerella cingulata, Uncinula necator, Phakopsora ampelopsidis, Guignardia bidwellii* and *Plasmopara viticola* on grape; *Gloeosporium kaki, Cercospora kaki* and *Mycosphaerella nawae* on persimmon, *Colletotrichum lagenarium, Sphaerotheca fuliginea, Mycosphaerella melonis, Fusarium oxysporum, Pseudoperonospora cubensis* and *Phytophthora* sp. on Cucurbitales vegetables, *Alternaria solani, Cladosporium fulvum* and *Phytophthora infestans* on tomato; *Phomopsis vexans* and *Erysiphe cichoracearum* on eggplant; *Alternaria japonica, Cercosporella brassicae, Plasmodiophora brassicae* and *Peronospora parasitica* on Brassicaceae vegetables; *Puccinia allii* and *Peronospora destructor* on leek; *Cercospora kikuchii, Elsinoe glycines, Diaporthe phaseolorum* var. *sojae, Phakopsora pachyrhizi* and *Phytophthora sojae* on soybean; *Colletotrichum lindemuthianum* of kidney bean; *Cercospora personata, Cercospora arachidicola* and *Sclerotium rolfsii* on peanut; *Erysiphe pisi* on pea; *Alternaria solani, Phytophthora infestans, Phytophthora erythroseptica* and *Spongospora subterranean* f. sp. *subterranean* on potato; *Sphaerotheca humuli* and *Glomerella cingulata* on strawberry; *Exobasidium reticulatum, Elsinoe leucospila, Pestalotiopsis* sp. and *Colletotrichum theae-sinensis* on tea; *Alternaria longipes, Erysiphe cichoracearum, Colletotrichum tabacum, Peronospora tabacina* and *Phytophthora nicotianae* on tobacco; *Cercospora beticola, Thanatephorus cucumeris*, and *Aphanidermatum cochlioides* on sugar beet; *Diplocarpon rosae, Sphaerotheca pannosa* and *Peronospora sparsa* on rose; *Bremia lactucae, Septoria chrysanthemi-indici* and *Puccinia horiana* on chrysanthemum and Compositae vegetables; *Alternaria brassicicola* on radish; *Sclerotinia homeocarpa* and *Rhizoctonia solani* on turf; *Mycosphaerella fijiensis* and *Mycosphaerella musicola* on banana; *Plasmopara halstedii* on sunflower; and various diseases on crops caused by *Aspergillus* spp., *Alternaria* spp., *Cephalosporium* spp., *Cercospora* spp., *Cochliobolus* spp., *Diaporthe* spp., *Phomopsis* spp., *Diplodia* spp., *Fusarium* spp., *Gibberella* spp., *Helminthosporium* spp., *Phakopsora* spp., *Phytophthora* spp., *Blumeria* spp., *Oidium* spp., *Erysiphe* spp., *Uncinula* spp., *Podosphaera* spp., *Microsphaera* spp., *Colletotrichum* spp., *Corynespora* spp., *Peronospora* spp., *Plasmopara* spp., *Pythium* spp., *Pyrenophora* spp., *Pythium* spp., *Rhizoctonia* spp., *Rhynchosporium* spp., *Botryotinia* spp., *Botrytis* spp., *Botryosphaeria* spp., *Sphaerotheca* spp., *Septoria* spp., *Thielaviopsis* spp., *Typhula* spp., *Pseudocercosporella* spp., *Cochliobolus* spp., *Gaeumannomyces* spp., *Mucor* spp., *Puccinia* spp., *Tilletia* spp., *Ustilago* spp., *Venturia* spp., *Gymnosporangium* spp., *Claviceps* spp., *Cladosporium* spp., *Physalospora* spp., *Pyricularia* spp., *Magnaporthe* spp., *Rhizopus* spp., *Monilinia* spp., *Cladosporium* spp., *Curvularia* spp., *Sclerotinia* spp., *Sclerotium* sp., *Corticum* spp., *Corticium* spp., *Phoma* spp., *Polymyxa* spp., and *Olpidium* spp.

Application to Plants and/or Soil

Generally, the methods described herein can be used to modulate, inhibit or eradicate fungal pathogens as described herein that cause disease on various parts of agricultural crop plants (e.g., fruit, blossoms, leaves, stems, tubers, roots) or other useful plants as described herein. For example, the methods described herein may be used to modulate, inhibit, and/or control any of the fungal pathogens and/or plant diseases listed above.

For example, methods described herein may be used to modulate, inhibit or eradicate plant fungal pathogens in vegetable crops, row crops, trees, nuts, vines, turf, and ornamental plants.

A composition comprising a compound as described herein may be supplied to a plant exogenously. The composition may be applied to the plant and/or the surrounding soil through sprays, drips, and/or other forms of liquid application.

The compounds described herein may penetrate the plant through the roots via the soil (systemic action); by drenching the locus of the plant with a liquid composition; or by applying the compounds in solid form to the soil, e.g. in granular form (soil application).

As used herein, the term "locus" broadly encompasses the fields on which the treated plants are growing, or where the seeds of cultivated plants are sown, or the place where the seed will be placed into the soil.

A composition as described herein may be applied to a plant, including plant leaves, shoots, roots, or seeds. For example, composition comprising a compound as described herein can be applied to a foliar surface of a plant. Foliar applications may require 50 to 500 g per hectare of a compound as described herein.

As used herein, the term "foliar surface" broadly refers to any green portion of a plant having surface that may permit absorption of silicon, including petioles, stipules, stems, bracts, flowerbuds, and leaves. Absorption commonly occurs at the site of application on a foliar surface, but in some cases, the applied composition may run down to other areas and be absorbed there.

Compositions described herein can be applied to the foliar surfaces of the plant using any conventional system for applying liquids to a foliar surface. For example, application by spraying will be found most convenient. Any conventional atomization method can be used to generate spray droplets, including hydraulic nozzles and rotating disk atomizers. In other instances, alternative application techniques, including application by brush or by rope-wick, may be utilized.

A composition comprising a compound as described herein can be directly applied to the soil surrounding the root zone of a plant. Soil applications may require 0.5 to 5 kg per hectare of a compound as described herein on a broadcast basis (rate per treated area if broadcast or banded).

For example, a composition may be applied directly to the base of the plants or to the soil immediately adjacent to the plants.

In some embodiments, a sufficient quantity of the composition is applied such that it drains through the soil to the root area of the plants.

Generally, application of a composition may be performed using any method or apparatus known in the art, including but not limited to hand sprayer, mechanical sprinkler, or irrigation, including drip irrigation.

A composition as provided herein can be applied to plants and/or soil using a drip irrigation technique. For example, the composition may be applied through existing drip irrigation systems. For example, this procedure can be used in connection with cotton, strawberries, tomatoes, potatoes, vegetables, and ornamental plants.

In other embodiments, a composition can be applied to plants and/or soil using a drench application. For example, the drench application technique may be used in connection with crop plants and turf grasses.

A composition as provided herein may be applied to soil after planting. Alternatively, a composition as provided herein may be applied to soil during planting, or may be applied to soil before planting.

For example, a composition as provided herein may be tilled into the soil or applied in furrow.

In crops of water, such as rice, solid granulates comprising the compounds described herein may be applied to the flooded field or locus of the crop plants to be treated.

Application to Seeds

Provided herein is a method of protecting a seed, and/or the roots of a plant grown from the seed, against damage by phytopathogenic *fungi*. The seed treatment methods described herein may be used to modulate, inhibit, and/or control any of the fungal pathogens and/or plant diseases described above. For example, the method may comprise treating a seed with a composition comprising a compound as described herein. As used herein, the term "seed" broadly encompasses plant propagating material such as, tubers cuttings, seedlings, seeds, and germinated or soaked seeds.

Provided herein is a method of administering to a seed a compound (e.g., a compound of Formula I) as described to control fungal pathogens in a composition as described herein, including using the compounds as described herein with the any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

For example, a compound as described herein may be applied to seeds or tubers by impregnating them with a liquid seed treatment composition comprising a compound described herein, or by coating them with a solid or liquid composition comprising a compound described herein.

Seed treatment methods described herein can be used in connection with any species of plant and/or the seeds thereof as described herein. Typically, the methods are used in connection with seeds of plant species that are agronomically important. In particular, the seeds can be of corn, peanut, canola/rapeseed, soybean, cucurbits, crucifers, cotton, beets, rice, *Sorghum*, sugar beet, wheat, barley, rye, sunflower, tomato, sugarcane, tobacco, oats, as well as other vegetable and leaf crops. For example, the seed can be corn, soybean, or cotton seed. The seed may be a transgenic seed from which a transgenic plant can grow and incorporate a transgenic event that confers, for example, tolerance to a particular herbicide or combination of herbicides, insect resistance, increased disease resistance, enhanced tolerance to stress and/or enhanced yield. Transgenic seeds include, but are not limited to, seeds of corn, soybean and cotton.

A seed treatment method may comprise applying the seed treatment composition to the seed prior to sowing the seed, so that the sowing operation is simplified. In this manner, seeds can be treated, for example, at a central location and then dispersed for planting. This permits the person who plants the seeds to avoid the complexity and effort associated with handling and applying the compositions, and to merely handle and plant the treated seeds in a manner that is conventional for regular untreated seeds.

A composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413; 5,891,246; 5,554,445; 5,389,399; 5,107,787; 5,080,925; 4,759,945 and 4,465,017, among others. Any conventional active or inert material can be used for contacting seeds with the composition, such as conventional film-coating materials including but not limited to water-based film coating materials.

For example, a composition can be introduced onto or into a seed by use of solid matrix priming. For example, a quantity of the composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Non-limiting examples of solid matrix materials which are useful include polyacrylamide, starch, clay, silica, alumina, soil, sand, polyurea, polyacrylate, or any other material capable of absorbing or adsorbing the composition for a time and releasing the active compound of the composition into or onto the seed. It is useful to make sure that the active compound and the solid matrix material are compatible with each other. For example, the solid matrix material should be chosen so that it can release the active compound at a reasonable rate, for example over a period of minutes, hours, days, or weeks.

Imbibition is another method of treating seed with the composition. For example, a plant seed can be directly immersed for a period of time in the composition. During the period that the seed is immersed, the seed takes up, or imbibes, a portion of the composition. Optionally, the mixture of plant seed and the composition can be agitated, for example by shaking, rolling, tumbling, or other means. After imbibition, the seed can be separated from the composition and optionally dried, for example by patting or air drying.

A composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds may be dried and then transferred to a sizing machine for sizing. Such procedures are generally known in the art.

If a composition is applied to the seed in the form of a coating, the seeds can be coated using a variety of methods known in the art. For example, the coating process can comprise spraying the composition onto the seed while agitating the seed in an appropriate piece of equipment such as a tumbler or a pan granulator.

When coating seed on a large scale (for example a commercial scale), the seed coating may be applied using a continuous process. For example, seed may be introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the fungicide and/or other active ingredients in a composition, the desired concentration on the finished seed, and the like. A composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the composition) and passed through the treater under continual movement/tumbling where it can be coated evenly and dried before storage or use.

The seed coating may be applied using a batch process. For example, a known weight of seeds can be introduced into the treatment equipment (such as a tumbler, a mixer, or a pan granulator). A known volume of the composition can be introduced into the treatment equipment at a rate that allows the composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

The seed coating may be applied using a semi-batch process that incorporates features from each of the batch processes and continuous processes set forth above.

In other embodiments, seeds can be coated in laboratory size commercial treatment equipment such as a tumbler, a mixer, or a pan granulator by introducing a known weight of seeds in the treater, adding the desired amount of the composition, tumbling or spinning the seed and placing it on a tray to thoroughly dry.

Seeds can also be coated by placing the known amount of seed into a narrow neck bottle or receptacle with a lid. While tumbling, the desired amount of the composition can be added to the receptacle. The seed is tumbled until it is coated with the composition. After coating, the seed can optionally be dried, for example on a tray.

The treated seeds may also be enveloped with a film overcoating to protect the fungicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Treated Seeds

Provided herein is a seed that has been treated with a composition as described herein comprising a compound (e.g., a compound of Formula I) as described herein. The seed may have been treated with the composition using one of the seed treatment methods set forth above, including but not limited to solid matrix priming, imbibition, coating, and spraying. The treated seed may be of any plant species, as described above.

A seed can be treated with a composition as described herein, including formulating, mixing in a seed treater tank, or combining on a seed by overcoating one or more additional active ingredients. The additional active ingredient may be, for example, an additional pesticide. The pesticide may be, for example, an insecticide, a fungicide, an herbicide, or an additional nematicide as described herein.

The amount of a compound present on a treated seed sufficient to protect the seed, and/or the roots of a plant grown from the seed, against damage by phytopathogenic *fungi* can be readily determined by one of ordinary skill in the art. In some embodiments, the treated seed comprises a compound of Formula I in an amount of at least about 0.005 mg/seed. For example, treated seeds can comprise a compound of Formula I in an amount of from about 0.005 to about 2 mg/seed, from about 0.005 to about 1 mg/seed, or from about 0.05 to about 0.5 mg/seed.

Having described the disclosure in detail, it will be apparent that modifications and variations are possible without departing from the scope of the claims.

General Methods for Providing the Present Compounds

The compounds of this invention may be prepared or isolated in general by synthetic and/or semi-synthetic methods known to those skilled in the art for analogous compounds and by methods described in detail herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

The amidation of a carboxylic acid with an amine is well established and known in the art. The use of amide coupling reagents is one of common approaches to form amide bonds known in the art and included those described in detail in *Handbook of Reagents for Organic Synthesis, Reagents for Glycoside, Nucleotide, and Peptide Synthesis*, D. Crich, 1$^{st}$ edition, John Wiley & Sons, 2005, the entirety of which is incorporated herein by reference. Suitable amide coupling reagents include, but are not limited to, (Benzotriazol-1-yloxy)tris(dimethylamino)phosphonium hexafluorophosphate (BOP), 3-(Diethoxyphosphoryloxy)-1,2,3-benzotriazin-4(3H)-one (DEPBT), N,N'-dicyclohexylcarbodiimide (DCC), N,N'-Diisopropylcarbodiimide (DIC), 1-[Bis(dimethylamino)methylene]-1H-1,2,3-triazolo[4,5-b]pyridinium 3-oxid hexafluorophosphate (HATU), 3-[Bis(dimethylamino)methyliumyl]-3H-benzotriazol-1-oxide hexafluorophosphate (HBTU), 3-Hydroxytriazolo[4,5-b]pyridine (HOAt), (7-Azabenzotriazol-1-yloxy)tripyrrolidinophosphonium hexafluorophosphate (PyAOP), (Benzotriazol-1-yloxy)tripyrrolidinophosphonium hexafluorophosphate (PyBOP), and propylphosphonic anhydride (T3P). It is also well known in the art, amidation can be achieved by converting carboxylic acids to corresponding acyl halides (e.g., acyl chloride) and then reacting with amines.

Oxazolyl Compounds

In certain embodiments, compounds of the present invention of formula I, where $R^2$ is 2-oxazolyl, are generally prepared by procedures described in U.S. Pat. No. 8,969,557, the entirety of which is incorporated herein by reference. Exemplative compounds listed in Table 1 can be prepared according to Scheme 1 or Scheme 2 set forth below:

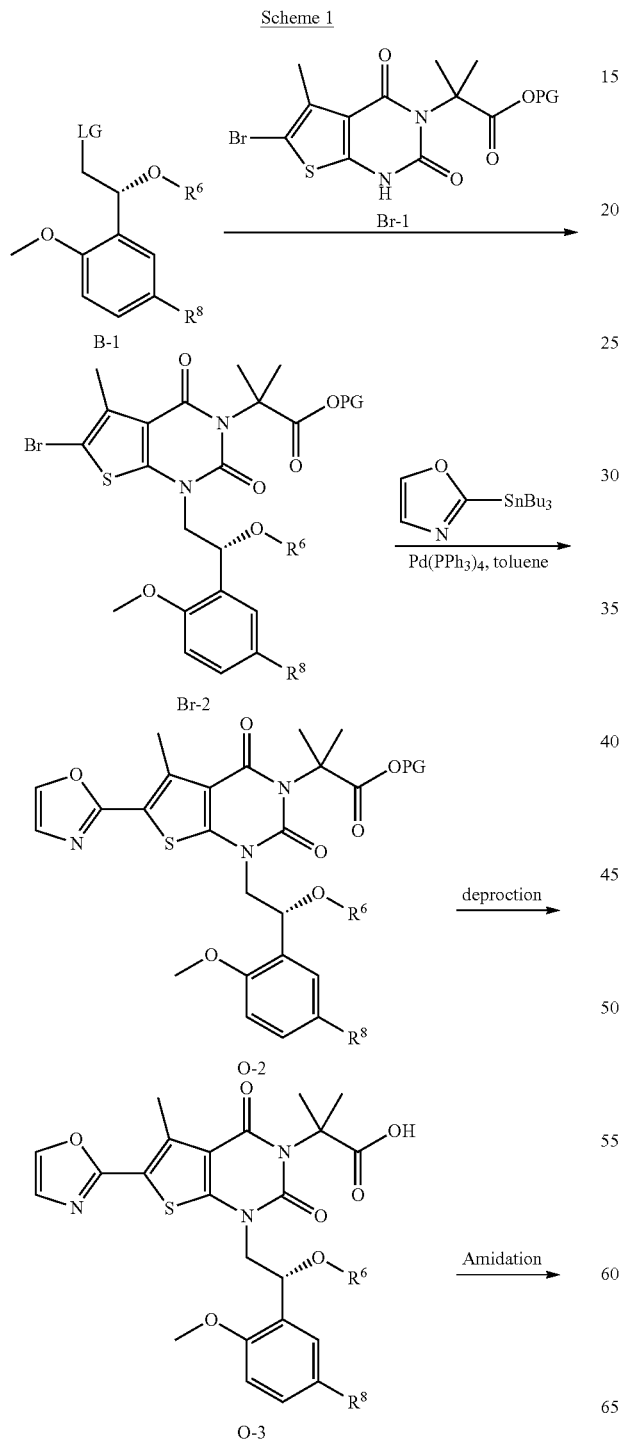

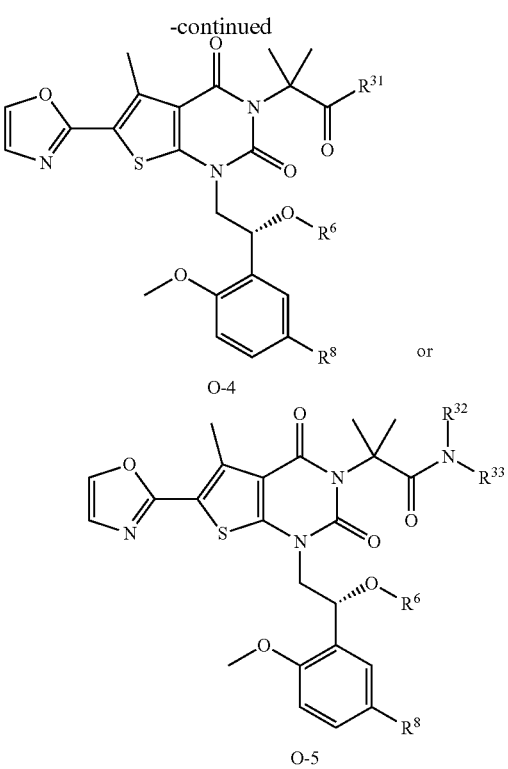

In Scheme 1 above, each of PG, LG, $R^6$, $R^8$, $R^{31}$, $R^{32}$, and $R^{33}$ is as defined above and below and in classes and subclasses as described herein.

In some embodiments, the first step comprises alkylating a compound of Formula Br-1 with a compound of Formula B-1, thereby forming a compound of Formula Br-2. In some embodiments, the compound of Formula B-1 is a halide wherein LG is chloride or bromide. In some embodiments, the compound of Formula B-1 is an alcohol wherein LG is —OH and the alkylation is accomplished by Mitsunobu reaction. In some embodiments, the Mitsunobu reaction is accomplished by the use of diisopropyl azodicarboxylate and triphenylphosine. In some embodiments, $R^6$ of the compound of Formula B-1 is isopropyl, tetrahydro-2H-pyran-4-yl; cis-4-hydroxycyclohexyl; 4-oxocyclohexyl; (4-oxocyclohexyl)methyl; or cis-4-hydroxycyclohexylmethyl. In some embodiments, $R^8$ of the compound of Formula B-1 is hydrogen or F.

In some embodiments, the oxazole moiety is installed by Stille coupling reaction to provide a compound of Formula O-2. In some embodiments, the Stille coupling reaction is accomplished by reacting the compound of Formula Br-2 with 2-(tributylstannyl)oxazole in the presence of a palladium complex, for example, tetrakis(triphenylphosphine)palladium(0).

In some embodiments, the carboxylic acid protection group of the compound of Formula O-1 is t-butyl and the deproction step comprises an acid treatment (e.g., trifluoroacetic acid in dichloromethane) to provide the carboxylic acid of Formula O-3. In some embodiment, the protection group of Formula O-2 is benzyl. In some embodiments, the protecting group is a silyl protecting group. In some embodiments, the protecting group is TBDPS and the deproction step comprises a fluoride treatment (e.g., tetrabutylammonium fluoride).

In some embodiments, the last step comprises an amidation of the carboxylic acid group of a compound of Formula O-3 with an amine, thereby providing a compound of Formula O-4 or Formula O-5. In some embodiments, the amine is ammonia (e.g., $R^{32}$ and $R^{33}$ are both hydrogen). In some embodiments, the amine is a primary amine (e.g., $R^{32}$ is hydrogen and $R^{33}$ is ethyl, isopropyl, or cyclobutyl). In some embodiments, the amine is a secondary amine. In some embodiments, the amine is a heterocycle (e.g., $R^{31}$ is 1-pyrrolidinyl, 1-piperidinyl, or 1-morpholinyl).

Alternatively, in some embodiments, the oxazole moiety is installed first by Stille coupling reaction to provide a compound of Formula O-1. Alkylation of the compound of Formula O-1 with a compound of Formula B-1, thereby forming a compound of Formula O-2, shown below:

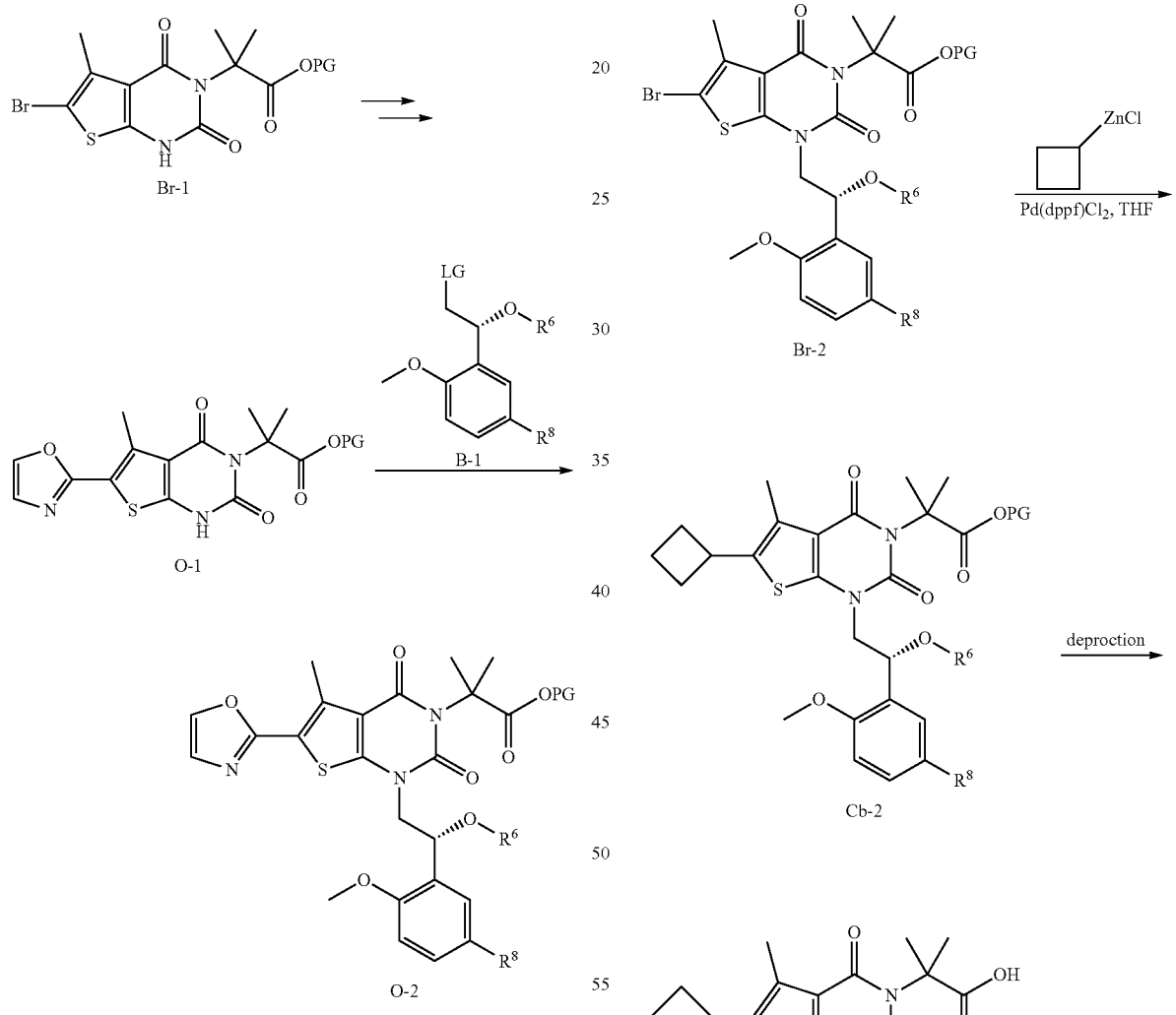

In Scheme 2 above, each of PG, LG, $R^6$, $R^8$, $R^{31}$, $R^{32}$, and $R^{33}$ is as defined and described above.

Cycloalkyl Compounds

In certain embodiments, compounds of the present invention of formula I, where $R^2$ is cycloalkyl, are generally prepared by procedures described in U.S. Pat. No. 8,969,557, the entirety of which is incorporated herein by reference. Exemplative compounds listed in Table 1 can be prepared according to Scheme 3 set forth below:

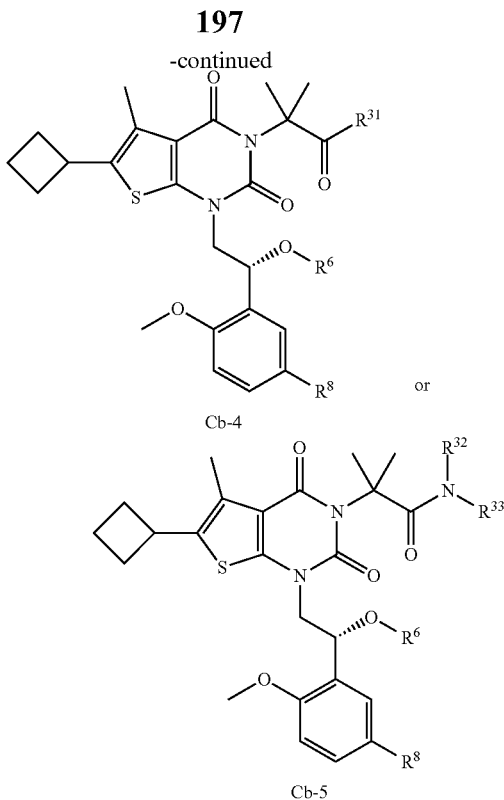

Cb-4 or

Cb-5

In Scheme 3 above, each of PG, LG, $R^6$, $R^8$, $R^{31}$, $R^{32}$, and $R^{33}$ is as defined above and below and in classes and subclasses as described herein.

In some embodiments, the first step comprises alkylating a compound of Formula Br-1 with a compound of Formula B-1, thereby forming a compound of Formula Br-2, as described above. In some embodiments, $R^6$ of the compound of Formula B-1 is tetrahydro-2H-pyran-4-yl. In some embodiments, $R^8$ of the compound of Formula B-1 is F.

In some embodiments, the oxazole moiety is installed by Negishi or Suzuki coupling reaction to provide a compound of Formula Cb-2. In some embodiments, the Negishi coupling reaction is accomplished by reacting the compound of Formula Br-2 with cycloalkylzinc(II) chloride in the presence of a palladium complex, for example, 1,1'-Bis(diphenylphosphino)ferrocene]palladium(II) dichloride. In some embodiments, the Suzuki coupling reaction is accomplished by reacting the compound of Formula Br-2 with a cycloalkylboronic compound in the presence of a palladium complex, for example, tetrakis(triphenylphosphine)palladium(0) or palladium(II) acetate.

In some embodiments, the carboxylic acid protection group of the compound of Formula Cb-2 is described above.

In some embodiments, the last step comprises an amidation of the carboxylic acid group of a compound of Formula Cb-3 with an amine, thereby providing a compound of Formula Cb-4 or Formula Cb-5, as described above. In some embodiments, the amine is ammonia (e.g., $R^{32}$ and $R^{33}$ are both hydrogen). In some embodiments, the amine is a primary amine (e.g., $R^{32}$ is hydrogen and $R^{33}$ is ethyl or isopropyl). In some embodiments, the amine is a secondary amine. In some embodiments, the amine is a heterocycle (e.g., $R^{31}$ is 1-pyrrolidinyl, 1-piperidinyl, or 1-morpholinyl).

Pyrazolyl Compounds

In certain embodiments, exemplative compounds in Table 1 of the present invention of formula I, where $R^2$ is 1-pyrazolyl, are generally prepared according to Scheme 4 set forth below:

Scheme 4

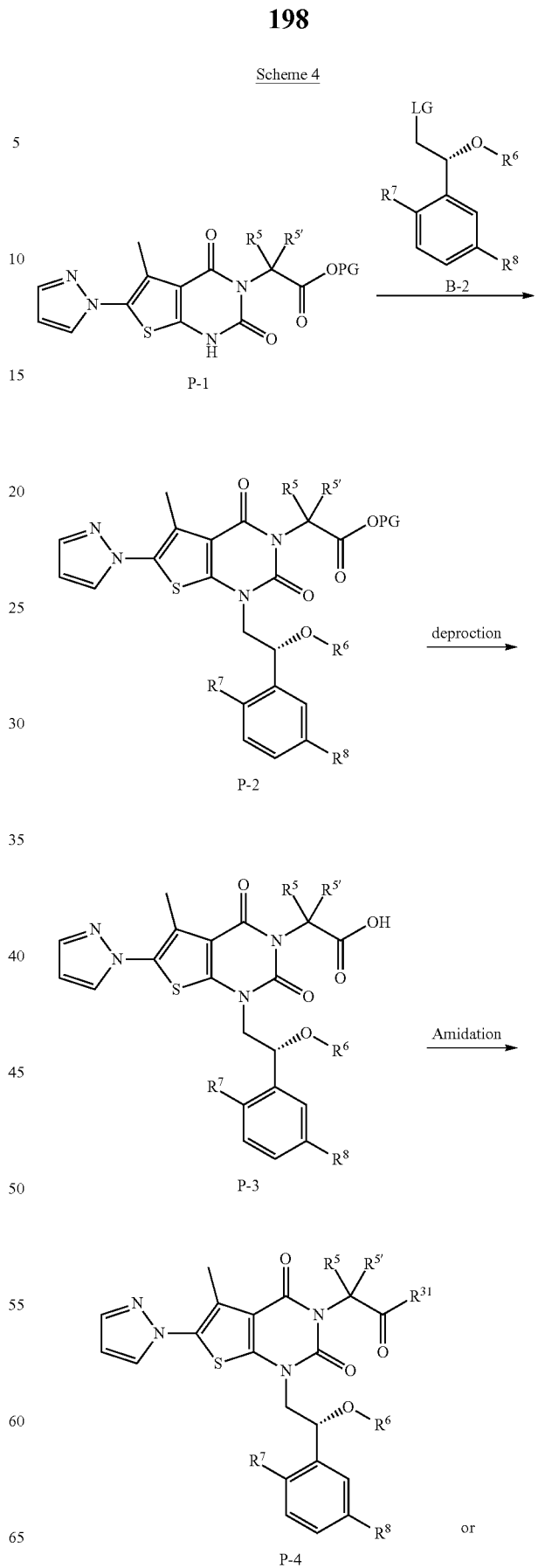

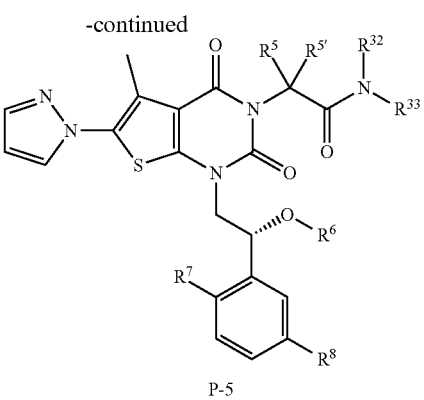

P-5

In Scheme 4 above, each of PG, LG, $R^5$, $R^{5'}$, $R^6$, $R^7$, $R^8$, $R^{31}$, $R^{32}$, and $R^{33}$ is as defined above and below and in classes and subclasses as described herein.

In some embodiments, the first step comprises alkylating a compound of Formula P-1 with a compound of Formula B-2, thereby forming a compound of Formula P-2. In some embodiments, the compound of Formula B-2 is a halide wherein LG is chloride or bromide. In some embodiments, the compound of Formula B-2 is an alcohol wherein LG is —OH and the alkylation is accomplished by Mitsunobu reaction. In some embodiments, the Mitsunobu reaction is accomplished by the use of diisopropyl azodicarboxylate and triphenylphosine. In some embodiments, $R^5$ and $R^{5'}$ of the compound of Formula P-1 or P-2 are both methyl. In some embodiments, $R^5$ of the compound of Formula P-1 or P-2 is methyl and $R^{5'}$ of the compound of Formula P-1 or P-2 is hydrogen. In some embodiments, $R^6$ of the compound of Formula B-2 is H, —CH$_2$CH$_3$, —CH(CH$_3$)$_2$, —CH$_2$CH(CH$_3$)$_2$, —CH$_2$CH=CH$_2$, —CH$_2$CH$_2$OH, —CH$_2$CH(R—CH$_3$)OH, —CH$_2$CH(S—CH$_3$)OH, —CH$_2$C(CH$_3$)$_2$(OH), —CH$_2$CH$_2$OCH$_3$, —CH$_2$CH$_2$CH$_2$OCH$_3$, —C(O)CH$_2$OH, —C(O)CH$_3$, —CH$_2$CN, —(CH$_2$)$_2$CN, —CH$_2$CH(CH$_3$)CN, —CH$_2$C(CH$_3$)$_2$CN, tetrahydro-2H-pyran-4-yl, cis-4-hydroxycyclohexyl, 4-oxocyclohexyl, (4-oxocyclohexyl) methyl, cis-4-hydroxycyclohexylmethyl, —CH$_2$CH$_2$C(O)NH$_2$, —CH$_2$CH$_2$N(CH$_3$)$_2$, or —CH$_2$CH$_2$SO$_2$CH$_3$. In some embodiments, $R^7$ of the compound of Formula B-2 or P-2 is —OMe or —OPG. In some embodiments, $R^8$ of the compound of Formula B-2 or P-2 is hydrogen or F.

In some embodiments, the carboxylic acid protection group of the compound of Formula P-3 is a silyl protecting group. In some embodiments, the protecting group is TBDPS and the deproction step comprises a fluoride treatment (e.g., tetrabutylammonium fluoride).

In some embodiments, the last step comprises an amidation of the carboxylic acid group of a compound of Formula P-3 with an amine, thereby providing a compound of Formula P-4 or Formula P-5. In some embodiments, the amine is ammonia (e.g., $R^{32}$ and $R^{33}$ are both hydrogen).

In some embodiments, the amine is a primary amine (e.g., $R^{32}$ is hydrogen and $R^{33}$ is methyl, ethyl, isopropyl, isobutyl, cyloropropyl, cyclobutyl, or cyclohexyl). In some embodiments, the amine is a secondary amine (e.g., $R^{32}$ is methyl and $R^{33}$ is methyl, isopropyl, or 2-propenyl). In some embodiments, the amine is a heterocycle (e.g., $R^{31}$ is 1-pyrrolidinyl, 1-piperidinyl, 1-morpholinyl, or 2,5-dihydro-1H-pyrrol-1-yl).

In some embodiments, if $R^7$ of the compound of Formula P-2 is —OPG, deprotection and O-alkylation provides $R^7$ as of —OCH$_2$CH$_2$OH, or —OCH$_2$CH$_2$CN in compounds of Formula P-4 or P-5.

One of skill in the art will appreciate that compounds of formula P-4 or P-5 may contain one or more stereocenters, and may be present as a racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

Ester Compounds

In certain embodiments, exemplative compounds in Table 1 of the present invention of Formula I, where $R^2$ is —C(O)OCH$_2$CH$_3$, are generally prepared according to Scheme 5 set forth below:

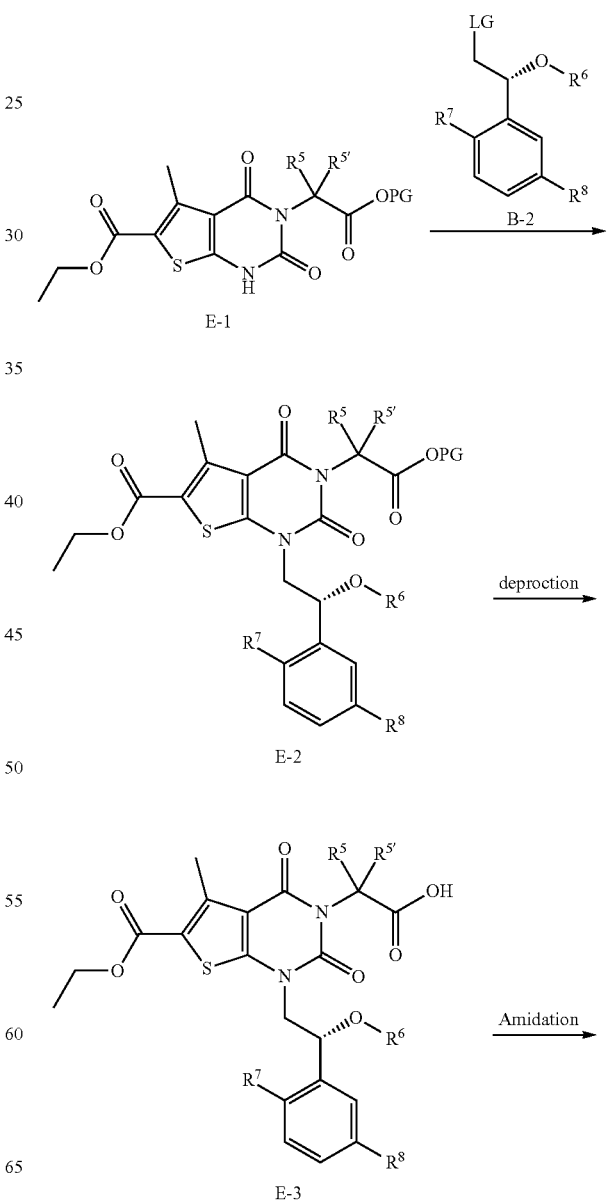

Scheme 5

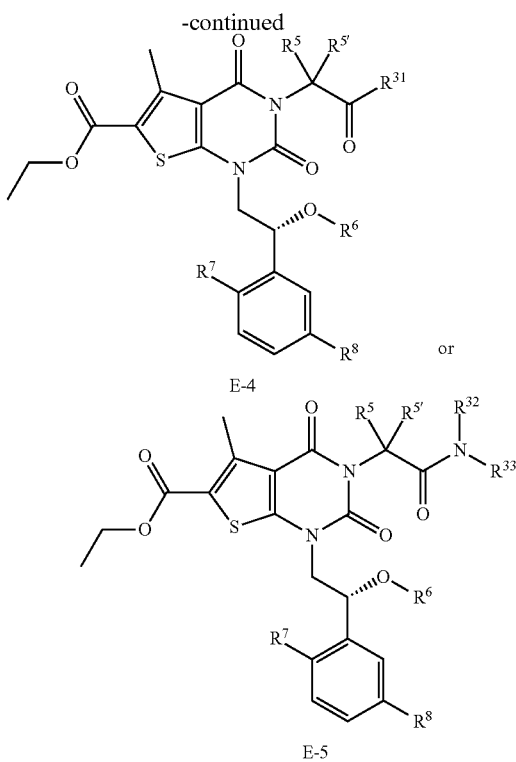

E-4 or

E-5

In Scheme 5 above, each of PG, LG, $R^5$, $R^{5'}$, $R^6$, $R^7$, $R^8$, $R^{31}$, $R^{32}$, and $R^{33}$ is as defined above and below and in classes and subclasses as described herein.

In some embodiments, the first step comprises alkylating a compound of Formula E-1 with a compound of Formula B-2, thereby forming a compound of Formula E-2. In some embodiments, the compound of Formula B-2 is a halide wherein LG is chloride or bromide. In some embodiments, the compound of Formula B-2 is an alcohol wherein LG is —OH and the alkylation is accomplished by Mitsunobu reaction. In some embodiments, the Mitsunobu reaction is accomplished by the use of diisopropyl azodicarboxylate and triphenylphosine. In some embodiments, $R^5$ and $R^{5'}$ of the compound of Formula E-1 or E-2 are both methyl. In some embodiments, $R^5$ of the compound of Formula E-1 or E-2 is methyl and $R^{5'}$ of the compound of Formula E-1 or E-2 is hydrogen. In some embodiments, $R^6$ of the compound of Formula B-2 is H, —CH$_2$CH$_3$, —CH(CH$_3$)$_2$, —CH$_2$CH (CH$_3$)$_2$, —CH$_2$CH═CH$_2$, —CH$_2$CH$_2$OH, —CH$_2$CH(R—CH$_3$)OH, —CH$_2$CH(S—CH$_3$)OH, —CH$_2$C(CH$_3$)$_2$(OH), —CH$_2$CH$_2$OCH$_3$, —CH$_2$CH$_2$CH$_2$OCH$_3$, —C(O)CH$_2$OH, —C(O)CH$_3$, —CH$_2$CN, —(CH$_2$)$_2$CN, —CH$_2$CH(CH$_3$)CN, —CH$_2$C(CH$_3$)$_2$CN, tetrahydro-2H-pyran-4-yl, cis-4-hydroxycyclohexyl, 4-oxocyclohexyl, (4-oxocyclohexyl) methyl, cis-4-hydroxycyclohexylmethyl, —CH$_2$CH$_2$C(O) NH$_2$, —CH$_2$CH$_2$N(CH$_3$)$_2$, or —CH$_2$CH$_2$SO$_2$CH$_3$. In some embodiments, $R^7$ of the compound of Formula B-2 or E-2 is —OMe or —OPG. In some embodiments, $R^8$ of the compound of Formula B-2 or E-2 is hydrogen or F.

In some embodiments, the carboxylic acid protection group of the compound of Formula E-3 is a silyl protecting group. In some embodiments, the protecting group is TBDPS and the deprotection step comprises a fluoride treatment (e.g., tetrabutylammonium fluoride).

In some embodiments, the last step comprises an amidation of the carboxylic acid group of a compound of Formula E-3 with an amine, thereby providing a compound of Formula E-4 or Formula E-5. In some embodiments, the amine is ammonia (e.g., $R^{32}$ and $R^{33}$ are both hydrogen). In some embodiments, the amine is a primary amine (e.g., $R^{32}$ is hydrogen and $R^{33}$ is methyl, ethyl, isopropyl, isobutyl, cyclopropyl, cyclobutyl, or cyclohexyl). In some embodiments, the amine is a secondary amine (e.g., $R^{32}$ is methyl and $R^{33}$ is methyl, ethyl, isopropyl, or 2-propenyl). In some embodiments, the amine is a heterocycle (e.g., $R^{31}$ is 1-pyrrolidinyl, 1-piperidinyl, 1-morpholinyl, or 2,5-dihydro-1H-pyrrol-1-yl).

In some embodiments, if $R^7$ of the compound of Formula E-2 is —OPG, deprotection and O-alkylation provides $R^7$ as of —OCH$_2$CH$_2$CN in compounds of Formula E-4 or E-5.

In some embodiments, the ester group (i.e., —C(O) OCH$_2$CH$_3$) in compounds of Formula E-4 or E-5 is further reduced to —CH$_2$OH as the $R^2$ in compounds of Formula I. In some embodiments, the —CH$_2$OH group is further alkylated to —CH$_2$OCH$_2$CH$_3$ as the $R^2$ in compounds of Formula I.

One of skill in the art will appreciate that compounds of formula E-4 or E-5 may contain one or more stereocenters, and may be present as a racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

Triazolyl Compounds

In certain embodiments, explemative compounds in Table 1 of the present invention of Formula I, where $R^2$ is 2H-1,2,3-triazol-2-yl, are generally prepared according to Scheme 6 set forth below:

Scheme 6

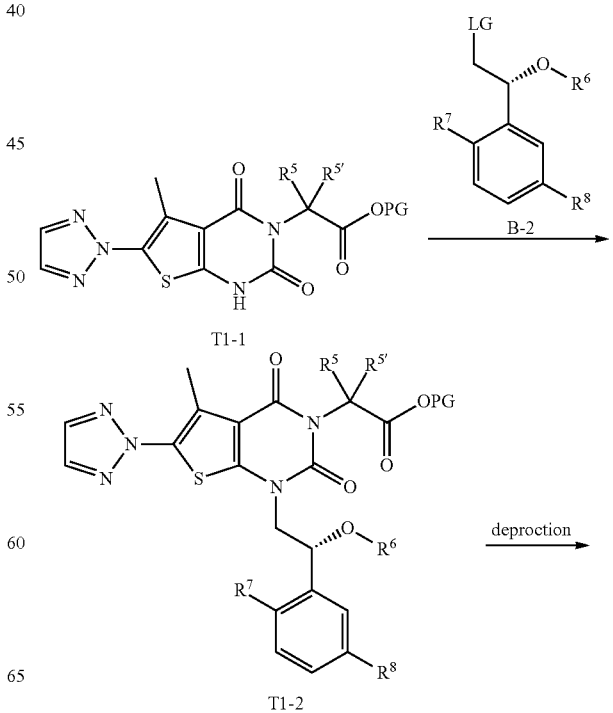

T1-1

T1-2

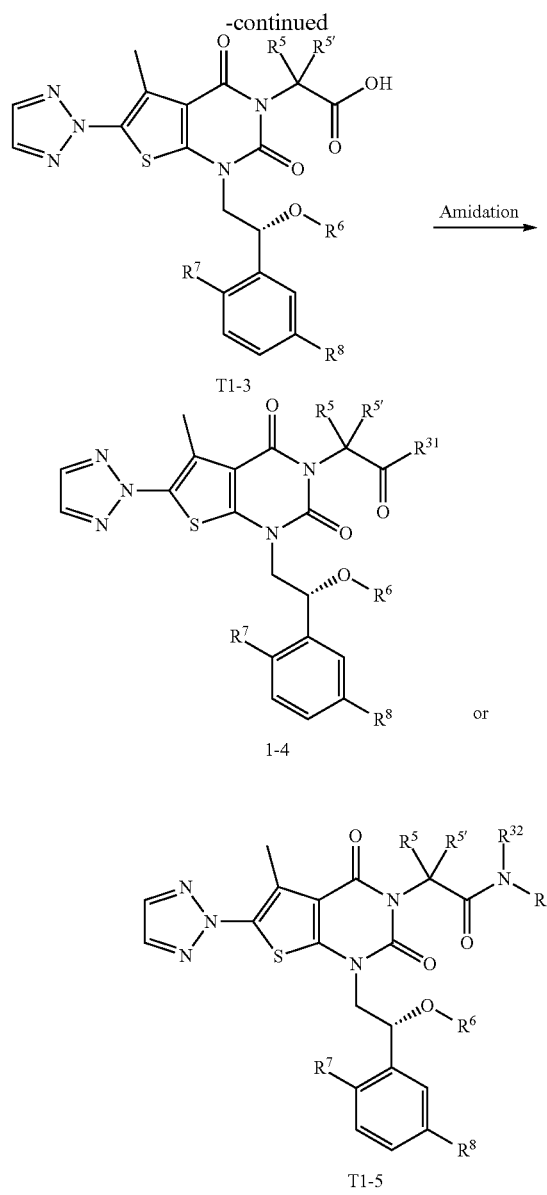

In Scheme 6 above, each of PG, LG, $R^5$, $R^{5'}$, $R^6$, $R^7$, $R^8$, $R^{31}$, $R^{32}$, and $R^{33}$ is as defined above and below and in classes and subclasses as described herein.

In some embodiments, the first step comprises alkylating a compound of Formula T1-1 with a compound of Formula B-2, thereby forming a compound of Formula T1-2. In some embodiments, the compound of Formula B-2 is a halide wherein LG is chloride or bromide. In some embodiments, the compound of Formula B-2 is an alcohol wherein LG is —OH and the alkylation is accomplished by Mitsunobu reaction. In some embodiments, the Mitsunobu reaction is accomplished by the use of diisopropyl azodicarboxylate and triphenylphosine. In some embodiments, $R^5$ and $R^{5'}$ of the compound of Formula T1-1 or T1-2 are both methyl. In some embodiments, $R^5$ of the compound of Formula T1-1 or T1-2 is methyl and $R^{5'}$ of the compound of Formula T1-1 or T1-2 is hydrogen. In some embodiments, $R^5$ and $R^{5'}$ of the compound of Formula T1-1 or T1-2 are both hydrogen. In some embodiments, $R^6$ of the compound of Formula B-2 is H, —CH$_2$CH$_3$, —CH(CH$_3$)$_2$, —CH$_2$CH(CH$_3$)$_2$, —CH$_2$CH═CH$_2$, —CH$_2$CH$_2$OH, —CH$_2$CH(R—CH$_3$)OH, —CH$_2$CH(S—CH$_3$)OH, —CH$_2$C(CH$_3$)$_2$(OH), —CH$_2$CH$_2$OCH$_3$, —CH$_2$CH$_2$CH$_2$OCH$_3$, —C(O)CH$_2$OH, —C(O)CH$_3$, —CH$_2$CN, —(CH$_2$)$_2$CN, —CH$_2$CH(CH$_3$)CN, —CH$_2$C(CH$_3$)$_2$CN, tetrahydro-2H-pyran-4-yl, cis-4-hydroxycyclohexyl, 4-oxocyclohexyl, (4-oxocyclohexyl)methyl, cis-4-hydroxycyclohexylmethyl, —CH$_2$CH$_2$C(O)NH$_2$, —CH$_2$CH$_2$N(CH$_3$)$_2$, or —CH$_2$CH$_2$SO$_2$CH$_3$. In some embodiments, $R^7$ of the compound of Formula B-2 or T1-2 is —OMe, methyl, ethyl, —(CH$_2$)$_3$CN, or —OPG. In some embodiments, $R^8$ of the compound of Formula B-2 or T1-2 is hydrogen or F.

In some embodiments, the carboxylic acid protection group of the compound of Formula T1-3 is a silyl protecting group. In some embodiments, the protecting group is TBDPS and the deproction step comprises a fluoride treatment (e.g., tetrabutylammonium fluoride).

In some embodiments, the last step comprises an amidation of the carboxylic acid group of a compound of Formula T1-3 with an amine, thereby providing a compound of Formula T1-4 or Formula T1-5. In some embodiments, the amine is ammonia (e.g., $R^{32}$ and $R^{33}$ are both hydrogen). In some embodiments, the amine is a primary amine (e.g., $R^{32}$ is hydrogen and $R^{33}$ is methyl, ethyl, isopropyl, isobutyl, cycloropropyl, cyclobutyl, cyclohexyl, or —CH$_2$CN). In some embodiments, the amine is a secondary amine (e.g., $R^{32}$ is methyl and $R^{33}$ is methyl, ethyl, isopropyl, or 2-propenyl). In some embodiments, the amine is a heterocycle (e.g., $R^{31}$ is 1-pyrrolidinyl, 1-piperidinyl, 1-morpholinyl, 2,5-dihydro-1H-pyrrol-1-yl, or 3-hydroxyazetidin-1-y).

In some embodiments, if $R^7$ of the compound of Formula T1-2 is —OPG, deprotection and O-alkylation provides $R^7$ as of —OCH(CH$_3$)$_2$, —OCH$_2$CH$_2$OH, —OCH$_2$CH$_2$OCH$_3$, —OCH$_2$CH(CH$_2$)$_2$O, —OCH$_2$CN, —OCH$_2$CH$_2$CN, —OC(O)CH$_3$; O-tetrahydro-2H-pyran-4-yl, or O-benzyl in compounds of Formula T1-4 or T1-5.

One of skill in the art will appreciate that compounds of formula T1-4 or T1-5 may contain one or more stereocenters, and may be present as a racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

In certain embodiments, exemplative triazolyl compounds in Table 1 of the present invention of Formula I, where $R^4$ is —O(CH$_2$)$_2$CN and $R^{4'}$ is CH$_3$ (I-273, I-274), $R^4$ is —OH and $R^{4'}$ is —CH$_2$CH$_2$OH (I-275, I-276), or $R^4$ is —OH and $R^{4'}$ is —CH$_2$OH (I-315) are prepared specifically with modified chemical steps. For example, $R^4$ of —O(CH$_2$)$_2$ CN and $R^{4'}$ of CH$_3$ in compounds I-273 and I-274 are installed at the benzylic position of the compound of 3-((2-(5-fluoro-2-methoxyphenyl)-1-hydroxypropan-2-yl)oxy)propanenitrile, shown in Scheme 7 below:

Scheme 7

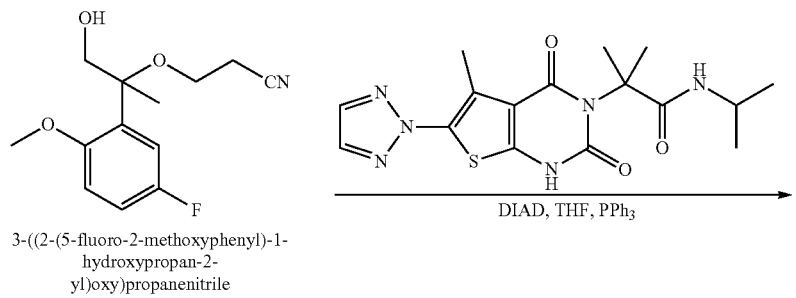

3-((2-(5-fluoro-2-methoxyphenyl)-1-hydroxypropan-2-yl)oxy)propanenitrile

DIAD, THF, PPh₃

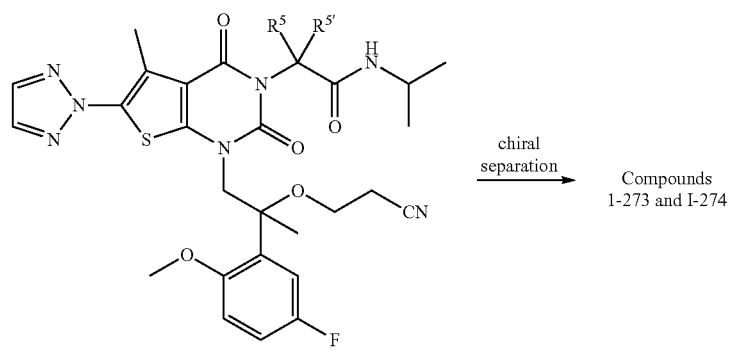

chiral separation → Compounds I-273 and I-274

Compounds I-273 and I-274 are prepared by alkylation, amidation, and chiral separation. For example, $R^4$ of —OH and $R^{4'}$ of —CH$_2$CH$_2$OH in compounds I-275 and I-276 are installed via a ketone intermediate, shown in Scheme 8 below:

Scheme 8

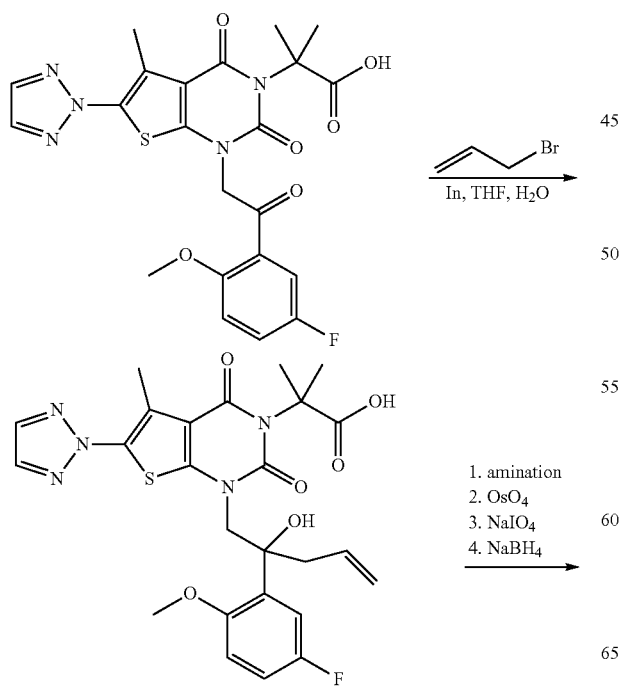

1. amination
2. OsO₄
3. NaIO₄
4. NaBH₄

-continued

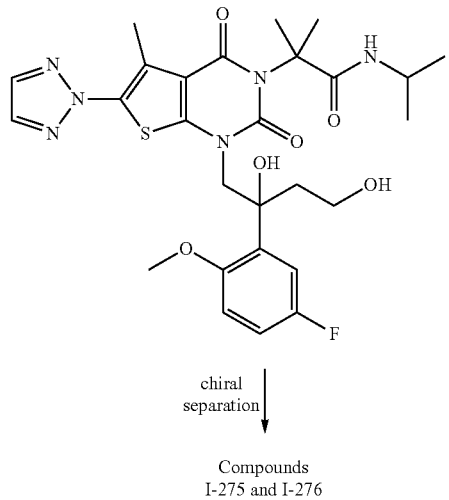

chiral separation ↓

Compounds I-275 and I-276

Compounds I-275 and I-276 are prepared by amidation, dihydroxylation of the double bond, oxidation of the diol to an aldehyde, reduction of the aldehyde to an alcohol, and chiral separation. For example, $R^4$ of —OH and $R^{4'}$ of —CH$_2$OH in the compound I-315 are installed via a ketone intermediate, shown in Scheme 9 below:

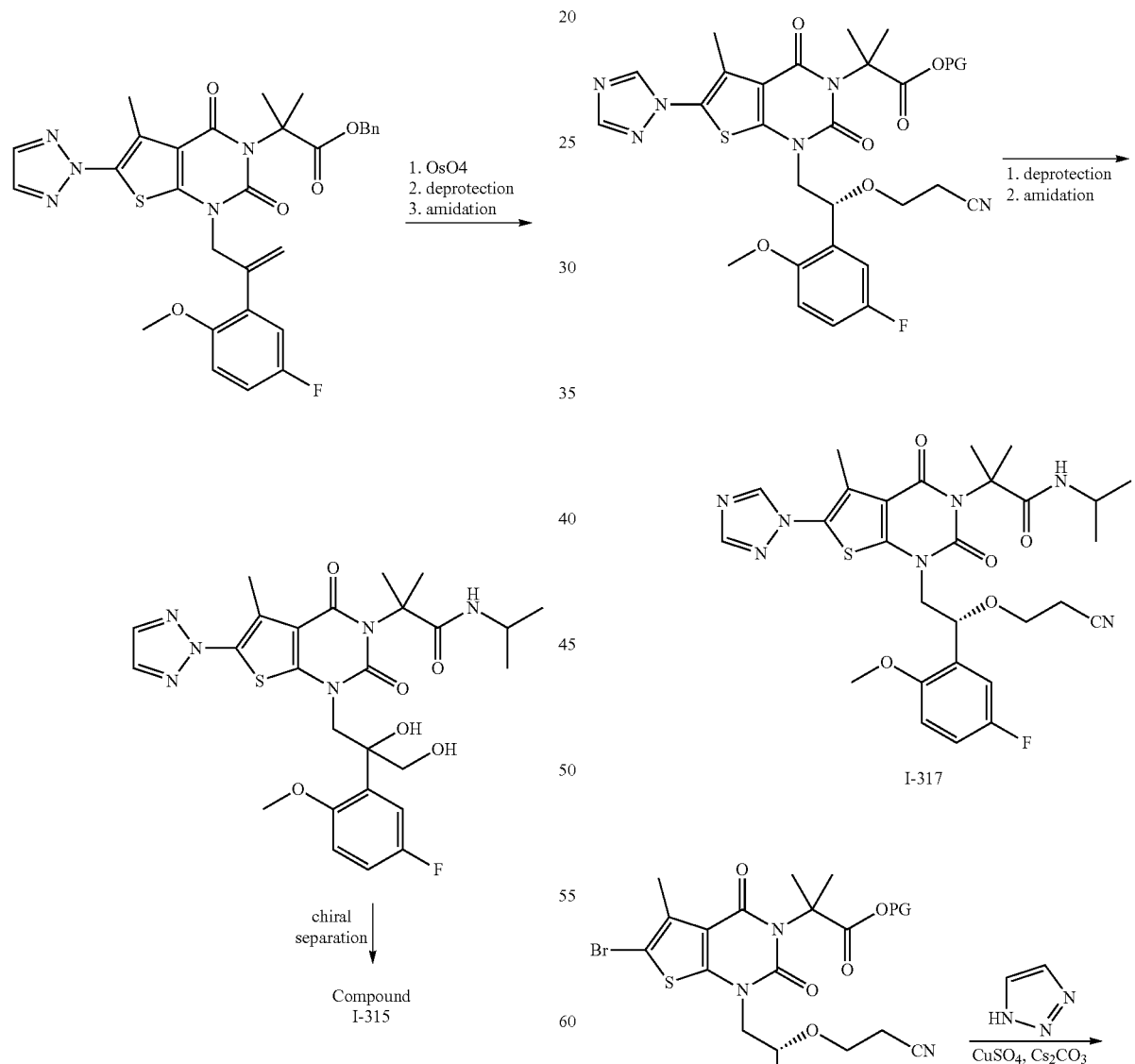
In certain embodiments, exemplative triazolyl compounds in Table 1 of the present invention of Formula I, where R² is 1H-1,2,4-triazol-1-yl (I-317) or 1H-1,2,3-triazol-1-yl (I-341) are generally prepared according to Scheme 10, shown below:

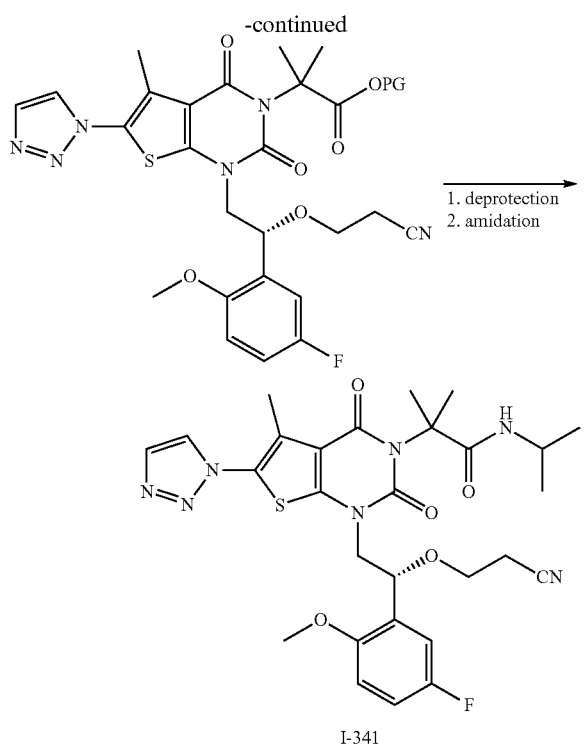

In some embodiments, the 1H-1,2,4-triazol-1-yl or 1H-1,2,3-triazol-1-yl moiety is installed by a metal-mediated coupling reaction.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See e.g. "March's Advanced Organic Chemistry", 5th Ed., Ed.: Smith, M. B. and March, J., John Wiley & Sons, New York: 2001, the entirety of which is incorporated herein by reference.

EXAMPLES

The following non-limiting examples are provided for further illustration.

Example 1: In Vitro Pathogen Growth Inhibition Assay

A growth inhibition assay was conducted to determine the ability of compounds to control the growth of fungal pathogens, such as *Botrtyis cinerea* (Bc), *Collectotrichum graminicola* (Cg), *Diplodia maydis* (Dm), *Fusarium moniliforme* (Fm), *Fusarium virguliforme* (Fv), *Phytophthora capsici* (Pc), *Rhizoctonia solani* (Rs), and *Septoria tritici* (St).

The compounds listed in Table 1 were each dissolved in DMSO at 2.5 mg/ml to produce compound stock solutions ("stocks"). Stocks were diluted with DMSO by a five-fold dilution in a 96-well stock plate, and two sets of final concentrations of 50, 10, and 2 ppm or 2, 0.4, and 0.08 ppm were obtained in vitro.

A set of positive controls was also prepared, with various concentrations of Soraphen (2, 0.4, and 0.08 ppm), Metalaxyl (1.1, 0.22, and 0.04 ppm), and Metconazole (2, 0.4, and 0.08 ppm or 0.2, 0.04, and 0.008 ppm) after the five-fold dilutions. Negative controls on each plate included 2% DMSO, water, and a blank (media+2% DMSO).

Fungal spores were isolated from previously sub-cultured plates of *Botrtyis cinerea* (Bc), *Collectotrichum graminicola* (Cg), *Diplodia maydis* (Dm), *Fusarium moniliforme* (Fm), *Fusarium virguliforme* (Fv), *Phytophthora capsici* (Pc), and *Septoria tritici* (St). The isolated spores were diluted to individual concentrations with a 17% V8 liquid media. For *Rhizoctonia solani* (Rs), 1.5 mm mycelial plugs were used in place of spores and ¼ Potato Dextrose Broth (PDB) was used for dilution. The spore concentrations and plug sizes were based on growth curves generated at 48 hours for each pathogen.

In a second 96-well plate, the spores or mycelial plugs, media, diluted compound solutions, and controls were combined. Once the compound was added, a true final concentration of compound in each well was measured by an OD600 reading, which adjusted for any compound precipitation that might have occurred in the well. Plate readings were repeated at both 24 and 48 hours. The blank negative control was used as a background subtraction. Additional visual ratings were performed at both 24 and 48 hours for checking on precipitation and confirming efficacy. Visual and OD600 ratings of the compounds at 48 hours were compared to the 2% DMSO negative control, and the percent of pathogen growth inhibition was determined based on those values.

A list of compounds that have an inhibition of ≥90% of *Fusarium moniliforme* (Fm) at a compound concentration of 2 ppm or lower is included in Table 2 below. Additional compounds that have an inhibition of ≥90% of *Fusarium moniliforme* (Fm) are included in Table 3 below. Both tables list the concentration of each compound that was sufficient to ≥90% inhibition of growth for each of the fungal pathogens listed above. In addition, some of compounds were tested in a yeast growth inhibition assay for *Saccharomyces cerevisiae* (Sc). Table 2 lists the concentration of the tested compound that was sufficient to ≥75% inhibition of *Saccharomyces cerevisiae* (Sc).

TABLE 2

In Vitro Pathogen Growth Inhibition Assay Results

| | Pathogens | | | | | | | | |
| --- | --- | --- | --- | --- | --- | --- | --- | --- | --- |
| | Bc | Cg | Dm | Fm | Fv | Pc | Rs | St | Sc |
| | Percentage of Inhibition | | | | | | | | |
| Cmpd. No. | ≥90% | ≥90% | ≥90% | ≥90% | ≥90% | ≥90% | ≥90% | ≥90% | ≥75% |
| | Compound Concentration (ppm) | | | | | | | | |
| I-001 | ≥0.4 | ≥2.0 | 2.0 | 0.080 | 0.40 | >50.0 | 50.0 | >10.0 | 1.2 |
| I-002 | 0.40 | 2.0 | 0.40 | 0.080 | 0.40 | >50.0 | 0.40 | >10.0 | — |

TABLE 2-continued

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | | | | | Percentage of Inhibition | | | | |
| | ≥90% | ≥90% | ≥90% | ≥90% | ≥90% | ≥90% | ≥90% | ≥90% | ≥75% |
| Cmpd. No. | | | | | Compound Concentration (ppm) | | | | |
| I-003 | 2.0 | 0.40 | 2.0 | 0.080 | 0.40 | >50.0 | 0.40 | ≥10.0 | 0.40 |
| I-004 | 0.40 | 2.0 | 2.0 | 0.080 | 2.0 | >50.0 | 10.0 | >10.0 | 3.7 |
| I-005 | 2.0 | 2.0 | 2.0 | 0.080 | 2.0 | >50.0 | 0.40 | >10.0 | 0.40 |
| I-006 | 0.40 | 0.40 | 0.40 | 0.080 | 0.40 | >50.0 | 0.40 | ≥2.0 | 1.2 |
| I-007 | 0.40 | 0.40 | 0.40 | 0.080 | 0.40 | >50.0 | 0.080 | ≥2.0 | 0.40 |
| I-008 | 0.40 | 2.0 | 2.0 | 0.080 | 2.0 | >50.0 | 10.0 | >10.0 | 3.7 |
| I-009 | 0.40 | 2.0 | 0.40 | 0.080 | 0.40 | >50.0 | 10.0 | >50.0 | 3.7 |
| I-010 | 0.40 | 50.0 | ≥2.0 | 0.080 | 2.0 | >50.0 | 50.0 | >50.0 | 0.40 |
| I-011 | 0.40 | 2.0 | 2.0 | 0.080 | 2.0 | >50.0 | 10.0 | 50.0 | 1.2 |
| I-012 | 0.40 | 10.0 | 2.0 | 0.080 | 2.0 | >50.0 | 50.0 | ≥10.0 | 0.14 |
| I-013 | 0.40 | 10.0 | 0.40 | 0.080 | 2.0 | >50.0 | 10.0 | ≥10.0 | 0.14 |
| I-014 | 0.40 | 2.0 | 2.0 | 0.080 | 0.40 | >50.0 | 2.0 | >10.0 | 1.2 |
| I-015 | 0.40 | 2.0 | ≥0.4 | 0.080 | 0.40 | >50.0 | 10.0 | >10.0 | — |
| I-016 | 0.40 | 2.0 | 0.40 | 0.080 | 0.40 | >50.0 | 0.40 | >10.0 | — |
| I-017 | 0.40 | 0.080 | ≥0.08 | 0.080 | 0.40 | >50.0 | 0.40 | >10.0 | — |
| I-018 | 0.40 | 0.40 | 0.40 | 0.080 | 0.40 | >50.0 | 0.080 | >10.0 | — |
| I-019 | ≥0.4 | ≥0.4 | ≥0.4 | 0.080 | 0.40 | >50.0 | 0.080 | >10.0 | — |
| I-020 | ≥0.08 | 0.080 | 0.080 | 0.080 | 0.40 | >50.0 | 0.080 | ≥2.0 | — |
| I-021 | 0.40 | 2.0 | 2.0 | 0.080 | 0.40 | >50.0 | 0.40 | >10.0 | — |
| I-022 | 0.080 | 0.080 | 0.080 | 0.080 | ≥0.08 | >50.0 | 0.080 | ≥2.0 | — |
| I-023 | 0.40 | 0.080 | 0.080 | 0.080 | ≥0.08 | >50.0 | 0.080 | >10.0 | — |
| I-024 | 0.40 | 2.0 | ≥2.0 | 0.080 | 2.0 | >50.0 | 0.40 | >50.0 | — |
| I-025 | 0.40 | 0.40 | 0.40 | 0.080 | 0.40 | >50.0 | 0.40 | >10.0 | — |
| I-026 | 0.40 | 0.080 | 0.080 | 0.080 | 0.40 | >50.0 | 0.40 | ≥2.0 | — |
| I-027 | 0.40 | 0.40 | 0.40 | 0.080 | 2.0 | >50.0 | 0.40 | >10.0 | — |
| I-028 | 0.40 | 0.080 | ≥0.08 | 0.080 | 0.40 | >50.0 | 0.080 | ≥2.0 | — |
| I-029 | 0.40 | ≥2.0 | ≥2.0 | 0.080 | 0.40 | 50.0 | 0.40 | >10.0 | — |
| I-030 | 0.40 | 0.40 | ≥0.4 | 0.080 | 0.40 | 50.0 | 0.080 | ≥2.0 | — |
| I-031 | 2.0 | 10.0 | 10.0 | 0.080 | 10.0 | >50.0 | 10.0 | >50.0 | — |
| I-032 | 0.40 | ≥2.0 | 10.0 | 0.080 | 10.0 | >50.0 | 10.0 | >50.0 | — |
| I-033 | 0.40 | ≥0.4 | ≥0.4 | 0.080 | 0.40 | >50.0 | 0.080 | >10.0 | — |
| I-034 | 0.40 | ≥0.4 | ≥0.4 | 0.080 | 0.40 | ≥10.0 | 0.080 | ≥2.0 | — |
| I-035 | 2.0 | ≥2.0 | 2.0 | 0.080 | 0.40 | >50.0 | 0.40 | >50.0 | — |
| I-036 | 0.40 | 0.080 | ≥0.08 | 0.080 | 0.40 | >50.0 | 0.080 | ≥2.0 | — |
| I-037 | ≥0.4 | ≥0.08 | ≥0.08 | 0.080 | 0.40 | 10.0 | 0.080 | ≥2.0 | — |
| I-038 | 0.40 | 0.40 | 0.40 | 0.080 | 0.40 | 10.0 | 0.080 | ≥2.0 | — |
| I-039 | 0.40 | 2.0 | 0.40 | 0.080 | 0.40 | >50.0 | 0.40 | ≥2.0 | — |
| I-040 | 0.40 | ≥0.4 | ≥0.4 | 0.080 | 0.40 | >50.0 | 2.0 | ≥10.0 | — |
| I-041 | 0.40 | 2.0 | ≥2.0 | 0.080 | 2.0 | >50.0 | 0.080 | >10.0 | — |
| I-042 | 0.40 | ≥0.4 | ≥0.4 | 0.080 | 0.40 | ≥10.0 | 0.080 | ≥10.0 | — |
| I-043 | 0.40 | >2.0 | 0.40 | 0.080 | 2.0 | >10.0 | 0.40 | >10.0 | — |
| I-044 | 0.40 | 0.40 | 2.0 | 0.080 | 0.40 | >50.0 | 0.40 | >50.0 | — |
| I-045 | 2.0 | ≥0.4 | ≥2.0 | 0.080 | 10.0 | >50.0 | 2.0 | >50.0 | — |
| I-046 | 2.0 | 2.0 | 2.0 | 0.080 | 0.40 | >50.0 | 0.40 | ≥50.0 | — |
| I-047 | 0.40 | ≥2.0 | 2.0 | 0.080 | 0.40 | >50.0 | 2.0 | >50.0 | — |
| I-048 | 0.40 | 10.0 | 2.0 | 0.080 | 2.0 | >50.0 | 2.0 | >50.0 | — |
| I-049 | 0.40 | 50.0 | 2.0 | 0.080 | 2.0 | >50.0 | 2.0 | >50.0 | — |
| I-050 | 0.080 | 2.0 | ≥0.08 | 0.080 | 0.40 | 50.0 | 0.080 | >50.0 | — |
| I-051 | 0.40 | 0.40 | ≥0.4 | 0.080 | 0.40 | >50.0 | 0.40 | >50.0 | — |
| I-052 | 0.40 | ≥0.4 | 2.0 | 0.080 | 0.40 | >50.0 | 2.0 | >50.0 | — |
| I-053 | 0.40 | 2.0 | ≥2.0 | 0.080 | 0.40 | >50.0 | 2.0 | ≥50.0 | — |
| I-054 | 0.40 | 0.40 | 0.40 | 0.080 | ≥0.08 | >50.0 | 0.40 | 10.0 | — |
| I-055 | 0.40 | 0.080 | ≥0.4 | 0.080 | ≥0.08 | >50.0 | 0.40 | ≥2.0 | — |
| I-056 | 0.40 | 0.080 | 0.080 | 0.080 | 0.24 | 30.0[a] | 0.24 | 26.0[a] | — |
| I-057 | 0.40 | 0.080 | 0.40 | 0.080 | 0.40 | 50.0[a] | 0.40 | 50.0[a] | — |
| I-058 | 0.40 | 0.080 | 0.080 | 0.080 | 0.080 | ≥10.0 | 0.40 | >50.0 | — |
| I-059 | 0.080 | 0.40 | 0.40 | 0.080 | ≥0.08 | >50.0 | 0.40 | 10.0 | — |
| I-060 | 0.40 | >50.0 | 0.40 | 0.080 | 0.40 | >50.0 | ≥2.0 | >50.0 | — |
| I-061 | 0.40 | 0.080 | 0.40 | 0.080 | 0.40 | >50.0 | 0.40 | >50.0 | — |
| I-062 | 0.40 | 0.40 | 1.2+ | 0.080 | 0.40 | 50.0[a] | 2.0 | 50.0[a] | — |
| I-063 | 0.40 | 0.40 | ≥0.4 | 0.080 | 0.40 | >50.0 | 2.0 | ≥50.0 | — |
| I-064 | 2.0 | 0.40 | 0.40 | 0.080 | 0.40 | ≥2.0 | ≥0.08 | ≥2.0 | — |
| I-065 | 2.0 | 0.40 | 0.40 | 0.080 | 0.40 | ≥2.0 | ≥0.08 | ≥2.0 | — |
| I-066 | ≥0.4 | ≥0.4 | ≥0.4 | 0.080 | 0.40 | 50.0 | ≥0.4 | ≥10.0 | — |
| I-067 | 0.40 | 0.080 | 0.080 | 0.080 | 0.40 | >50.0 | 0.40 | ≥2.0 | — |
| I-068 | 0.40 | 0.40 | ≥0.08 | 0.080 | 0.40 | >50.0 | 0.40 | ≥50.0 | — |
| I-069 | 0.40 | 0.40 | 0.40 | 0.080 | 0.40 | >50.0 | ≥0.4 | ≥50.0 | — |
| I-070 | 0.40 | 2.0 | 0.40 | 0.080 | 0.080 | >50.0 | 2.0 | ≥10.0 | — |
| I-071 | 0.40 | 0.40 | 0.40 | 0.080 | 0.40 | ≥50.0 | ≥0.08 | ≥50.0 | — |
| I-072 | 2.0 | ≥0.08 | 0.40 | 0.080 | 0.40 | 10.0 | ≥0.4 | ≥2.0 | — |

TABLE 2-continued

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | | | | Percentage of Inhibition | | | | | |
| | ≥90% | ≥90% | ≥90% | ≥90% | ≥90% | ≥90% | ≥90% | ≥90% | ≥75% |
| Cmpd. No. | | | | Compound Concentration (ppm) | | | | | |
| I-073 | 2.0 | 0.40 | 2.0 | 0.080 | 0.40 | >50.0 | ≥0.4 | ≥10.0 | — |
| I-074 | 2.0 | 2.0 | 2.0 | 0.080 | 0.40 | ≥50.0 | 0.40 | >50.0 | — |
| I-075 | 2.0 | 0.40 | 0.40 | 0.080 | 0.40 | >50.0 | 0.080 | >50.0 | — |
| I-076 | 2.0 | 0.40 | 0.40 | 0.080 | 0.40 | ≥50.0 | 0.080 | ≥10.0 | — |
| I-077 | 2.0 | 2.0 | 2.0 | 0.080 | 0.40 | >50.0 | 0.40 | >50.0 | — |
| I-078 | 2.0 | 2.0 | 2.0 | 0.080 | 0.40 | >50.0 | 0.40 | >50.0 | — |
| I-079 | 2.0 | 2.0 | 2.0 | 0.080 | 0.40 | >50.0 | 0.40 | >50.0 | — |
| I-080 | 0.40 | 0.080 | 0.40 | 0.080 | 2.0 | >50.0 | 0.080 | >50.0 | — |
| I-081 | 2.0 | 0.40 | 2.0 | 0.080 | 0.40 | ≥50.0 | 0.40 | >50.0 | — |
| I-082 | 2.0 | 0.40 | 0.40 | 0.080 | 0.40 | 10.0[a] | 0.24 | 30.0[a] | — |
| I-083 | 2.0 | 2.0 | 2.0 | 0.080 | 0.40 | >50.0 | 0.40 | ≥50.0 | — |
| I-084 | 0.40 | 0.40 | 0.080 | 0.080 | 0.080 | >50.0 | 0.40 | ≥10.0 | — |
| I-085 | >0.08 | 0.40 | 0.40 | 0.080 | 0.40 | >50.0 | 0.080 | ≥10.0 | — |
| I-086 | >50.0 | >50.0 | >50.0 | 0.080 | ≥2.0 | >50.0 | 10.0 | >50.0 | — |
| I-087 | 2.0 | 2.0 | >50.0 | 0.080 | 2.0 | >50.0 | 2.0 | >50.0 | — |
| I-088 | 0.080 | 2.0 | 2.0 | 0.080 | 0.40 | >50.0 | 0.080 | >50.0 | — |
| I-089 | >0.4 | >0.4 | 2.0 | 0.080 | >0.4 | ≥50.0 | 0.080 | ≥10.0 | — |
| I-090 | 2.0 | 0.080 | >0.08 | 0.080 | >0.4 | 2.0 | 0.080 | ≥2.0 | — |
| I-091 | 0.40 | ≥2.0 | 2.0 | 0.080 | 0.40 | >50.0 | 2.0 | >50.0 | — |
| I-092 | 0.40 | 0.080 | 0.40 | 0.080 | >0.40 | 2.0 | 0.080 | ≥2.0 | — |
| I-093 | 0.40 | 10.0 | 2.0 | 0.080 | 10.0 | >50.0 | 2.0 | >50.0 | — |
| I-094 | 0.080 | 0.080 | >0.4 | 0.080 | 0.080 | >50.0 | 0.080 | ≥10.0 | — |
| I-095 | 0.40 | 0.080 | 0.08 | 0.080 | 0.080 | ≥2.0 | 0.080 | >50 | — |
| I-096 | 2.0 | 0.080 | 0.40 | 0.080 | 2.0 | 2.0 | 0.080 | ≥2.0 | — |
| I-097 | 0.40 | 50.0 | ≥2.0 | 0.080 | 2.0 | >50.0 | 2.0 | >50.0 | — |
| I-098 | 2.0 | 10.0 | 2.0 | 0.40 | 10.0 | >50.0 | 10.0 | >50.0 | 11.0 |
| I-099 | 10.0 | 50.0 | 10.0 | 0.40 | 50.0 | >50.0 | 50.0 | >50.0 | 33.0 |
| I-100 | 2.0 | 50.0 | 2.0 | 0.40 | 10.0 | >50.0 | 50.0 | ≥50.0 | 1.2 |
| I-101 | 10.0 | 10.0 | 10.0 | 0.40 | 10.0 | 50.0 | 50.0 | >50.0 | 3.7 |
| I-102 | 2.0 | 2.0 | 2.0 | 0.40 | 2.0 | 10.0 | ≥2.0 | ≥50.0 | 1.2 |
| I-103 | 2.0 | 50.0 | 10.0 | 0.40 | 2.0 | >50.0 | 50.0 | >10.0 | 1.2 |
| I-104 | 2.0 | >50.0 | 10.0 | 0.40 | 10.0 | >10.0 | 10.0 | >50.0 | 11.0 |
| I-105 | 2.0 | 50.0 | 10.0 | 0.40 | 10.0 | >50.0 | >50.0 | >50.0 | 1.2 |
| I-106 | 2.0 | 10.0 | 2.0 | 0.40 | 2.0 | >50.0 | 50.0 | >50.0 | 33.3 |
| I-107 | 0.40 | >50.0 | ≥0.4 | 0.40 | >50.0 | >50.0 | >50.0 | >50.0 | >33.3 |
| I-108 | 2.0 | 10.0 | 10.0 | 0.40 | 2.0 | >50.0 | 50.0 | >50.0 | 11.1 |
| I-109 | 0.40 | 10.0 | 2.0 | 0.40 | 10.0 | >50.0 | 50.0 | >50.0 | 11.1 |
| I-110 | 2.0 | >50.0 | 10.0 | 0.40 | 2.0 | >50.0 | 50.0 | >50.0 | 33.3 |
| I-111 | 2.0 | 10.0 | 10.0 | 0.40 | 2.0 | >50.0 | 10.0 | 50.0 | 3.7 |
| I-112 | 2.0 | ≥2.0 | 10.0 | 0.40 | 10.0 | >50.0 | 50.0 | 50.0 | 3.7 |
| I-113 | 2.0 | 2.0 | 2.0 | 0.40 | 0.40 | >50.0 | 0.080 | 50.0 | — |
| I-114 | 2.0 | 10.0 | 10.0 | 0.40 | 2.0 | >50.0 | 10.0 | >50.0 | — |
| I-115 | 2.0 | ≥2.0 | ≥2.0 | 0.40 | 2.0 | >50.0 | 10.0 | ≥50.0 | — |
| I-116 | 10.0 | ≥2.0 | 10.0 | 0.40 | 10.0 | >50.0 | 2.0 | ≥50.0 | — |
| I-117 | 2.0 | 10.0 | 10.0 | 0.40 | 10.0 | >50.0 | 10.0 | >50.0 | — |
| I-118 | 2.0 | 10.0 | 2.0 | 0.40 | 0.40 | >50.0 | 50.0 | ≥50.0 | — |
| I-119 | 2.0 | 10.0 | ≥2.0 | 0.40 | 10.0 | >50.0 | 2.0 | >50.0 | — |
| I-120 | 2.0 | 2.0 | 2.0 | 0.40 | 10.0 | >50.0 | 2.0 | >50.0 | — |
| I-121 | 2.0 | 10.0 | ≥2.0 | 0.40 | >50.0 | >50.0 | 50.0 | >50.0 | — |
| I-122 | 2.0 | ≥2.0 | 10.0 | 0.40 | ≥2.0 | >50.0 | 2.0 | >50.0 | — |
| I-123 | 2.0 | ≥10.0 | 10.0 | 0.40 | 2.0 | >50.0 | 10.0 | >50.0 | — |
| I-124 | ≥0.4 | 10.0 | ≥2.0 | 0.40 | 10.0 | 50.0 | 2.0 | >50.0 | — |
| I-125 | 2.0 | ≥2.0 | >50.0 | 0.40 | 0.40 | >50.0 | ≥2.0 | >50.0 | — |
| I-126 | 2.0 | 2.0 | 2.0 | 0.40 | 1.2 | 50.0[a] | 2.0 | 50.0[a] | — |
| I-127 | 2.0 | 2.0 | 2.0 | 0.40 | 0.40 | >50.0 | 2.0 | >50.0 | — |
| I-128 | 2.0 | 10.0 | >10.0 | 0.40 | 2.0 | >50.0 | ≥2.0 | >50.0 | — |
| I-129 | 2.0 | 2.0 | 10.0 | 0.40 | 2.0 | 50.0 | 2.0 | >50.0 | — |
| I-130 | 2.0 | 2.0 | ≥2.0 | 0.40 | ≥0.4 | 50.0 | ≥2.0 | ≥50.0 | — |
| I-131 | 0.40 | 10.0 | 2.0 | 0.40 | 0.40 | >50.0 | ≥0.4 | >50.0 | — |
| I-132 | 2.0 | ≥2.0 | 10.0 | 0.40 | 0.40 | >50.0 | ≥2.0 | >50.0 | — |
| I-133 | 2.0 | 0.40 | 2.0 | 0.40 | 0.40 | 50.0 | ≥2.0 | ≥50.0 | — |
| I-134 | 2.0 | 0.40 | ≥2.0 | 0.40 | 2.0 | ≥10.0 | ≥0.4 | ≥10.0 | — |
| I-135 | 2.0 | 10.0 | ≥10.0 | 0.40 | 2.0 | >50.0 | ≥2.0 | 50.0 | — |
| I-136 | 2.0 | 10.0 | ≥10.0 | 0.40 | 2.0 | >50.0 | ≥2.0 | >50.0 | — |
| I-137 | 2.0 | 2.0 | 2.0 | 0.40 | ≥0.4 | ≥50.0 | ≥2.0 | ≥10.0 | — |
| I-138 | 10.0 | 10.0 | ≥10.0 | 0.40 | 10.0 | >50.0 | ≥2.0 | >50.0 | — |
| I-139 | 2.0 | 10.0 | 10.0 | 0.40 | 0.40 | 50.0[a] | 2.0 | 50.0[a] | — |
| I-140 | 2.0 | 10.0 | 10.0 | 0.40 | 0.40 | >50.0 | 2.0 | >50.0 | — |
| I-141 | 2.0 | ≥2.0 | 2.0 | 0.40 | ≥2.0 | >50.0 | 10.0 | >50.0 | — |
| I-142 | 2 | 10 | 50 | 0.4 | 0.4 | ≥50 | 2 | >50 | — |

TABLE 2-continued

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | Percentage of Inhibition | | | | | | | | |
| | ≥90% | ≥90% | ≥90% | ≥90% | ≥90% | ≥90% | ≥90% | ≥90% | ≥75% |
| Cmpd. No. | Compound Concentration (ppm) | | | | | | | | |
| I-143 | 2.0 | 50.0 | 10.0 | 2.0 | ≥10.0 | >50.0 | >50.0 | >50.0 | 11.0 |
| I-144 | 10.0 | 50.0 | 10.0 | 2.0 | 10.0 | >50.0 | >50.0 | >50.0 | 11.0 |
| I-145 | 50.0 | 50.0 | 50.0 | 2.0 | >50.0 | >50.0 | >50.0 | >50.0 | >33.0 |
| I-146 | 2.0 | 10.0 | 50.0 | 2.0 | 50.0 | >50.0 | 50.0 | >50.0 | — |
| I-147 | 10.0 | 50.0 | >50.0 | 2.0 | 2.0 | >50.0 | 50.0 | >50.0 | 33.0 |
| I-148 | 10.0 | 50.0 | >10.0 | 2.0 | 50.0 | >50.0 | 50.0 | >50.0 | 33.0 |
| I-149 | 10.0 | 50.0 | 50.0 | 2.0 | 2.0 | >50.0 | >50.0 | >50.0 | 11.0 |
| I-150 | 2.0 | 50.0 | ≥10.0 | 2.0 | 10.0 | >50.0 | 10.0 | >50.0 | — |
| I-151 | 10.0 | 50.0 | 10.0 | 2.0 | 2.0 | >50.0 | >50.0 | >50.0 | 11.0 |
| I-152 | 10.0 | 50.0 | 50.0 | 2.0 | >50.0 | >50.0 | >50.0 | >50.0 | >33.0 |
| I-153 | 2.0 | >50.0 | 50.0 | 2.0 | >50.0 | >50.0 | 50.0 | >50.0 | >33.3 |
| I-154 | 2.0 | 50.0 | 10.0 | 2.0 | 50.0 | >50.0 | >50.0 | >50.0 | 3.7 |
| I-155 | 2.0 | 50.0 | 10.0 | 2.0 | 10.0 | >50.0 | 50.0 | >50.0 | 33.3 |
| I-156 | 10.0 | 50.0 | 50.0 | 2.0 | 10.0 | >50.0 | 10.0 | >50.0 | — |
| I-157 | 10.0 | ≥10.0 | 10.0 | 2.0 | ≥10.0 | >50.0 | 50.0 | ≥50.0 | — |
| I-158 | 10.0 | >50.0 | 50.0 | 2.0 | >50.0 | 50.0 | 10.0 | >50.0 | — |
| I-159 | 10.0 | ≥10.0 | ≥50.0 | 2.0 | 2.0 | >50.0 | ≥10.0 | >50.0 | — |
| I-160 | 2.0 | ≥10.0 | 10.0 | 2.0 | 2.0 | >50.0 | ≥50.0 | >50.0 | — |
| I-161 | 10.0 | 10.0 | 50.0 | 2.0 | 10.0 | >50.0 | ≥2.0 | >50.0 | — |
| I-162 | 10.0 | 2.0 | 10.0 | 2.0 | 10.0 | >50.0 | 2.0 | >50.0 | — |
| I-163 | 10.0 | 50.0 | ≥10.0 | 2.0 | 2.0 | >50.0 | 10.0 | >50.0 | — |
| I-164 | 50.0 | 10.0 | 10.0 | 2.0 | 2.0 | >50.0 | 50.0 | >50.0 | — |
| I-165 | 2.0 | 2.0 | 2.0 | ≥0.08 | 2.0 | >50.0 | 2.0 | >50.0 | — |
| I-166 | 2.0 | 2.0 | ≥2.0 | ≥0.08 | 2.0 | >50.0 | 10.0 | ≥50.0 | — |
| I-167 | 2.0 | ≥0.4 | 2.0 | ≥0.08 | 2.0 | 50.0 | ≥0.4 | >50.0 | — |
| I-168 | 0.40 | 0.40 | 2.0 | ≥0.4 | ≥0.4 | >50.0 | 2.0 | ≥10.0 | 1.2 |
| I-169 | 10.0 | 50.0 | ≥10.0 | ≥0.4 | 50.0 | >50.0 | >50.0 | >50.0 | 11.0 |
| I-170 | 10.0 | ≥50.0 | 50.0 | ≥2.0 | >50.0 | >50.0 | 50.0 | >50.0 | — |
| I-171 | 0.08 | 0.08 | 0.08 | 0.08 | ≥0.4 | ≥10.0 | 0.08 | ≥2.0 | — |
| I-172 | 2.0 | 50.0 | 10.0 | 2.0 | 50.0 | >50.0 | 10.0 | >50.0 | — |
| I-177 | 2.0 | 2.0 | 2.0 | 0.08 | 0.4 | >50.0 | 10.0 | >50.0 | — |
| I-178 | 2.0 | ≥0.4 | 2.0 | 0.4 | 2.0 | >50.0 | 0.4 | ≥50.0 | — |
| I-179 | 2.0 | ≥2.0 | 10.0 | 0.4 | >2.0 | >50.0 | 10.0 | >50.0 | — |
| I-180 | 2.0 | 50.0 | >50.0 | 0.4 | 10.0 | >50.0 | 10.0 | >50.0 | — |
| I-181 | 0.4 | 0.08 | ≥0.08 | 0.08 | 0.4 | 10.0 | 0.08 | ≥10.0 | — |
| I-182 | 2.0 | 2.0 | 2.0 | 0.08 | 2.0 | >50.0 | 0.4 | >50.0 | — |
| I-183 | 10.0 | >50.0 | >50.0 | 2.0 | 50.0 | >50.0 | 2.0 | >50.0 | — |
| I-184 | 2.0 | 0.4 | 0.4 | 0.08 | 2.0 | 50.0 | 0.08 | >50.0 | — |
| I-185 | 0.4 | 0.4 | 0.4 | 0.08 | 0.08 | ≥10 | 0.08 | ≥50.0 | — |
| I-186 | 0.4 | 2 | 2 | 0.08 | 0.08 | >50.0 | 0.4 | >50.0 | — |
| I-187 | 2 | 10 | 10 | 0.4 | 0.4 | ≥50.0 | 0.4 | >50.0 | — |
| I-188 | 0.4 | 2 | 2 | 0.08 | 0.4 | >50.0 | 0.4 | >50.0 | — |
| I-189 | 0.4 | 0.4 | 0.4 | 0.08 | 0.4 | >50.0 | 0.08 | 50.0 | — |
| I-191 | 0.4 | ≥0.4 | ≥0.4 | 0.08 | 0.4 | 50 | 0.08 | ≥10 | — |
| I-192 | 0.4 | ≥2 | 2 | 0.08 | 0.4 | 50 | 0.08 | ≥50 | — |
| I-193 | ≥0.08 | ≥0.08 | 0.08 | 0.08 | 0.4 | 2 | 0.08 | ≥2 | — |
| I-194 | 10 | 50 | 50 | 2 | ≥10 | >50 | 10 | >50 | — |
| I-195 | 2 | 2 | ≥2 | 2 | 2 | >50 | 2 | >50 | — |
| I-196 | 2 | 10 | 10 | 0.4 | 2 | >50 | 2 | >50 | — |
| I-197 | 0.4 | 10 | 10 | 0.4 | ≥2 | >50 | 0.4 | ≥50 | — |
| I-198 | 0.4 | 0.08 | 0.08 | 0.08 | 0.4 | 2 | 0.08 | ≥2 | — |
| I-200 | 2 | >50 | >50 | 2 | 2 | >50 | 2 | >50 | — |
| I-201 | 2 | 10 | ≥2 | 0.4 | ≥0.4 | >50 | 0.08 | >50 | — |
| I-202 | ≥0.4 | 2 | 2 | 0.08 | 0.4 | ≥50 | 0.4 | >50 | — |
| I-204 | 2 | 10 | 2 | 0.4 | 2 | >50 | 2 | >50 | — |
| I-205 | 0.4 | 0.4 | ≥0.08 | 0.4 | 0.4 | >50 | 0.08 | >50 | — |
| I-206 | 0.4 | 0.4 | 0.4 | 0.08 | 0.4 | >50 | 0.08 | >50 | — |
| I-207 | 2 | 10 | ≥2 | 0.08 | 2 | >50 | 0.08 | >50 | — |
| I-208 | 0.4 | 2 | 2 | 0.4 | 0.4 | >50 | 0.08 | >50 | — |
| I-209 | 2 | 50 | ≥10 | 0.08 | 10 | >50 | 0.08 | >50 | — |
| I-210 | 0.4 | ≥0.4 | 0.4 | 2 | 0.4 | >50 | 0.08 | >50 | — |
| I-211 | 0.4 | 0.08 | 0.08 | 0.08 | 0.4 | >50 | 0.08 | >50 | — |
| I-212 | 0.4 | 0.08 | ≥0.08 | 0.08 | 0.4 | >50 | 0.08 | >50 | — |
| I-213 | 0.4 | 0.4 | ≥0.08 | 0.08 | 0.4 | >50 | 0.08 | >50 | — |
| I-214 | 2 | 2 | ≥10 | 0.4 | 2 | >50 | 2 | >50 | — |
| I-218 | 10 | 10 | 50 | 2 | 2 | ≥50 | 2 | >50 | — |
| I-219 | 2 | 10 | >10 | 0.4 | ≥10 | >50 | >50 | >50 | — |
| I-220 | 0.4 | 0.4 | 0.4 | 0.08 | 0.4 | ≥10 | 0.08 | >50 | — |
| I-222 | 2 | 2 | 10 | 0.40 | 0.4 | >50 | 0.4 | 50 | — |
| I-224 | 2 | 10 | >50 | 2 | 2 | >50 | 0.08 | >50 | — |

TABLE 2-continued

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | | | | Percentage of Inhibition | | | | | |
| | ≥90% | ≥90% | ≥90% | ≥90% | ≥90% | ≥90% | ≥90% | ≥90% | ≥75% |
| Cmpd. No. | | | | Compound Concentration (ppm) | | | | | |
| I-225 | 10 | >50 | >10 | 2 | ≥50 | >50 | 10 | >50 | — |
| I-226 | 2 | 2 | ≥2 | 0.08 | 2 | >50 | 0.08 | >50 | — |
| I-229 | 2 | 2 | 2 | 0.08 | 0.4 | >50 | 2 | >50 | — |
| I-230 | 2 | 10 | ≥10 | 0.4 | 0.4 | >50 | 0.08 | ≥10 | — |
| I-231 | 2 | 0.4 | 0.4 | 0.08 | 2 | >50 | 0.08 | ≥10 | — |
| I-232 | 10 | 10 | 50 | 2 | 0.4 | >50 | 2 | >50 | — |
| I-233 | 0.4 | 0.4 | 0.4 | 0.08 | 0.4 | ≥2 | 2.0 | ≥10 | — |
| I-234 | 2 | 2 | 2 | 0.08 | 2 | >50 | 2 | >10 | — |
| I-235 | 2 | 2 | ≥2 | 0.4 | 2 | >50 | 2 | >50 | — |
| I-238 | 2 | 10 | 10 | 2 | 10 | >50 | 10 | >50 | — |
| I-239 | 2 | 2 | 2 | 0.08 | 0.08 | ≥10 | 0.08 | ≥10 | — |
| I-242 | 2 | 2 | 2 | 0.4 | 2 | >50 | 2 | ≥50 | — |
| I-243 | 10 | 2 | 10 | 2 | 50 | >50 | 2 | ≥50 | — |
| I-244 | 2 | 2 | 10 | 0.4 | 2 | 10 | 0.4 | ≥50 | — |
| I-245 | 0.4 | 0.40 | 2.0 | 0.08 | 0.08 | 50 | 0.08 | ≥2 | — |
| I-246 | 0.4 | 0.08 | 0.4 | 0.08 | 0.08 | 10 | 0.1 | ≥2 | — |
| I-247 | 0.4 | 0.4 | 2.0 | 0.08 | 0.4 | >50 | 2 | ≥10 | — |
| I-248 | 2.0 | 2.0 | ≥10 | 0.4 | 0.4 | >50 | 10 | ≥10 | — |
| I-249 | 2.0 | 2.0 | ≥10 | 2.0 | 2.0 | >50 | 10 | >50 | — |
| I-250 | 2.0 | 10.0 | >50 | 2.0 | 2.0 | >50 | 2 | >50 | — |
| I-251 | 0.4 | 2.0 | 2.0 | 0.08 | 0.4 | >50 | 0.4 | >10 | — |
| I-253 | 0.4 | 0.4 | 0.4 | 0.08 | 0.4 | ≥50 | 0.08 | ≥2 | — |
| I-254 | 2.0 | >50 | ≥10 | 2.00 | >50 | >50 | >50 | >50 | — |
| I-255 | 2.0 | ≥10 | ≥10 | 2.00 | ≥10 | >50 | 2 | >50 | — |
| I-257 | 2.0 | 2.0 | 50.0 | 0.4 | 0.40 | >50 | 2 | >50 | — |
| I-258 | 0.4 | 0.08 | 0.4 | 0.08 | 0.40 | ≥10 | 0.08 | ≥2 | — |
| I-259 | 0.4 | 0.08 | 0.4 | 0.08 | 0.40 | >50 | 0.08 | >10 | — |
| I-262 | 0.4 | 0.08 | 2.0 | ≥0.08 | 0.40 | ≥10 | 0.08 | ≥2 | — |
| I-263 | 0.4 | 0.4 | 2.0 | ≥0.08 | 0.40 | ≥50 | 0.4 | >10 | — |
| I-264 | 0.4 | 2 | 2 | 0.08 | 0.4 | 50 | 0.08 | >50 | — |
| I-265 | 0.4 | 2 | 2 | 0.08 | 0.4 | ≥50 | 0.08 | ≥50 | — |
| I-266 | 2 | 10 | 10 | 2 | 2 | ≥50 | 2 | >50 | — |
| I-267 | 0.4 | 2 | 2 | 0.08 | 0.4 | >50 | 0.4 | >50 | — |
| I-268 | 2 | 2 | ≥2 | 0.08 | 2 | >50 | 0.4 | >50 | — |
| I-269 | 10 | >50 | >50 | 0.4 | 10 | >50 | 2 | >50 | — |
| I-270 | 0.4 | 2 | 2 | 0.08 | 0.4 | >50 | >50 | >50 | — |
| I-271 | 10 | ≥10 | 50 | 2.0 | 10 | 50 | 2 | >50 | — |
| I-272 | 2 | 2 | 2 | 2.0 | 2 | >50 | 2 | >50 | — |
| I-273 | 0.4 | 2 | 50 | 0.08 | 0.4 | >50 | 2 | >50 | — |
| I-274 | 0.4 | 0.08 | 0.4 | 0.08 | 0.4 | 2 | 0.08 | >50 | — |
| I-276 | 2 | 2 | 2 | 0.4 | 2 | 10 | 0.08 | >50 | — |
| I-277 | 0.4 | 0.4 | 2 | 0.08 | 0.08 | >50 | 0.08 | >50 | — |
| I-278 | 2 | 0.4 | 2 | 0.4 | 2 | 10 | 0.4 | >50 | — |
| I-279 | 0.08 | 0.08 | 2 | 0.08 | 0.08 | >50 | 0.08 | >50 | — |
| I-280 | 2 | 2 | 2 | 0.08 | 0.4 | 50 | 0.08 | ≥50 | — |
| I-281 | 0.08 | 0.08 | 2 | 0.08 | 0.08 | >50 | 0.08 | >50 | — |
| I-282 | 2 | 2 | ≥10 | 0.4 | 2 | 10 | 0.4 | >50 | — |
| I-283 | 10 | 50 | >50 | 2 | 10 | >50 | 2 | >50 | — |
| I-284 | 0.4 | 0.08 | 2 | 0.08 | 0.40 | >50 | 0.08 | >50 | — |
| I-285 | 2 | 0.4 | ≥2 | 0.4 | 2 | 50 | 0.4 | ≥50 | — |
| I-286 | 2 | 2 | ≥50 | 2 | 2 | ≥50 | 2 | >50 | — |
| I-287 | 2 | 0.4 | 0.4 | 0.4 | 2 | 10 | 0.08 | ≥50 | — |
| I-289 | 2 | 0.08 | 0.4 | 0.08 | 0.4 | ≥10 | 0.08 | >50 | — |
| I-290 | 2 | 10 | ≥10 | 0.4 | 10 | >50 | 2 | >50 | — |
| I-292 | 2 | 2 | 2 | 0.08 | 0.4 | >50 | 0.4 | >50 | — |
| I-293 | 10 | >50 | >50 | 2 | 50 | >50 | >50 | >50 | — |
| I-294 | 0.4 | 10 | 10 | 0.4 | 0.08 | >50 | 2.0 | >50 | — |
| I-295 | 2 | 2 | 10 | 0.4 | 2 | >50 | 2.0 | >50 | — |
| I-296 | 2 | 2 | 10 | 2 | 2 | >50 | 2.0 | >50 | — |
| I-297 | 10 | 10 | >50 | 2 | >50 | >50 | >50 | >50 | — |
| I-298 | 2 | 10 | ≥10 | 2 | 2 | >50 | >50 | >50 | — |
| I-299 | 2 | 10 | 50 | 0.4 | 2 | >50 | 50.0 | >50 | — |
| I-300 | 2 | 2 | 50 | 0.08 | 0.4 | >50 | 0.08 | >50 | — |
| I-301 | 10 | >50 | >50 | 2 | ≥2 | >50 | 10.0 | >50 | — |
| I-302 | 10 | 50 | 50 | ≥2 | 2 | >50 | 0.08 | >50 | — |
| I-303 | 0.4 | 2 | ≥2 | 0.08 | 2 | >50 | 2.00 | >50 | — |
| I-304 | 2 | 2 | ≥10 | 0.08 | 0.4 | >50 | 2.0 | >50 | — |
| I-305 | 0.4 | 2 | 2 | 0.08 | 0.4 | >50 | 0.4 | >50 | — |
| I-307 | ≥0.4 | 2 | 2 | 0.08 | 0.4 | >50 | 0.08 | >50 | — |
| I-308 | 0.4 | 2 | 2 | 0.4 | 2 | 50 | 0.08 | >50 | — |

TABLE 2-continued

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | Percentage of Inhibition | | | | | | | | |
| | ≥90% | ≥90% | ≥90% | ≥90% | ≥90% | ≥90% | ≥90% | ≥90% | ≥75% |
| Cmpd. No. | Compound Concentration (ppm) | | | | | | | | |
| I-310 | 2 | 2 | ≥2 | 0.08 | 0 | >50 | 0.08 | >50 | — |
| I-313 | >50 | 50 | >50 | 2 | 50 | >50 | 50.0 | >50 | — |
| I-314 | >50 | 50 | >50 | 2 | 10 | >50 | >50 | >50 | — |
| I-315 | 0.4 | 0.08 | 0.4 | 0.08 | 0.4 | 2 | 0.08 | >50 | — |
| I-316 | 0.4 | 2 | 2 | 0.08 | 0.08 | ≥10 | 0.08 | >50 | — |
| I-319 | 50 | >50 | >50 | 2 | 10 | >50 | >50 | >50 | — |
| I-321 | 0.4 | 0.4 | ≥0.4 | 0.08 | 0.4 | >50 | 2.0 | >50 | — |
| I-323 | 0.4 | 0.4 | ≥0.4 | 0.08 | 0.08 | >50 | 0.08 | >50 | — |
| I-324 | 2 | 10 | 10 | 0.4 | 2 | >50 | 2.0 | >50 | — |
| I-325 | 50 | >50 | >50 | 2 | 50 | >50 | >50 | >50 | — |
| I-326 | 2 | 2 | 2 | 0.08 | 0.08 | >50 | 10 | >50 | — |
| I-328 | 2 | 10 | 2 | 0.4 | 0.4 | >50 | 10 | >50 | — |
| I-329 | 10 | 50 | 50 | 2 | 2 | >50 | 50 | >50 | — |
| I-330 | 2 | 10 | 10 | 0.08 | 0.4 | >50 | 2 | >50 | — |
| I-331 | 2 | 10 | >50 | 0.08 | 0.08 | >50 | 10 | >50 | — |
| I-332 | >50 | >50 | >50 | 2 | 2 | >50 | >50 | >50 | — |
| I-333 | 2 | 2 | 10 | 0.4 | 10 | 50 | 2 | >50 | — |
| I-335 | 10 | 50 | 50 | 2 | 2 | >50 | 10 | >50 | — |
| I-338 | 2 | 10 | 2 | 0.08 | 0.08 | >50 | 10 | >50 | — |
| I-339 | 10 | >50 | >50 | 2 | 2 | >50 | 50 | >50 | — |
| I-340 | 10 | 50 | 50 | 2 | 2 | >50 | 50 | >50 | — |

[a]Denotes an average value derived from two experimental trials

TABLE 3

In Vitro Pathogen Growth Inhibition Assay Results

| | Pathogens | | | | | | | | |
|---|---|---|---|---|---|---|---|---|---|
| | Bc | Cg | Dm | Fm | Fv | Pc | Rs | St | Sc |
| | Percentage of Inhibition | | | | | | | | |
| | ≥90% | ≥90% | ≥90% | ≥90% | ≥90% | ≥90% | ≥90% | ≥90% | ≥75% |
| Cmpd. No. | Compound Concentration (ppm) | | | | | | | | |
| I-173 | 50 | ≥50 | >50 | 50.0 | >50 | >50 | 10 | >50 | — |
| I-174 | 10 | 50 | 10 | 10 | 10 | >50 | 50 | >50 | — |
| I-175 | 2 | 50 | 10 | 10 | >50 | >50 | >50 | >50 | — |
| I-190 | 10 | >50 | >50 | 10 | 50 | >50 | 10 | >50 | — |
| I-199 | 10 | 50 | 50 | 10 | 10 | >50 | 50 | >50 | — |
| I-203 | 50 | 50 | 50 | 10 | 50 | >50 | 10 | >50 | — |
| I-215 | 10 | 50 | >50 | 10 | 10 | >50 | 0.08 | >50 | — |
| I-221 | 10 | 50 | >50 | 10 | 50 | >50 | >50 | >50 | — |
| I-227 | 50 | >50 | >50 | 10 | >50 | >50 | 0.4 | >50 | — |
| I-228 | 10 | >50 | >50 | 10 | 10 | >50 | 2 | >50 | — |
| I-256 | 50.0 | 50.0 | 50.0 | 10.0 | 50.0 | >50 | 50 | >50 | — |
| I-275 | 50 | 50 | >50 | 50 | >50 | >50 | 50 | >50 | — |
| I-291 | 50 | >50 | 50 | 10 | 50 | >50 | 2 | >50 | — |
| I-306 | 50 | >50 | >50 | 10 | >50 | >50 | >50 | >50 | — |
| I-309 | 50 | >50 | >50 | 10 | 10 | >50 | >50 | >50 | — |
| I-311 | 50 | >50 | >50 | 50 | >50 | >50 | >50 | >50 | — |
| I-312 | >50 | >50 | >50 | 10 | >50 | >50 | 2.0 | >50 | — |
| I-317 | 50 | 50 | >50 | 10 | ≥10 | >50 | >50 | >50 | — |
| I-318 | 50 | >50 | >50 | 10 | >50 | >50 | >50 | >50 | — |
| I-320 | 50 | >50 | >50 | 50 | 50 | >50 | >50 | >50 | — |
| I-322 | 10 | >50 | >50 | 10 | ≥10 | >50 | >50 | >50 | — |
| I-334 | >50 | >50 | >50 | 50 | >50 | >50 | >50 | >50 | — |
| I-336 | 50 | >50 | >50 | 10 | 10 | >50 | >50 | >50 | — |
| I-337 | 50 | >50 | >50 | 10 | 10 | >50 | 10 | >50 | — |
| I-341 | >50 | >50 | >50 | >50 | >50 | >50 | >50 | >50 | — |

Example 2: Foliar Protection Test for Barley Powdery Mildew Control

Plants (*Hordeum vulgare* cv. Perry) were grown for 6 days in 2-inch square pots containing Metromix 200 medium amended with fertilizer. For propagation, plants were maintained in a growth chamber at conditions of 20 to 21° C., 16 hour light cycle, 400 uM of light, 70% humidity, and with sub-irrigation as needed. After inoculation with the pathogen of *Blumeria graminis* f. sp. *hordei*, plants were kept at conditions of 20 to 22° C., 70% relative humidity, and 200 uM of light to facilitate infection and disease development.

At 6 days after planting (1st true leaf fully expanded), the test compounds were dissolved in a solution of 5% acetone and 0.005% Tween 80 surfactant. An atomizer was used for applying the solution onto both sides of the leaves until thoroughly wetted. The amount of the compound applied to the leaves was typically 200, 100, 50, 10, or 2 ppm, but it may vary.

At 24 hours after treatment, the plants were moved to a cooler chamber and inoculated by shaking well-colonized, untreated stock plants above the treated plants. This allowed producing a settling cloud of spores and resulting in uniform infection.

Efficacy was evaluated in 7 days later by examining leaves for colonization and growth of mildew. Table 4 lists the results of barley powdery mildew control at a compound concentration of 10 ppm or lower. Compounds having an activity designated as "AA" provided a compound having ≥85% control of barley powdery mildew; compounds having an activity designated as "A" provided a compound having from 70% to 84% control of barley powdery mildew; compounds having an activity designated as "B" provided a compound having from 50 to 69% control of barley powdery mildew; compounds having an activity designated as "C" provided a compound having from 25 to 49% control of barley powdery mildew; and compounds having an activity designated as "D" provided a compound having <25% control of barley powdery mildew.

TABLE 4

Compounds with Barley Powdery Mildew Control at 10 ppm or Lower

| Cmpd. No. | Barley Powdery Mildew Control at a compound concentration of 10 ppm or lower |
| --- | --- |
| I-003 | A |
| I-014 | AA |
| I-020 | AA |
| I-030 | AA |
| I-034 | AA |
| I-035 | A |
| I-064 | A |
| I-074 | AA |
| I-082 | AA |
| I-084 | AA |
| I-089 | B |
| I-090 | A |
| I-092 | C |
| I-094 | AA |
| I-095 | AA |
| I-096 | B |
| I-171 | AA |
| I-181 | AA |
| I-184 | A |
| I-185 | AA |
| I-186 | A |
| I-188 | AA |
| I-189 | AA |
| I-191 | AA |
| I-192 | AA |
| I-193 | AA |
| I-198 | AA |
| I-202 | A |
| I-205 | AA |
| I-206 | AA |
| I-208 | AA |
| I-210 | AA |
| I-211 | AA |
| I-212 | AA |
| I-213 | A |
| I-220 | AA |
| I-229 | AA |
| I-231 | AA |
| I-233 | AA |
| I-234 | AA |
| I-239 | AA |
| I-246 | A |
| I-251 | AA |
| I-253 | A |
| I-258 | A |
| I-259 | A |
| I-262 | A |
| I-263 | A |
| I-274 | AA |
| I-281 | AA |
| I-284 | AA |
| I-285 | A |
| I-287 | AA |
| I-289 | AA |
| I-292 | AA |
| I-307 | AA |
| I-308 | AA |
| I-310 | AA |
| I-316 | AA |
| I-323 | AA |

Example 3: Foliar Protection for Cucumber Powdery Mildew Control

Plants (*Cucumis sativus* cv. Straight Eight) were grown for 10 days in 2.5-inch square pots containing Metromix 200 medium amended with fertilizer. For propagation, plants were maintained in a growth chamber at conditions of 23 to 27° C., 16 hour light cycle, ambient humidity, and with sub-irrigation as needed. After inoculation with the pathogen of *Sphaerotheca fuliginea*, plants were kept at conditions of 23 to 27° C., 16 hour light cycle, 60% relative humidity, and with sub-irrigation as needed to facilitate infection and disease development.

At 10 days after planting ($1^{st}$ true leaf 75% expanded and $2^{nd}$ leaf not yet emerged) the test compounds were dissolved in 5% acetone and 0.05% Tween 20 surfactant. An atomizer was used for applying the solution onto both sides of the leaves until thoroughly wetted. The amount of the compound applied to the leaves was typically 200, 100, 50, or 10 ppm, but it may vary.

At 24 hours after treatment, the plants were moved to a cooler chamber and inoculated by shaking well-colonized, untreated stock plants above the treated plants. This allowed producing a settling cloud of spores and resulting in uniform infection. Inoculated plants were kept near other sporulating stock plants to allow for infection of newly emerging leaves.

Efficacy was evaluated in 7 days later by examining leaves for colonization and growth of mildew. Table 5 lists the results of cucumber powdery mildew control at a compound concentration of 10 ppm or lower. Compounds having an activity designated as "AA" provided a compound having ≥85% control of cucumber powdery mildew; compounds having an activity designated as "A" provided a compound having from 70% to 84% control of cucumber powdery mildew; compounds having an activity designated as "B" provided a compound having from 50 to 69% control of cucumber powdery mildew; compounds having an activity designated as "C" provided a compound having from 25 to 49% control of cucumber powdery mildew; and compounds having an activity designated as "D" provided a compound having <25% control of cucumber powdery mildew.

TABLE 5

Compounds with Cucumber Powdery Mildew Control at 10 ppm or Lower

| Cmpd. No. | Cucumber Powdery Mildew Control at a compound concentration of 10 ppm or lower |
|---|---|
| I-003 | AA |
| I-014 | AA |
| I-020 | AA |
| I-030 | AA |
| I-034 | AA |
| I-035 | AA |
| I-064 | AA |
| I-074 | AA |
| I-082 | AA |
| I-089 | AA |
| I-090 | A |
| I-092 | AA |
| I-094 | AA |
| I-095 | AA |
| I-096 | AA |
| I-171 | AA |
| I-181 | AA |
| I-184 | AA |
| I-185 | AA |
| I-186 | C |
| I-188 | AA |
| I-189 | AA |
| I-191 | AA |
| I-192 | AA |
| I-193 | AA |
| I-198 | AA |
| I-202 | AA |
| I-205 | AA |
| I-206 | AA |
| I-208 | AA |
| I-210 | AA |
| I-211 | AA |
| I-212 | AA |
| I-213 | AA |
| I-220 | AA |
| I-229 | AA |
| I-231 | AA |
| I-233 | A |
| I-234 | AA |
| I-239 | AA |
| I-246 | AA |
| I-251 | AA |
| I-253 | AA |
| I-258 | AA |
| I-259 | AA |
| I-262 | AA |
| I-263 | AA |
| I-274 | AA |
| I-281 | AA |
| I-284 | AA |
| I-285 | AA |
| I-287 | AA |
| I-289 | AA |
| I-292 | AA |
| I-307 | AA |
| I-308 | AA |
| I-310 | AA |
| I-316 | AA |
| I-323 | AA |

Example 4: Foliar Protection Test for Wheat Septoria Leaf Blotch Control

Plants (*Triticum aestivum* cv. WinterHawk) were grown for 14 days in 2-inch square pots containing Metromix 200 medium amended with fertilizer. For propagation, plants were maintained at in a growth chamber at conditions of 24 to 26° C., 16 hour light cycle, 400 uM of light, 60% humidity, and with sub-irrigation as needed. After inoculation with the pathogen of *Mycosphaerella graminicola* (synthetic *Septoria tritici*), plants were kept at conditions of 16 to 20° C., 75% relative humidity, and 200 uM of light to facilitate infection and disease development.

Cultures of the pathogen were maintained on oatmeal agar amended with cefotaxime (200 mg/L) at an ambient temperature, and the 14-day old cultures were used for preparing spore suspensions at a concentration of $1 \times 10^7$ million spores/ml in a solution of 0.01% Tween 20 in water.

At 14 days after planting (2 true leaves fully expanded), the test compounds were dissolved in a solution of 5% acetone and 0.01% Tween 20 surfactant. An atomizer was used for applying the solution onto both sides of the leaves until thoroughly wetted. The amount of the compound applied to the leaves was typically 100, or 25 ppm, but it may vary.

At 1 hour after treatment, the plants were moved to a cooler chamber and inoculated by spraying the spore suspension until all leaf surfaces were wetted. The inoculated plants were then incubated for 3 days in a misting tent covered with a thin shade cloth. After misting for 3 days, they were removed from the mist tent and grown for 16 days before rating.

Efficacy was evaluated in 16 days later by examining the two treated leaves for diseased area. Table 6 lists the results of wheat *septoria* leaf blotch control at a compound concentration of 25 ppm or lower. Compounds having an activity designated as "AA" provided a compound having ≥85% control of wheat *septoria* leaf blotch; compounds having an activity designated as "A" provided a compound having from 70% to 84% control of wheat *septoria* leaf blotch; compounds having an activity designated as "B" provided a compound having from 50 to 69% control of wheat *septoria* leaf blotch; compounds having an activity designated as "C" provided a compound having from 25 to 49% control of wheat *septoria* leaf blotch; and compounds having an activity designated as "D" provided a compound having <25% control of wheat *septoria* leaf blotch.

TABLE 6

Compounds with Wheat *Septoria* Leaf Blotch Control at 25 ppm or Lower

| Cmpd. No. | *Septoria* Leaf Blotch Control at a compound concentration of 25 ppm or lower |
|---|---|
| I-003 | C |
| I-014 | D |
| I-020 | B |
| I-030 | B |
| I-034 | B |

TABLE 6-continued

Compounds with Wheat *Septoria* Leaf Blotch Control at 25 ppm or Lower

| Cmpd. No. | *Septoria* Leaf Blotch Control at a compound concentration of 25 ppm or lower |
|---|---|
| I-035 | C |
| I-064 | A |
| I-074 | AA |
| I-082 | AA |
| I-084 | AA |
| I-089 | C |
| I-090 | A |
| I-092 | B |
| I-094 | A |
| I-095 | AA |
| I-096 | B |
| I-171 | AA |
| I-181 | B |
| I-184 | C |
| I-185 | AA |
| I-186 | D |
| I-188 | C |
| I-189 | A |
| I-191 | AA |
| I-192 | A |
| I-193 | AA |
| I-198 | AA |
| I-202 | D |
| I-205 | AA |
| I-206 | AA |
| I-208 | AA |
| I-210 | AA |
| I-211 | AA |
| I-212 | AA |
| I-213 | AA |
| I-220 | B |
| I-229 | D |
| I-231 | C |
| I-233 | C |
| I-234 | C |
| I-239 | D |
| I-246 | A |
| I-251 | C |
| I-253 | AA |
| I-258 | B |
| I-259 | C |
| I-262 | AA |
| I-263 | D |
| I-274 | AA |
| I-281 | AA |
| I-284 | AA |
| I-285 | C |
| I-287 | AA |
| I-289 | AA |
| I-292 | B |
| I-307 | B |
| I-308 | AA |
| I-310 | B |
| I-316 | A |
| I-323 | AA |

Example 5: Foliar Protection Test for Wheat *Fusarium* Head Blight Control

Plants (*Triticum aestivum* cv. Samson) were grown until flowing in 4.5-inch square pots containing Metromix 200 medium amended with fertilizer. For propagation, plants were maintained at in a growth chamber at conditions of 20 to 21° C., 16 hour light cycle, 400 uM of light, 70% humidity, and with sub-irrigation as needed. After inoculation with the pathogen of *Fusarium graminearum*, plants were kept at the same conditions to facilitate disease development.

Cultures of the pathogen were maintained on ¼ strength potato dextrose agar at conditions of 21° C. and 16 hour light cycle. New cultures were started at regular intervals so spores were readily available. Conidia were harvested by flooding the plates with distilled water, scraping, and then filtering through cheesecloth. Spore concentration is adjusted to $5\times10^5$ conidia per ml in water.

When wheat plants were flowering, the test compounds were dissolved in a solution of 5% acetone and 0.02% Tween 20 surfactant. An atomizer was used for applying the solution onto both sides of the leaves until thoroughly wetted. The amount of the compound applied to the leaves was typically 100, or 25 ppm, but it may vary.

At 24 hours after treatment, the plants were inoculated by spraying the conidial suspension until the heads were thoroughly wetted. The inoculated plants were then placed for 3 days in a misting tent at 22° C. during the day and 17° C. during the night with 15 hours of light. After misting, they remained in these same growth conditions for further disease development Efficacy was evaluated in 14 days later by examining plant heads for symptom development in terms of necrotic spikelets. Table 7 lists the results of wheat *fusarium* head blight control at a compound concentration of 25 ppm or lower. Compounds having an activity designated as “AA” provided a compound having ≥85% control of wheat *fusarium* head blight; compounds having an activity designated as “A” provided a compound having from 70% to 84% control of wheat *fusarium* head blight; compounds having an activity designated as “B” provided a compound having from 50 to 69% control of wheat *fusarium* head blight; compounds having an activity designated as “C” provided a compound having from 25 to 49% control of wheat *fusarium* head blight; and compounds having an activity designated as “D” provided a compound having <25% control of wheat *fusarium* head blight.

TABLE 7

Compounds with Wheat *Fusarium* Head Blight Control at 25 ppm or Lower

| Cmpd. No. | Wheat *Fusarium* Head Blight Control at a compound concentration of 25 ppm or lower |
|---|---|
| I-003 | B |
| I-014 | C |
| I-020 | B |
| I-030 | B |
| I-034 | C |
| I-035 | B |
| I-064 | C |
| I-074 | C |
| I-082 | C |
| I-089 | D |
| I-090 | D |
| I-092 | C |
| I-094 | A |
| I-095 | B |
| I-096 | D |
| I-171 | C |
| I-181 | B |
| I-184 | A |
| I-185 | A |
| I-186 | B |
| I-188 | D |
| I-189 | C |
| I-191 | C |
| I-192 | D |
| I-193 | B |
| I-198 | C |
| I-202 | D |
| I-205 | C |
| I-206 | B |
| I-208 | C |
| I-210 | C |

TABLE 7-continued

Compounds with Wheat *Fusarium* Head Blight Control at 25 ppm or Lower

| Cmpd. No. | Wheat *Fusarium* Head Blight Control at a compound concentration of 25 ppm or lower |
|---|---|
| I-211 | C |
| I-212 | B |
| I-213 | B |
| I-220 | C |
| I-229 | C |
| I-231 | C |
| I-233 | C |
| I-234 | C |
| I-239 | C |
| I-246 | B |
| I-251 | C |
| I-253 | B |
| I-258 | C |
| I-259 | B |
| I-262 | B |
| I-263 | B |
| I-274 | C |
| I-281 | C |
| I-284 | C |
| I-285 | C |
| I-287 | C |
| I-289 | C |
| I-292 | C |
| I-307 | C |
| I-308 | C |
| I-310 | C |
| I-316 | C |
| I-323 | C |

Example 6: Foliar Protection Test for Wheat Leaf Rust Control

Plants (*Triticum aestivum* cv. Winterhawk) were grown for 11 days in 2.5-inch square pots containing Metromix 200 medium amended with fertilizer. For propagation, plants were maintained in a growth chamber at conditions of 20 to 21° C., 16 hour light cycle, 400 uM of light, 60% humidity, and with sub-irrigation as needed. After inoculation with the pathogen of *Puccinia triticina*, plants were kept at conditions of 20 to 20° C. and 80% relative humidity to facilitate infection and disease development.

At 11 days after planting ($3^{rd}$ leaf fully expanded), the test compounds were dissolved in a solution of 5% acetone and 0.02% Tween 20 surfactant. An atomizer was used for applying the solution onto both sides of the leaves until thoroughly wetted. The amount of the compound applied to the leaves was typically 25 or 10 ppm, but it may vary.

Spores were collected from untreated, previously inoculated plants. The spore was suspended in a solution of 0.01% Tween 20 or 0.1% water agar.

At three hours after treatment, plants were inoculated by spraying the spore suspension on the underside of the leaves until they are wetted. Inoculated plants were then incubated for 24 hours in a misting tent at 20° C. After misting, they were grown at the same conditions as the incubation conditions with exception of having a 85% relative humidity.

Efficacy was evaluated in 10 days later by examining leaves for pustule formation and sporulation. Table 8 lists the results of wheat leaf rust control at a compound concentration of 10 ppm or lower. Compounds having an activity designated as "AA" provided a compound having ≥85% control of wheat leaf rust; compounds having an activity designated as "A" provided a compound having from 70% to 84% control of wheat leaf rust; compounds having an activity designated as "B" provided a compound having from 50 to 69% control of wheat leaf rust; compounds having an activity designated as "C" provided a compound having from 25 to 49% control of wheat leaf rust; and compounds having an activity designated as "D" provided a compound having <25% control of wheat leaf rust.

TABLE 8

Compounds with Wheat Leaf Rust Control at 10 ppm or Lower

| Cmpd. No. | Wheat Leaf Rust Control at a compound concentration of 10 ppm or lower |
|---|---|
| I-003 | AA |
| I-014 | A |
| I-020 | B |
| I-030 | AA |
| I-034 | AA |
| I-035 | AA |
| I-064 | AA |
| I-074 | A |
| I-082 | B |
| I-084 | A |
| I-089 | AA |
| I-090 | AA |
| I-092 | AA |
| I-094 | C |
| I-095 | AA |
| I-096 | A |
| I-171 | B |
| I-181 | AA |
| I-184 | AA |
| I-185 | AA |
| I-186 | C |
| I-188 | AA |
| I-189 | AA |
| I-191 | AA |
| I-192 | AA |
| I-193 | AA |
| I-198 | AA |
| I-202 | A |
| I-205 | AA |
| I-206 | AA |
| I-208 | AA |
| I-210 | A |
| I-211 | A |
| I-212 | AA |
| I-213 | B |
| I-220 | C |
| I-229 | B |
| I-231 | AA |
| I-233 | AA |
| I-234 | AA |
| I-239 | AA |
| I-246 | A |
| I-251 | D |
| I-253 | AA |
| I-258 | A |
| I-259 | C |
| I-262 | AA |
| I-263 | AA |
| I-274 | AA |
| I-281 | AA |
| I-284 | AA |
| I-285 | AA |
| I-287 | AA |
| I-289 | AA |
| I-292 | AA |
| I-307 | AA |
| I-308 | AA |
| I-310 | C |
| I-316 | AA |
| I-323 | AA |

Example 7: Foliar Protection Test for Asian Soybean Rust Control

Plants (*Glycine max* AG4832) were grown in 2.5-inch square pots containing Fafard germination mix amended with fertilizer. For propagation, plants were maintained in a growth chamber at conditions of 21 to 26° C., 16 hour light cycle, 600 uM of light, 65% humidity, and with sub-irrigation as needed. To maintain the pathogen stocks, plants are inoculated with the pathogen of *Phakopsora pachyrhizi* and placed in a mist tent for 24 hours. After inoculation with the pathogen, plants were grown at conditions of 20 to 24° C., 12 hour light cycle, 400 uE of light, and 80 to 85% relative humidity to facilitate infection and disease development. At 10 to 28 days after inoculation, spores were collected and stored at 4° C. before use.

At 16 to 19 days after planting, the test compounds were dissolved in a solution of 5% acetone and 0.02% Tween 20 surfactant. An air brush sprayer was used for applying the solution to the plant. Because of plant stature and angle of the leaves, chemistry accumulated mainly on the top of the leaf; leaves were wet but not dripping. The amount of the compound applied to the leaves was typically 25 or 100 ppm, but it may vary.

At 24 hours after treatment, the left lateral leaf from the first or second trifoliate (dependent upon the purpose of the experiment) was removed and placed in a petri dish with moist filter paper and inoculated. Leaflets were inoculated by spraying the spore suspension in a solution of 0.1% water agar on the bottom/abaxial side of the leaflet until they were covered with a fine mist. Typically, approximately 1 ml/leaflet was applied.

Percent disease area was evaluated in 14 days later via a software program, and efficacy was calculated based on the control leaves that were treated with the formulation without a test compound. Table 9 lists the results of Asian soybean rust control at a compound concentration of 25 ppm or lower. Compounds having an activity designated as "AA" provided a compound having ≥85% control of Asian soybean rust; compounds having an activity designated as "A" provided a compound having from 70% to 84% control of Asian soybean rust; compounds having an activity designated as "B" provided a compound having from 50 to 69% control of Asian soybean rust; compounds having an activity designated as "C" provided a compound having from 25 to 49% control of Asian soybean rust; and compounds having an activity designated as "D" provided a compound having <25% control of Asian soybean rust.

TABLE 9

Compounds with Asian Soybean Rust Control at 25 ppm or Lower

| Cmpd. No. | Asian Soybean Rust Control at a compound concentration of 25 ppm or lower |
|---|---|
| I-003 | A |
| I-014 | A |
| I-020 | B |
| I-030 | A |
| I-034 | AA |
| I-035 | A |
| I-064 | A |
| I-074 | C |
| I-082 | B |
| I-089 | A |
| I-090 | B |
| I-092 | B |
| I-094 | C |
| I-095 | AA |
| I-096 | A |
| I-171 | A |
| I-181 | B |
| I-184 | B |
| I-185 | AA |
| I-186 | D |
| I-188 | B |
| I-189 | A |
| I-191 | A |
| I-192 | AA |
| I-193 | AA |
| I-198 | AA |
| I-202 | A |
| I-205 | AA |
| I-206 | AA |
| I-208 | AA |
| I-210 | AA |
| I-211 | AA |
| I-212 | AA |
| I-213 | B |
| I-220 | B |
| I-229 | C |
| I-231 | A |
| I-233 | A |
| I-234 | A |
| I-239 | AA |
| I-246 | AA |
| I-251 | C |
| I-253 | A |
| I-258 | C |
| I-259 | B |
| I-262 | AA |
| I-263 | AA |
| I-274 | A |
| I-281 | D |
| I-284 | B |
| I-285 | C |
| I-287 | AA |
| I-289 | AA |
| I-292 | B |
| I-307 | C |
| I-308 | C |
| I-310 | C |
| I-316 | A |
| I-323 | AA |

Example 8: Seed Protectant for Soybean Seedling Disease

The pathogen of *Rhizoctonia solani* inoculum was grown on sterile *sorghum*; and the pathogen of *Pythium ultimum* inoculum was grown on white millet.

Soybean seeds (*Glycine max* cv. AG4832) were planted in 2.5-inch square pots containing Berger BM2 germination mix amended with fertilizer (e.g., 14-14-14). Pots with soil were inoculated with the pathogen of *R. solani* or *P. ultimum* at time of planting. A hole was pressed into the soil to a depth of about 2 to 3 cm; the inoculum was added to the hole, followed by the seed which was then covered with soil. Two seeds per pot were planted. Plants were grown in a growth chamber at conditions of 20 to 24° C., 14 hour light cycle, 500 uM of light, and 65% humidity. The pots inoculated with *P. ultimum* were sub-irrigated every day; and the pots inoculated with *R. solani* were sub-irrigated every other day.

Seedling emergence was captured at 7 and 14 days after seeding. At 14 days, the top of the plant was removed and fresh weight was recorded. The plant weights from the seeds treated with test compounds (e.g., in formulations) were compared to the ones either from the inoculated non-treated seeds or non-inoculated non-treated seeds. Table 10 lists the results of the *R. solani* control in soybean upon seed treatment with test compounds, and Table 11 lists the results of the *P. ultimum* control in soybean upon seed treatment with test compounds, respectively.

TABLE 10

*R. solani* Control in Soybean from Treated Seeds

| Treatment | Treatment Rate (mg/seed) | Plant Weight (g) | Improvement in plant weight (%)[a] |
|---|---|---|---|
| Inoculated non-treated seeds | — | 0.74 | 9.2 |
| I-064 | 0.025 | 6.41 | 79.9 |
| I-074 | 0.025 | 2.06 | 25.7 |
| I-095 | 0.025 | 7.54 | 93.9 |
| I-181 | 0.025 | 3.16 | 39.4 |
| I-191 | 0.025 | 6.39 | 79.6 |
| I-193 | 0.025 | 6.83 | 85.0 |
| Non-inoculated non-treated seeds | — | 8.03 | 100 |

[a]Expressed as a percentage of the maximum possible; Calculated by (weight of treated inoculated plants/weight of non-inoculated non-treated controls) × 100%.

TABLE 11

*P. ultimum* Control in Soybean from Treated Seeds

| Treatment | Treatment Rate (mg/seed) | Plant Weight (g) | Improvement in plant weight (%)[a] |
|---|---|---|---|
| Inoculated non-treated seeds | — | 3.16 | 48 |
| I-064 | 0.025 | 5.49 | 88 |
| I-074 | 0.025 | 4.33 | 69 |
| I-095 | 0.025 | 4.65 | 74 |
| I-181 | 0.025 | 4.73 | 76 |
| I-191 | 0.025 | 5.00 | 80 |
| I-193 | 0.025 | 5.36 | 86 |
| Non-inoculated non-treated seeds | — | 6.25 | 100 |

[a]Expressed as a percentage of the maximum possible; Calculated by (weight of treated inoculated plants/weight of non-inoculated non-treated controls) × 100%.

Example 9: Seed Protectant for Corn Seedling Disease

The pathogen of *Fusarium graminearum* was cultured aseptically on whole *sorghum* using standard mycological techniques and air-dried. The *sorghum* inoculum was then coarsely ground using a coffee mill before use.

Two corn seeds (*Zea mays* cv. DKC 36-34 or DKC 63-33) were planted in 2.5-inch square pots containing Berger BM6 15P germination mix amended with fertilizer (e.g., 19-6-12). The soil pots were pre-drenched and two two-inch holes were pressed into the soil. The *sorghum* inoculums (1/16 teaspoon) was added to each hole, followed by one corn seed (treated with or without test compounds). The two seeds were sown in opposite corners of the pot. Plants were grown in a growth chamber at conditions of 20 to 24° C., 16 hour light cycle, 500 uM of light, 65% humidity, and with sub-irrigation twice daily.

Seedling emergence and total plant height (cm) were recorded at 7 and 14 days after planting.

The plant heights from the seeds treated with test compounds (e.g., in formulations) were compared to the ones either from the inoculated non-treated seeds or non-inoculated non-treated seeds. Tables 12 and 13 list the results of the *F. graminearum* control in corn upon seed treatment with test compounds.

TABLE 12

*F. graminearum* Control in Corn from Treated Seeds

| Treatment | Treatment Rate (mg/seed) | Plant Height (cm) | Improvement in plant weight (%)[a] |
|---|---|---|---|
| Inoculated non-treated seeds | | 18.91 | 41 |
| I-020 | 0.025 | 40.53 | 87 |
| I-095 | 0.025 | 39.41 | 85 |
| I-181 | 0.025 | 47.63 | 103 |
| I-185 | 0.025 | 45.66 | 99 |
| I-191 | 0.025 | 35.50 | 77 |
| Non-inoculated Non-treated seeds | | 46.34 | 100 |

[a]Expressed as a percentage of the maximum possible; Calculated by (height of treated inoculated plants/height of non-inoculated non-treated controls) × 100%.

TABLE 13

*F. graminearum* Control in Corn from Treated Seeds

| Treatment | Treatment Rate (mg/seed) | Plant Height (cm) | Improvement in plant weight (%)[a] |
|---|---|---|---|
| Inoculated non-treated seeds | | 20.75 | 51 |
| I-095 | 0.025 | 43.97 | 109 |
| I-193 | 0.025 | 40.66 | 101 |
| I-205 | 0.025 | 41.47 | 103 |
| I-206 | 0.025 | 42.72 | 106 |
| I-253 | 0.025 | 37.81 | 94 |
| Non-inoculated non-treated seeds | | 40.41 | 100 |

[a]Expressed as a percentage of the maximum possible; Calculated by (height of treated inoculated plants/height of non-inoculated non-treated controls) × 100%.

Example 10: Early Foliar Disease Control Via Seed Treatment

Barley seeds (*Hordeum vulgare* cv. Perry or Conlon) were treated with a test compound dissolved in pure acetone, in which the acetone solution (1 mL) was used per 50 seeds in glass jars in a fume hood. The seeds were swirled in the glass jars by hand until no obvious presence of acetone remained and the seeds were mostly dry.

Plants were grown for 7 days in 2-inch square pots containing Metromix 200 medium amended with fertilizer. For propagation, plants were maintained in a growth chamber at conditions of 20 to 21° C., 16 hour light cycle, 400 uM of light, 50% humidity, and with sub-irrigation as needed. After inoculation with the pathogen of *Blumeria graminis* f. sp. *hordei*, plants were kept at conditions of 20 to 22° C., 200 uM of light, 70% humidity to facilitate infection and disease development.

At 7 days after planting (1$^{st}$ true leaf fully expanded), the plants were moved to the cooler chamber and inoculated by shaking well-colonized, untreated stock plants above the treated material. By doing so, it produced a settling cloud of spores and resulted in uniform infection.

Efficacy was evaluated in 7 days later by examining leaves for colonization and growth of powdery mildew. Each side of each leaf was assigned a severity rating of 0, 1, 5, 10, 25, 50, 75, or 100 percent diseased area. Table 14 lists the results of barley powdery mildew control upon seed treatment with test compounds.

TABLE 14

Barley Powdery Mildew control via Seed Treatment

| Treatment | Treatment Rate (mg/seed) | Barley Powdery Mildew Reduction (%) |
|---|---|---|
| I-020 | 0.025 | 91 |
| I-181 | 0.025 | 57 |
| I-191 | 0.025 | 94 |
| I-193 | 0.025 | 96 |

Embodiments

For further illustration, additional non-limiting embodiments of the present disclosure are set forth below.

For example, embodiment 1 is a composition for agricultural use comprising an effective amount of a fungicidal compound of Formula I:

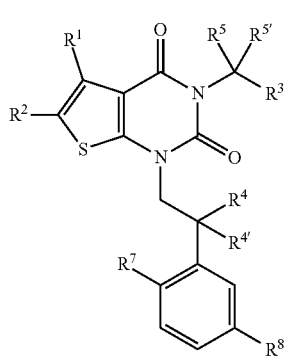

Formula I or a salt thereof, wherein:

$R^1$ is hydrogen, $C_1$-$C_4$ alkyl, $C_1$-$C_4$ alkoxy, $C_1$-$C_4$ haloalkyl, or $C_1$-$C_4$ haloalkoxy;

$R^2$ is heteroaryl, alkyl, cycloalkyl, or heterocyclyl, each of which may be optionally independently substituted with one or more of hydroxyl, halogen, $C_1$-$C_4$ alkyl, $C_1$-$C_4$ alkoxy, $C_1$-$C_4$ haloalkyl, $C_1$-$C_4$ haloalkoxy, oxo, or cyano; or $R^2$ is —C(O)$R^{21}$, wherein $R^{21}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or heterocyclyl, each of which may be optionally independently substituted with one or more of hydroxyl, $C_1$-$C_4$ alkyl, $C_1$-$C_4$ alkoxy, oxo, or cyano;

$R^3$ is —C(O)$R^{31}$, —C(O)N($R^{32}R^{33}$), or —$R^{34}$SO$_2$N($R^{32}R^{33}$), wherein $R^{31}$ is hydroxyl, $C_1$-$C_6$ alkoxy, $C_1$-$C_6$ haloalkoxy, $C_3$-$C_6$ cycloalkoxy, arylalkoxy, heteroarylalkoxy, or 1-heterocycl-1-yl, each of which may be optionally independently substituted with one or more of hydroxyl, $C_1$-$C_4$ alkyl, $C_1$-$C_4$ alkoxy, oxo, or cyano; $R^{32}$ and $R^{33}$ are each independently hydrogen, $C_1$-$C_6$ alkyl, $C_2$-$C_6$ alkenyl, or $C_3$-$C_6$ cycloalkyl, each of which may be optionally independently substituted with one or more of hydroxyl, halogen, $C_1$-$C_4$ alkoxy, oxo, or cyano; and $R^{34}$ is a bond, $C_1$-$C_4$ alkyl, $C_1$-$C_4$ haloalkyl, or $C_2$-$C_4$ alkenyl;

$R^4$ is hydrogen or —O$R^6$, wherein $R^6$ is hydrogen, $C_1$-$C_6$ alkyl, $C_2$-$C_6$ alkenyl, $C_3$-$C_6$ cycloalkyl, $C_4$-$C_{10}$ cycloalkylalkyl, or heterocyclyl, each of which may be optionally independently substituted with one or more of an oxygen atom, hydroxyl, $C_1$-$C_4$ alkyl, $C_1$-$C_4$ alkoxy, oxo, cyano, —N($R^{61}R^{62}$), —C(O)N($R^{61}R^{62}$), or SO$_2R^{63}$, wherein $R^{61}$ and $R^{62}$ are each independently hydrogen or $C_1$-$C_6$ alkyl, and $R^{63}$ is $C_1$-$C_6$ alkyl;

$R^{4'}$ is hydrogen or $C_1$-$C_4$ alkyl, which may be optionally substituted with one or more of hydroxyl, $C_1$-$C_4$ alkoxy, or cyano;

$R^5$ and $R^{5'}$ are each independently hydrogen or $C_1$-$C_4$ alkyl;

$R^7$ is hydroxyl or $C_1$-$C_4$ alkyl, which may be optionally substituted with one or more of hydroxyl, $C_1$-$C_4$ alkoxy, oxo, or cyano; or $R^7$ is —O$R^{10}$, wherein $R^{10}$ is $C_1$-$C_4$ alkyl, $C_1$-$C_4$ haloalkyl, $C_3$-$C_6$ cycloalkylmethyl, heterocyclyl, or aryl($C_1$-$C_4$)alkyl, each of which may be optionally independently substituted with one or more of hydroxyl, an oxygen atom, $C_1$-$C_4$ alkyl, $C_1$-$C_4$ alkoxy, oxo, or cyano; and $R^8$ is hydrogen, halogen, or cyano.

Embodiment 2 is the composition of embodiment 1 wherein $R^1$ is $C_1$-$C_4$ alkyl.

Embodiment 3 is the composition of embodiment 2 wherein $R^1$ is methyl.

Embodiment 4 is the composition of any one of embodiments 1 to 3 wherein $R^2$ is —C(O)$R^{21}$, wherein $R^{21}$ is $C_1$-$C_4$ alkoxy.

Embodiment 5 is the composition of any one of embodiments 1 to 3 wherein $R^2$ is —CH$_2$OH.

Embodiment 6 is the composition of any one of embodiments 1 to 3 wherein $R^2$ is —CH$_2$O($C_1$-$C_4$)alkyl.

Embodiment 7 is the composition of any one of embodiments 1 to 3 wherein $R^2$ is cyclobutyl.

Embodiment 8 is the composition of any one of embodiments 1 to 3 wherein $R^2$ is unsubstituted heteroaryl.

Embodiment 9 is the composition of embodiment 8 wherein $R^2$ is a 5-membered heteroaryl.

Embodiment 10 is the composition of embodiment 9 wherein $R^2$ is oxazolyl, pyrazolyl, triazolyl, isoxazolyl, or thienyl.

Embodiment 11 is the composition of embodiment 10 wherein $R^2$ is oxazolyl, pyrazolyl, or triazolyl.

Embodiment 12 is the composition of embodiment 11 wherein $R^2$ is 2-oxazolyl.

Embodiment 13 is the composition of embodiment 11 wherein $R^2$ is 1-pyrazolyl.

Embodiment 14 is the composition of embodiment 11 wherein $R^2$ is 2H-1,2,3-triazol-2-yl.

Embodiment 15 is the composition of any one of embodiments 1 to 14 wherein $R^3$ is —C(O)$R^{31}$, wherein $R^{31}$ is hydroxyl, alkoxy, or an optionally independently substituted 1-heterocycl-1-yl.

Embodiment 16 is the composition of embodiment 15 wherein $R^{31}$ is hydroxyl.

Embodiment 17 is the composition of embodiment 15 wherein $R^{31}$ is ethoxy or benzoxy.

Embodiment 18 is the composition of embodiment 15 wherein $R^{31}$ is 2,5-dihydro-1H-pyrrolyl, 1-piperidinyl, 1-pyrrolidinyl, 1-morpholinyl, or 1-azetidinyl, each of which may be optionally independently substituted with hydroxyl, methoxy, or methyl.

Embodiment 19 is the composition of any one of embodiments 1 to 14 wherein $R^3$ is —C(O)N($R^{32}R^{33}$), wherein $R^{32}$ and $R^{33}$ are independently hydrogen, $C_1$-$C_6$ alkyl, $C_2$-$C_6$ alkenyl, or $C_3$-$C_6$ cycloalkyl.

Embodiment 20 is the composition of embodiment 19 wherein $R^{32}$ is hydrogen or methyl, and $R^{33}$ is hydrogen, methyl, ethyl, propyl, isopropyl, butyl, isobutyl, t-butyl, cyclopropyl, cyclobutyl, 2-propenyl, or —CH$_2$CN.

Embodiment 21 is the composition of embodiment 20 wherein $R^{32}$ is hydrogen, and $R^{33}$ is hydrogen, methyl, ethyl, isopropyl, isobutyl, cyclopropyl, cyclobutyl, 2-propenyl, or —CH$_2$CN.

Embodiment 22 is the composition of embodiment 20 wherein $R^{32}$ is methyl, and $R^{33}$ is methyl, isopropyl, or 2-propenyl.

Embodiment 23 is the composition of any one of embodiments 1 to 14 wherein $R^3$ is —R$^{34}$SO$_2$N(R$^{32}$R$^{33}$), wherein $R^{34}$ is a bond or $C_1$-$C_4$ alkyl, and $R^{32}$ and $R^{33}$ are each hydrogen.

Embodiment 24 is the composition of any one of embodiments 1 to 14 wherein $R^3$ is —CH$_2$SO$_2$NH$_2$.

Embodiment 25 is the composition of any one of embodiments 1 to 24 wherein $R^4$ and $R^{4'}$ are both hydrogen.

Embodiment 26 is the composition of any one of embodiments 1 to 24 wherein $R^4$ is —OR$^6$ and $R^{4'}$ is hydrogen, wherein $R^6$ is hydrogen, $C_1$-$C_6$ alkyl, $C_2$-$C_6$ alkenyl, $C_3$-$C_6$ cycloalkyl, $C_4$-$C_{10}$ cycloalkylalkyl, or heterocyclyl, each of which may be optionally independently substituted with hydroxyl, methoxy, oxo, cyano, —N(CH$_3$)$_2$, —C(O)NH$_2$, or —SO$_2$CH$_3$.

Embodiment 27 is the composition of embodiment 26 wherein $R^6$ is hydrogen.

Embodiment 28 is the composition of embodiment 26 wherein $R^6$ is $C_1$-$C_6$ alkyl or $C_2$-$C_6$ alkenyl, each of which may be optionally independently substituted with hydroxyl, methoxy, oxo, cyano, —N(CH$_3$)$_2$, —C(O)NH$_2$, or —SO$_2$CH$_3$.

Embodiment 29 is the composition of embodiment 28 wherein $R^6$ is ethyl, isopropyl, isobutyl, —CH$_2$CH$_2$OH, —CH$_2$CH$_2$OCH$_3$, —(CH$_2$)$_3$OCH$_3$, —CH$_2$CH(CH$_3$)OH, —CH$_2$C(CH$_3$)$_2$OH, —CH$_2$CH=CH$_2$, —C(O)CH$_3$, —C(O)CH$_2$OH, —CH$_2$CN, —CH$_2$CH$_2$CN, —CH$_2$CH(CH$_3$)CN, —CH$_2$C(CH$_3$)$_2$CN, —CH$_2$CH$_2$N(CH$_3$)$_2$, —CH$_2$CH$_2$C(O)NH$_2$, or —CH$_2$CH$_2$SO$_2$CH$_3$.

Embodiment 30 is the composition of embodiment 26 wherein $R^6$ is $C_3$-$C_6$ cycloalkyl or $C_4$-$C_{10}$ cycloalkylalkyl, which may be optionally independently substituted with hydroxyl or oxo.

Embodiment 31 is the composition of embodiment 30 wherein $R^6$ is 4-hydroxycyclohexyl, 4-oxycyclohexyl, (4-oxocyclohexyl)methyl, or (4-hydroxycyclohexyl)methyl.

Embodiment 32 is the composition of embodiment 26 wherein $R^6$ is tetrahydro-2H-pyran-4-yl.

Embodiment 33 is the composition of any one of embodiments 1 to 24 wherein $R^4$ is —OH or —OCH$_2$CH$_2$CN, and $R^{4'}$ is methyl, —CH$_2$OH, or —CH$_2$CH$_2$OH.

Embodiment 34 is the composition of embodiment 33 wherein $R^4$ is —OH and $R^{4'}$ is —CH$_2$OH.

Embodiment 35 is the composition of embodiment 33 wherein $R^4$ is —OH and $R^{4'}$ is —CH$_2$CH$_2$OH.

Embodiment 36 is the composition of embodiment 33 wherein $R^4$ is —OCH$_2$CH$_2$CN and $R^{4'}$ is methyl.

Embodiment 37 is the composition of any one of embodiments 1 to 36 wherein $R^5$ and $R^{5'}$ are independently hydrogen or methyl.

Embodiment 38 is the composition of embodiment 37 wherein $R^5$ and $R^{5'}$ are both methyl.

Embodiment 39 is the composition of embodiment 37 wherein $R^5$ is methyl and $R^{5'}$ is hydrogen.

Embodiment 40 is the composition of embodiment 37 wherein $R^5$ and $R^{5'}$ are both hydrogen.

Embodiment 41 is the composition of any one of embodiments 1 to 40 wherein $R^7$ is hydroxyl.

Embodiment 42 is the composition of any one of embodiments 1 to 40 wherein $R^7$ is $C_1$-$C_4$ alkyl, which may be optionally independently substituted with cyano.

Embodiment 43 is the composition of embodiment 42 wherein $R^7$ is methyl, ethyl, or —(CH$_2$)$_3$CN.

Embodiment 44 is the composition of any one of embodiments 1 to 40 wherein $R^7$ is —OR$^{10}$, wherein $R^{10}$ is $C_1$-$C_4$ alkyl, heterocyclyl, or benzyl, each of which may be optionally independently substituted with hydroxyl, methoxy, oxo, oxetanyl, or cyano.

Embodiment 45 is the composition of embodiment 44 wherein $R^{10}$ is methyl, —CH(CH$_3$)$_2$, —CH$_2$CH$_2$OH, —CH$_2$CH$_2$OCH$_3$, —C(O)CH$_3$, —CH$_2$(oxetan-3-yl), —CH$_2$CN, or —CH$_2$CH$_2$CN.

Embodiment 46 is the composition of embodiment 45 wherein $R^{10}$ is methyl.

Embodiment 47 is the composition of embodiment 44 wherein $R^{10}$ is tetrahydro-2H-pyran-4-yl or benzyl.

Embodiment 48 is the composition of any one of embodiments 1 to 47 wherein $R^8$ is hydrogen or fluorine.

Embodiment 49 is a composition for agricultural use comprising an effective amount of a fungicidal compound of Formula Ia, or Ib:

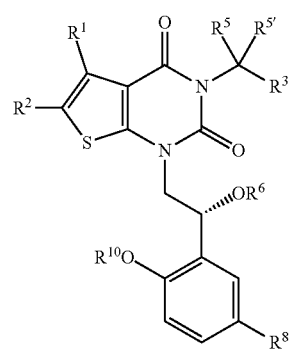

Formula Ia

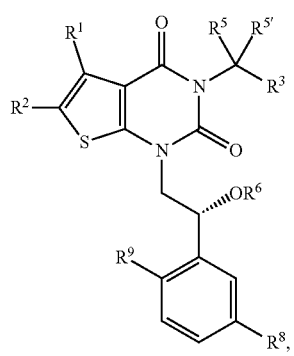

Formula Ib or a salt thereof, wherein:

$R^1$ is methyl;

$R^2$ is oxazolyl, pyrazolyl, triazolyl, cyclobutyl, —CH$_2$OH, —CH$_2$O($C_1$-$C_4$)alkyl, or —C(O)R$^{21}$ wherein $R^{21}$ is $C_1$-$C_4$ alkoxy;

$R^3$ is —C(O)R$^{31}$, —C(O)N(R$^{32}$R$^{33}$), or —R$^{34}$SO$_2$N(R$^{32}$R$^{33}$), wherein $R^{31}$ is hydroxyl, ethoxy, benzoxy, 1-pyrrolidinyl, 1-piperidinyl, 1-morpholinyl, 2,5-dihydro-1H-pyrrol-1-yl, or 3-hydroxyazetidin-1-yl, $R^{32}$ is hydrogen or methyl, and $R^{33}$ is hydrogen, methyl, ethyl, isopropyl, isobutyl, 2-propenyl, or cyclobutyl; or $R^{34}$ is a bond, or $C_1$-$C_4$ alkyl;

$R^5$ and $R^{5'}$ are each independently hydrogen or methyl;

$R^6$ is hydrogen, $C_1$-$C_4$ alkyl, which may be substituted with one or more of hydroxyl, methoxy, oxo, cyano, or —$SO_2CH_3$; $R^6$ is cyclohexyl or cyclohexylmethyl, which may be substituted with one or more of hydroxyl or oxo; $R^6$ is 2-propenyl; or $R^6$ is tetrahydropyranyl;

$R^8$ is hydrogen or F;

$R^9$ is hydroxyl, methyl, ethyl, or —$(CH_2)_3CN$; and $R^{10}$ is methyl or ethyl, each of which may be substituted with one or more of hydroxyl, methyl, methoxy, cyano, phenyl, oxo, or oxetan-3-yl; or $R^{10}$ is tetrahydropyranyl.

Embodiment 50 is the composition of embodiment 49 wherein $R^2$ is 1-pyrazolyl, 2H-1,2,3-triazol-2-yl, 2-oxazolyl, or —$C(O)OCH_2CH_3$.

Embodiment 51 is the composition of embodiment 50 wherein $R^2$ is 1-pyrazolyl.

Embodiment 52 is the composition of embodiment 50 wherein $R^2$ is 2H-1,2,3-triazol-2-yl.

Embodiment 53 is the composition of embodiment 50 wherein $R^2$ is 2-oxazolyl.

Embodiment 54 is the composition of embodiment 50 wherein $R^2$ is —$C(O)OCH_2CH_3$.

Embodiment 55 is the composition of any one of embodiment 49 to 54 wherein $R^3$ is —$C(O)R^{31}$, wherein $R^{31}$ is 1-pyrrolidinyl or 1-piperidinyl.

Embodiment 56 is the composition of embodiment 55 wherein $R^3$ is —$C(O)R^{31}$ wherein $R^{31}$ is 1-pyrrolidinyl.

Embodiment 57 is the composition of any one of embodiment 49 to 54 wherein $R^3$ is —$C(O)N(R^{32}R^{33})$, $R^{32}$ is hydrogen or methyl, and $R^{33}$ is ethyl, isopropyl, or cyclobutyl.

Embodiment 58 is the composition of embodiment 57 wherein $R^{32}$ is hydrogen, and $R^{33}$ is ethyl.

Embodiment 59 is the composition of embodiment 57 wherein $R^{32}$ is hydrogen, and $R^{33}$ is isopropyl.

Embodiment 60 is the composition of embodiment 57 wherein $R^{32}$ is methyl, and $R^{33}$ is isopropyl.

Embodiment 61 is the composition of embodiment 57 wherein $R^{32}$ is hydrogen, and $R^{33}$ is cyclobutyl.

Embodiment 62 is the composition of any one of embodiments 49 to 61 wherein $R^5$ and $R^{5'}$ are each methyl.

Embodiment 63 is the composition of any one of embodiments 49 to 61 wherein $R^5$ is methyl and $R^{5'}$ is hydrogen.

Embodiment 64 is the composition of any one of embodiments 49 to 63 wherein $R^6$ is hydrogen, isopropyl, —$CH_2CH_2OH$, —$CH_2CH_2OCH_3$, —$(CH_2)_3OCH_3$, —$C(O)CH_3$, —$CH_2CN$, —$CH_2CH_2CN$, —$CH_2CH(CH_3)CN$, —$CH_2C(CH_3)_2CN$, —$CH_2CH_2SO_2CH_3$, or tetrahydro-2H-pyran-4-yl.

Embodiment 65 is the composition of any one of embodiments 49 to 64 wherein $R^8$ is hydrogen.

Embodiment 66 is the composition of any one of embodiments 49 to 64 wherein $R^8$ is F.

Embodiment 67 is the composition of any one of embodiments 49 to 66 wherein $R^9$ is ethyl.

Embodiment 68 is the composition of any one of embodiments 49 to 66 wherein $R^{10}$ is methyl.

Embodiment 69 is a composition for agricultural use comprising an effective amount of a fungicidal compound selected from the group consisting of:

(R)-ethyl-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-2,4-dioxo-1,2,3,4-tetrahydrothieno[2,3-d]pyrimidine-6-carboxylate;

(R)-2-(1-(2-(5-fluoro-2-methoxyphenyl)-2-isopropoxyethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-isopropoxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-6-(2H-1,2,3-triazol-2-yl)thieno[2,3-d]pyrimidine-2,4(1H,3H)-dione;

(R)—N-ethyl-2-(1-(2-(5-fluoro-2-methoxyphenyl)-2-((tetrahydro-2H-pyran-4-yl)oxy)ethyl)-5-methyl-2,4-dioxo-6-(2H-1,2,3-triazol-2-yl)-1,4-dihydrothieno[2,3-d]pyrimidin-3 (2H)-yl)-2-methylpropanamide;

(R)-2-(1-(2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-(2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-2-(1-(2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3(2H)-yl)-N-isopropyl-2-methylpropanamide;

(S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3(2H)-yl)-N-isopropyl-N-methylpropanamide;

(R)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)—N-cyclobutyl-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)propanamide;

(R)-2-(1-((R)-2-(5-fluoro-2-methoxyphenyl)-2-(3-methoxypropoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(S)-2-(1-((R)-2-(5-fluoro-2-methoxyphenyl)-2-(2-hydroxyethoxy)ethyl)-5-methyl-2,4-dioxo-6-(2H-1,2,3-triazol-2-yl)-1,4-dihydrothieno[2,3-d]pyrimidin-3(2H)-yl)-N-isopropylpropanamide;

(R)-2-(1-((R)-2-(5-fluoro-2-methoxyphenyl)-2-(2-methoxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

(R)-ethyl 1-(2-(2-cyanoethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl 1-(2-(5-fluoro-2-methoxyphenyl)-2-(2-hydroxyethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(5-fluoro-2-methoxyphenyl)-2-hydroxyethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(S)-2-(1-((R)-2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(R)-2-(1-(2-(2-cyanoethoxy)-2-(2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide;

(R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropylpropanamide;

3-((R)-1-(5-fluoro-2-methoxyphenyl)-2-(5-methyl-2,4-dioxo-3-((R)-1-oxo-1-(pyrrolidin-1-yl)propan-2-yl)-6-(2H-1,2,3-triazol-2-yl)-3,4-dihydrothieno[2,3-d]pyrimidin-1 (2H)-yl)ethoxy)propanenitrile;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide;

(R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethyl-2-methylpropanamide;

(R)-2-(1-(2-(cyanomethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((S)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin (2H)-yl)-N-isopropyl-2-methylpropanamide;

(R)-2-(1-(2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(2-cyanoethoxy)-2-(5-fluoro-2-methoxyphenyl)ethyl)-3-((R)-1-(isopropylamino)-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(5-fluoro-2-methoxyphenyl)ethyl)-3-((R)-1-(isopropyl(methyl)amino)-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(5-fluoro-2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-(2-cyanoethoxy)-2-(2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;

(S)-2-(1-((R)-2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-N-methylpropanamide;

(R)-2-(1-(2-(2-ethyl-5-fluorophenyl)-2-(2-hydroxyethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(cyanomethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-((R)-2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-isopropylpropanamide;

(R)-ethyl-1-(2-((S)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-ethyl-1-(2-((R)-2-cyanopropoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

2-(1-((R)-2-((S)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-isopropyl-2-methylpropanamide;

(S)-2-(1-(2-(2-cyanoethoxy)-2-(5-fluoro-2-methoxyphenyl)propyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((S)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

2-(1-((R)-2-((R)-2-cyanopropoxy)-2-(2-ethyl-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-ethyl-1-(2-(5-fluoro-2-methoxyphenyl)-2-(2-(methylsulfonyl)ethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;

(R)-2-(1-(2-(5-fluoro-2-methoxyphenyl)-2-(2-(methylsulfonyl)ethoxy)ethyl)-5-methyl-2,4-dioxo-6-(2H-1,2,3-triazol-2-yl)-1,4-dihydrothieno[2,3-d]pyrimidin-3 (2H)-yl)-N-isopropyl-2-methylpropanamide;

(R)-2-(1-((R)-2-(2-cyanoethoxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3 (2H)-yl)-N-ethylpropanamide;

(R)—N-ethyl-2-(1-(2-(5-fluoro-2-methoxyphenyl)-2-hydroxyethyl)-5-methyl-2,4-dioxo-6-(2H-1,2,3-triazol-2-yl)-1,4-dihydrothieno[2,3-d]pyrimidin-3 (2H)-yl)-2-methylpropanamide;

(R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutyl-2-methylpropanamide;

(R)-2-(1-((R)-2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3 (2H)-yl)-N-cyclobutylpropanamide;

(R)-2-(1-((R)-2-(5-fluoro-2-methoxyphenyl)-2-(2-methoxyethoxy)ethyl)-5-methyl-2,4-dioxo-6-(1H-pyrazol-1-yl)-1,4-dihydrothieno[2,3-d]pyrimidin-3 (2H)-yl)-N-isopropylpropanamide;

(R)-2-(1-(2-hydroxy-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-isopropyl-2-methylpropanamide; and (R)-1-(5-fluoro-2-methoxyphenyl)-2-(3-(1-(isopropylamino)-2-methyl-1-oxopropan-2-yl)-5-methyl-2,4-dioxo-6-(2H-1,2,3-triazol-2-yl)-3,4-dihydrothieno[2,3-d]pyrimidin-1(2H)-yl)ethyl acetate.

Embodiment 70 is the composition of any one of embodiments 1 to 69 further comprising a surfactant.

Embodiment 71 is the composition of any one of embodiments 1 to 69 further comprising a co-solvent.

Embodiment 72 is the composition of any one of embodiments 1 to 69 further comprising a biological control agent, microbial extract, natural product, plant growth activator or plant defense agent or mixtures thereof.

Embodiment 73 is the composition of embodiment 72 wherein the biological control agent comprises a bacterium, a fungus, a beneficial nematode, or a virus.

Embodiment 74 is the composition of embodiment 73 wherein the biological control agent comprises a bacterium of the genus *Actinomycetes, Agrobacterium, Arthrobacter, Alcaligenes, Aureobacterium, Azobacter, Bacillus, Beijerinckia, Bradyrhizobium, Brevibacillus, Burkholderia, Chromobacterium, Clostridium, Clavibacter, Comamonas, Corynebacterium, Curtobacterium, Enterobacter, Flavobacterium, Gluconobacter, Hydrogenophage, Klebsiella, Metarhizium, Methylobacterium, Paenibacillus, Pasteuria, Photorhabdus, Phyllobacterium, Pseudomonas, Rhizobium, Serratia, Sphingobacterium, Stenotrophomonas, Streptomyces, Variovax*, or *Xenorhabdus*.

Embodiment 75 is the composition of embodiment 73 wherein the biological control agent comprises a fungus of the genus *Alternaria, Ampelomyces, Aspergillus, Aureobasidium, Beauveria, Colletotrichum, Coniothyrium, Gliocladium, Metarhizium, Muscodor, Paecilomyces, Penicillium, Trichoderma, Typhula, Ulocladium*, and *Verticillium*.

Embodiment 76 is the composition of embodiment 73 wherein the biological control agent is a plant growth activator or plant defense agent selected from the group consisting of harpin, *Reynoutria sachalinensis*, jasmonate, lipochitooligosaccharides, salicylic acid, and isoflavones.

Embodiment 77 is the composition of any one of embodiments 1 to 76 further comprising one or more additional pesticides, wherein the additional pesticide comprises a fungicide, an insecticide and a herbicide or a mixture thereof.

Embodiment 78 is the composition of embodiment 77 wherein the additional pesticide is a fungicide selected from the group consisting of acibenzolar-S-methyl, azoxystrobin, benalaxyl, benzovindiflupyr, bixafen, boscalid, carbendazim, cyproconazole, dimethomorph, epoxiconazole, fluindapyr, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, oxathiapiprolin, penflufen, penthiopyrad, picoxystrobin, propiconazole, prothioconazole, pyraclostrobin, pydiflumetofen, sedaxane, silthiofam, tebuconazole, thifluzamide, thiophanate, tolclofos-methyl, trifloxystrobin, and triticonazole.

Embodiment 79 is the composition of embodiment 77 wherein the additional pesticide is an insecticide or nematicide selected from the group consisting of abamectin, aldicarb, aldoxycarb, bifenthrin, broflanilide, carbofuran, chlorantraniliprole, clothianidin, cyantraniliprole, cyclaniliprole, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, 3-phenyl-5-(2-thienyl)-1,2,4-oxadiazole, nitenpyram, oxamyl, permethrin, spinetoram, spinosad, spirodichlofen, spirotetramat, tefluthrin, tetraniliprole, thiacloprid, thiamethoxam, thiodicarb, tioxazafen, and mixtures thereof.

Embodiment 80 is the composition of embodiment 77 wherein the additional pesticide is an herbicide selected from the group consisting of acetochlor, clethodim, dicamba, 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione (trifludimoxazin), ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy) acetate, flumioxazin, fomesafen, glyphosate, glufosinate, halauxifen, isoxaflutole, mesotrione, metolachlor, quizalofop, saflufenacil, sulcotrione, tembotrione, topramezone, and 2,4-D and mixtures thereof.

Embodiment 81 is the composition of embodiment 77 or 80 wherein the additional pesticide is an ACCase inhibitor.

Embodiment 82 is the composition of embodiment 81 wherein the additional pesticide is an ACCase inhibitor selected from the group consisting of chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, and pinoxaden.

Embodiment 83 is the composition of embodiment 77 wherein the additional pesticide is selected from the group consisting of fluoxastrobin, fluxapyroxad, ipconazole, mefenoxam, metalaxyl, penflufen, prothioconazole, pyraclostrobin, trifloxystrobin, abamectin, *Bacillus firmus*, clothianidin, imidacloprid, thiamethoxam and mixtures thereof.

Embodiment 84 is the composition of embodiment 77 wherein the treatment composition comprises tioxazafen.

Embodiment 85 is a treated seed comprising a composition as set forth in any one of embodiments 1 to 84.

Embodiment 86 is the seed of embodiment 85, wherein the treated seed comprises: a seed and a coating comprising a composition as set forth in any one of embodiments 1 to 84.

Embodiment 87 is the seed of embodiment 86, wherein the coating comprises the fungicidal compound of Formula I, Formula Ia, or a salt thereof in an amount of at least about 0.005 mg/seed, from about 0.005 to about 1 mg/seed, or from about 0.05 to about 0.5 mg/seed.

Embodiment 88 is a method of controlling agricultural fungal pathogens, the method comprising administering to a plant, a seed or soil a composition as set forth in any one of embodiments 1 to 84.

Embodiment 89 is the method of embodiment 88 wherein the method comprises administering the composition to a seed.

Embodiment 90 is a treated seed prepared according to the method of embodiment 89.

Embodiment 91 is the method of embodiment 88 wherein the method comprises exogenously administering the composition to a plant.

Embodiment 92 is the method of embodiment 91 wherein the composition is applied to the foliage of a plant.

Embodiment 93 is the method of embodiment 91 wherein the method comprises applying the composition to the soil surrounding the root zone of a plant.

Embodiment 94 is the method of embodiment 91 wherein the composition is applied directly to the base of the plant or to the soil immediately adjacent to the plant.

Embodiment 95 is the method of embodiment 93 or 94 wherein the composition is applied such that it drains through the soil to the root area of the plant.

Embodiment 96 is the method of any one of embodiments 91 to 95 wherein the composition is applied using a sprayer, a mechanical sprinkler, a drench application, drip irrigation technique, or tilled into the soil or applied in furrow.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method of controlling an agricultural fungal pathogen, the method comprising administering to a plant, a seed or soil a composition comprising a compound selected from the group consisting of:
   (R)-ethyl-1-(2-(2-cyanoethoxy)-2-(5-fluoro-2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;
   (R)-ethyl-1-(2-(5-fluoro-2-methoxyphenyl)-2-(2-hydroxyethoxy)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate;
   (R)-2-(1-(2-(2-cyanoethoxy)-2-(2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide;
   (R)-2-(1-(2-(2-cyanoethoxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-isopropyl-2-methylpropanamide;
   (R)-2-(1-(2-(2-cyano-2-methylpropoxy)-2-(5-fluoro-2-methoxyphenyl)ethyl)-5-methyl-2,4-dioxo-6-(2H-1,2,3-triazol-2-yl)-1,4-dihydrothieno [2,3-d]pyrimidin-3(2H)-yl)-N-isopropyl-2-methylpropanamide;
   (R)-ethyl-1-(2-(2-cyanoethoxy)-2-(5-fluoro-2-methoxyphenyl)ethyl)-3-((R)-1-(isopropylamino)-1-oxopropan-2-yl)-5-methyl-2,4-dioxo-1,2,3,4-tetrahydrothieno[2,3-d]pyrimidine-6-carboxylate;
   (R)-ethyl-1-(2-(2-cyanoethoxy)-2-(5-fluoro-2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;
   (R)-ethyl-1-(2-(2-cyanoethoxy)-2-(2-methoxyphenyl)ethyl)-3-(1-(isopropylamino)-2-methyl-1-oxopropan-2-yl)-5-methyl-2,4-dioxo-1,2,3,4-tetrahydrothieno[2,3-d]pyrimidine-6-carboxylate; and
   (R)-ethyl-1-(2-(2-cyanoethoxy)-2-(2-methoxyphenyl)ethyl)-3-(1-(ethylamino)-2-methyl-1-oxopropan-2-yl)-5-methyl-2,4-dioxo-1,2,3,4-tetrahydrothieno[2,3-d]pyrimidine-6-carboxylate;
   or a salt thereof.

2. The method of claim 1, wherein the composition further comprises a surfactant.

3. The method of claim 1, wherein the composition further comprises a co-solvent.

4. The method of claim 1, wherein the composition further comprises a biological control agent, microbial extract, natural product, plant growth activator plant defense agent, or a mixture thereof.

5. The method of claim 1, wherein the composition further comprises an additional pesticide, wherein the additional pesticide is a fungicide, an insecticide, a herbicide, or a mixture thereof.

6. The method of claim 1, wherein the composition further comprises an additional pesticide, wherein the additional pesticide is fluoxastrobin, fluxapyroxad, ipconazole, mefenoxam, metalaxyl, penflufen, prothioconazole, pyraclostrobin, trifloxystrobin, abamectin, clothianidin, imidacloprid, thiamethoxam, or a mixture thereof.

7. The method of claim 1, wherein the composition further comprises tioxazafen.

8. The method of 1, wherein the method comprises administering the composition to a seed.

9. A treated seed prepared according to the method of claim 1.

10. The method of claim 1, wherein the method comprises exogenously administering the composition to a plant.

11. The method of claim 10, wherein the composition is applied to foliage of the plant.

12. The method of claim 10, wherein the method comprises applying the composition to soil surrounding a root zone of the plant.

13. The method of claim 10, wherein the composition is applied directly to a base of the plant or to soil immediately adjacent to the plant.

14. The method of claim 1, wherein the agricultural fungal pathogen is selected from Ascomycetes, Deuteromycetes, Oomycetes, and Basidiomycetes.

15. The method of claim 1, wherein the agricultural fungal pathogen is *Blumeria graminis, Microsphaera* spp., *Podosphaera* spp., *Uncinula necator, Fusarium graminearum, Fusarium moniliforme, Fusarium virguliforme, Botrtyis cinerea, Sclerotinia sclerotiorum, Alternaria alternata, Alternaria solani, Collectotrichum graminicola, Cercospora* spp., *Septoria* (Zymoseptoria) *tritici, Rhizoctonia solani, Puccinia* spp., *Puccinia triticina, Phakopsora pachyrhizi, Diplodia maydis, Phytophthora capsici, Pythium* spp., or *Pythium ultimum*.

16. The method of claim 1, wherein the composition further comprises a biological control agent, wherein the biological control agent is *Bacillus firmus*.

\* \* \* \* \*